United States Patent
Koide et al.

(10) Patent No.: US 12,084,500 B2
(45) Date of Patent: Sep. 10, 2024

(54) ANTIBODIES SPECIFIC TO DELTA 1 CHAIN OF T CELL RECEPTOR

(71) Applicants: New York University, New York, NY (US); PureTech LYT, Inc., Boston, MA (US)

(72) Inventors: Shohei Koide, New York, NY (US); George Miller, Englewood, NJ (US); Akiko Koide, New York, NY (US); Tatyana Panchenko, New York, NY (US); Takamitsu Hattori, West New York, NJ (US); Aleksandra Filipovic, London (GB); Eric Elenko, Boston, MA (US); Joseph Bolen, Boston, MA (US)

(73) Assignees: New York University, New York, NY (US); PureTech LYT, Inc., Boston, MA (US)

( * ) Notice: Subject to any disclaimer, the term of this patent is extended or adjusted under 35 U.S.C. 154(b) by 643 days.

(21) Appl. No.: 17/424,474

(22) PCT Filed: Jan. 23, 2020

(86) PCT No.: PCT/US2020/014858
§ 371 (c)(1),
(2) Date: Jul. 20, 2021

(87) PCT Pub. No.: WO2020/154548
PCT Pub. Date: Jul. 30, 2020

(65) Prior Publication Data
US 2022/0073612 A1    Mar. 10, 2022

Related U.S. Application Data

(60) Provisional application No. 62/959,648, filed on Jan. 10, 2020, provisional application No. 62/932,156, filed on Nov. 7, 2019, provisional application No. 62/931,149, filed on Nov. 5, 2019, provisional application No. 62/896,235, filed on Sep. 5, 2019, provisional application No. 62/874,313, filed on Jul. 15, 2019, provisional application No. 62/847,888, filed on May 14, 2019, provisional application No. 62/823,353, filed on Mar. 25, 2019, provisional application No. 62/796,061, filed on Jan. 23, 2019.

(51) Int. Cl.
*C07K 16/28* (2006.01)
*A61P 35/00* (2006.01)
*A61K 39/00* (2006.01)

(52) U.S. Cl.
CPC .......... *C07K 16/2809* (2013.01); *A61P 35/00* (2018.01); *C07K 16/2818* (2013.01); *A61K 2039/507* (2013.01); *C07K 2317/21* (2013.01); *C07K 2317/24* (2013.01); *C07K 2317/565* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 7,582,300 B2 | 9/2009 | Gelfand et al. | |
| 8,722,049 B2 | 5/2014 | Getts et al. | |
| 2008/0248025 A1 | 10/2008 | Roark et al. | |
| 2014/0294759 A1 | 10/2014 | Chu et al. | |
| 2014/0322235 A1 | 10/2014 | Olive et al. | |
| 2018/0028566 A1 | 2/2018 | Miller et al. | |

FOREIGN PATENT DOCUMENTS

| | | | | |
|---|---|---|---|---|
| CN | 102532269 A | 7/2012 | | |
| WO | 2007/064919 A2 | 6/2007 | | |
| WO | WO-2011119661 A1 * | 9/2011 | ............ | A61K 38/17 |
| WO | 2011/130499 A1 | 10/2011 | | |
| WO | 2014180577 A1 | 11/2014 | | |
| WO | 2015035112 A1 | 3/2015 | | |
| WO | 2016005752 A1 | 1/2016 | | |
| WO | 2016/198480 A1 | 12/2016 | | |
| WO | WO-2017058866 A1 * | 4/2017 | | |
| WO | 2017/197347 A1 | 11/2017 | | |
| WO | 2017223422 A1 | 12/2017 | | |
| WO | 2018/023111 A1 | 2/2018 | | |
| WO | 2019147735 A1 | 8/2019 | | |
| WO | 2021032960 A1 | 2/2021 | | |

OTHER PUBLICATIONS

Castella, B. et al., Anergic bone marrow Vγ9Vγ δ2 T cells as early and long-lasting markers of PD-1-targetable microenvironment-induced immune suppression in human myeloma, OncoImmunology, Sep. 14, 2015, vol. 4, No. 11, article e1047580, 12 pages.

Correia, D.V., et al., Differentiation of human peripheral blood Vδ1+ T cells expressing the natural cytotoxicity receptor NKp30 for recognition of lymphoid leukemia cells, Blood, Jul. 28, 2011, vol. 118, No. 4, pp. 992-1001.

Mao, Y., et al., A new effect of IL-4 on human γδ T cells: promoting regulatory Vδ1 T cells via IL-10 production and inhibiting function of Vδ2 T cells, Cellular & Molecular Immunology, Mar. 16, 2015, vol. 13, pp. 217-228.

(Continued)

*Primary Examiner* — Daniel E Kolker
*Assistant Examiner* — Lea S O'Brien
(74) *Attorney, Agent, or Firm* — Hodgson Russ LLP

(57) ABSTRACT

Disclosed herein are antibodies specific to a delta-1 chain of a γδ T cell receptor and methods of using such for modulating γδ T cell bioactivity. Such anti-Delta 1 antibodies may also be used to treat diseases associated with γδ T cell activation, such as solid tumors, or for detecting presence of γδ1 T cells.

32 Claims, 67 Drawing Sheets

Specification includes a Sequence Listing.

(56) References Cited

OTHER PUBLICATIONS

Peng, G., et al., Tumor-Infiltrating γδ T Cells Suppress T and Dendritic Cell Function via Mechanisms Controlled by a Unique Toll-like Receptor Signaling Pathway, Immunity, Aug. 24, 2007, vol. 27, pp. 334-348.

Peters, C. et al., Phenotype and regulation of immunosuppressive Vδ2-expressing γδ T cells, Cell and Molecular Life Sciences, Oct. 4, 2013, vol. 71, No. 10, pp. 1943-1960.

Ramstead, A.G., et al., Complex Role of γδ T-Cell-Derived Cytokines and Growth Factors in Cancer, Journal of Interferon & Cytokine Research, Dec. 1, 2012, vol. 32, No. 12, pp. 563-569.

Wang, L. et al., Significance of Programmed Death Ligand 1 (PD-L1) Immunohistochemical Expression in Colorectal Cancer, Mol Diagn Ther, Feb. 18, 2016, vol. 20, pp. 175-181.

Wu, P. et al., γδT17 Cells Promote the Accumulation and Expansion of Myeloid-Derived Suppressor Cells in Human Colorectal Cancer, Immunity, May 15, 2014, vol. 40, pp. 785-800.

Yang, Y., et al., Challenges and Opportunities of Allogeneic Donor-Derived CAR T Cells, Curr Opin Hematol, Nov. 2015, vol. 22, No. 6, pp. 509-515.

UniProtKB Accession No. F6TAN7, Ig-like domain-containing protein, Ornithorynchus anatinus (*Duckbill platypus*), 2017 Jul. 2011, 2 pages. https://www.uniprot.org/uniprot/F6TAN7.

Bottino, C., et al., Two Subsets of Human T Lymphocytes Expressing Gamma/Delta Antigen Receptor Are Identifiable by Monoclonal Antibodies Directed to Two Distinct Molecular Forms of the Receptor, Journal of Experimental Medicine, vol. 168, No. 2, pp. 491-505.

Dechanet, J., et al., Implication of gamma-delta T cells in the human immune response to cytomegalovirus, The Journal of Clinical Investigation, vol. 103, No. 10, pp. 1437-1449.

Ye, J., et al., Specific recruitment of gamma delta regulatory T cells in human breast cancer, Cancer Res., Oct. 15, 2013, vol. 73, No. 20, pp. 6137-6148.

Ma, C., et al., Tumor-Infiltrating gamma delta T Lymphocytes Predict Clinical Outcome in Human Breast Cancer, The Journal of Immunology, Oct. 3, 2012, vol. 189, pp. 5029-5036.

Wistuba-Hamprecht, K., et al., Proportions of blood-borne V delta 1+ and V delta 2+ T-cells are associated with overall survival of melanoma patients treated with ipilimumab, European Journal of Cancer, Jul. 9, 2016, vol. 64, pp. 116-126.

Hidalgo, J.V., et al., Histological analysis of gamma delta T lymphocytes infiltrating human triple-negative breast carcinomas, Frontiers in Immunology, Dec. 10, 2014, vol. 5, No. 632, pp. 1-7.

Daley, D., et al., Gamma Delta T Cells Support Pancreatic Oncogenesis by Restraining alpha beta T Cell Activation, Cell, Sep. 8, 2016, vol. 166, No. 6, pp. 1485-1499.

Fleming, C, et al., Gamma Delta T Cells: Unexpected Regulators of Cancer Development and Progression, Trends in Cancer, Aug. 2017, vol. 3, No. 8, pp. 561-570.

Lo Presti, E., et al., Gamma Delta T Cells and Tumor Microenvironment: From Immunosurveillance to Tumor Evasion, Front. Immunol., Jun. 15, 2018, vol. 9, No. 1395, pp. 1-10.

Morrow, E.S., et al., The role of gamma delta T lymphocytes in breast cancer: a review, Translational Research, Jan. 2019, vol. 203, pp. 88-96.

Chen, X., et al., Distribution and functions of gamma delta T cells infiltrated in the ovarian cancer microenvironment, J. Transl. Med., May 7, 2019, vol. 17, No. 144, pp. 1-13.

Raverdeau, M., et al., gamma delta T cells in cancer: a small population of lymphocytes with big implications, Clinical & Translational Immunology, Oct. 10, 2019, vol. 8, No. 10, pp. 1-15.

Miller, K.R., et al., T Cell Receptor-Like Recognition of Tumor In Vivo by Synthetic Antibody Fragment, PLoS One, Aug. 20, 2012, vol. 7, No. 8, pp. 1-14.

Jenkins, R.W., et al., Ex Vivo Profiling of PD-1 Blockade Using Organotypic Tumor Spheroids, Cancer Discovery, Feb. 2018, vol. 8, No. 2, pp. 196-215.

Frerichs, K.A., et al., CD38-targeting antibodies in multiple myeloma: mechanisms of action and clinical experience, Expert Review of Clinical Immunology, Mar. 2018, vol. 14, No. 3, pp. 197-206.

Labani-Motlagh, A., et al., The Tumor Microenvironment: A Milieu Hindering and Obstructing Antitumor Immune Responses, Frontiers in Immunology, May 15, 2020, vol. 11, No. 940, pp. 1-22.

Ni, C., et al., Breast cancer-derived exosomes transmit lncRNA SNHG16 to induce CD73+gamma delta 1 Treg cells, Signal Transduction and Targeted Therapy, Apr. 29, 2020, vol. 5, No. 41, pp. 1-14.

Hu, G., et al., Tumor-infiltrating CD39+ gamma-deltaTregs are novel immunosuppressive T cells in human colorectal cancer, Oncoimmunology, 2017, vol. 6, No. 2, e1277305, 32 pages.

Zhao, Y., et al., Gamma-delta T Cells: friend or foe in cancer development?, Journal of Translational Medicine, 2018, vol. 16, No. 3, 13 pages.

Rong, L., et al., Analysis of tumor-infiltrating gamma delta T cells in rectal cancer, World Journal of Gastroenterology, Apr. 7, 2016, vol. 22, No. 13, pp. 3573-3580.

Braster, R., et al., Myeloid cells as effector cells for monoclonal antibody therapy of cancer, Methods, vol. 65, No. 1, pp. 28-37.

Natsume, A., et al., Improving effector functions of antibodies for cancer treatment: Enhancing ADCC and CDC, Drug Design, Development and Therapy, 2009, vol. 3, pp. 7-16.

Padlan, E.A., Anatomy of the Antibody Molecule, Molecular Immunology, 1994, vol. 31, No. 3, pp. 169-217.

Portolano, S., et al., Lack of Promiscuity in Autoantigen-Specific H and L Chani Combinations as Revealed by Human H and L Chain "Roulette", The Journal of Immunology, Feb. 1, 1993, vol. 150, No. 3, pp. 880-887.

McKinney, P.A., Brain Tumours: Incidence, Survival, and Aetiology, J. Neurol. Neurosurg. Psychiatry, 2004, vol. 75 (Suppl. II), pp. ii12-ii17.

* cited by examiner

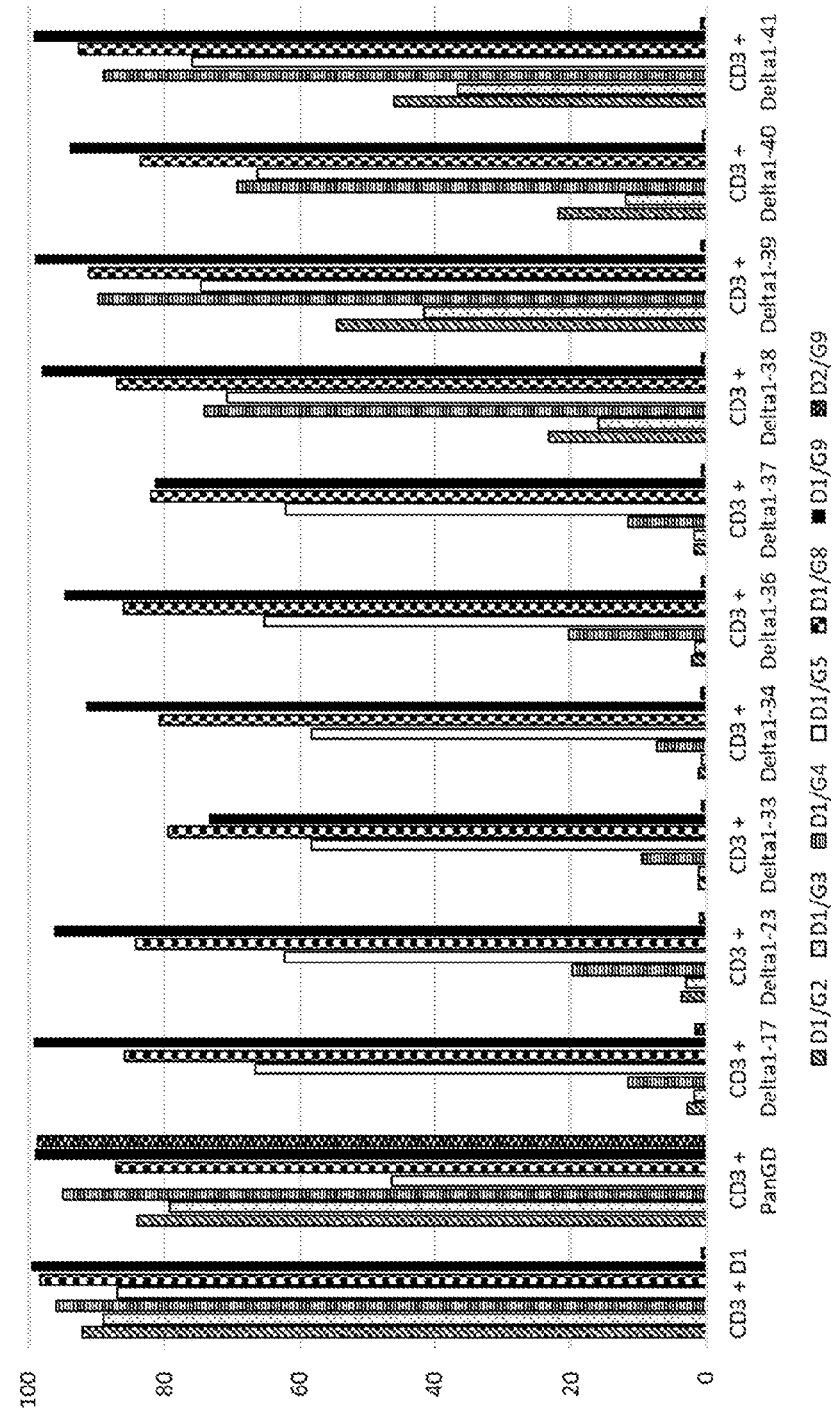

Figure 22C

| | KD (M) | KD Error | kon(1/Ms) | kon Error | kdis(1/s) | kdis Error | RMax | RMax Error | kobs(1/s) | Full R^2 |
|---|---|---|---|---|---|---|---|---|---|---|
| Human | 2.31e-010 | 1.14e-012 | 407000.00 | 895.00 | 9.40e-005 | 4.13e-007 | 0.4780 | 0.0002 | 0.0815 | 0.9945 |
| Cyno | 2.85e-010 | 1.33e-012 | 317000.00 | 632.00 | 9.05e-005 | 3.81e-007 | 0.5339 | 0.0002 | 0.0635 | 0.9960 |

*note: 0 hr time point is extrapolated from the "No Antibody" group

ANTIBODIES SPECIFIC TO DELTA 1 CHAIN OF T CELL RECEPTOR

SEQUENCE LISTING

The instant application contains a Sequence Listing which has been submitted in .txt format and is hereby incorporated by reference in its entirety. Said .txt copy was created on Jul. 20, 2021, is named "Delta_1_Cyno_Sequence_Listing.txt", and is 105,084 bytes in size.

BACKGROUND OF INVENTION

Immune checkpoint blockade has demonstrated unprecedented success in the past few years as cancer treatment. Often antibodies are used to block immune inhibitory pathways, such as the cytotoxic T-lymphocyte-associated protein 4 (CTLA-4) and programmed death 1 (PD-1) pathways. While therapies targeting those two pathways have shown success in treating several cancer types, anti-CTLA-4 and anti-PD-1 therapies have a response rate of 10 to 60% of treated patients, depending on cancer type, and have not yet shown the ability to exceed a response rate of 60%, even when used in combination (Kyvistborg et al., Enhancing responses to cancer immunotherapy; Science. 2018 Feb. 2; 359(6375):516-517). Additionally, a large number of cancer types are refractory to these therapies.

γδ T cells are a subgroup of T cells which have distinct T cell receptor (TCR) γ and δ chains on their surface. This sets them apart from CD4+ helper T cells and CD8+ cytotoxic T cells, which express αβ TCRs on their cell surfaces. Recent studies have found that γδ T cells have protumor activity (Zhao et al. J Transl Med (2018) 16:3). For example, in human pancreatic ductal carcinoma, γδ T cells have been found to constitute a substantial fraction of tumor-infiltrating T cells and to inhibit the anti-cancer immune response mediated by alpha beta (αβ) T cells (Daley et al., *Cell*, 2016, 166: 1485-1499). In the tumor microenvironment (TME), γδ T cells have been shown to express IL-4, IL-10, and TGF-β, leading to suppression of the anti-tumor response (Kuhl et al., *Immunol.*, 2009, 128(4): 580-588). The expression of both IL-10 and TGF-β has been shown to be increased in a variety of cancer types (Lafont et al., *Front Immunol.*, 2014, 5: 622). γδ T17 cells are a major source of IL-17 in the tumor microenvironment, where they function to promote angiogenesis in a number of cancer types (Silva-Santos B. Eur J Immunol. 2010; 40:1873-6; Zhao et al. J Transl Med (2018) 16:3, and references therein). Additionally, γδ T cells have been found to induce senescence of naïve and effector T cells, which become suppressive and increase immunosuppression in the TME (Ye et al., *J Immunol.*, 2013, 190(5): 2403-2414). Finally, studies have shown that γδ T cells increase the presence of myeloid derived suppressor cells (MDSCs) in the TME, promoting a pro-tumor microenvironment (Yan and Huang, Oncoimmunology. 2014;3: e953423; Qu P, et al., Cancer Lett. 2016; 380:253-6, and references therein).

Given the average response rate and the large number of cancer types that are refractory to current treatment, there remains a need for new cancer therapies. Modulating the activity of gamma delta T cells and/or one or more of its T cell receptors provides a novel cancer therapy approach.

SUMMARY OF INVENTION

The modulation of gamma delta T cell activity and/or one or more of its T cell receptors may be used alone or in combination with existing therapies as a means for cancer treatment. Described herein are novel human antibodies which bind to human gamma delta T cell receptors and their therapeutic use in the treatment of cancer. The present disclosure is based, at least in part, on the development of antibodies that specifically bind to delta-1 chains of γδ T cell receptors (TCRs). Such antibodies were found to effectively suppress γδ T cells, thereby rescuing immune suppression mediated by the γδ T cells.

Accordingly, one aspect of the present disclosure provides an isolated antibody, which specifically binds a delta-1 chain of a T cell receptor. In some instances, the antibody comprises a heavy chain variable region ($V_H$) that comprises a HC CDR1, a HC CDR2, and a HC CDR3. In some embodiments, the HC CDR1 comprises a motif of $FTX_1X_2X_3X_4X_5IH$ (SEQ ID NO: 46), in which $X_1$ is F or V, $X_2$ is S or T, $X_3$ is G, A, or S, $X_4$ is T, N, or S, and $X_5$ is D or S. In some embodiments, the HC CDR2 comprises SIYSSSGYTYYADSVKG (SEQ ID NO: 53). Alternatively, or in addition, in some embodiments, the HC CDR3 comprises $PGX_6YYWYYSGSAYEGYGLDY$ (SEQ ID NO: 48), in which $X_6$ comprises S or M.

Alternatively or in addition, the isolated antibody disclosed herein comprises a light chain variable region ($V_L$) that comprises a LC CDR1, a LC CDR2, and a LC CDR3. In some embodiments, the LC CDR1 comprises RASQSVSSAVA (SEQ ID NO: 55). In some embodiments, the LC CDR2 comprises $X_7ASSLX_8S$ (SEQ ID NO: 50), in which $X_7$ is S or A and $X_8$ is Y or Q. Alternatively or in addition, in some embodiments, the LC CDR3 comprises $QQX_9X_{10}X_{11}X_{12}X_{13}X_{14}LIT$ (SEQ ID NO: 51), in which $X_9$ is S or Q, $X_{10}$ is G, S, or T, $X_{11}$ is D, K, or S, $X_{12}$ is Y, W, or absent, $X_{13}$ is P or absent, and $X_{14}$ is D, F, or Y. In some instances, the isolated antibody does not comprise the same heavy chain and light chain CDRs as Delta1-17.

In some embodiments, the antibody comprises a heavy chain variable region ($V_H$) that comprises a HC CDR1, a HC CDR2, and a HC CDR3, wherein the HC CDR1 comprises a motif of $FTFX_1X_2X_3X_4IH$ (SEQ ID NO: 93), in which $X_1$ is S or T, $X_2$ is S, G or A, $X_3$ is T, N, or S, and $X_4$ is D or S. Alternatively, or in addition, in some embodiments, the HC CDR2 comprises SIYSSSGYTYYADSVKG (SEQ ID NO: 53). Alternatively, or in addition, the HC CDR3 comprises DPGSYYWYYSGSAYEGYGLDY (SEQ ID NO: 54). Alternatively or in addition, in some embodiments, the isolated antibody disclosed herein comprises a light chain variable region ($V_L$) that comprises a LC CDR1, a LC CDR2, and a LC CDR3, wherein the LC CDR1 comprises RASQSVSSAVA (SEQ ID NO: 55). Alternatively or in addition, in some embodiments, the LC CDR2 comprises AASSLQS (SEQ ID NO: 56). Alternatively or in addition, in some embodiments, the LC CDR3 comprises QQQSKYPFLIT (SEQ ID NO: 57).

In some embodiments, the antibody comprises a heavy chain variable region ($V_H$) that comprises a HC CDR1, a HC CDR2, and a HC CDR3, wherein the HC CDR1 comprises a motif of $FTFX_1X_2X_3X_4IH$ (SEQ ID NO: 93), in which $X_1$ is S or T, $X_2$ is S, G or A, $X_3$ is T, N, or S, and $X_4$ is D or S, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody comprises a light chain variable region ($V_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the antibody comprises a heavy chain variable region (V$_H$) that comprises a HC CDR1, a HC CDR2, and a HC CDR3, wherein the HC CDR1 is selected from the group consisting of SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72. Alternatively or in addition, the HC CDR2 comprises SIYSSSGYTYYADSVKG (SEQ ID NO: 53). Alternatively, or in addition, the HC CDR3 comprises DPGSYYWYYSGSAYEGYGLDY (SEQ ID NO: 54). Alternatively or in addition, the isolated antibody disclosed herein comprises a light chain variable region (V$_L$) that comprises a LC CDR1, a LC CDR2, and a LC CDR3, wherein the LC CDR1 comprises RASQSVSSAVA (SEQ ID NO: 55). Alternatively or in addition, the LC CDR2 comprises AASSLQS (SEQ ID NO: 56). Alternatively or in addition, the LC CDR3 comprises QQQSKYPFLIT (SEQ ID NO: 57).

In some embodiments, the antibody comprises a heavy chain variable region (V$_H$) that comprises a HC CDR1, a HC CDR2, and a HC CDR3, wherein the HC CDR1 is selected from the group consisting of SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody further comprises a light chain variable region (V$_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the antibody comprises a heavy chain variable region (V$_H$) that comprises a HC CDR1, a HC CDR2, and a HC CDR3, wherein the HC CDR1 comprises a motif of FTFX$_1$X$_2$X$_3$X$_4$IH (SEQ ID NO: 94), in which X$_1$ is S or T, X$_2$ is S, or A, X$_3$ is N, or S, and X$_4$ is D or S, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody comprises a light chain variable region (V$_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the antibody comprises a heavy chain variable region (V$_H$) that comprises a HC CDR1, a HC CDR2, and a HC CDR3, wherein the HC CDR1 is selected from the group consisting of SEQ ID NO: 68, SEQ ID NO: 69, SEQ ID NO: 70, SEQ ID NO: 71, and SEQ ID NO: 72. Alternatively or in addition, the HC CDR2 comprises SIYSSSGYTYYADSVKG (SEQ ID NO: 53). Alternatively, or in addition, the HC CDR3 comprises DPGSYYWYYSGSAYEGYGLDY (SEQ ID NO: 54). Alternatively or in addition, the isolated antibody disclosed herein comprises a light chain variable region (V$_L$) that comprises a LC CDR1, a LC CDR2, and a LC CDR3, wherein the LC CDR1 comprises RASQSVSSAVA (SEQ ID NO: 55). Alternatively or in addition, the LC CDR2 comprises AASSLQS (SEQ ID NO: 56). Alternatively or in addition, the LC CDR3 comprises QQQSKYPFLIT (SEQ ID NO: 57).

In some embodiments, the antibody comprises a heavy chain variable region (V$_H$) that comprises a HC CDR1, a HC CDR2, and a HC CDR3, wherein the HC CDR1 is selected from the group consisting of SEQ ID NO: 68, SEQ ID NO: 69, SEQ ID NO: 70, SEQ ID NO: 71, and SEQ ID NO: 72, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody further comprises a light chain variable region (V$_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the HC CDR1, the HC CDR2, and the HC CDR3 of the anti-Delta1 antibody disclosed herein collectively contain no more than 10 amino acid variations (e.g., no more than 9, 8, 7, 6, 5, 4, 3, 2, or 1 amino acid variations) relative to the HC CDRs of a reference antibody. Alternatively or in addition, the LC CDR1, the LC CDR2, and the LC CDR3 of the antibody collectively contain no more than 8 amino acid variations (e.g., no more than 7, 6, 5, 4, 3, 2, or 1 amino acid variations) relative to the light chain CDRs of a reference antibody, selected from the group consisting of Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43.

In some embodiments, the HC CDR1, the HC CDR2, and the HC CDR3 of the anti-Delta1 antibody disclosed herein collectively contain no more than 10 amino acid variations (e.g., no more than 9, 8, 7, 6, 5, 4, 3, 2, or 1 amino acid variations) relative to the HC CDRs of a reference antibody. Alternatively or in addition, the LC CDR1, the LC CDR2, and the LC CDR3 of the antibody collectively contain no more than 8 amino acid variations (e.g., no more than 7, 6, 5, 4, 3, 2, or 1 amino acid variations) relative to the light chain CDRs of a reference antibody, selected from the group consisting of Delta1-32, Delta1-33, Delta1-34, Delta1-35, Delta1-36, Delta1-37, Delta1-38, Delta1-39, Delta1-40, Delta1-41, Delta1-42, and Delta1-43.

In some embodiments, the HC CDR1, the HC CDR2, and the HC CDR3 of the anti-Delta1 antibody disclosed herein collectively contain no more than 10 amino acid variations (e.g., no more than 9, 8, 7, 6, 5, 4, 3, 2, or 1 amino acid variations) relative to the HC CDRs of a reference antibody. Alternatively or in addition, the LC CDR1, the LC CDR2, and the LC CDR3 of the antibody collectively contain no more than 8 amino acid variations (e.g., no more than 7, 6, 5, 4, 3, 2, or 1 amino acid variations) relative to the light chain CDRs of a reference antibody, selected from the group consisting Delta1-38, Delta1-39, Delta1-40, and Delta1-41.

In some embodiments, the HC CDR1, the HC CDR2, and the HC CDR3 of the antibody have at least 90% (e.g., at least 91%, 92%, 93%, 94%, 95%, 96%, 97%, 98%, 99%, or 100% identity to the heavy chain CDRs of a reference antibody and/or CDR1, CDR2, CDR3 collectively share at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%).

In some examples, the anti-Delta1 antibody may comprise the same heavy chain complementarity determining regions (CDRs) and the same light chain CDRs as the reference antibody. In one specific example, the anti-Delta1 antibody comprises the same heavy chain variable region and the same light chain variable region as the reference antibody.

In some embodiments, the anti-Delta1 antibody disclosed herein binds a human delta1 chain. In some embodiments, the anti-Delta1 antibody disclosed herein is selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. Each of these antibodies are referred to herein as a "reference antibody". In some embodiments, the anti-Delta1 antibody disclosed herein binds to the same epitope as any one of the Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies and/or competes against any of the just-noted reference antibodies from binding to the epitope.

In some embodiments, the anti-Delta1 antibody disclosed herein is selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. Each of these antibodies are referred to herein as a "reference antibody". In some embodiments, the anti-Delta1 antibody disclosed herein binds to the same epitope as any one of the Delta1-32, Delta1-33, Delta1-34, Delta1-35, Delta1-36, Delta1-37, Delta1-38, Delta1-39, Delta1-40, Delta1-41, Delta1-42, and Delta1-43 antibodies and/or competes against any of the just-noted reference antibodies from binding to the epitope.

In some embodiments, the anti-Delta1 antibody disclosed herein is selected from Delta1-38, Delta1-39, Delta1-40, and Delta1-41 antibodies. Each of these antibodies are referred to herein as a "reference antibody". In some embodiments, the anti-Delta1 antibody disclosed herein binds to the same epitope as any one of the Delta1-38, Delta1-39, Delta1-40, and Delta1-41 antibodies and/or competes against any of the just-noted reference antibodies from binding to the epitope.

In some embodiments, the anti-Delta1 antibody comprises a heavy chain variable domain ($V_H$) comprising a heavy chain complementarity determining region 1 (HC CDR1), a heavy chain complementary determining region 2 (HC CDR2), and a heavy chain complementary determining region 3 (HC CDR3), which collectively are at least 90% (e.g., at least 91%, 92%, 93%, 94%, 95%, 96%, 97%, 98%, 99%, or 100%) identical to the heavy chain CDRs of a reference antibody; and/or the antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of a reference antibody.

In some embodiments, the anti-Delta1 antibody comprises a heavy chain variable domain ($V_H$) comprising a heavy chain complementarity determining region 1 (HC CDR1), a heavy chain complementary determining region 2 (HC CDR2), and a heavy chain complementary determining region 3 (HC CDR3), which collectively are at least 90% (e.g., at least 91%, 92%, 93%, 94%, 95%, 96%, 97%, 98%, 99%, or 100%) identical to the heavy chain CDRs of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies; and/or the antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody comprises a heavy chain variable domain ($V_H$) comprising a heavy chain complementarity determining region 1 (HC CDR1), a heavy chain complementary determining region 2 (HC CDR2), and a heavy chain complementary determining region 3 (HC CDR3), which collectively are at least 90% (e.g., at least 91%, 92%, 93%, 94%, 95%, 96%, 97%, 98%, 99%, or 100%) identical to the heavy chain CDRs of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies; and/or the antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody comprises a heavy chain variable domain ($V_H$) comprising a heavy chain complementarity determining region 1 (HC CDR1), a heavy chain complementary determining region 2 (HC CDR2), and a heavy chain complementary determining region 3 (HC CDR3), which collectively are at least 90% (e.g., at least 91%, 92%, 93%, 94%, 95%, 96%, 97%, 98%, 99%, or 100%) identical to the heavy chain CDRs of an antibody selected from Delta1-38, Delta1-39, Delta1-40, and Delta1-41 antibodies; and/or the antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody comprises the same heavy chain complementarity determining regions (CDRs) and the same light chain CDRs as a reference antibody. In some embodiments, the anti-Delta1 antibody comprises the same heavy chain variable region and the same light chain variable region as an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. In some embodiments, the anti-Delta1 antibody comprises the same heavy chain variable region and the same light chain variable region as an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In one specific embodiment, the anti-Delta1 antibody comprises a heavy chain variable domain (V$_H$) comprising a heavy chain complementarity determining region 1 (HC CDR1), a heavy chain complementary determining region 2 (HC CDR2), and a heavy chain complementary determining region 3 (HC CDR3) identical to the heavy chain CDRs of Delta1-39. In some embodiments, the anti-Delta1 antibody comprises a light chain variable domain (V$_L$) comprising a light chain CDR1, a light CDR2, and a light chain CDR3, identical to the light chain CDRs of Delta1-39. In some embodiments, the anti-Delta1 antibody comprises a heavy chain variable domain (V$_H$) comprising a heavy chain complementarity determining region 1 (HC CDR1), a heavy chain complementary determining region 2 (HC CDR2), and a heavy chain complementary determining region 3 (HC CDR3), which collectively are at least 90% (e.g., at least 90%, 91%, 92%, 93%, 94%, 95%, 96%, 97%, 98%, 99%, or 100%) identical to the heavy chain CDRs of Delta1-39; and/or the antibody comprises a light chain variable domain (V$_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of Delta1-39.

In some embodiments, the anti-Delta1 antibody comprises a VH CDR1 having a sequence selected from SEQ ID NOs: 52, 61, 62, 63, 64, 65, 66, 67, 68, 69, 70, 71, and 72. In some embodiments, the anti-Delta1 antibody comprises a VH CDR1 having the sequence of SEQ ID NO: 68. In some embodiments, the anti-Delta1 antibody comprises a VH CDR2 having the sequence of SEQ ID NO: 53. In some embodiments, the anti-Delta1 antibody comprises a VH CDR3 having the sequence of SEQ ID NO: 54. In some embodiments, the anti-Delta1 antibody comprises a VH CDR1 having the sequence of SEQ ID NO: 68, a V$_H$ CDR2 having the sequence of SEQ ID NO: 53, and a VH CDR3 having the sequence of SEQ ID NO: 54. In some embodiments, the anti-Delta1 antibody comprises a light chain variable domain (V$_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 68, 53, and 54, respectively.

In some embodiments, the anti-Delta1 antibody comprises a VL CDR1 having the sequence of SEQ ID NO: 55. In some embodiments, the anti-Delta1 antibody comprises a VL CDR2 having a sequence of SEQ ID NO: 56 or 58. In some embodiments, the anti-Delta1 antibody comprises a VL CDR3 having a sequence selected from any of SEQ ID NO: 83, 84, 85, 86, 87, 57, 88, 89, 90, 91, 92, 59, and 60. In some embodiments, the anti-Delta1 antibody comprises a VL CDR1 having the sequence of SEQ ID NO: 55, a VL CDR2 having the sequence of SEQ ID NO: 56 or 58, and a VL CDR3 having a sequence selected from any of SEQ ID NO: 83, 84, 85, 86, 87, 57, 88, 89, 90, 91, 92, 59, and 60. In some embodiments, the anti-Delta1 antibody comprises a VL CDR1 having the sequence of SEQ ID NO: 55, a VL CDR2 having the sequence of SEQ ID NO: 56, and a VL CDR3 having a sequence selected from any of SEQ ID NO: 57. In some embodiments, the anti-Delta1 antibody comprises a light chain variable domain (V$_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having a sequence selected from SEQ ID NOs: 61, 62, 63, 64, 65, 66, 67, 68, 69, 70, 71, and 72. In some embodiments, the anti-Delta1 antibody comprises a VH CDR2 having the sequence of SEQ ID NO: 53. In some embodiments, the anti-Delta1 antibody comprises a VH CDR3 having the sequence of SEQ ID NOs:54. In some embodiments, the anti-Delta1 antibody comprises a VH CDR1 having the sequence of SEQ ID NO: 68. In some embodiments, the anti-Delta1 antibody comprises a VH CDR1 having the sequence of SEQ ID NO: 68, a V$_H$ CDR2 having the sequence of SEQ ID NO: 53, and a VH CDR3 having the sequence of SEQ ID NO: 54. In some embodiments, the anti-Delta1 antibody comprises a heavy chain variable domain (V$_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 68, 53, and 54, respectively.

In some embodiments, the anti-Delta1 antibody comprises a VL CDR1 having the sequence of SEQ ID NO: 55. In some embodiments, the anti-Delta1 antibody comprises a VL CDR2 having the sequence of SEQ ID NO: 56. In some embodiments, the anti-Delta1 antibody comprises a VL CDR3 having the sequence of SEQ ID NO: 57. In some embodiments, the anti-Delta1 antibody comprises a VL CDR1 having the sequence of SEQ ID NO: 55, a VL CDR2 having the sequence of SEQ ID NO: 56, and a VL CDR3 having the sequence of SEQ ID NO: 57. In some embodiments, the anti-Delta1 antibody comprises a light chain variable domain (V$_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having a sequence selected from SEQ ID NOs: 67, 68, 69, and 70. In some embodiments, the anti-Delta1 antibody comprises a VH CDR2 having the sequence of SEQ ID NO: 53. In some embodiments, the anti-Delta1 antibody comprises a VH CDR3 having the sequence of SEQ ID NOs:54. In some embodiments, the anti-Delta1 antibody comprises a VH CDR1 having the sequence of SEQ ID NO: 68. In some embodiments, the anti-Delta1 antibody comprises a VH CDR1 having the sequence of SEQ ID NO: 68, a VH CDR2 having the sequence of SEQ ID NO: 53, and a VH CDR3 having the sequence of SEQ ID NO: 54. In some embodiments, the anti-Delta1 antibody comprises a heavy chain variable domain (V$_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 68, 53, and 54, respectively.

In some embodiments, the anti-Delta1 antibody comprises a VL CDR1 having the sequence of SEQ ID NO: 55. In some embodiments, the anti-Delta1 antibody comprises a VL CDR2 having the sequence of SEQ ID NO: 56. In some embodiments, the anti-Delta1 antibody comprises a VL CDR3 having the sequence of SEQ ID NO: 57. In some embodiments, the anti-Delta1 antibody comprises a VL CDR1 having the sequence of SEQ ID NO: 55, a VL CDR2 having the sequence of SEQ ID NO: 56, and a VL CDR3 having the sequence of SEQ ID NO: 57. In some embodiments, the anti-Delta1 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having a sequence selected from SEQ ID NOs: 52, 61, 62, 63, 64, 65, 66, 67, 68, 69, 70, 71, and 72, a VH CDR2 having the sequence of SEQ ID NO: 53 and a VH CDR3 having the sequence of SEQ ID NOs:54. Alternatively or in addition, the anti-Delta1 antibody comprises a $V_L$ CDR1 having the sequence of SEQ ID NO: 55, a VL CDR2 having a sequence of SEQ ID NO: 56 or 58, and a VL CDR3 having a sequence selected from any of SEQ ID NO: 83, 84, 85, 86, 87, 57, 88, 89, 90, 91, 92, 59, and 60. In some embodiments, the anti-Delta1 antibody comprises a light chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 52, 61, 62, 63, 64, 65, 66, 67, 68, 69, 70, 71, and 72 (CDR1), 53 (CDR2), and 54 (CDR3), respectively. Alternatively or in addition, the anti-Delta1 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55(CDR1), 56 or 58 (CDR2), and 83, 84, 85, 86, 87, 57, 88, 89, 90, 91, 92, 59, and 60 (CDR3), respectively.

In some embodiments, the anti-Delta1 antibody comprises a VH CDR1 having a sequence selected from SEQ ID NOs: 61, 62, 63, 64, 65, 66, 67, 68, 69, 70, 71, and 72, a $V_H$ CDR2 having the sequence of SEQ ID NO: 53, and a VH CDR3 having the sequence of SEQ ID NOs:54. Alternatively or in addition, the anti-Delta1 antibody comprises a VL CDR1 having the sequence of SEQ ID NO: 55, a VL CDR2 having the sequence of SEQ ID NO: 56, and a VL CDR3 having the sequence of SEQ ID NO: 57. In some embodiments, the anti-Delta1 antibody comprises a heavy chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 61, 62, 63, 64, 65, 66, 67, 68, 69, 70, 71, and 72 (CDR1), 53 (CDR2), and 54 (CDR3), respectively. Alternatively or in addition, the anti-Delta1 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having a sequence selected from SEQ ID NOs: 67, 68, 69, and 70, a VH CDR2 having the sequence of SEQ ID NO: 53, and a VH CDR3 having the sequence of SEQ ID NOs:54. Alternatively or in addition, the anti-Delta1 antibody comprises a VL CDR1 having the sequence of SEQ ID NO: 55, a VL CDR2 having the sequence of SEQ ID NO: 56, and a VL CDR3 having the sequence of SEQ ID NO: 57. In some embodiments, the anti-Delta1 antibody comprises a heavy chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs67, 68, 69, and 70 (CDR1), 53 (CDR2), and 54 (CDR3), respectively. Alternatively or in addition, the anti-Delta1 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having a sequence set forth in SEQ ID NOs: 68, a VH CDR2 having the sequence of SEQ ID NO: 53, and a VH CDR3 having the sequence of SEQ ID NOs:54. Alternatively or in addition, the anti-Delta1 antibody comprises a VL CDR1 having the sequence of SEQ ID NO: 55, a VL CDR2 having the sequence of SEQ ID NO: 56, and a VL CDR3 having the sequence of SEQ ID NO: 57. In some embodiments, the anti-Delta1 antibody comprises a heavy chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOL 68 (CDR1), 53 (CDR2), and 54 (CDR3), respectively. Alternatively or in addition, the anti-Delta1 antibody comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In some embodiments, the anti-Delta1 antibody comprises a VH CDR1 having the sequence of SEQ ID NO: 68, a VH CDR2 having the sequence of SEQ ID NO: 53, and a $V_H$ CDR3 having the sequence of SEQ ID NO: 54, and further comprises a VL CDR1 having the sequence of SEQ ID NO: 55, a VL CDR2 having the sequence of SEQ ID NO: 56, and a $V_L$ CDR3 having the sequence of SEQ ID NO: 57. In some embodiments, the anti-Delta1 antibody comprises a light chain variable domain ($V_H$) comprising a heavy chain CDR1, a heavy CDR2, and a heavy chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the heavy chain CDRs of SEQ ID NOs: 68, 53, and 54, respectively, and further comprises a light chain variable domain ($V_L$) comprising a light chain CDR1, a light CDR2, and a light chain CDR3, which collectively are at least 80% (e.g., at least 81%, 82%, 83%, 84%, 85%, 86%, 87%, 88%, 89%, 90%, 91%, 92%, 93%, 94%, 95%, 96%, 97%, 98%, 99%, or 100%) identical to the light chain CDRs of SEQ ID NOs: 55, 56, and 57, respectively.

In any of these embodiments, the anti-Delta1 antibody binds to delta1. In some embodiments, the anti-Delta1 antibody comprises a HC CDR1, a HC CDR2, and a HC CDR3, which collectively contains no more than 10 (e.g., no more than 9, 8, 7, 6, 5, 4, 3, 2, or 1) amino acid variations relative to the HC CDRs of the reference antibody; and/or wherein the antibody comprises a LC CDR1, a LC CDR2, and a LC CDR3, which collectively contains no more than 8 (e.g., no more than 7, 6, 5, 4, 3, 2, or 1) amino acid variations relative to the light chain CDRs of the reference antibody. In some embodiments, the reference antibody is Delta1-39.

In some embodiments, the anti-Delta1 antibody comprises a HC CDR1, a HC CDR2, and a HC CDR3, which collectively contains no more than 10 (e.g., no more than 9, 8, 7, 6, 5, 4, 3, 2, or 1) amino acid variations relative to the HC CDRs of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43; and/or wherein the antibody comprises a LC CDR1, a LC CDR2, and a LC CDR3, which collectively contains no more than 8 (e.g., no more than 7, 6, 5, 4, 3, 2, or 1) amino acid variations relative to the light chain CDRs of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43.

In some embodiments, the anti-Delta1 antibody comprises a HC CDR1, a HC CDR2, and a HC CDR3, which collectively contains no more than 10 (e.g., no more than 9, 8, 7, 6, 5, 4, 3, 2, or 1) amino acid variations relative to the HC CDRs of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43; and/or wherein the antibody comprises a LC CDR1, a LC CDR2, and a LC CDR3, which collectively contains no more than 8 (e.g., no more than 7, 6, 5, 4, 3, 2, or 1) amino acid variations relative to the light chain CDRs of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43.

In some embodiments, the anti-Delta1 antibody comprises a HC CDR1, a HC CDR2, and a HC CDR3, which collectively contains no more than 10 (e.g., no more than 9, 8, 7, 6, 5, 4, 3, 2, or 1) amino acid variations relative to the HC CDRs of an antibody selected from Delta1-38, Delta1-39, Delta1-40, and Delta1-41 and/or wherein the antibody comprises a LC CDR1, a LC CDR2, and a LC CDR3, which collectively contains no more than 8 (e.g., no more than 7, 6, 5, 4, 3, 2, or 1) amino acid variations relative to the light chain CDRs of an antibody selected from Delta1-38, Delta1-39, Delta1-40, and Delta1-41.

In some embodiments, the anti-Delta1 antibody comprises a HC CDR1, a HC CDR2, and a HC CDR3, which collectively contains no more than 10 (e.g., no more than 9, 8, 7, 6, 5, 4, 3, 2, or 1) amino acid variations relative to the HC CDRs of Delta1-39; and/or wherein the antibody comprises a LC CDR1, a LC CDR2, and a LC CDR3, which collectively contains no more than 8 (e.g., no more than 7, 6, 5, 4, 3, 2, or 1) amino acid variations relative to the light chain CDRs of Delta1-39.

In some embodiments, the anti-Delta1 antibody comprises a $V_L$ that is at least 85% (e.g., at least 85%, 86%, 87%, 88%, 89%, 90%, 91%, 92%, 93%, 94%, 95%, 96%, 97%, 98%, 99%, or 100%) identical to the $V_L$ of the reference antibody, and/or a $V_H$ that is at least 85% (e.g., at least 85%, 86%, 87%, 88%, 89%, 90%, 91%, 92%, 93%, 94%, 95%, 96%, 97%, 98%, 99%, or 100%) identical to the $V_H$ of the reference antibody.

In some embodiments, the anti-Delta1 antibody has a $V_H$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_H$ sequence of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 7 antibodies, and/or a $V_L$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_L$ sequence of an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody has a $V_H$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_H$ sequence of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 7 antibodies, and/or a $V_L$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_L$ sequence of an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody has a $V_H$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_H$ sequence of an antibody selected from Delta1-38, Delta1-39, Delta1-40, and Delta1-41 antibodies, and/or a $V_L$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_L$ sequence of an antibody selected from Delta1-38, Delta1-39, Delta1-40, and Delta1-41 antibodies.

In some embodiments, the anti-Delta1 antibody has a $V_L$ sequence that is at least 85% (e.g., at least 85%, 86%, 87%, 88%, 89%, 90%, 91%, 92%, 93%, 94%, 95%, 96%, 97%, 98%, 99%, or 100%) identical to the $V_L$ sequence of Delta1-39, and/or a $V_H$ that is at least 85% (e.g., at least 85%, 86%, 87%, 88%, 89%, 90%, 91%, 92%, 93%, 94%, 95%, 96%, 97%, 98%, 99%, or 100%) identical to the $V_H$ of Delta1-39 antibody.

In some embodiments, the anti-Delta1 antibody disclosed herein has the same VL sequence as an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. In some embodiments, the anti-Delta1 antibody disclosed herein is an antibody having the same $V_L$ sequence as an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. In some embodiments, the anti-Delta1 antibody disclosed has the same $V_H$ sequence and the same $V_L$ sequence as an antibody selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody disclosed herein has the same VL sequence as an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. In some embodiments, the anti-Delta1 antibody disclosed herein is an antibody having the same $V_L$ sequence as an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies. In some embodiments, the anti-Delta1 antibody disclosed has the same $V_H$ sequence and the same $V_L$ sequence as an antibody selected from Delta1-32, Delta1-33, Delta1-34, Delta1-35, Delta1-36, Delta1-37, Delta1-38, Delta1-39, Delta1-40, Delta1-41, Delta1-42, and Delta1-43 antibodies.

In some embodiments, the anti-Delta1 antibody disclosed herein has the same VL sequence as an antibody selected from Delta1-38, Delta1-39, Delta1-40, and Delta1-41 antibodies. In some embodiments, the anti-Delta1 antibody disclosed herein is an antibody having the same VL sequence as an antibody selected from Delta1-38, Delta1-39, Delta1-40, and Delta1-41 antibodies. In some embodiments, the anti-Delta1 antibody disclosed has the same VH sequence and the same VL sequence as an antibody selected from Delta1-38, Delta1-39, Delta1-40, and Delta1-4 antibodies.

In some embodiments, the anti-Delta1 antibody is selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, and Delta1-43. In some embodiments, the anti-Delta1 antibody is selected from Delta1-32, Delta1-33, Delta1-34, Delta1-35, Delta1-36, Delta1-37, Delta1-38, Delta1-39, Delta1-40, Delta1-41, Delta1-42, and Delta1-43 In some embodiments, the anti-Delta1 antibody is selected from Delta1-38, Delta1-39, Delta1-40, and Delta1-41. In one specific embodiment, the anti-Delta-1 antibody is Delta1-39.

In some embodiments, the anti-Delta1 antibody comprises a VH region having a sequence selected from SEQ ID NOs: 3, 17, 18, 19, 20, 21, 22, 23, 24, 25, 43, 44, and 45. In some embodiments, the anti-Delta1 antibody comprises a VL region having a sequence selected from SEQ ID NOs: 4, 5, 6, 7, 8, 9, 10, 11, 12, 13, 14, 15, 2, 16, and 9. In some embodiments, the anti-Delta1 antibody comprises a VH region a sequence selected from SEQ ID NOs: 3, 17, 18, 19, 20, 21, 22, 23, 24, 25, 43, 44, and 45 and a VL region having a sequence selected from SEQ ID NOs: 4, 5, 6, 7, 8, 9, 10, 11, 12, 13, 14, 15, 2, 16, and 9. In some embodiments, the anti-Delta1 antibody comprises a VH region having a sequence selected from SEQ ID NOs: 17, 18, 19, 20, 21, 22, 23, 24, 25, 43, 44, and 45. In some embodiments, the anti-Delta1 antibody comprises a VL region having a sequence of SEQ ID NO: 9. In some embodiments, the anti-Delta1 antibody comprises a VH region a sequence selected from SEQ ID NOs: 17, 18, 19, 20, 21, 22, 23, 24, 25, 43, 44, and 45 and a VL region having a sequence of SEQ ID NO: 9.

In some embodiments, the anti-Delta1 antibody comprises a VH region having the sequence of SEQ ID NO: 24. In some embodiments, the anti-Delta1 antibody comprises a VL region having the sequence of SEQ ID NO: 9. In some embodiments, the anti-Delta1 antibody comprises a VHregion having the sequence of SEQ ID NO: 24 and a VL region having the sequence of SEQ ID NO: 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 3, 17, 18, 19, 20, 21, 22, 23, 24, 25, 43, 44, and 45. In some embodiments, the anti-Delta1 antibody has a $V_L$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 4, 5, 6, 7, 8, 9, 10, 11, 12, 13, 14, 15, 2, 16, and 9. In some embodiments, the anti-Delta1 antibody has a $V_H$ sequence comprising a sequence selected from SEQ ID NOs: 3, 17, 18, 19, 20, 21, 22, 23, 24, 25, 43, 44, and 45. In some embodiments, the anti-Delta1 antibody has a $V_L$ sequence comprising a sequence selected from SEQ ID NOs: 4, 5, 6, 7, 8, 9, 10, 11, 12, 13, 14, 15, 2, 16, and 9. In some embodiments, the isolated antibody has a $V_H$ sequence consisting essentially of or consisting of a sequence selected from SEQ ID NOs: 3, 17, 18, 19, 20, 21, 22, 23, 24, 25, 43, 44, and 45. In some embodiments, the isolated antibody has a $V_L$ sequence consisting essentially of or consisting of a sequence selected from SEQ ID NOs: 4, 5, 6, 7, 8, 9, 10, 11, 12, 13, 14, 15, 2, 16, and 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 3, 17, 18, 19, 20, 21, 22, 23, 24, 25, 43, 44, and 45 and has a $V_L$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 4, 5, 6, 7, 8, 9, 10, 11, 12, 13, 14, 15, 2, 16, and 9. In some embodiments, the isolated antibody has a $V_H$ sequence comprising a sequence selected from SEQ ID NOs: 3, 17, 18, 19, 20, 21, 22, 23, 24, 25, 43, 44, and 45 and a $V_L$ sequence comprising a sequence selected from SEQ ID NOs: 4, 5, 6, 7, 8, 9, 10, 11, 12, 13, 14, 15, 2, 16, and 9. In some embodiments, the isolated antibody has a $V_H$ sequence consisting essentially of a sequence selected from SEQ ID NOs: 3, 17, 18, 19, 20, 21, 22, 23, 24, 25, 43, 44, and 45 and a $V_L$ sequence consisting essentially of a sequence selected from SEQ ID NOs: 4, 5, 6, 7, 8, 9, 10, 11, 12, 13, 14, 15, 2, 16, and 9. In some embodiments, the isolated antibody has a $V_H$ sequence consisting of a sequence selected from SEQ ID NOs: 3, 17, 18, 19, 20, 21, 22, 23, 24, 25, 43, 44, and 45 and a $V_L$ sequence consisting of a sequence selected from SEQ ID NOs: 4, 5, 6, 7, 8, 9, 10, 11, 12, 13, 14, 15, 2, 16, and 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs:

17, 18, 19, 20, 21, 22, 23, 24, 25, 43, 44, and 45. In some embodiments, the anti-Delta1 antibody has a $V_L$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the sequence of SEQ ID NO: 9. In some embodiments, the anti-Delta1 antibody has a $V_H$ sequence comprising a a sequence selected from SEQ ID NOs: 17, 18, 19, 20, 21, 22, 23, 24, 25, 43, 44, and 45. In some embodiments, the anti-Delta1 antibody has a $V_L$ sequence comprising the sequence of SEQ ID NO: 9. In some embodiments, the isolated antibody has a $V_H$ sequence consisting essentially of or consisting of a sequence selected from SEQ ID NOs: 17, 18, 19, 20, 21, 22, 23, 24, 25, 43, 44, and 45. In some embodiments, the isolated antibody has a $V_L$ sequence consisting essentially of or consisting of the sequence of SEQ ID NO: 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 17, 18, 19, 20, 21, 22, 23, 24, 25, 43, 44, and 45 and has a $V_L$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the sequence of SEQ ID NO: 9. In some embodiments, the isolated antibody has a $V_H$ sequence comprising a sequence selected from SEQ ID NOs: 17, 18, 19, 20, 21, 22, 23, 24, 25, 43, 44, and 45 and a $V_L$ sequence comprising the sequence of SEQ ID NO: 9. In some embodiments, the isolated antibody has a $V_H$ sequence consisting essentially of a sequence selected from SEQ ID NOs: 17, 18, 19, 20, 21, 22, 23, 24, 25, 43, 44, and 45 and a $V_L$ sequence consisting essentially of the sequence of SEQ ID NO: 9. In some embodiments, the isolated antibody has a $V_H$ sequence consisting of a sequence selected from SEQ ID NOs: 17, 18, 19, 20, 21, 22, 23, 24, 25, 43, 44, and 45 and a $V_L$ sequence consisting of the sequence of SEQ ID NO: 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 22, 23, 24, 25, and 43. In some embodiments, the anti-Delta1 antibody has a $V_L$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the sequence of SEQ ID NO: 9. In some embodiments, the anti-Delta1 antibody has a $V_H$ sequence comprising a a sequence selected from SEQ ID NOs: 22, 23, 24, 25, and 43. In some embodiments, the anti-Delta1 antibody has a $V_L$ sequence comprising the sequence of SEQ ID NO: 9. In some embodiments, the isolated antibody has a $V_H$ sequence consisting essentially of or consisting of a sequence selected from SEQ ID NOs: 22, 23, 24, 25, and 43. In some embodiments, the isolated antibody has a $V_L$ sequence consisting essentially of or consisting of the sequence of SEQ ID NO: 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a sequence selected from SEQ ID NOs: 22, 23, 24, 25, and 43 and has a $V_L$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the sequence of SEQ ID NO: 9. In some embodiments, the isolated antibody has a $V_H$ sequence comprising a sequence selected from SEQ ID NOs: 22, 23, 24, 25, and 43 and a $V_L$ sequence comprising the sequence of SEQ ID NO: 9. In some embodiments, the isolated antibody has a $V_H$ sequence consisting essentially of a sequence selected from SEQ ID NOs: 22, 23, 24, 25, and 43 and a $V_L$ sequence consisting essentially of the sequence of SEQ ID NO: 9. In some embodiments, the isolated antibody has a $V_H$ sequence consisting of a sequence selected from SEQ ID NOs: 22, 23, 24, 25, and 43 and a $V_L$ sequence consisting of the sequence of SEQ ID NO: 9.

In some embodiments, the anti-Delta1 antibody has a $V_H$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 24. In some embodiments, the anti-Delta1 antibody has a $V_L$ sequence that is at least 80% or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 9. In some embodiments, the anti-Delta1 antibody has a $V_H$ sequence comprising SEQ ID NO: 24. In some embodiments, the anti-Delta1 antibody has a $V_L$ sequence comprising SEQ ID NO: 9. In some embodiments, the isolated antibody has a $V_H$ sequence consisting essentially of or consisting of SEQ ID NO: 24. In some embodiments, the isolated antibody has a $V_L$ sequence consisting essentially of or consisting of SEQ ID NO: 9.

In some embodiments, the anti-Delta1 antibody has a $V_H$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 24 and has a $V_L$ sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 9. In some embodiments, the isolated antibody has a $V_H$ sequence comprising SEQ ID NO: 24 and a $V_L$ sequence comprising SEQ ID NO: 9. In some embodiments, the isolated antibody has a $V_H$ sequence consisting essentially of SEQ ID NO: 24 and a $V_L$ sequence consisting essentially of SEQ ID NO: 9. In some embodiments, the isolated antibody has a $V_H$ sequence consisting of SEQ ID NO: 24 and a $V_L$ sequence consisting of SEQ ID NO: 9.

In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 78. In some embodiments, the anti-Delta1 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 79. In some embodiments, the anti-Delta1 antibody has a light chain sequence comprising SEQ ID NO: 78. In some embodiments, the anti-Delta1 antibody has a heavy chain sequence comprising SEQ ID NO: 79. In some embodiments, the isolated antibody has a light chain sequence consisting essentially of SEQ ID NO: 78 or consisting of SEQ ID NO: 78. In some embodiments, the isolated antibody has a heavy chain sequence consisting essentially of SEQ ID NO: 79 or consisting of SEQ ID NO: 79.

In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 78 and a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 79. In some embodiments, the isolated antibody has a light chain sequence comprising SEQ ID NO: 78 and a heavy chain sequence comprising SEQ ID NO: 79. In some embodiments, the isolated antibody has a light chain sequence consisting essentially of SEQ ID NO: 78 and a heavy chain sequence consisting essentially of SEQ ID NO: 79. In some embodiments, the isolated antibody has a light chain sequence consisting of SEQ ID NO: 78 and a heavy chain sequence consisting of SEQ ID NO: 79.

In some embodiments, the anti-Delta1 antibody preferentially binds a γδ1 TCR as relative to a γδ2 TCR or a or γδ3 TCR. In one particular embodiment, the anti-Delta1 antibody does not bind a T cell receptor comprising a delta-2 chain and a gamma chain.

In some embodiments, the anti-Delta1 antibody described herein cross-reacts with a human delta-1 chain and a non-human mammalian delta-1 chain; for example, a non-human primate delta-1 chain. In one particular example, the non-human primate delta-1 chain is a cynomolgus monkey delta-1 chain.

In some embodiments, the anti-Delta1 antibody described herein is capable of binding to γδ1 TCRs containing various gamma chains, including gamma 3, 4, 5, 8, or 9. In some embodiments, the anti-Delta1 antibody described herein is capable of binding to γδ1 TCRs containing various gamma chains, including gamma 3, 4, 5, and 8. In some embodiments, the anti-Delta1 antibody described herein cross-reacts with a human delta-1 chain and a non-human mammalian delta-1 chain, e.g., a non-human primate delta-1 chain, and is capable of binding to γδ1 TCRs containing various gamma chains, including gamma 3, 4, 5, and 8. Non-limiting examples of such antibodies described herein include Delta1-39 and Delta1-41. IN some examples, such antibodies are Delta1-38, Delta1-39, Delta1-40, and Delta1-41.

Any of the anti-Delta1 antibodies described herein may be a full-length antibody (e.g., an IgG molecule) or an antigen-binding fragment thereof. In some examples, the antibody is a Fab, a F(ab')$_2$, or a single-chain antibody. In any instances, the antibody can be a human antibody or a humanized antibody. In some embodiments, the antibody is an antibody drug conjugate. In some embodiments, the antibody is an antibody mimetic.

In another aspect, the present disclosure provides an isolated nucleic acid or set of nucleic acids which encode or collectively encode any of the anti-Delta1 antibodies disclosed herein. In some instances, the heavy chain and light chain of the antibody are encoded by two separate nucleic acid molecules (a set of nucleic acids). In other instances, the heavy chain and light chain of the antibody are encoded by one nucleic acid molecule, which may be in multicistronic format, or under the control of distinct promoters. Accordingly, in one aspect the disclosure provides an isolated nucleic acid molecule comprising one or more nucleic acid sequence(s) encoding a heavy chain variable region (VH) and/or a light chain variable region (VL) of an anti-Delta1 antibody described herein. In some embodiments, the nucleic acid molecule comprises one or more nucleic acid sequence(s) encoding a heavy chain variable region (VH) of an anti-Delta1 antibody described herein. Alternatively or in addition, in some embodiments, the nucleic acid molecule comprises one or more nucleic acid sequence(s) encoding a Light chain variable region (VL) of an anti-Delta1 antibody described herein. In one specific embodiment, the nucleic acid molecule comprises one or more nucleic acid sequences encoding a VH and/or VL (or a heavy chain and/or light chain) of an antibody comprising a heavy chain complementarity determining region 1 (CDR1) set forth as SEQ ID NO: 68, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56, and a light chain complementary determining region 3 (CDR3) set forth as SEQ ID NO: 57. Accordingly, in some embodiments, the nucleic acid molecule comprises one or more nucleic acid sequence(s) encoding a VH and/or VL (or a heavy chain and/or light chain) of an antibody comprising a VH set forth as SEQ ID NO: 24 and/or a VL set forth as SEQ ID NO: 9. In one example, the one or more nucleic acid sequences encode a VH and/or VL (or a heavy chain and/or light chain) of G9.2-17.

In some embodiments, the nucleic acid or set of nucleic acids are located on one or two vectors, for example, the one or two vectors may be one or two expression vectors. Accordingly, a vector may comprise any of the isolated nucleic acid molecule(s) described herein. Further, the present disclosure provides a host cell comprising any of the isolated nucleic acid or set of nucleic acids coding for the anti-Delta1 antibodies described herein. In some embodiments, the host cell is selected from the group consisting of E. coli cells, simian COS cells, Chinese hamster ovary (CHO) cells, or myeloma cells.

Also provided herein is a method for producing the anti-Delta1 antibodies, comprising culturing the host cell described herein under suitable conditions allowing for expressing of the antibody, and harvesting the antibody thus produced from the cell culture (e.g., from the culture medium).

Further, the present disclosure provides a pharmaceutical composition, comprising any of the anti-Delta1 antibodies or a nucleic acid(s) encoding such, and a pharmaceutically acceptable carrier.

In yet another aspect, the present disclosure features a method of inhibiting activity and function of immunosuppressive γδ T cells, e.g,. γδ1 T cells, in a subject, the method comprising administering to a subject in need thereof an effective amount of any of the anti-Delta1 antibodies disclosed herein or a pharmaceutical composition comprising such. Alternatively or in addition, the present disclosure features a method of eliminating or depleting immunosuppressive γδ T cells, e.g,. γδ1 T cells, in a subject, the method comprising administering to a subject in need thereof an effective amount of any of the anti-Delta1 antibodies disclosed herein or a pharmaceutical composition comprising such. In some embodiments, the subject in need thereof is a human patient having, suspected of having, or at risk for having a solid cancer. In some embodiments, the present disclosure features a method of treating a cancer in a subject, the method comprising administering to a subject in need thereof an effective amount of any of the anti-Delta1 antibodies disclosed herein or a pharmaceutical composition comprising such. Exemplary solid tumors include, but are not limited to, pancreatic ductal adenocarcinoma (PDA), colorectal cancer (CRC), melanoma, breast cancer, lung cancer, glioblastoma, upper and lower gastrointestinal malignancies, squamous cell head and neck cancer, genitourinary cancer, ovarian cancer, endometrial cancer, renal cancer, bladder cancer, prostate cancer, neuroendocrine cancer, adrenocortical cancer, or sarcomas. In some examples, the effective amount of the pharmaceutical composition is sufficient to inhibit or block the activity and function of immunosuppressive γδ T cells, e.g., γδ1 T cells.

Any of the treatment methods described herein may further comprise administering to the subject an inhibitor of a checkpoint molecule, an activator of a co-stimulatory receptor, an inhibitor of an innate immune cell target, a chemotherapeutic agent, and/or any other anti-cancer treatment agent, including, but not limited to, a biologic, a small molecule inhibitor, and/or any form of radiation therapy, and/or cell based therapy. Examples of checkpoint molecules include, but are not limited to, PD-1, PD-L1, PD-L2, CTLA-4, LAG3, TIM-3, A2aR, TIGIT and VISTA. Examples of co-stimulatory receptors include, but are not limited to, OX40, GITR, CD137, CD40, CD27, and ICOS. Examples of innate immune cell targets include, but are not limited to, KTR, NKG2A, CD96, TLR, IDO, and galectin-9.

Also within the scope of the present disclosure are (i) pharmaceutical compositions for use in treating a disease associated with activation of immune suppressive γδ T cells (e.g., γδ1 T cells, wherein the pharmaceutical composition comprises any of the anti-Delta1 antibodies described herein or a nucleic acid(s) encoding such, and a pharmaceutically acceptable carrier; and (ii) uses of the anti-Delta1 antibodies or the encoding nucleic acids for manufacturing a medicament for use in treating the target diseases as described herein.

Another aspect of the present disclosure provides a method for analyzing a biological sample from a subject suspected of having a solid tumor (e.g., a metastatic solid tumor or a relapsed or refractory solid tumor), the method comprising: (i) providing a biological sample of a subject suspected of having a solid tumor; and (ii) measuring a level of Delta1 in the biological sample with an antibody that specifically binds Delta1. In some embodiments, the subject is suspected of having a solid tumor, for example, a metastatic solid tumor or a relapsed or refractory solid tumor. Examples include, but are not limited to, pancreatic adenocarcinoma (PDA), colorectal cancer (CRC), hepatocellular carcinoma (HCC), breast cancer (e.g., ductal carcinoma), and cholangiocarcinoma. In some embodiments, the subject is suspected of having a metastatic solid tumor. In other embodiments, the subject is suspected of having relapsed or refractory solid tumor. Examples include, but are not limited to, metastatic pancreatic adenocarcinoma (PDA), metastatic colorectal cancer (CRC), metastatic hepatocellular carcinoma (HCC), breast cancer (e.g., ductal carcinoma), and cholangiocarcinoma.

In some embodiments, the biological sample can be a serum sample or a plasma sample. In other embodiments, the biological sample can be a tumor biopsy sample. For example, in some embodiments, the tumor biopsy sample comprises patient-derived organotypic tumor spheroids (PDOT). For example, in some embodiments, the tumor biopsy sample comprises TILs.

The antibody can be any of those described herein, for example, comprising the same heavy chain and light chain complementary determining regions (CDRs) as reference antibody Delta1-39, e.g., comprising a heavy chain variable domain of SEQ ID NO: 24, and/or a light chain variable domain of SEQ ID NO: 9. In some instances, the antibody can be a Fab molecule. In some embodiments, the antibody a different anti-Delta1 antibody known in the art.

In some embodiments, an immunoassay is used to determine levels of Delta1 in the biological sample. In some embodiments, the assay is flow cytometry.

In some embodiments, the methods disclosed herein further comprise identifying the subject as a suitable candidate for a treatment involving an anti-Delta1 antibody if the level of Delta1 measured in step (ii) is elevated relative to a control level. The suitable candidate is given an effective amount of the anti-Delta1 antibody, e.g., those described herein, either taken alone or in combination with a checkpoint inhibitor such as those described herein.

In some embodiments, level of Delta1 measured in step (ii) is used to identify or select a cancer patient that is likely to respond to anti-Delta1 targeting therapy. In some embodiments, Delta1 levels are measured in blood, serum and/or plasma. In some embodiments, Delta1 levels are measured on the surface of cancer cells or immune cells derived from the tumor and/or the blood of a cancer patient. In some examples, the cancer cells are in tumor organoids derived from the human patient. In some examples, the immune cells are in tumor organoids derived from the human patient. In some embodiments, the immune cells comprise macrophages, alpha/beta T cells, and/or gamma/delta T cells.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to the drawing in combination with the detailed description of specific embodiments presented herein.

FIG. 3A: Cells derived from colorectal cancer patient. FIGS. 3B and 3C: cells derived from two individual pancreatic cancer patients.

Figure 5A:
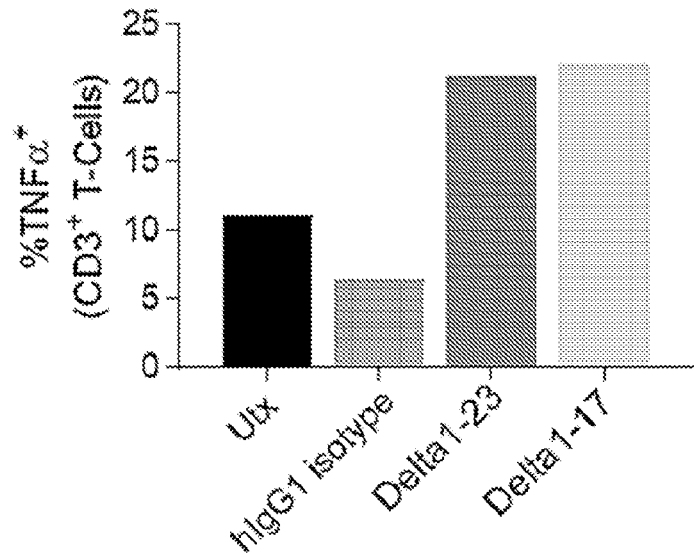
Figure 5B:
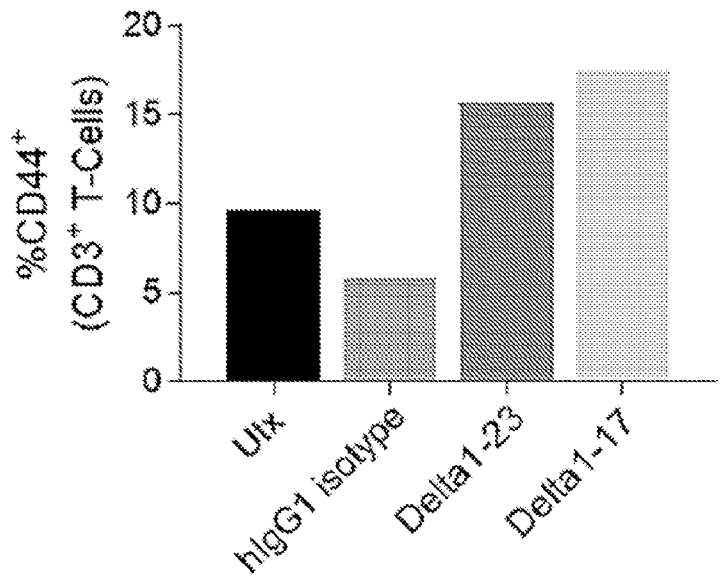

FIGS. 5A and 5B depict bar graphs showing immune profile expression in a breast cancer liver metastasis tumor sample (PDOTS) untreated (Utx) and treated with isotype (hIgG1), as compared to two anti-Delta1 IgG1 antibodies (Delta1-23 and Delta1-17 as examples). The percent TNF-α in CD3+ T cells (FIG. 5A) and percent CD44 in CD3+ T cells (FIG. 5B) are shown.

Figure 6A:
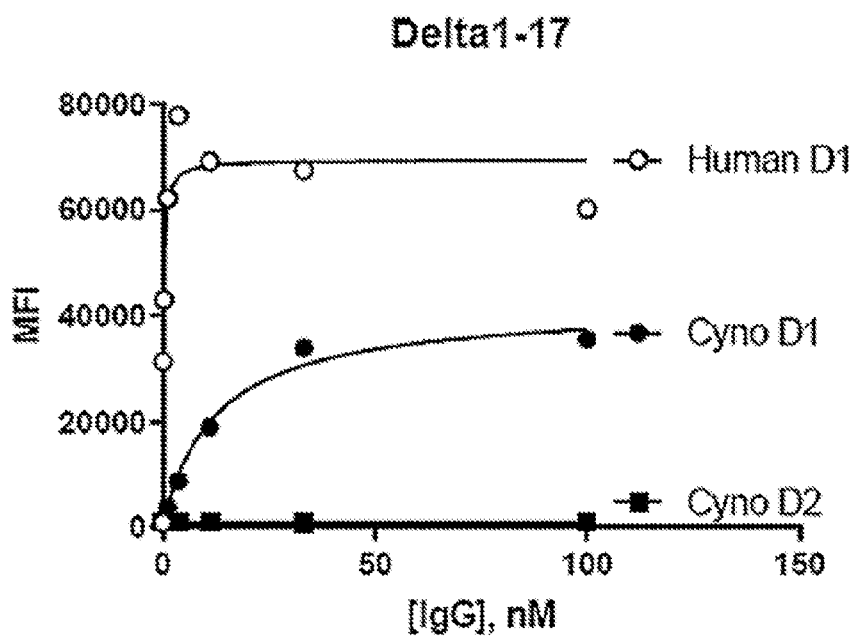
Figure 6B:
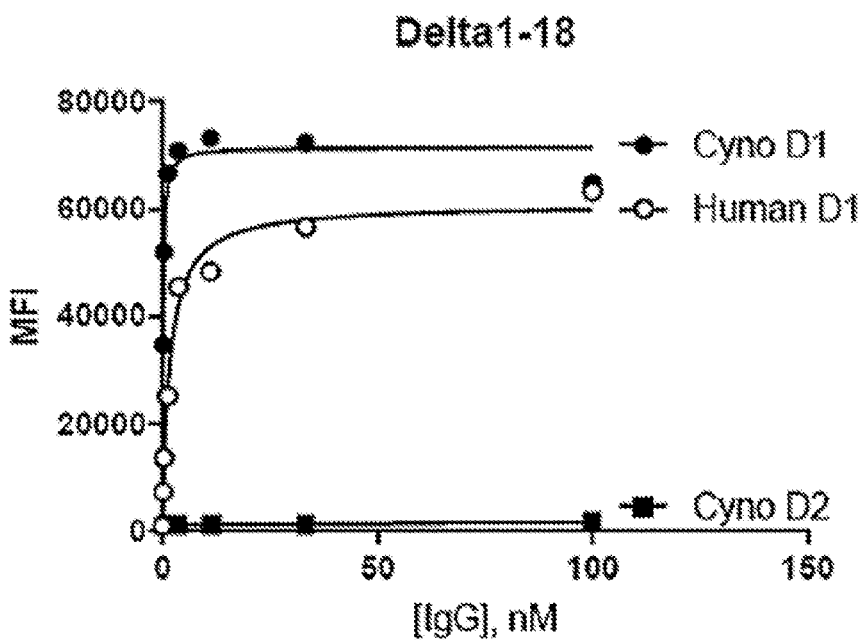
Figure 6C:
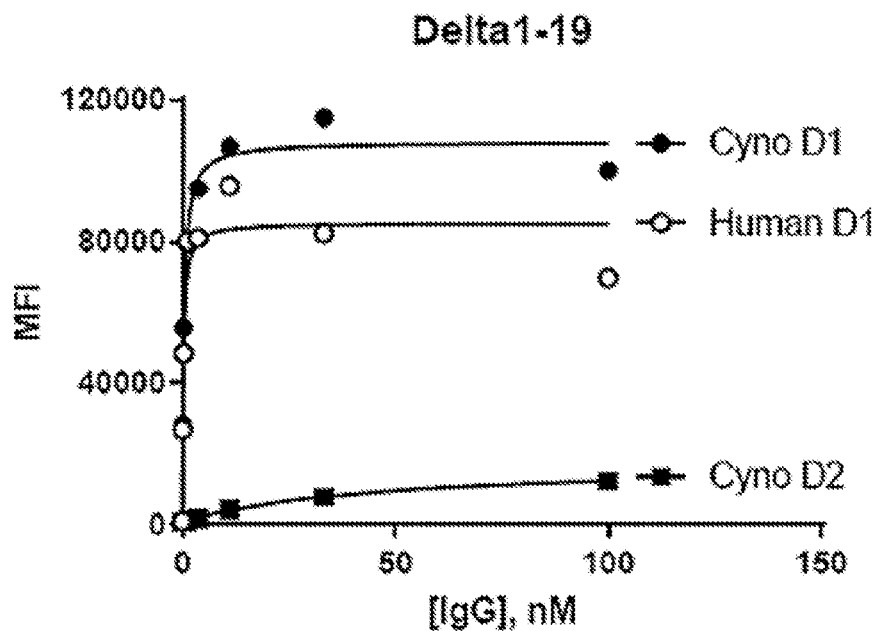
Figure 6D:
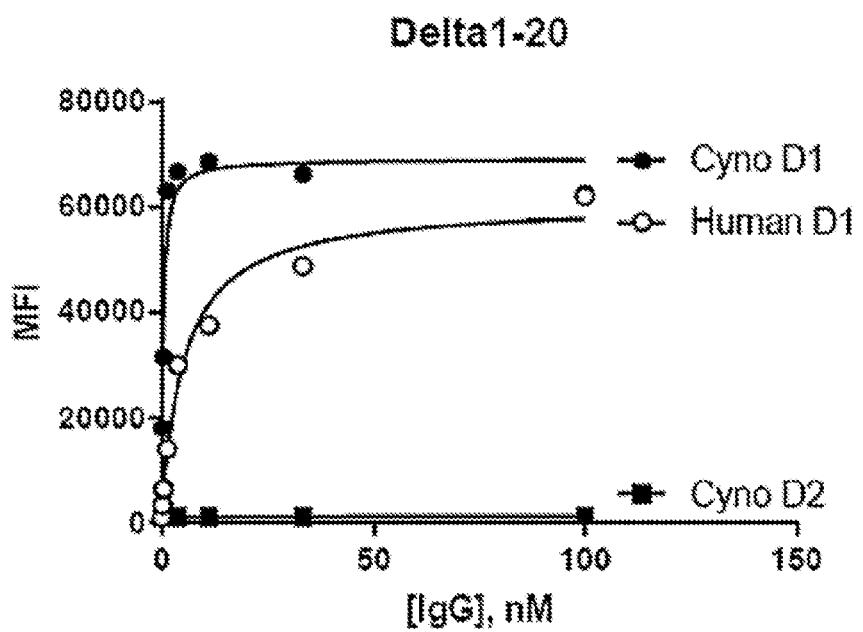
Figure 6E:
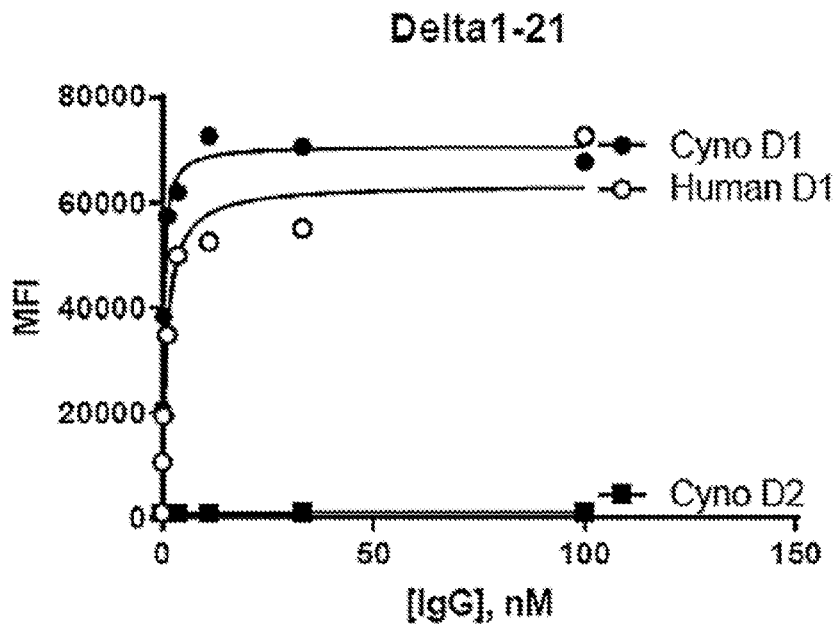
Figure 6F:
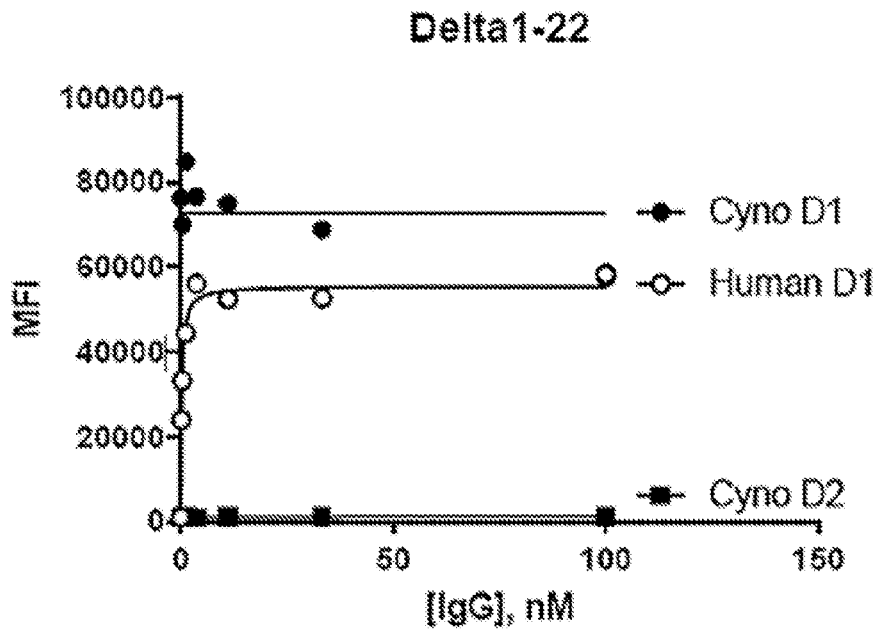
Figure 6G:
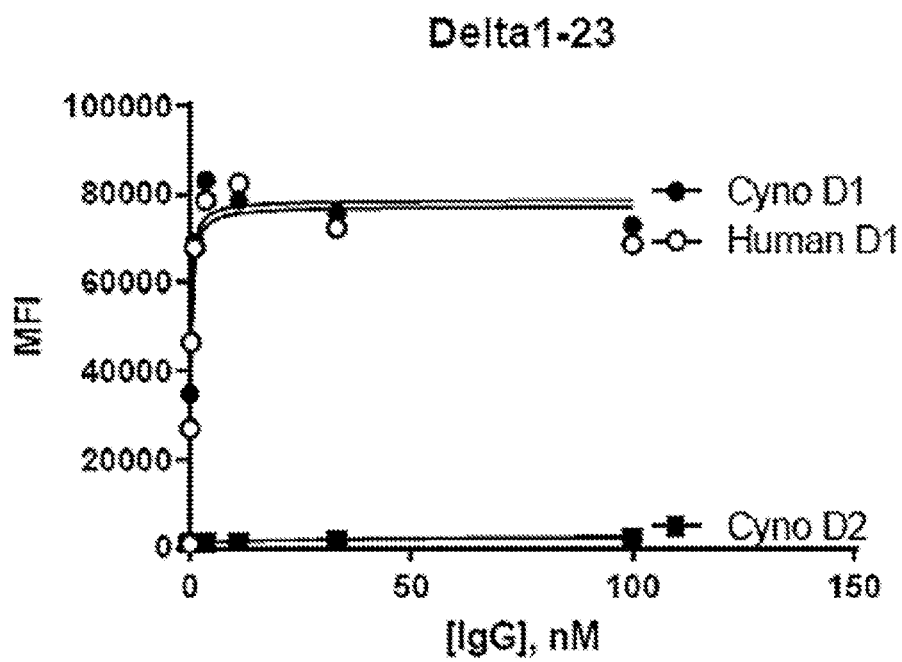
Figure 6H:
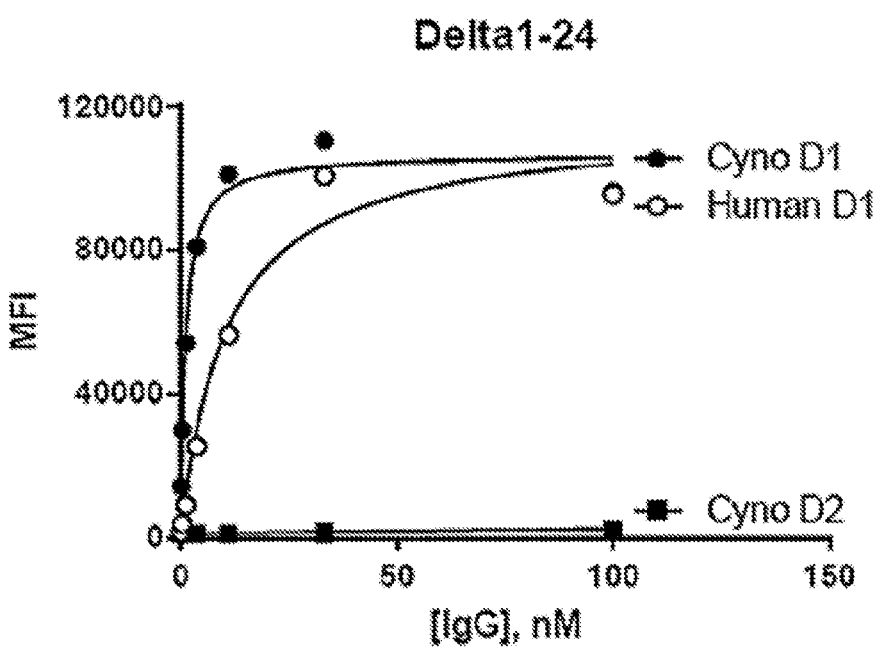
Figure 6I:
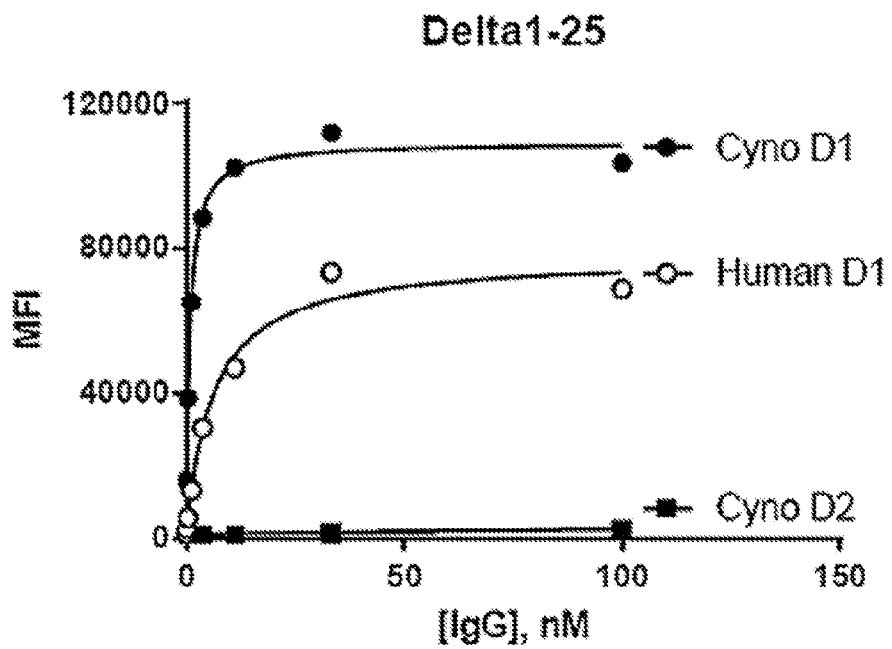
Figure 6J:
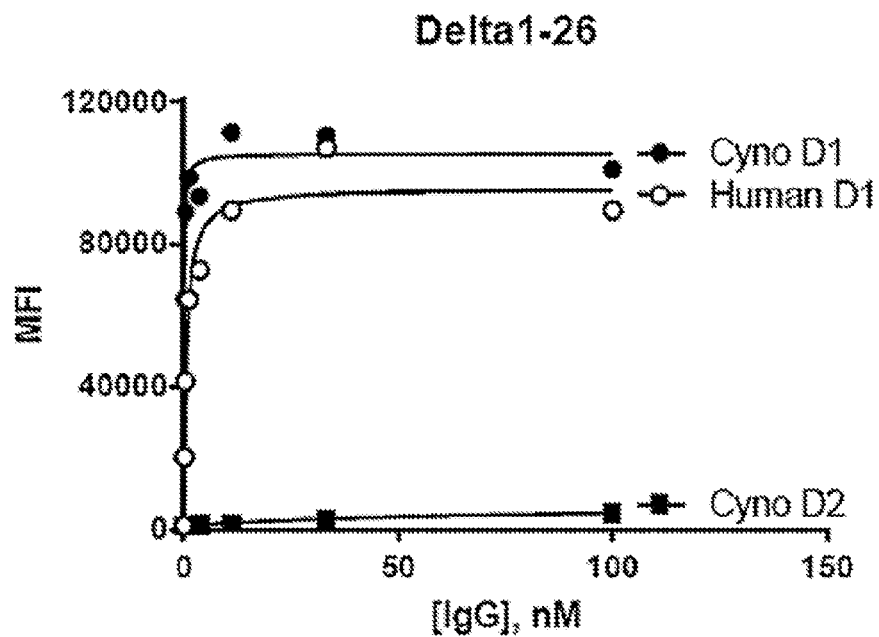
Figure 6K:
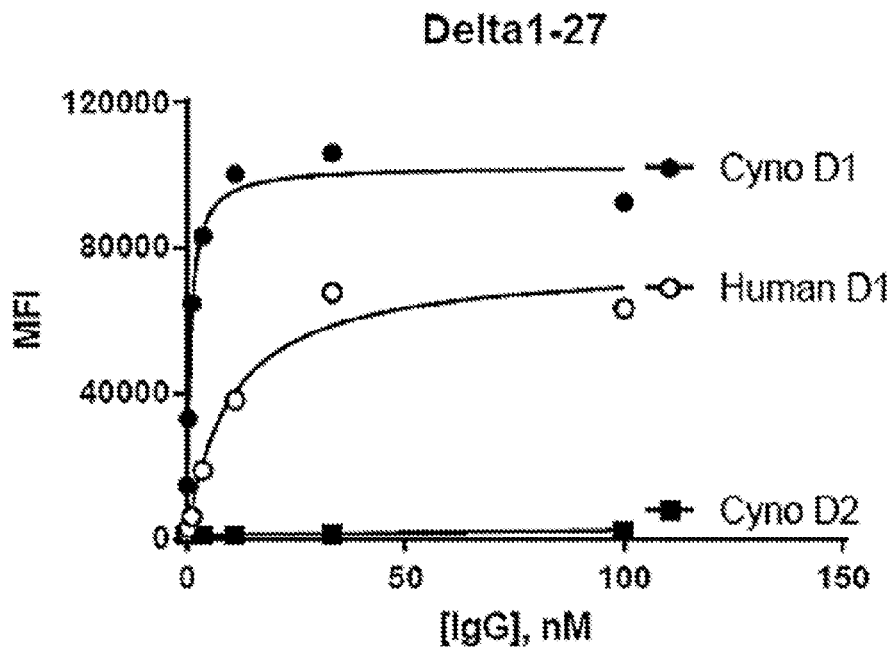
Figure 6L:
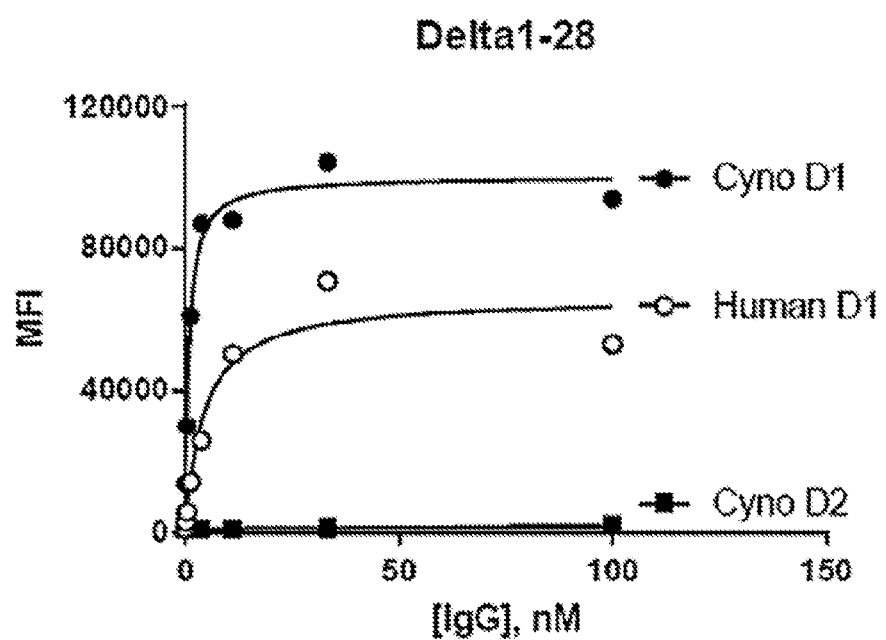
Figure 6M:
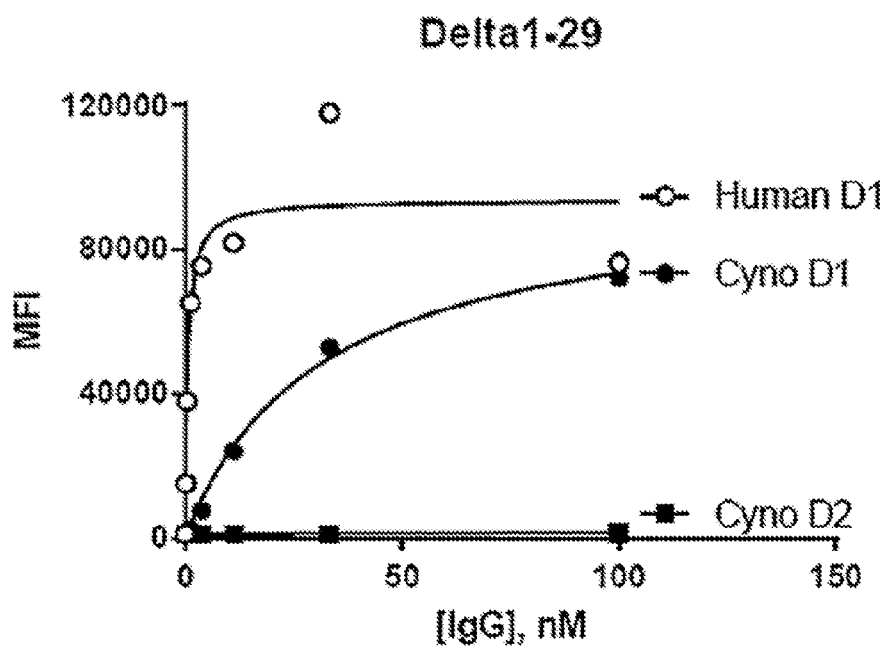
Figure 6N:
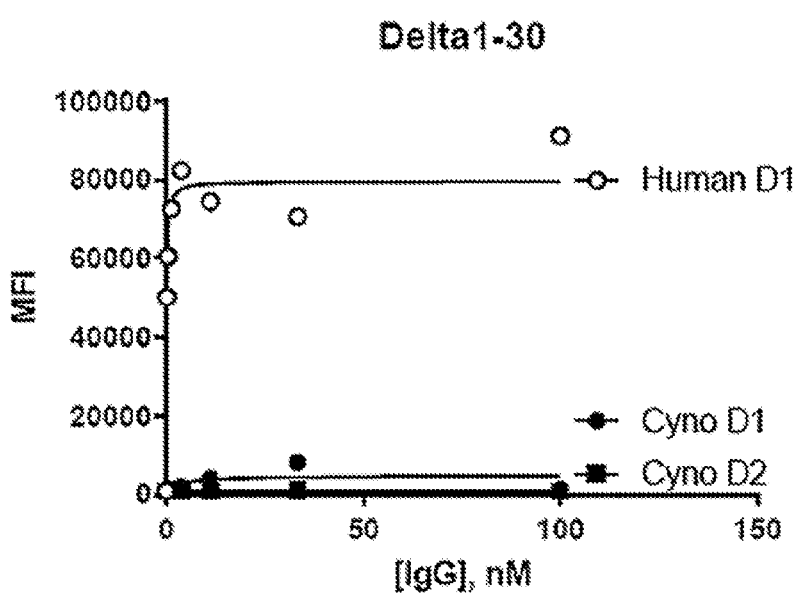
Figure 7A:
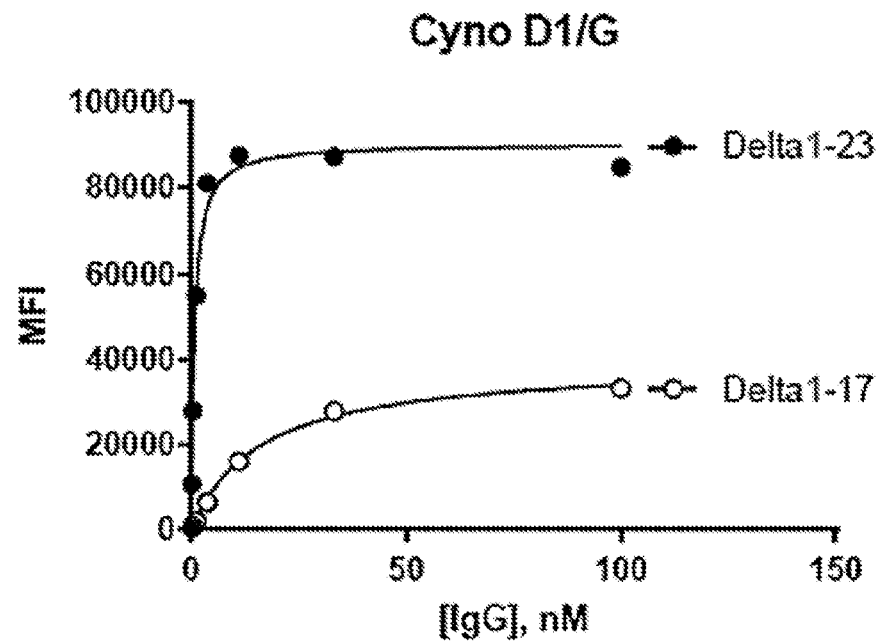
Figure 7B:
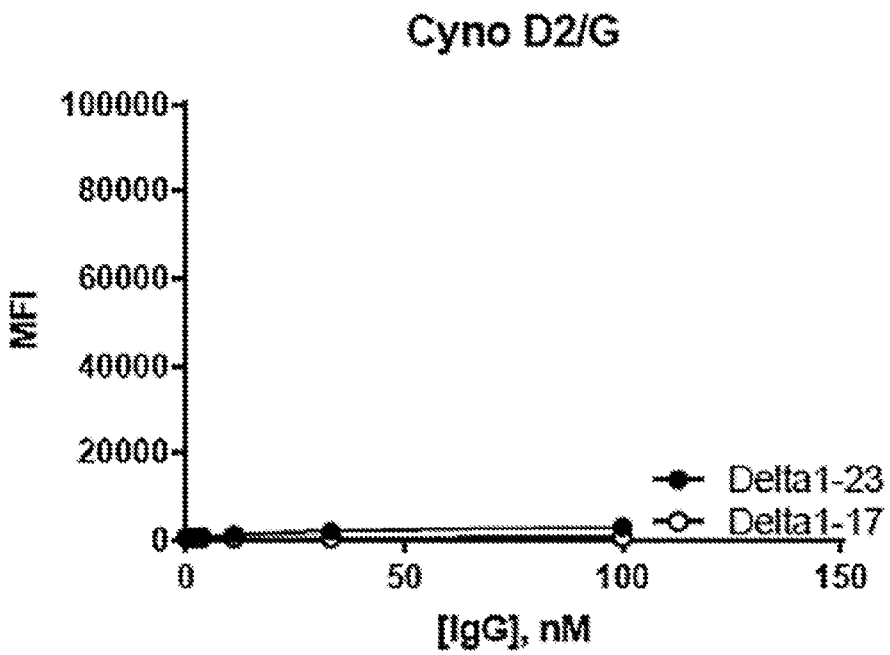
Figure 7C:
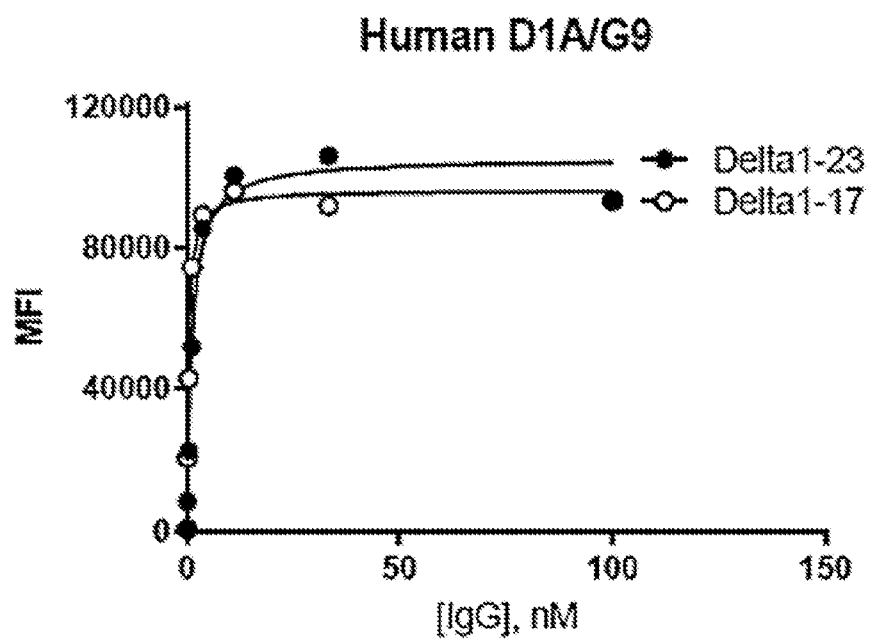
Figure 7D:
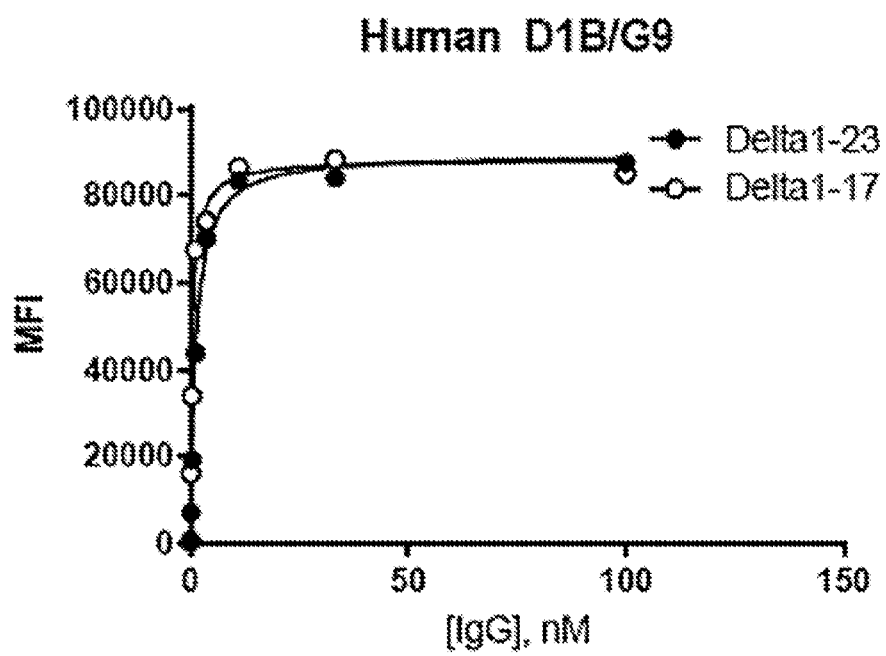
Figure 7E:
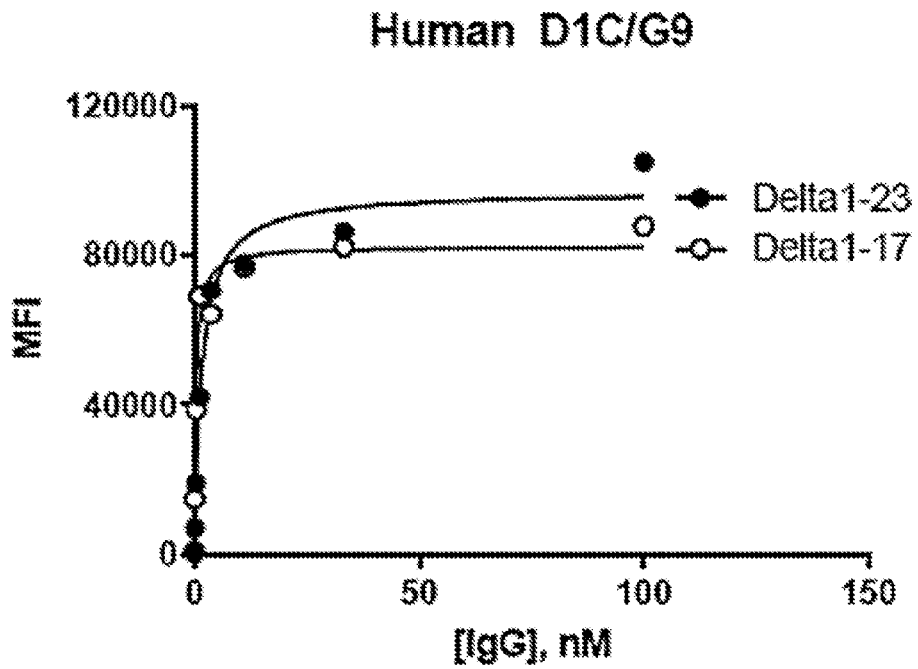
Figure 7F:
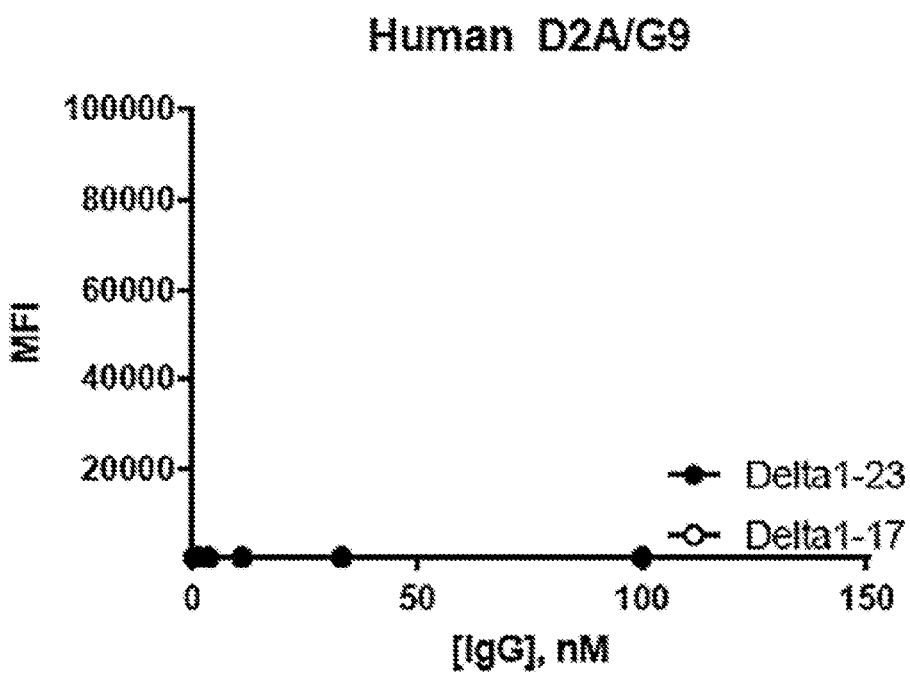
Figure 7G:
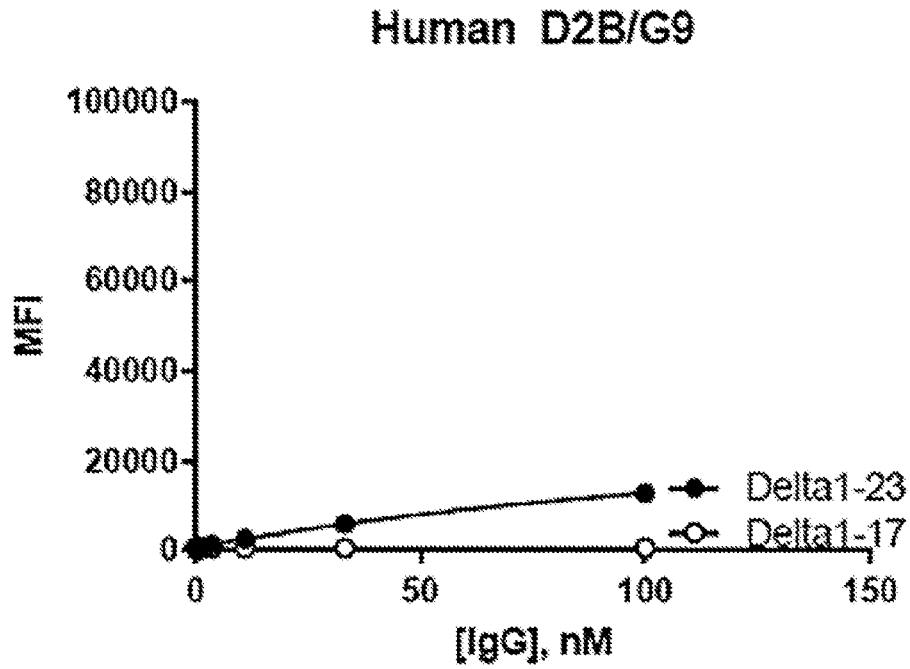
Figure 7H:
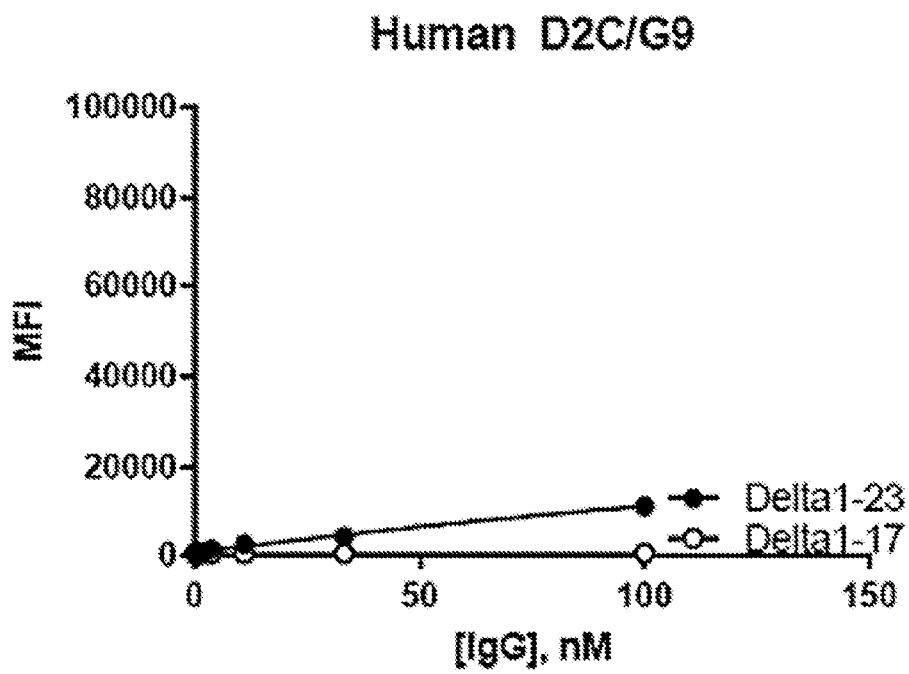
Figure 7I:
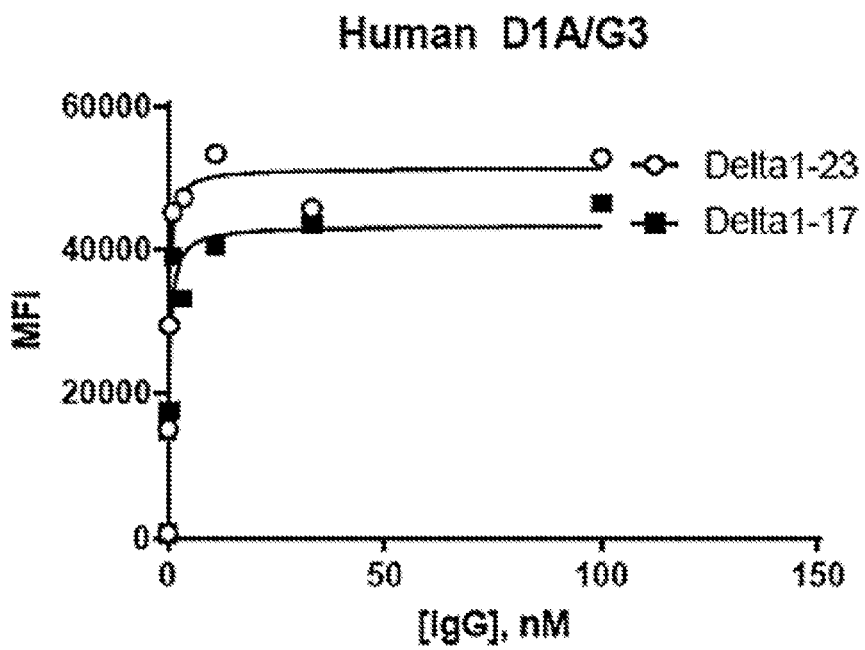
Figure 7J:
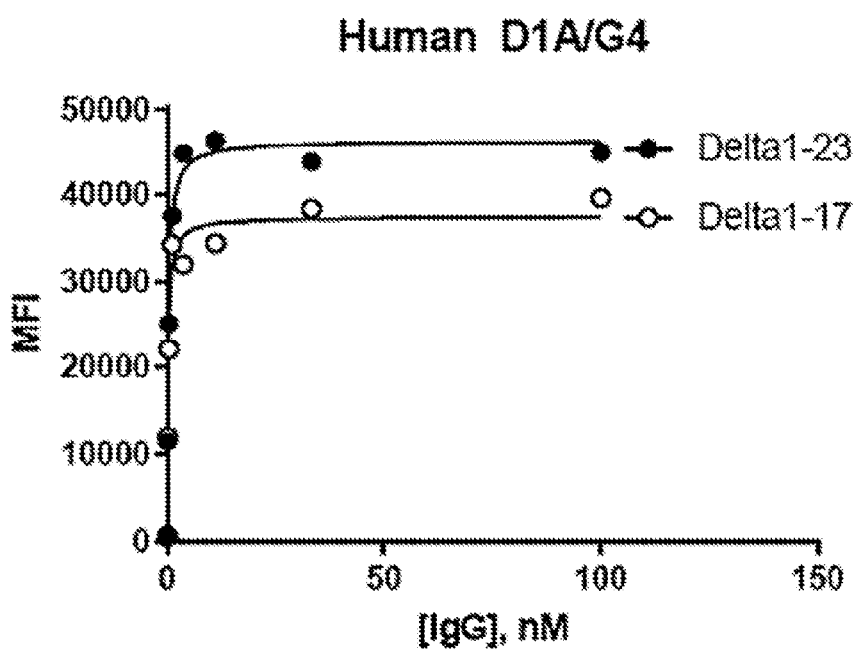
Figure 7K:
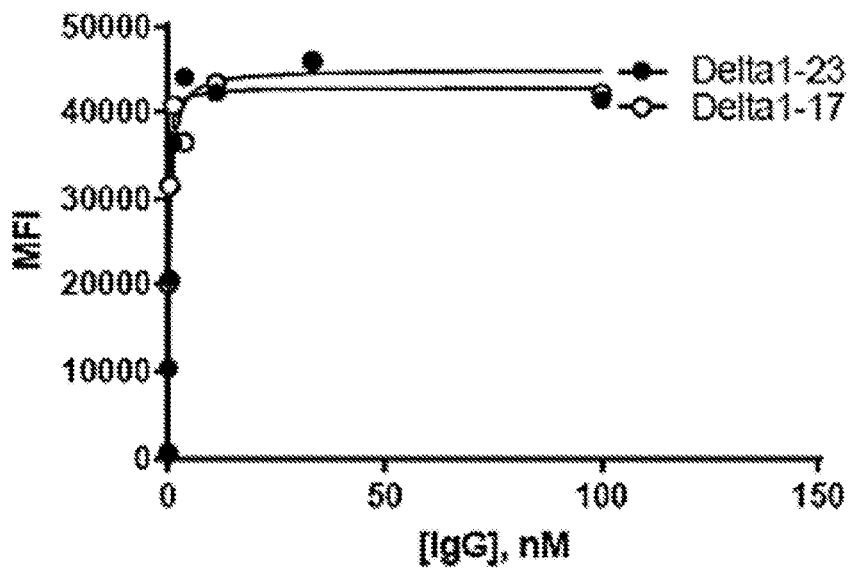
Figure 7L:
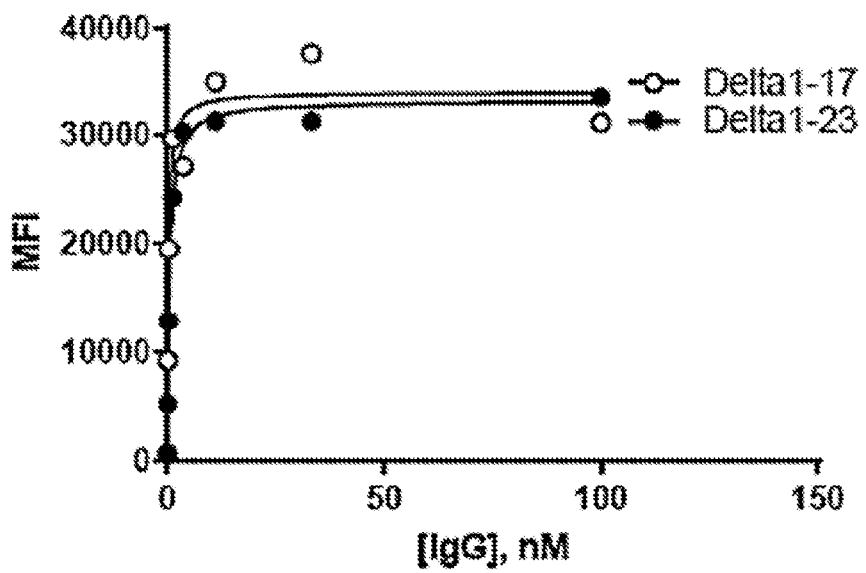

FIGS. 6A-6N depict binding titrations of anti-Delta1 antibodies to purified gamma/delta TCRs, as measured using a bead binding assay. Human Gamma9/Delta1C (denoted "Human D1"), cynomolgus Gamma/Delta1A ("Cyno D1") and cynomolgus Gamma/Delta2 ("Cyno D2") were tested.

FIGS. 7A-7L depict binding titrations of anti-Delta1 antibodies, Delta1-17 and Delta1-23, to purified Gamma/Delta TCRs consisting of different subunits.

Figure 8:
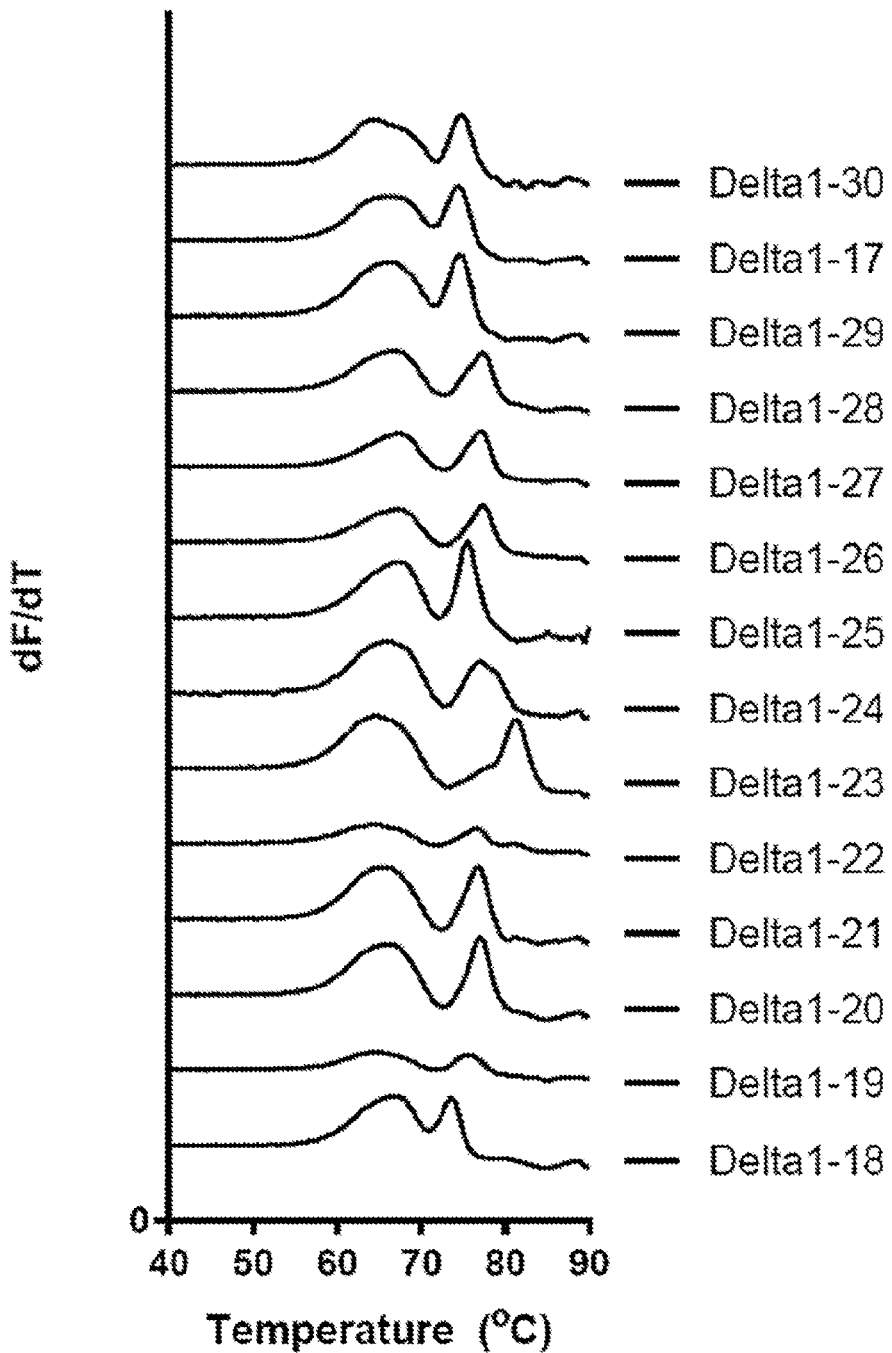

FIG. 8 shows traces from thermal shift assays used to determine the thermostability of Delta1-specific IgGs.

FIGS. 9A-9I show binding titrations of anti-Delta1 antibodies to purified gamma/delta TCRs, as measured by a bead binding assay. Human Gamma9/Delta1C (denoted "Human D1") and cynomolgus Gamma/Delta1A ("cyno D1") were tested.

Figure 10A:
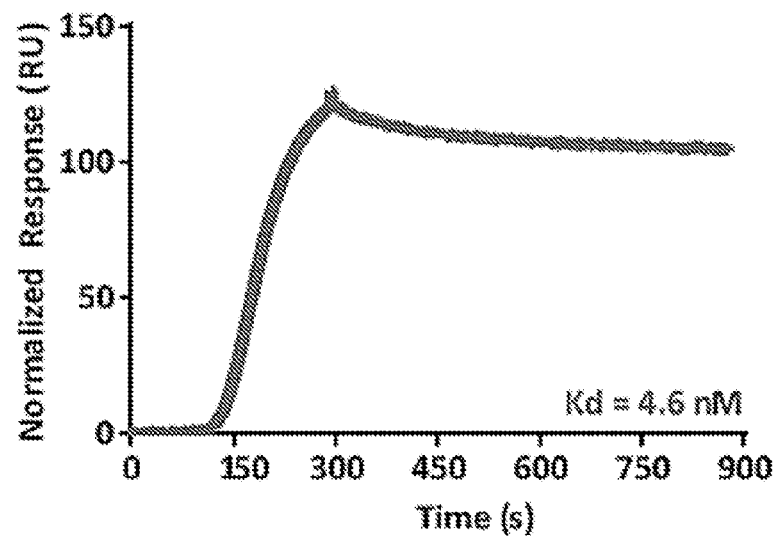
Figure 10B:
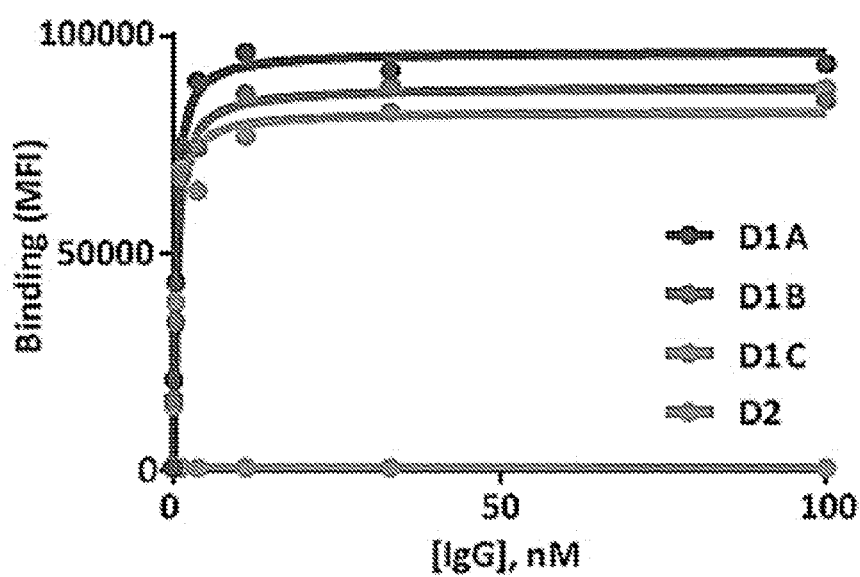
Figure 10C:
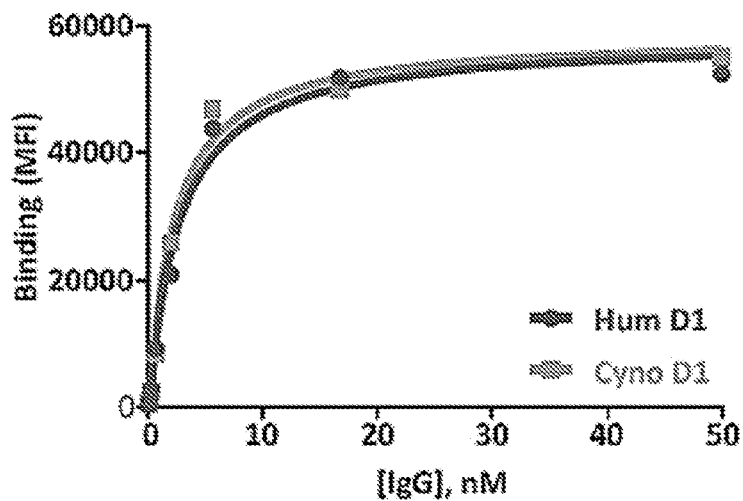
Figure 10D:
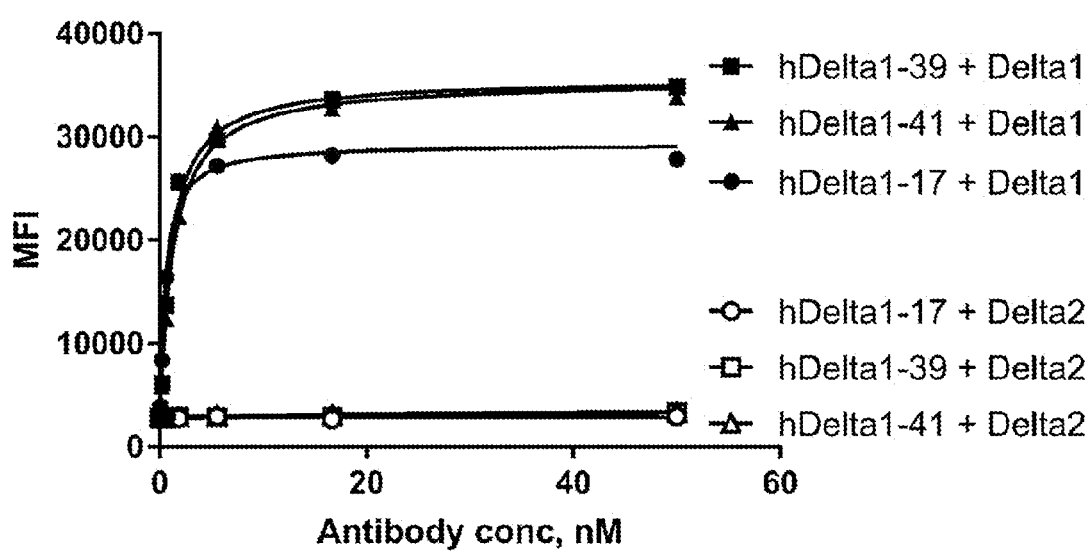

FIGS. 10A-10D show that anti-Delta1 antibodies disclosed herein have high affinity and specificity for Delta1. FIG. 10A is a surface plasmon resonance (SPR) graph showing that anti-Delta1-17 antibody for example, has high affinity for human Delta1 TCR. FIG. 10B is a graph showing that Delta1-17 antibody is specific for Delta1 TCR and does not bind to (cross-react with) Delta 2 TCR. Three different Delta1 variants (D1A, D1B, and D1C), which differ from one another only in the CDR3 loop, were produced. Delta1 and Delta2 Fc fusion proteins were attached to streptavidin-coated beads and binding titrations were performed with Delta1-17 hIgG1. FIG. 10C is a graph showing that Delta1-41 antibody is cross-reactive between human and monkey ("cyno"). FIG. 10D is a graph showing that Delta1 antibodies Delta1-17, Delta1-39, and Delta1-41 are specific for Delta1 TCR as relative to Delta2 TCR.

Figure 11A:
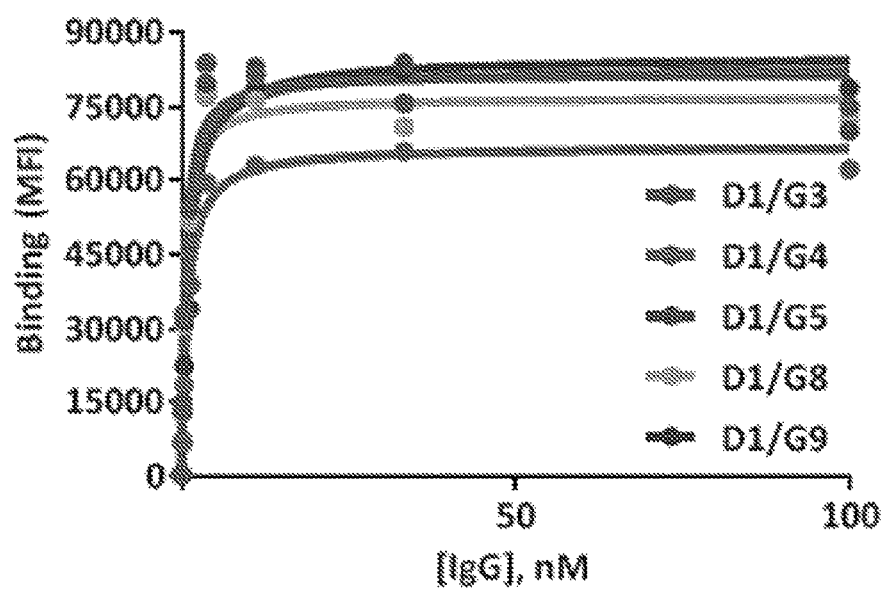

FIGS. 11A and 11B show that anti-Delta1 antibodies disclosed herein are γ-independent. FIG. 11A is a graph showing that Delta1-17 is Delta1-specific, regardless of the γ chain in purified δγ TCRs. FIG. 11B is a graph demonstrating that several anti Delta1 antibodies, including Delta1-39 and Delta1-41 is Delta1-specific, using cell surface δγ TCRs. Un-transduced J.RT3-T3.5 (TIB153) was used as a control to show that there is no background binding to any other cell surface receptors found on T cells (data not shown).

Figure 12A:
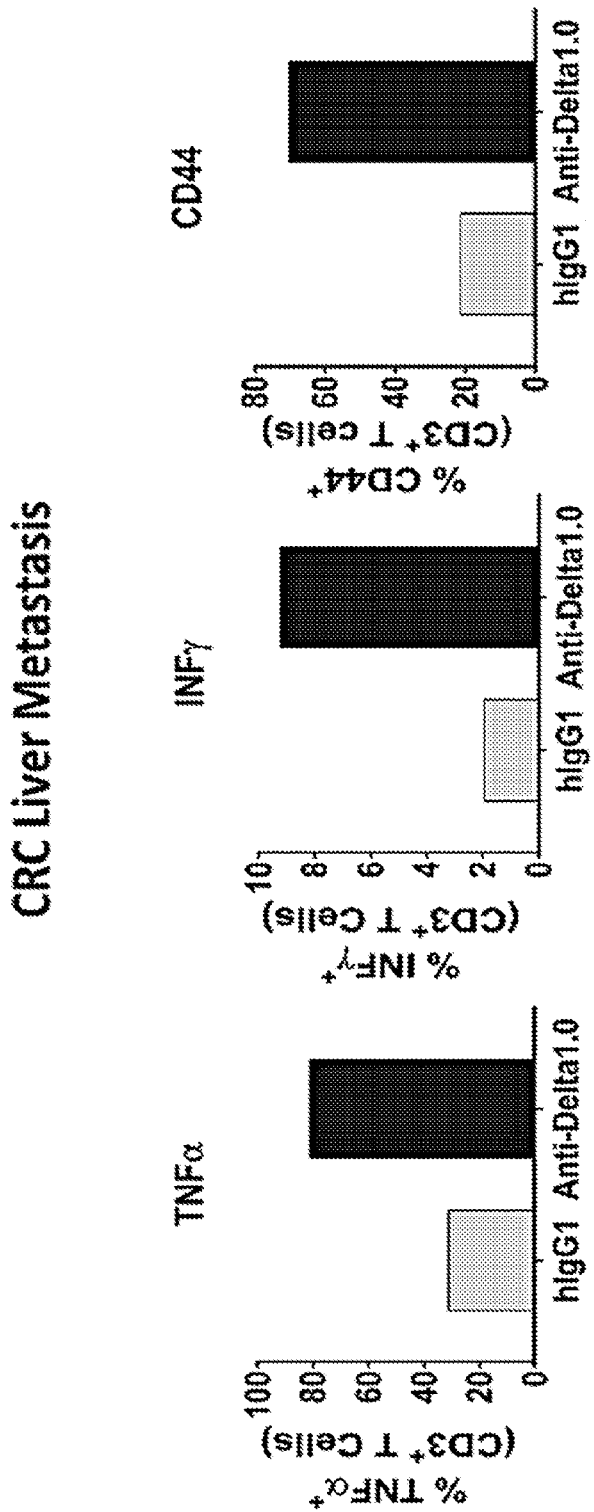
Figure 12B:
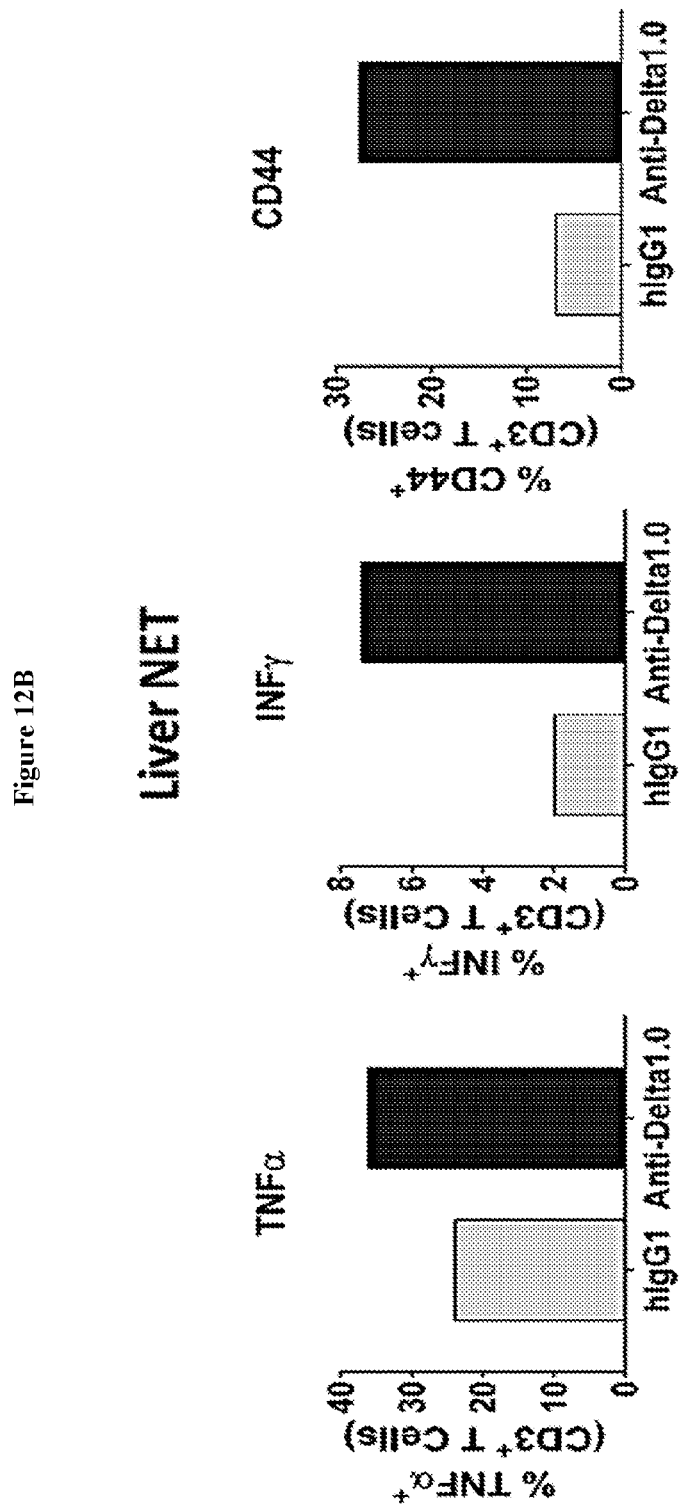
Figure 12C:
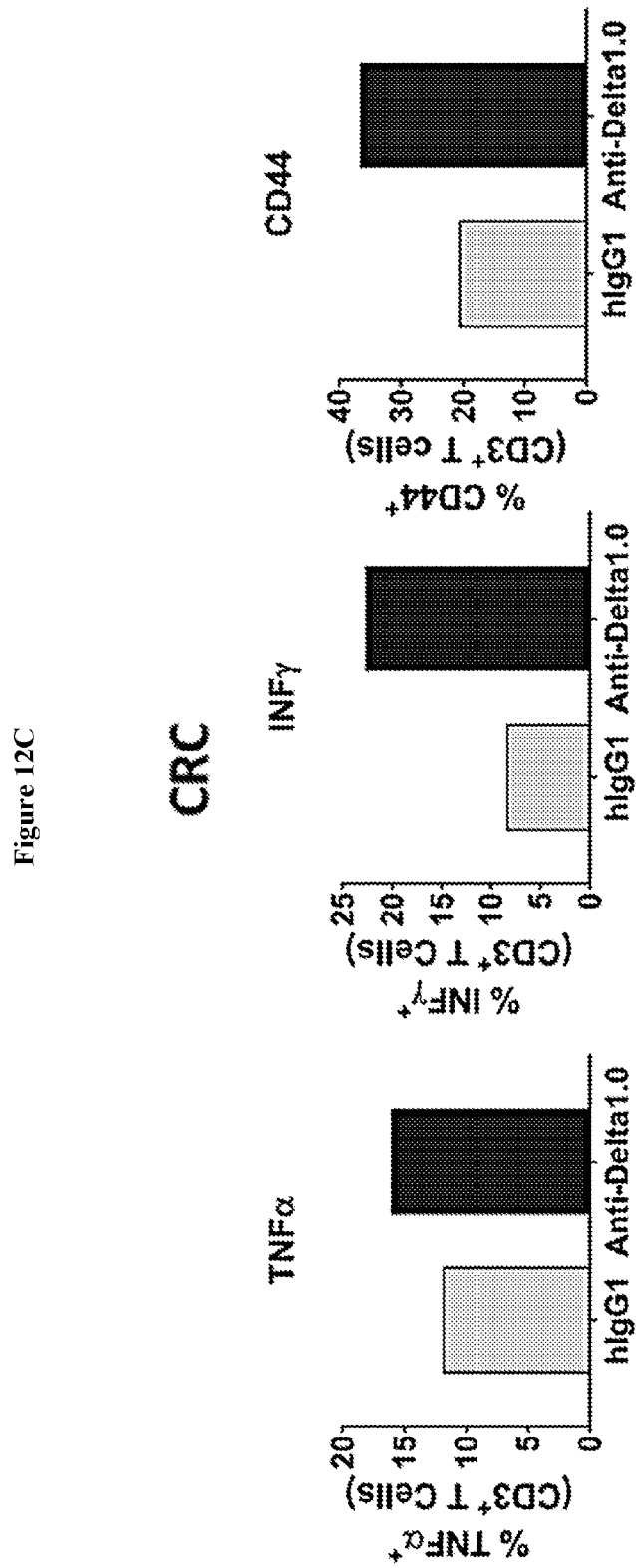
Figure 12D:
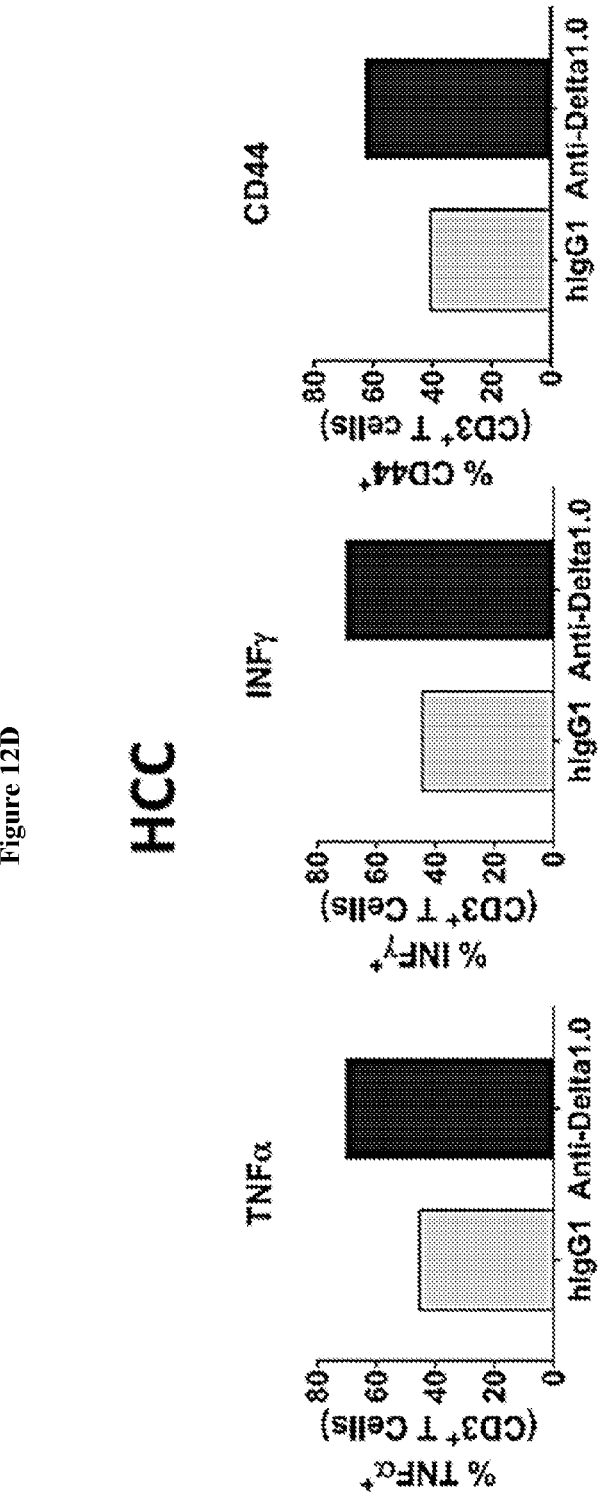

FIGS. 12A-12D include bar graphs showing immune profile expression in tumor samples (PDOTS) treated with isotype (hIgG1) as compared to an anti-Delta1 IgG1 antibody (Delta1-17 as an example). The percent TNF-α in CD3+ T cells, percent IFNγ in CD3+ T cells, and percent CD44 in CD3+ T cells are shown for colorectal carcinoma liver metastasis (FIG. 12A), liver neuroendocrine tumor (FIG. 12B), colorectal carcinoma neuroendocrine tumor (FIG. 12C), and hepatocellular carcinoma (FIG. 12D).

Figure 13A:
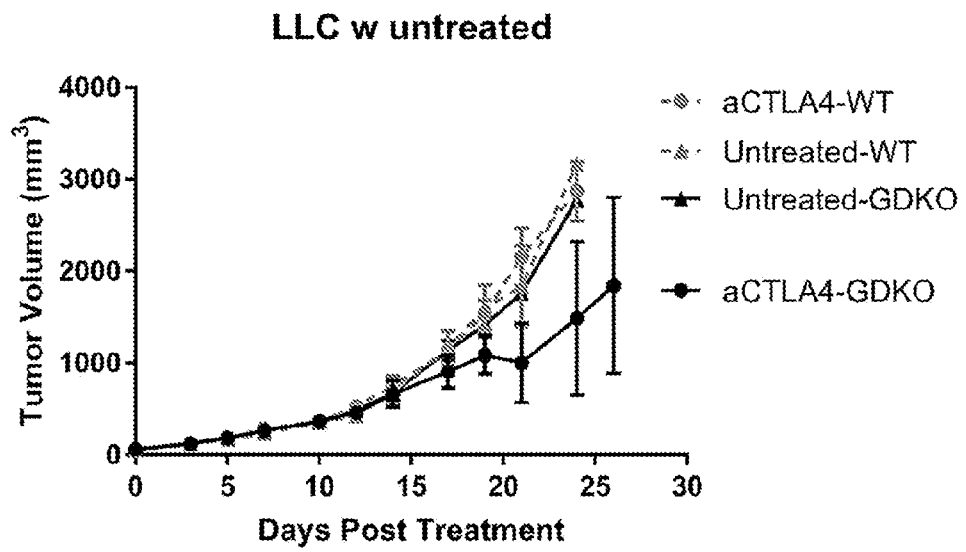
Figure 13B:
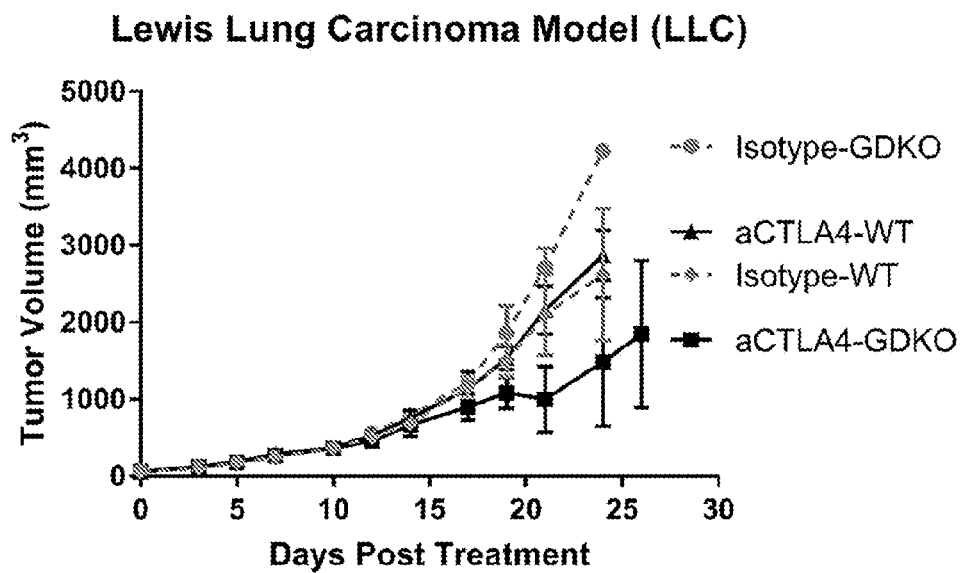
Figure 13C:
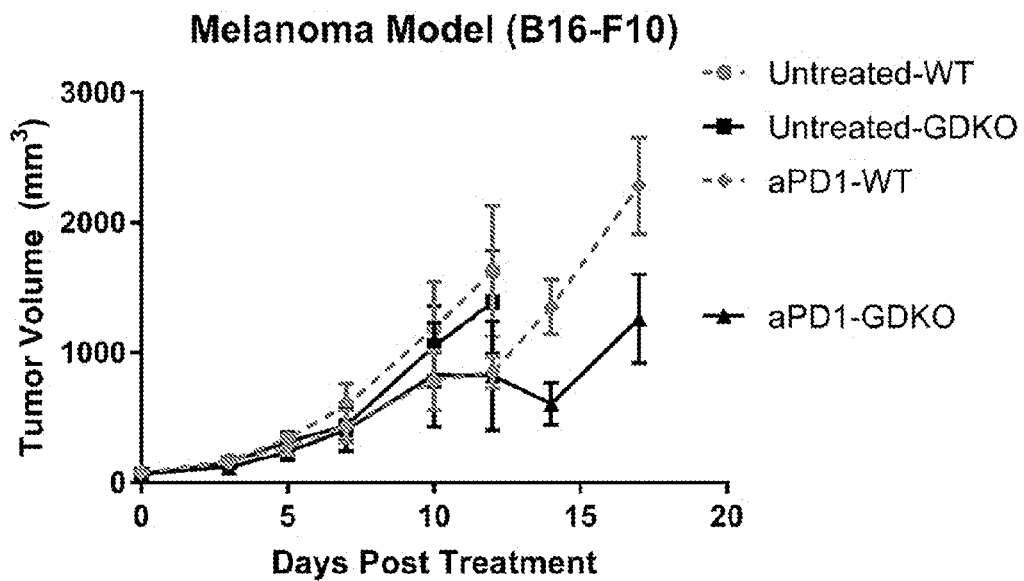
Figure 13D:
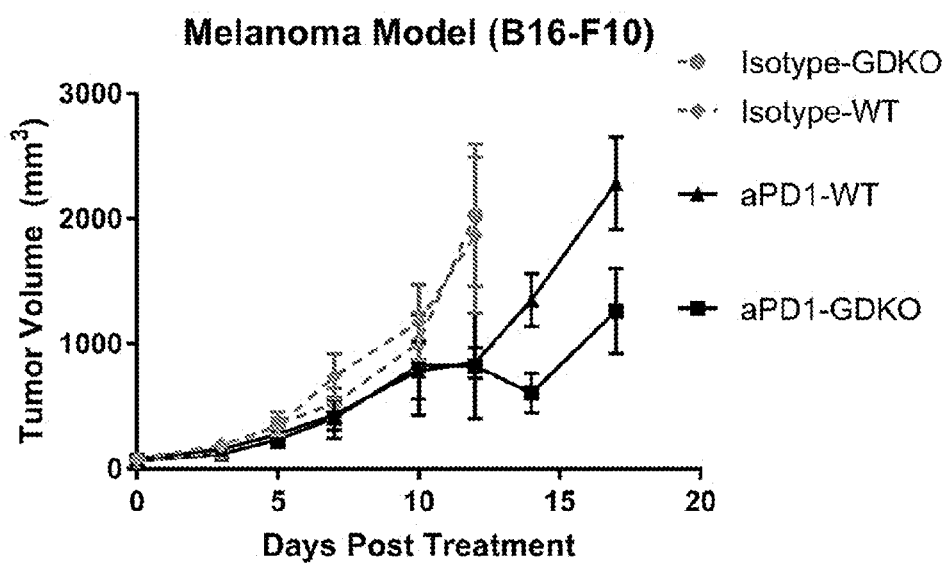

FIGS. 13A-13D include graphs showing impact of γδ T cells on response to checkpoint inhibition in the lung (LLC) and the melanoma (B16F10) subcutaneous syngeneic models. FIGS. 13A and 13B: graphs showing anti-tumor effects of an anti-CTLA-4 antibody versus untreated (13A) or an IgG isotype control (13B) in a γδ knock-out Lewis lung carcinoma mouse model as compared to the in the wild-type counterpart. FIGS. 13C and 13D: graphs showing anti-tumor effects of an anti-PD-1 antibody versus untreated (13C) or an IgG isotype control (13D) in a γδ knock-out melanoma mouse model as compared to the wild-type counterpart.

Figure 14A:
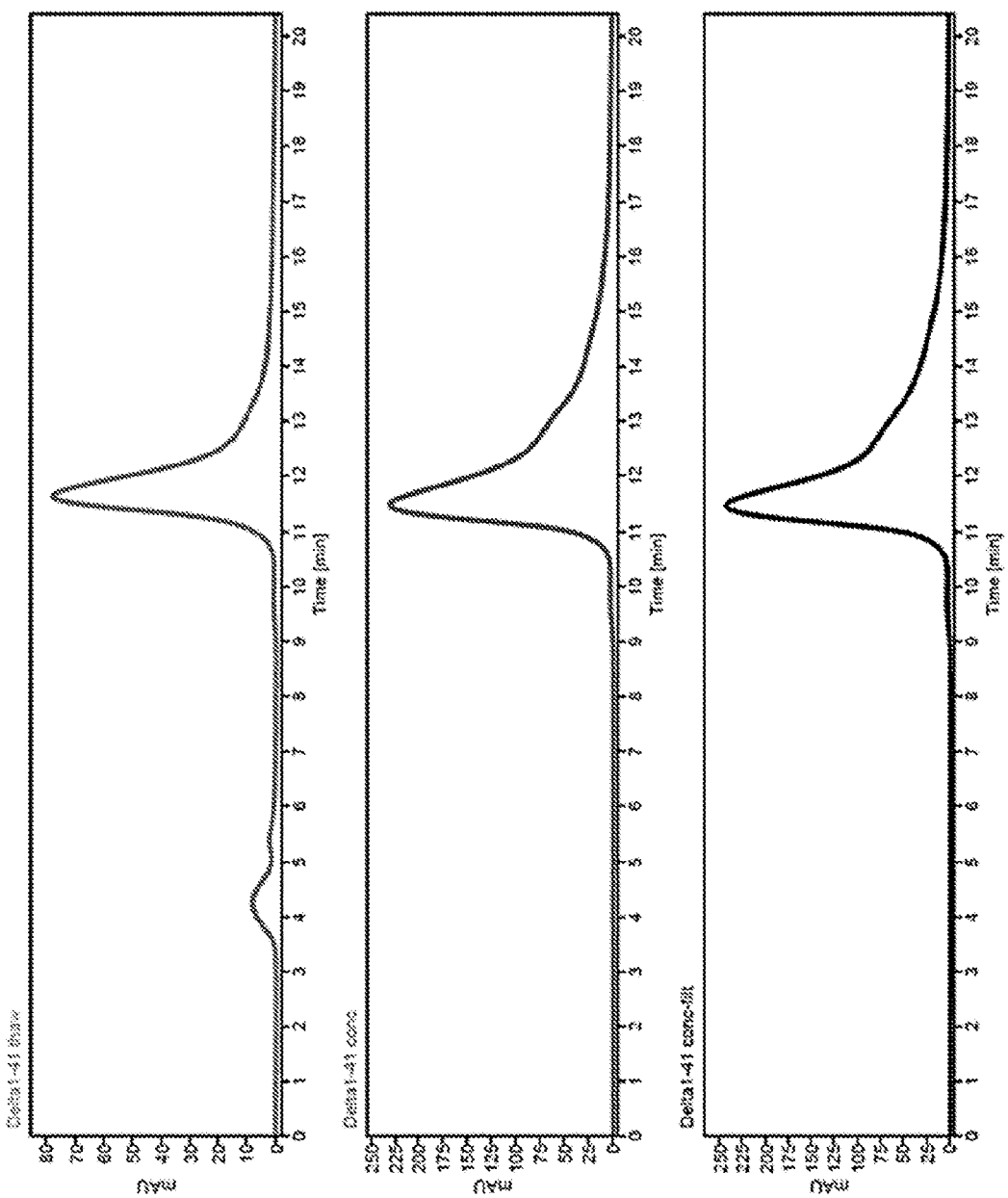
Figure 14B:
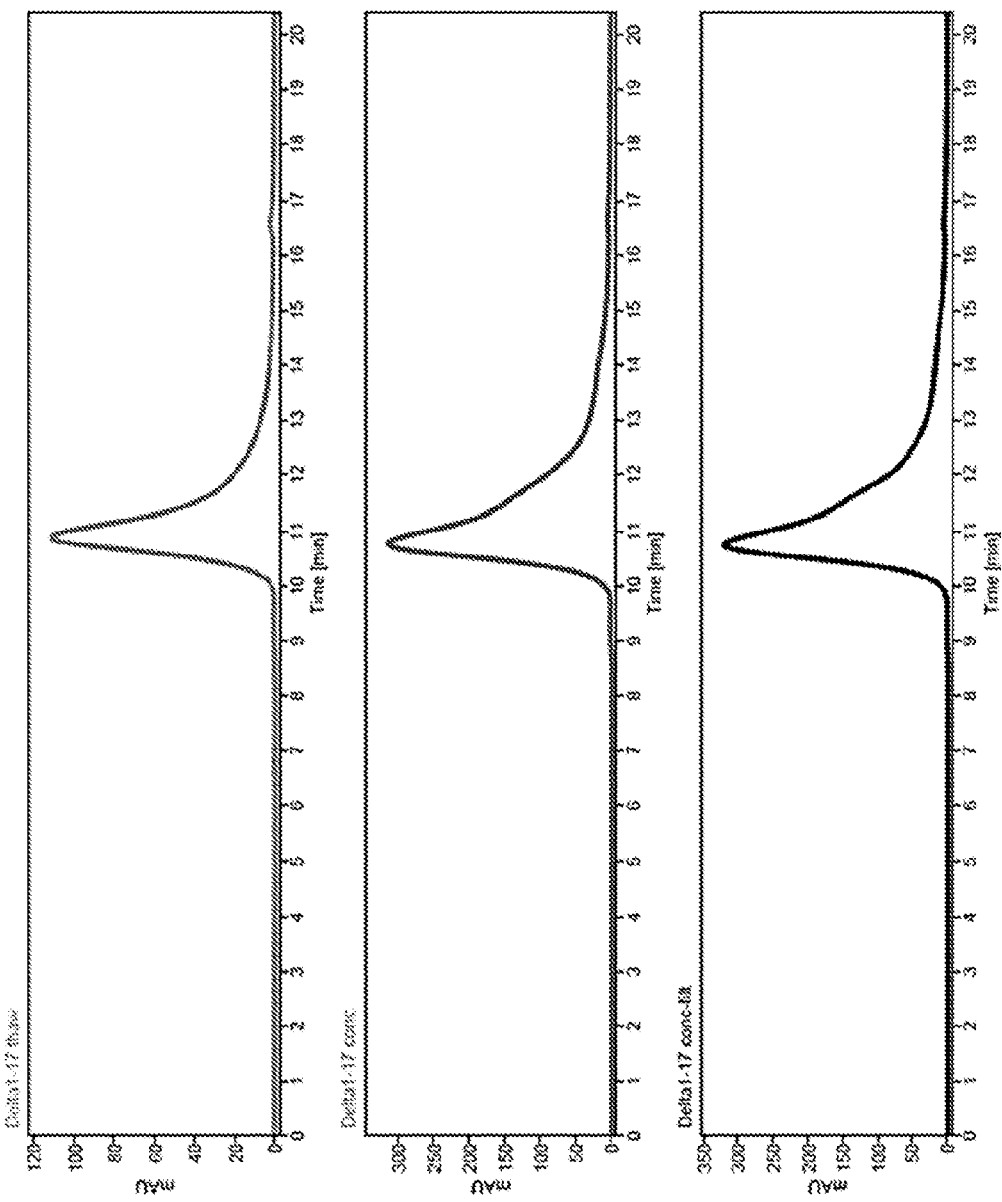
Figure 14C:
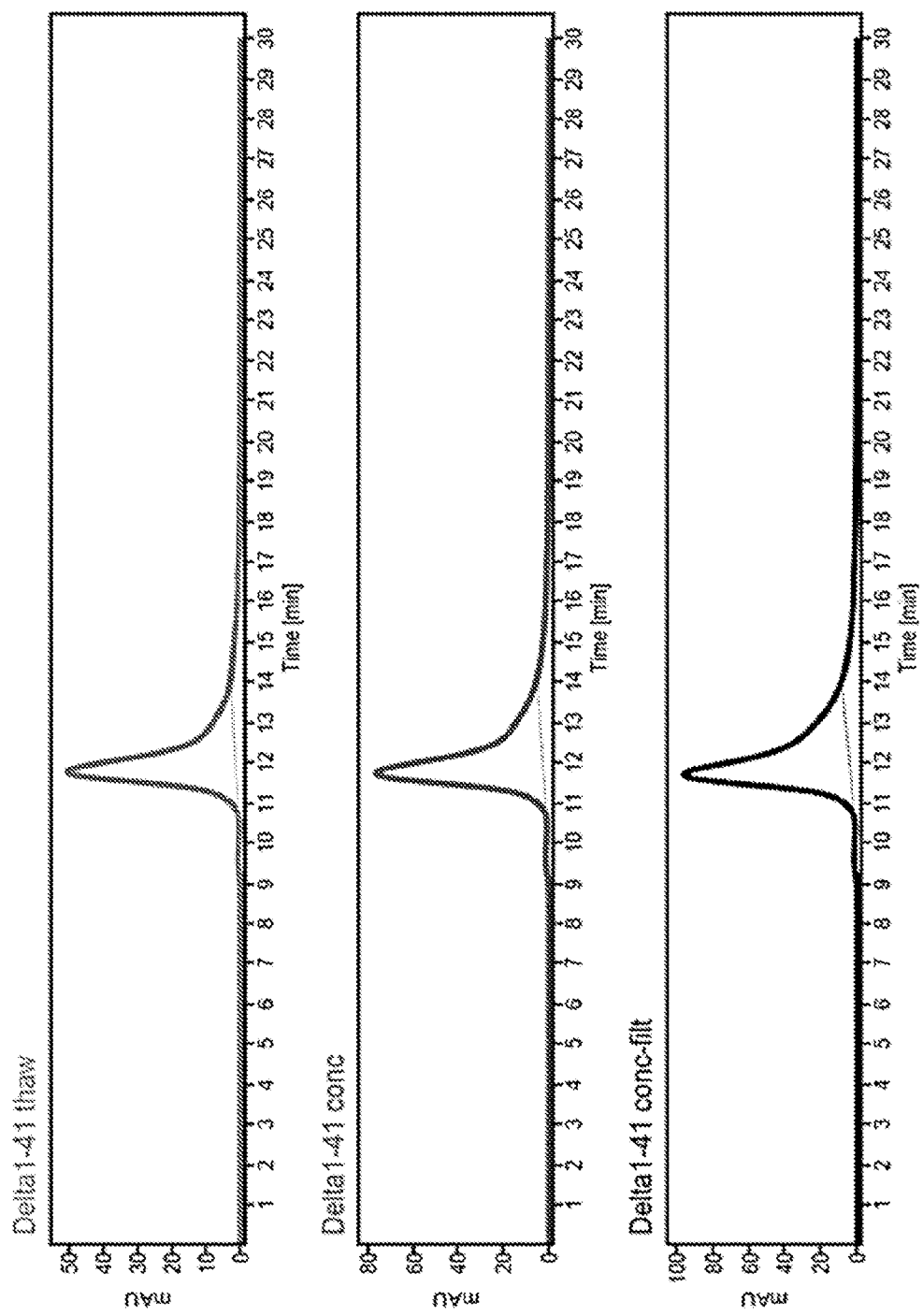
Figure 14D:
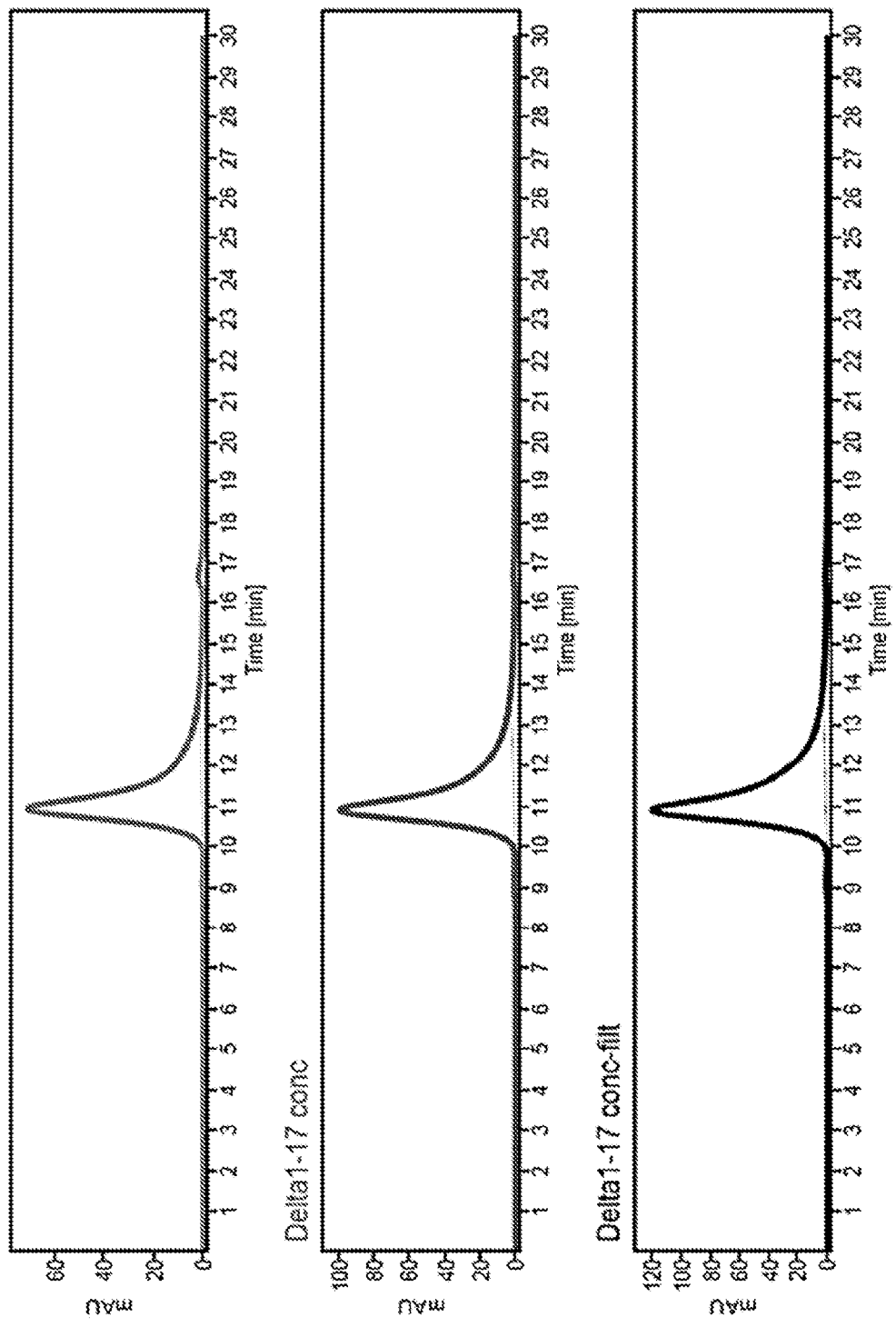
Figure 14E:
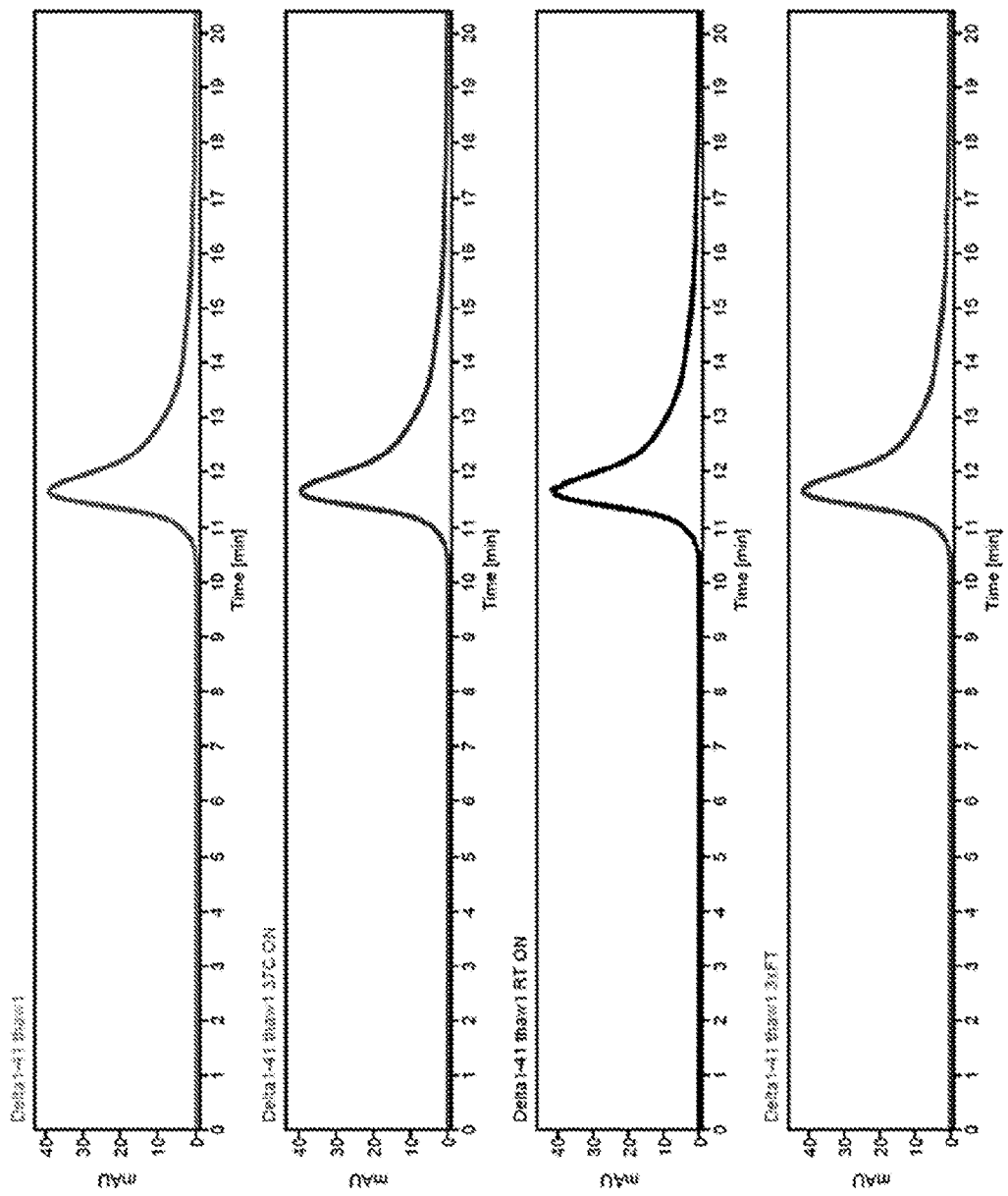
Figure 14F:
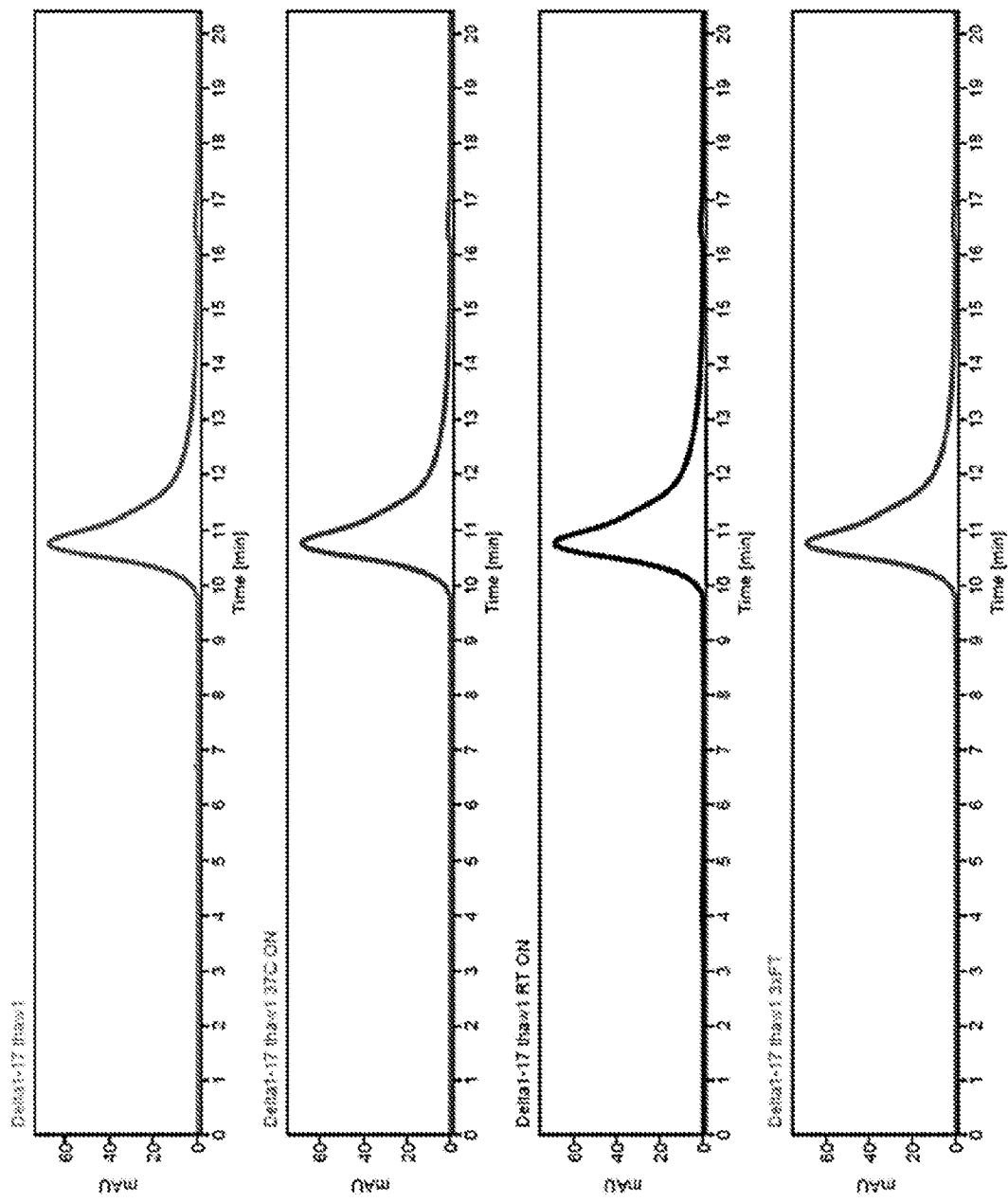
Figure 14G:
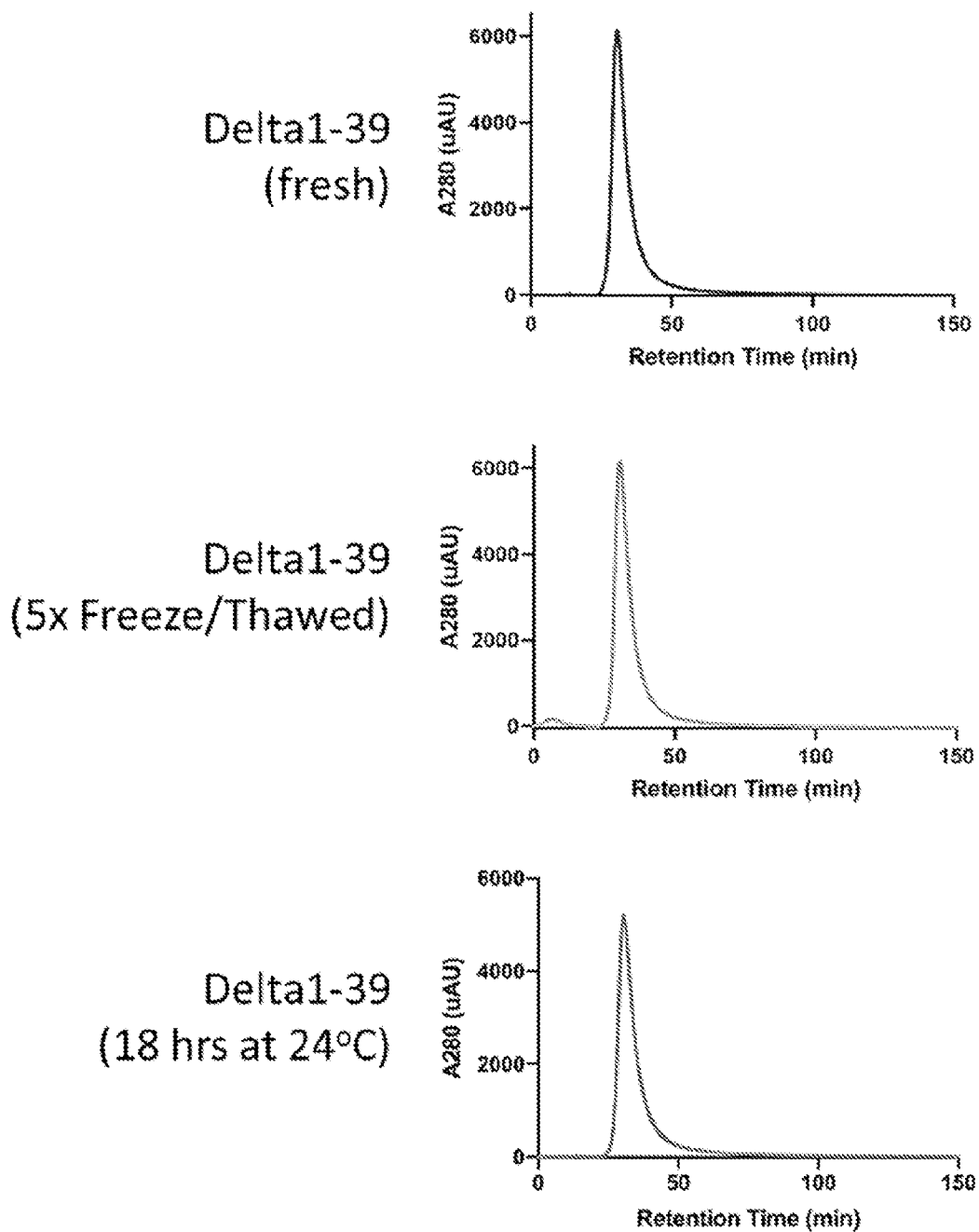

FIGS. 14A-14G include graphs showing stability of anti-Delta1 antibodies Delta1-17, Delta1-41, and Delta1-39 after freeze/thaw, concentration, and filteration. FIGS. 14A and 14B are stability curves of Delta1-41 and Delta1-17, respectively. From top panel to bottom panel: Freeze/thaw 1x, 3 mg/ml; Freeze/thaw 1x, concentrated to 12 mg/ml; and Freeze/thaw 1x, concentrated to 12 mg/ml, and filtered. FIGS. 14C and 14D are stability curves of Delta1-41 and Delta1-17, respectively, after being inducated at 4° C. for 10 days. From top panel to bottom panel: Freeze/thaw 1x, 3 mg/ml; Freeze/thaw 1x, concentrated to 12 mg/ml; and Freeze/thaw 1x, concentrated to 12 mg/ml, and filtered. FIG. 14E and FIG. 14F are stability curves of Delta1-41 and Delta1-17, respectively, after high temperature storage and freeze and thaw. From top to bottom panels: Freeze/Thaw 1x; 37° C. overnight (O/N); Room temperature (RT) overnight (O/N); and Freeze/Thaw 4x. FIG. 14G shows stability curves of Delta1-39 fresh, freeze thawed 5 times, and after 18 hours and 24 C.

Figure 15A:
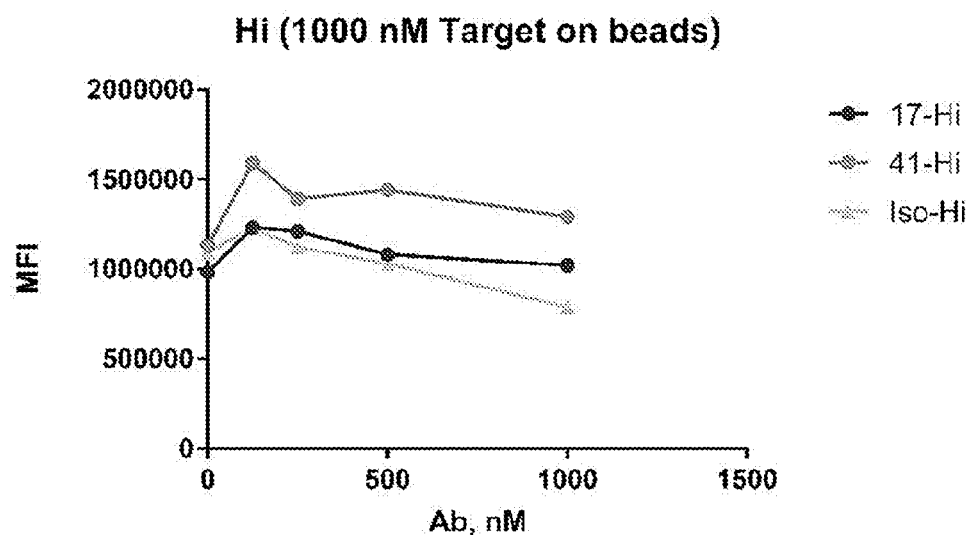
Figure 15B:
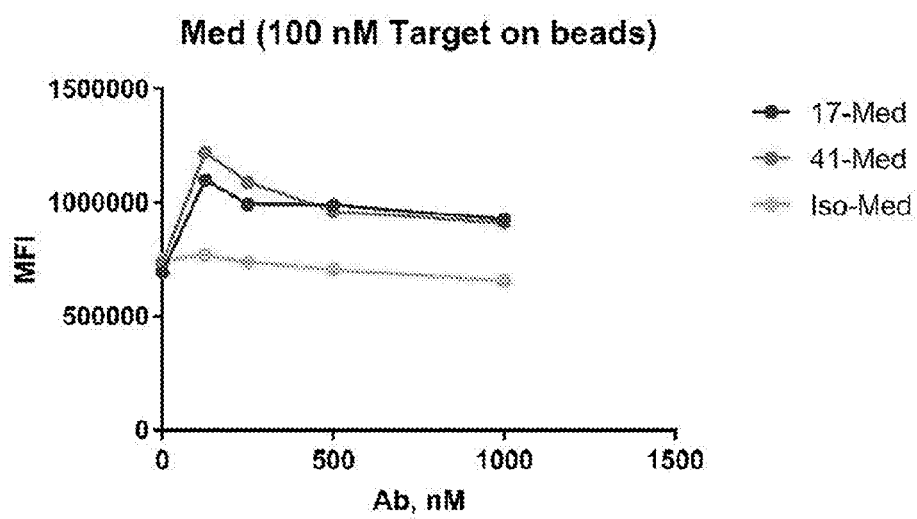
Figure 15C:
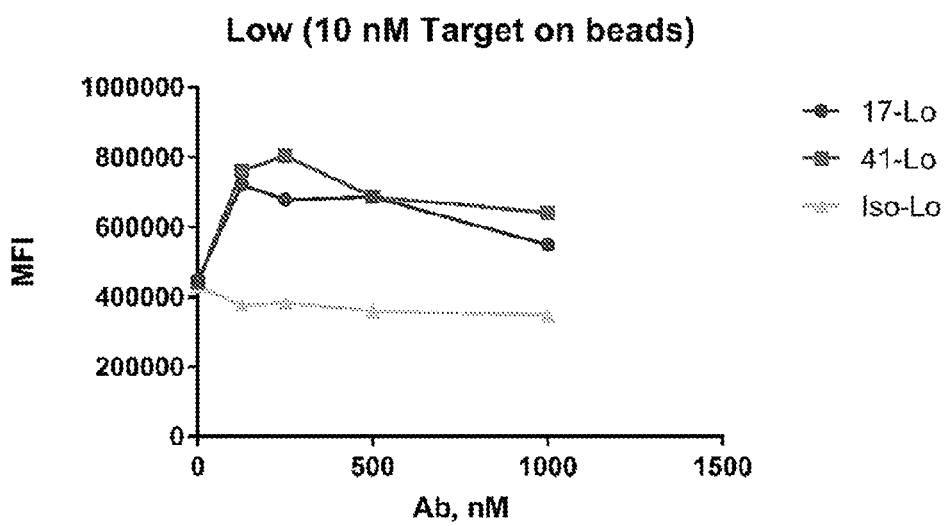

FIGS. 15A-15C include charts showing antibody-dependent cellular phagocytosis (ADCP) effects of Delta1-17 and Delta1-41 against target immobilized on beads. 15A: 1000 nM target on beads. 15B: 100 nM target on beads. 15C: 10 nM target on beads.

Figure 16A:
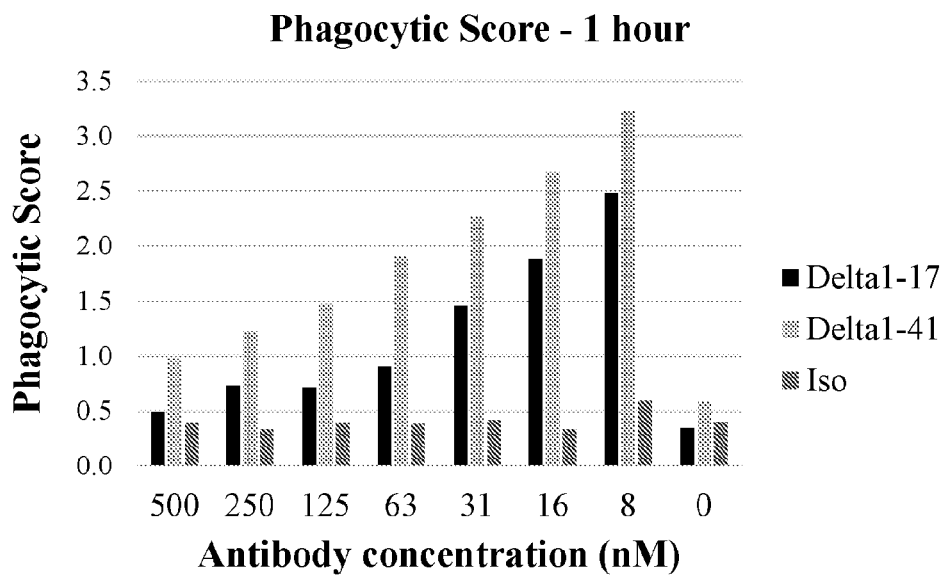
Figure 16B:
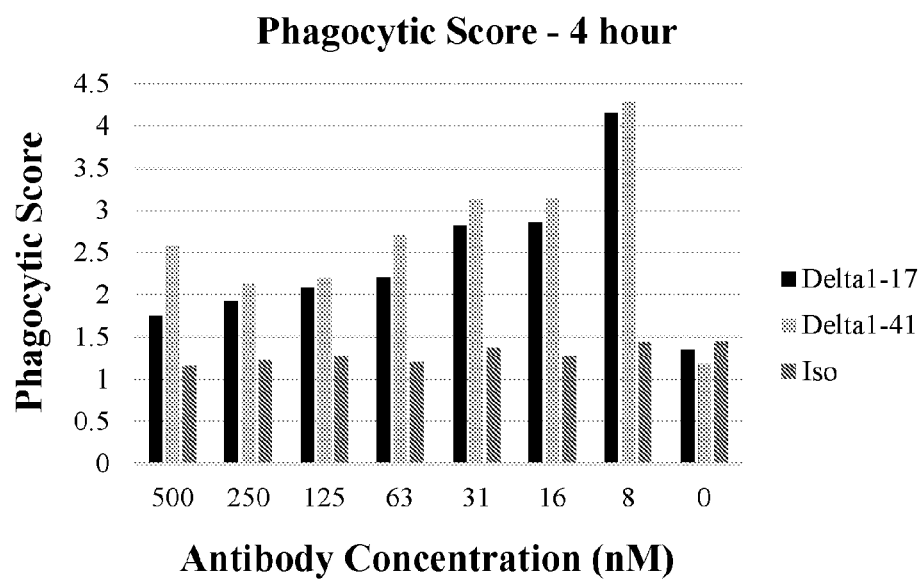
Figure 16C:
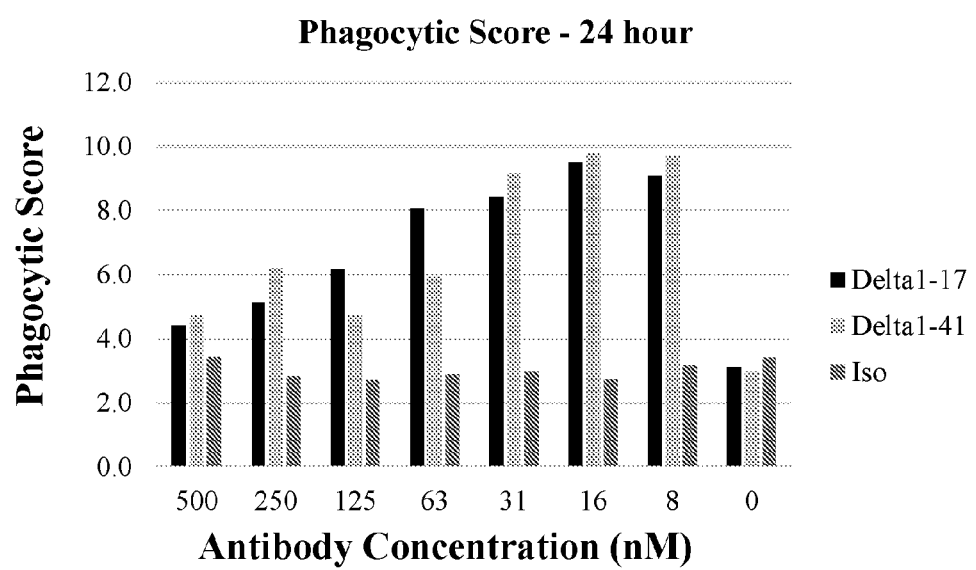

FIGS. 16A-16C include diagrams showing ADCP effects of Delta1-17 and Delta1-41 at different time point, including 1 hour (16A), 4 hours (16B), and 24 hours (16C), different antibody concentrations as indicated.

Figure 17:
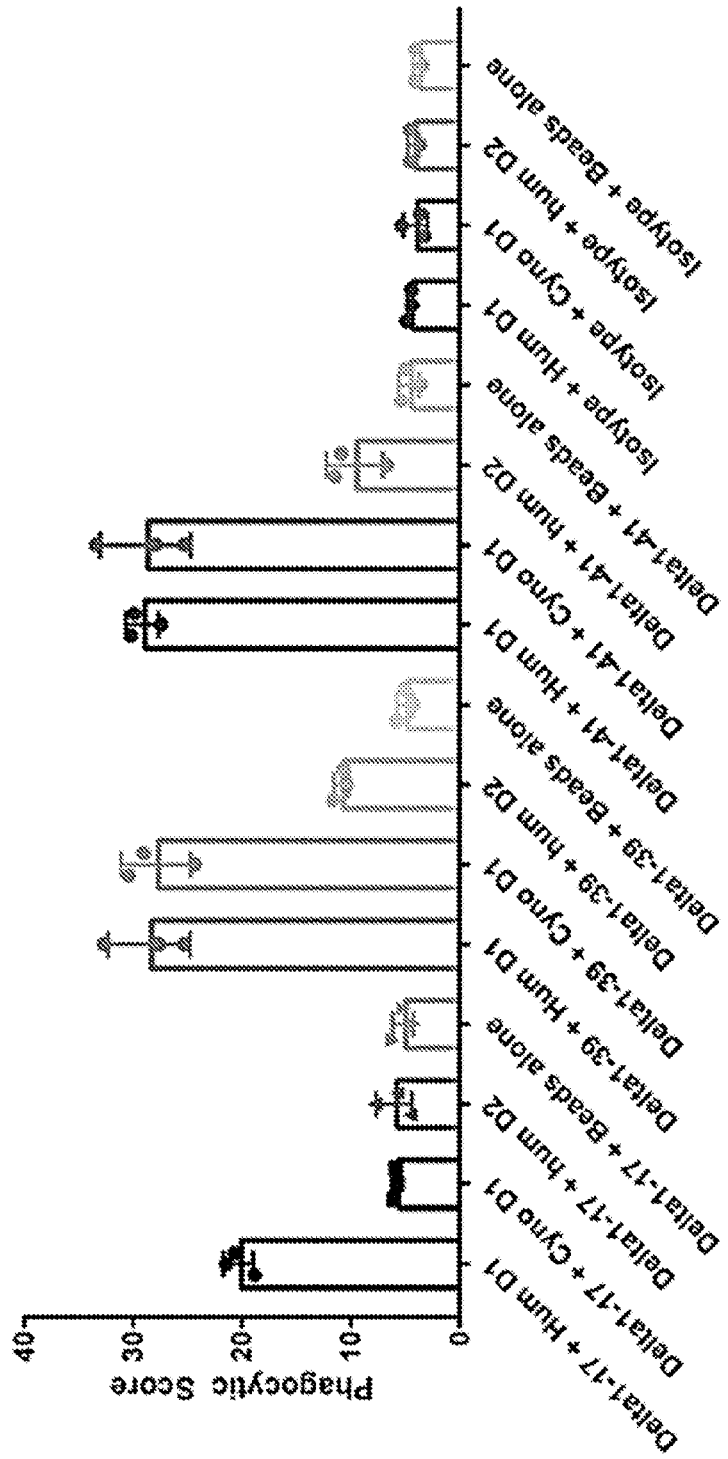

FIG. 17 is a diagram showing ADCP effects of various anti-Delta1 antibodies (e.g., Delta1-17, Delta1-39, and Delta1-41) against different target proteins observed in a bead-based ADCP assay.

Figure 18A:
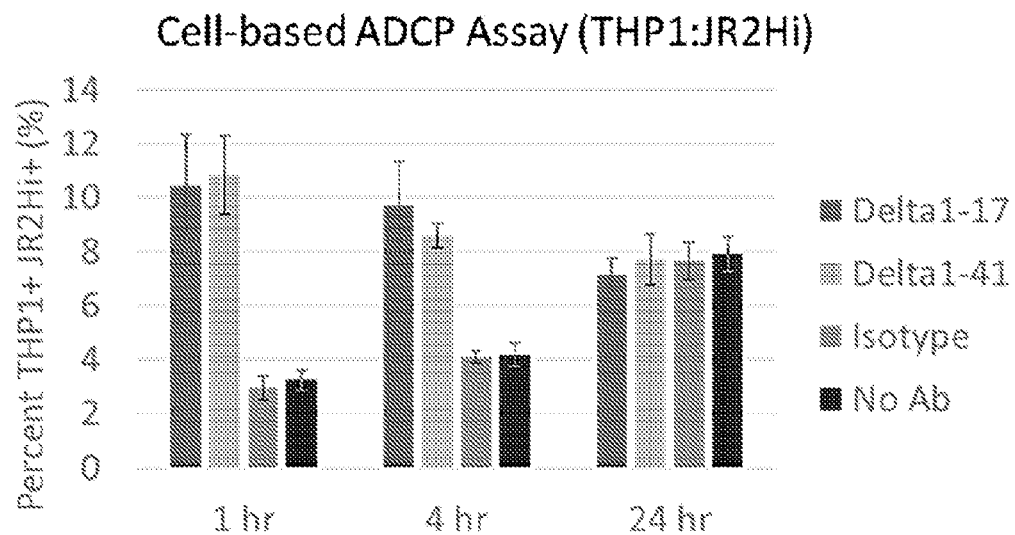
Figure 18B:
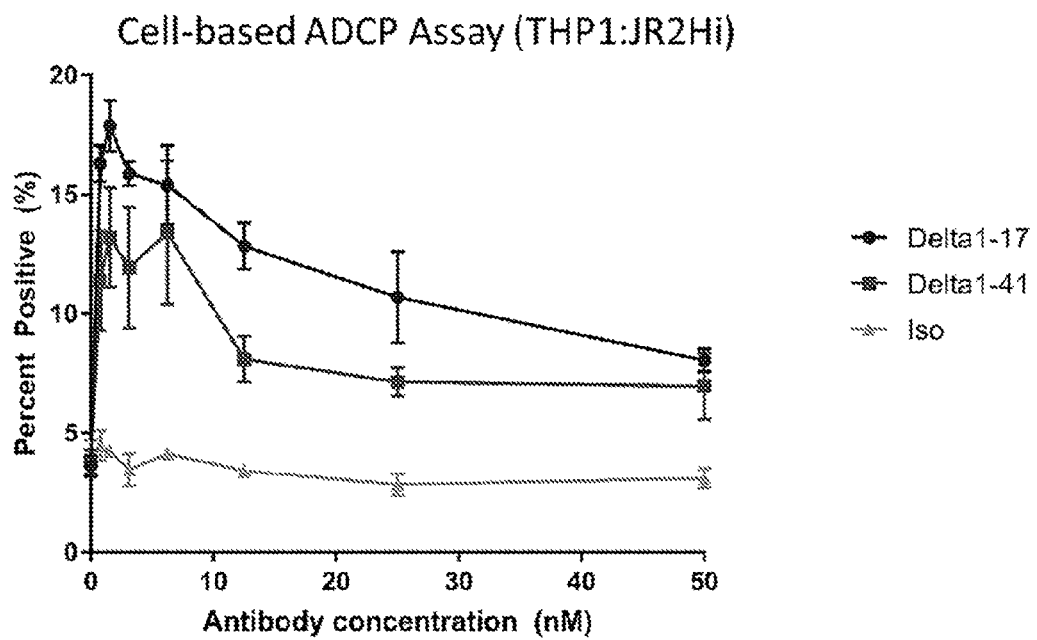

FIGS. 18A and 18B include diagrams showing ADCP effect of anti-Delta1 antibodies in a cell-based ADCP assay. FIG. 18A: ADCP effects at different time points as indicated. FIG. 18B: ADCP effects at different antibody concentrations.

Figure 19:
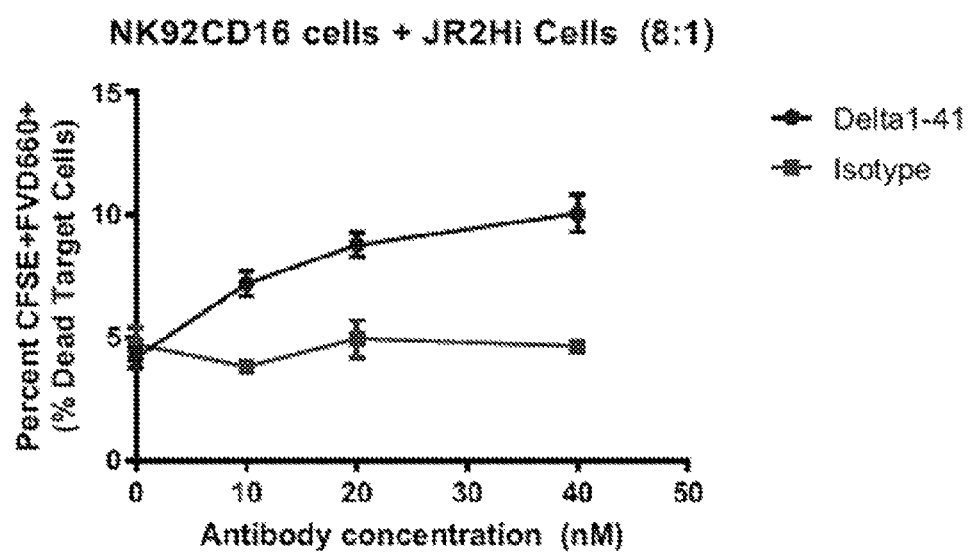

FIG. 19 includes a diagram showing the antibody-dependent cell cytotoxicity (ADCC) effects of Delta1-41 at different antibody concentrations as indicated).

Figure 20A:
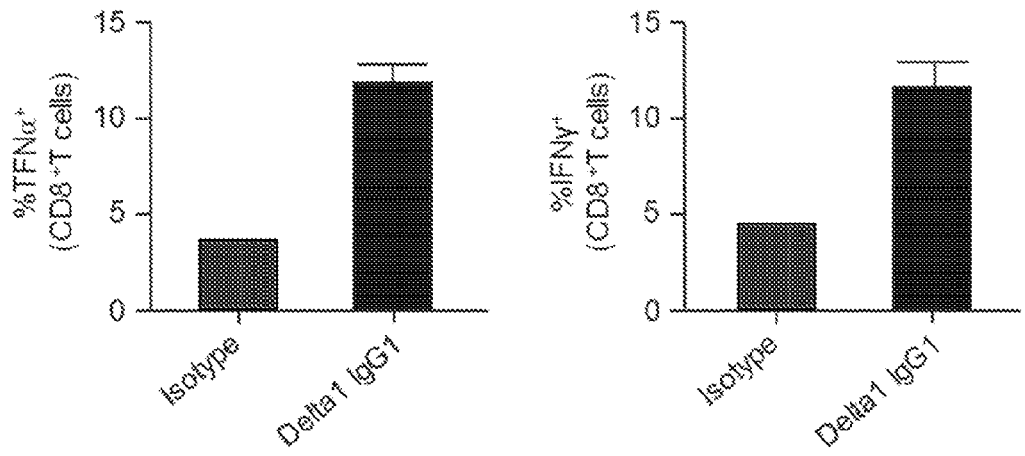
Figure 20B:
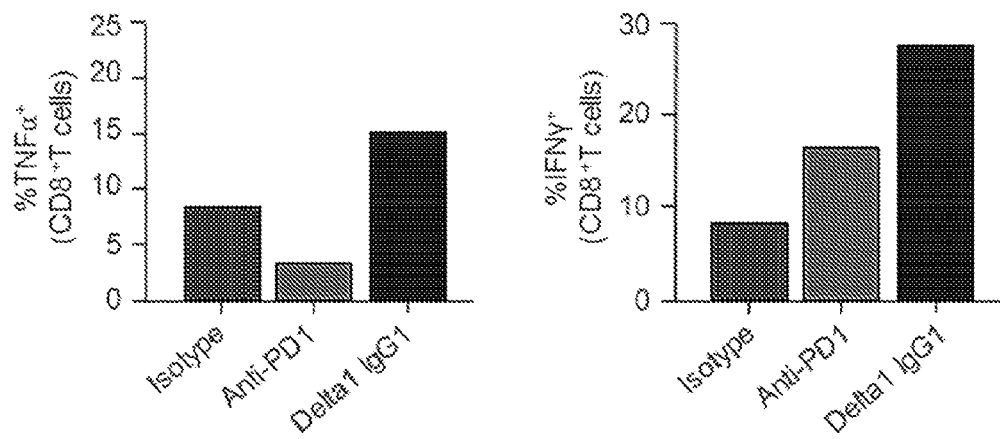

FIGS. 20A-20B include bar graphs showing levels of αβ T cell activation in tumor samples (PDOTS) treated with isotype (hIgG1) as compared to an anti-Delta1 IgG1 antibody (Delta1-41 as an example), or an anti-PD1 antibody. The percent TNF-α in CD8+ T cells, percent IFNγ in CD8+ T cells, and percent CD44 in CD8+ T cells are shown for colorectal cancer (FIG. 20A) and hepatocellular carcinoma (FIG. 20B).

Figure 21A:
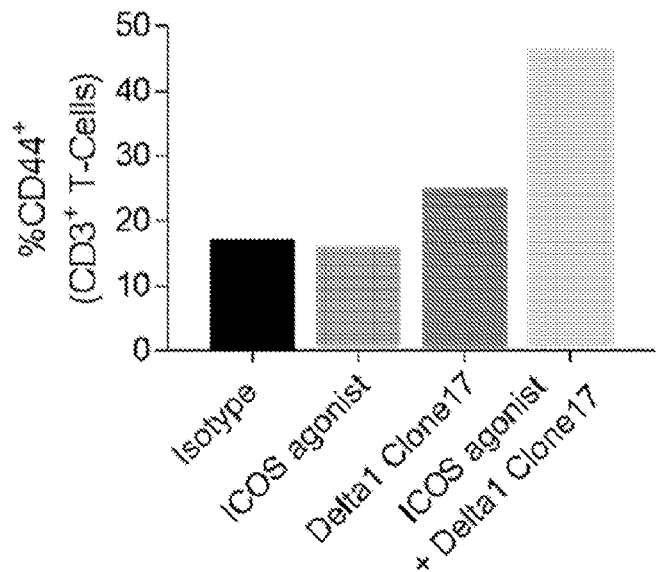
Figure 21B:
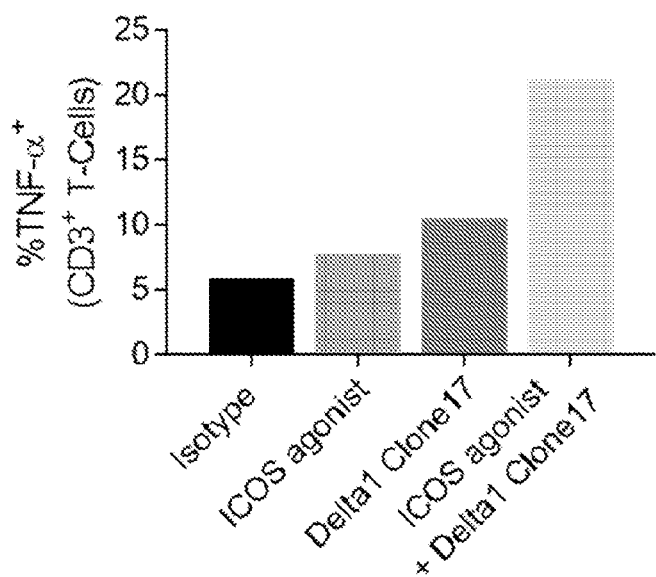
Figure 21C:
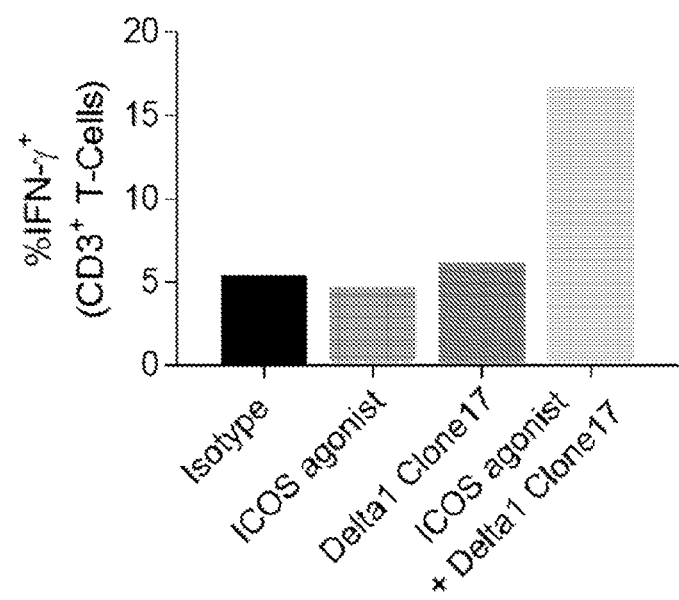

FIGS. 21A-21C include bar graphs showing levels of αβ T cell activation in tumor samples (PDOTS) from hepatocellular carcinoma treated an anti-Delta1 IgG1 antibody (Delta1-17 as an example) in the presence of a co-stimulatory receptor agonist (ICOS agonist) as compared to an isotype (hIgG1) (as a control). The percent CD44 in CD3+ T cells (FIG. 21A), percent TNF-α in CD3+ T cells (FIG. 21B), and percent IFNγ in CD3+ T cells (FIG. 21C) are shown.

Figure 22A:
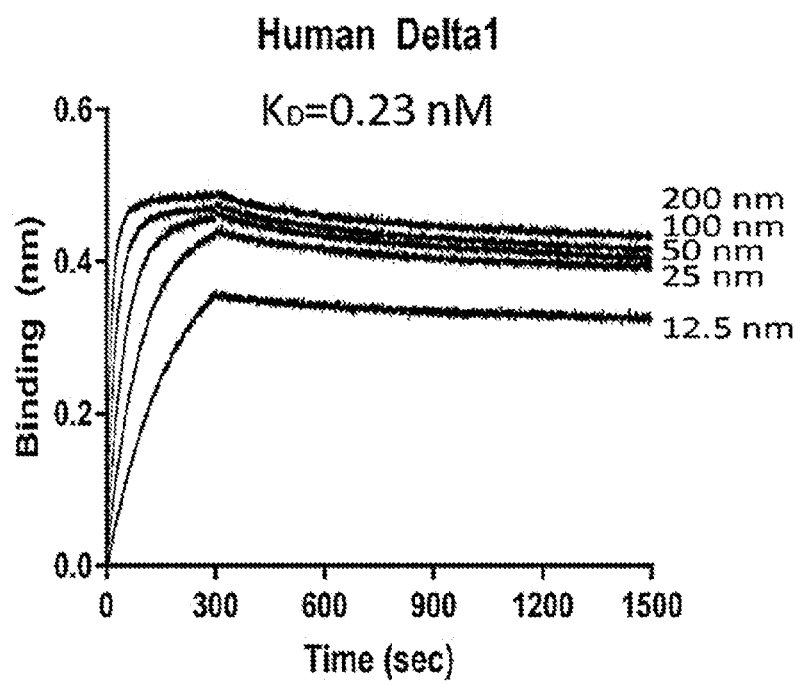
Figure 22B:
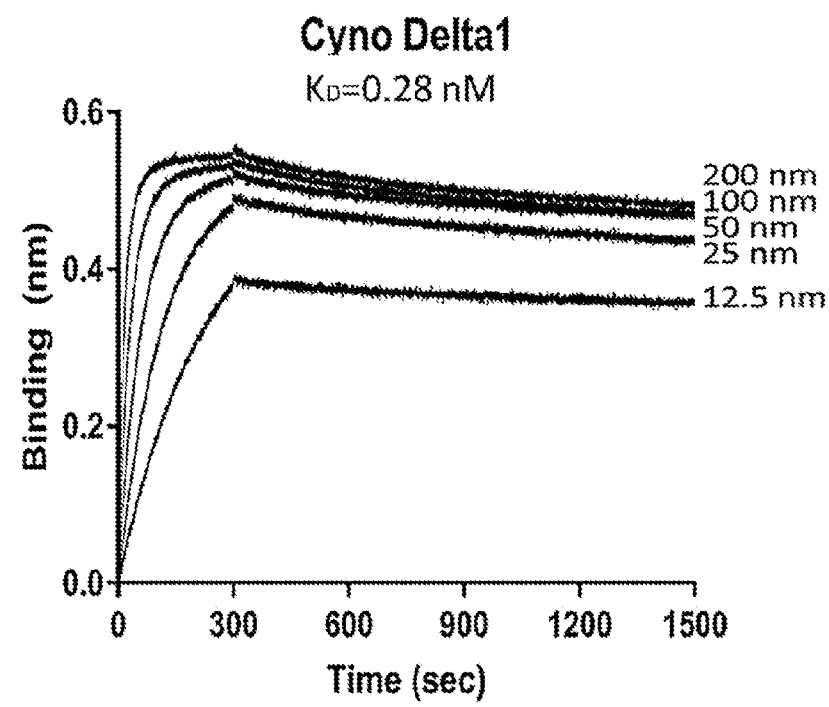

FIGS. 22A-22C show that anti-Delta1 antibody Delta1-39 disclosed herein is cross-reactive between human and monkey and has high affinity for Delta1. FIG. 22A: binding of Delta1-39 antibody to human delta-1 chain. FIG. 22B:

binding of anti-Delta1-39 to monkey ("cyno") delta-1 chain. FIG. 22C: Table listing $K_D$ values, rate constants and fitting parameters.

Figure 23:
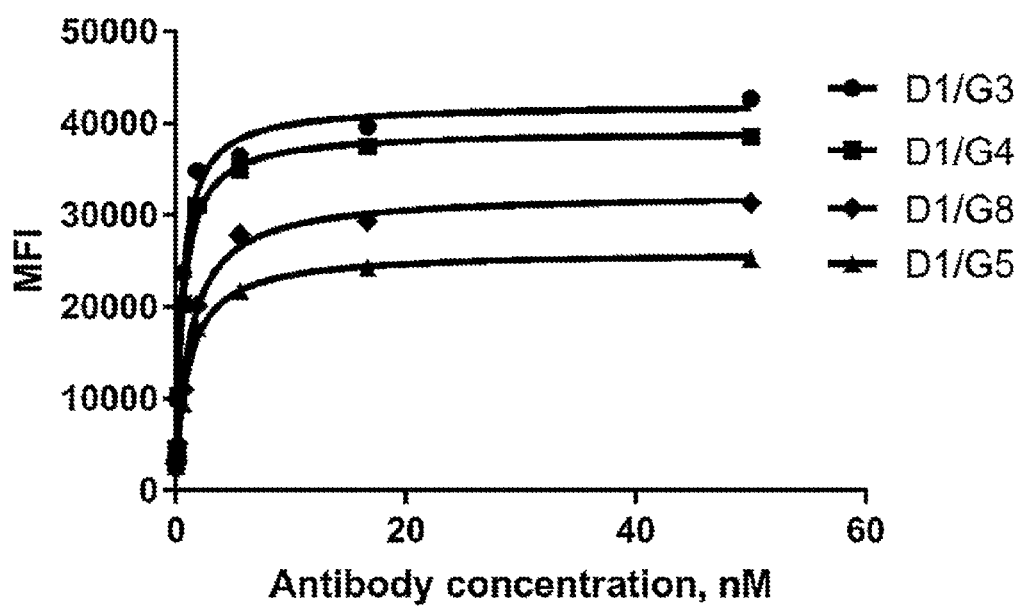

FIG. 23 shows that Delta1-39 is Delta1-specific, regardless of the γ chain in purified δγ TCRs.

Figure 24A:
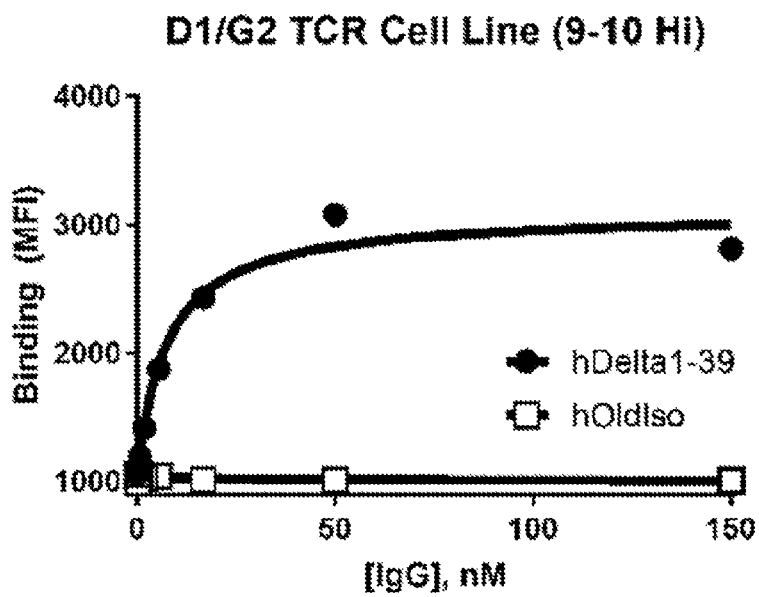
Figure 24B:
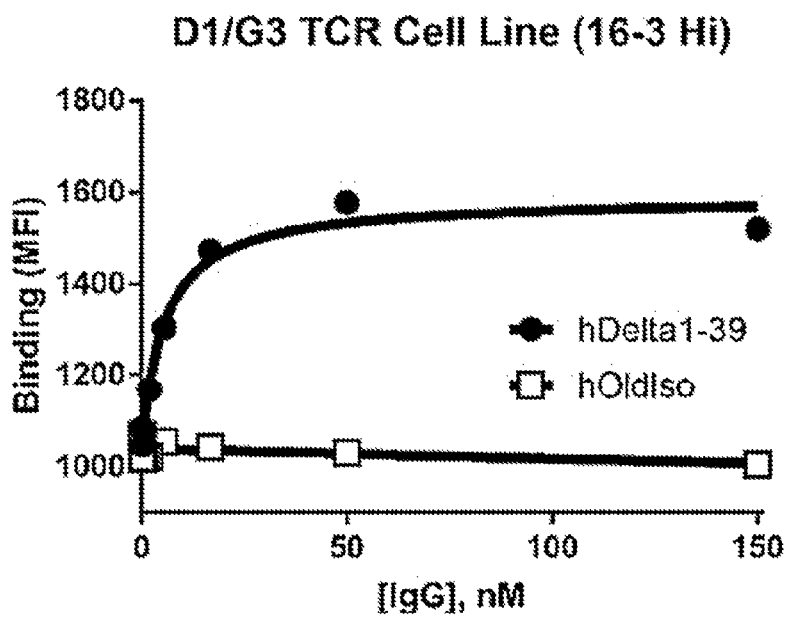
Figure 24C:
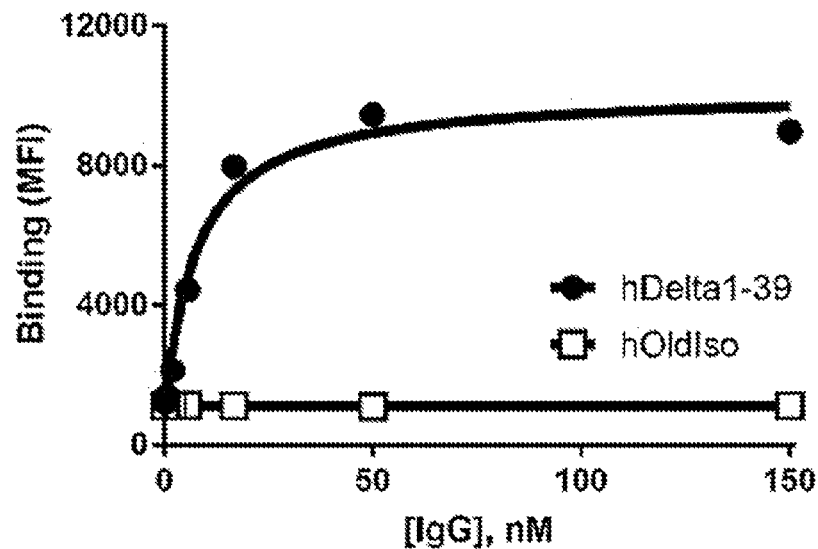
Figure 24D:
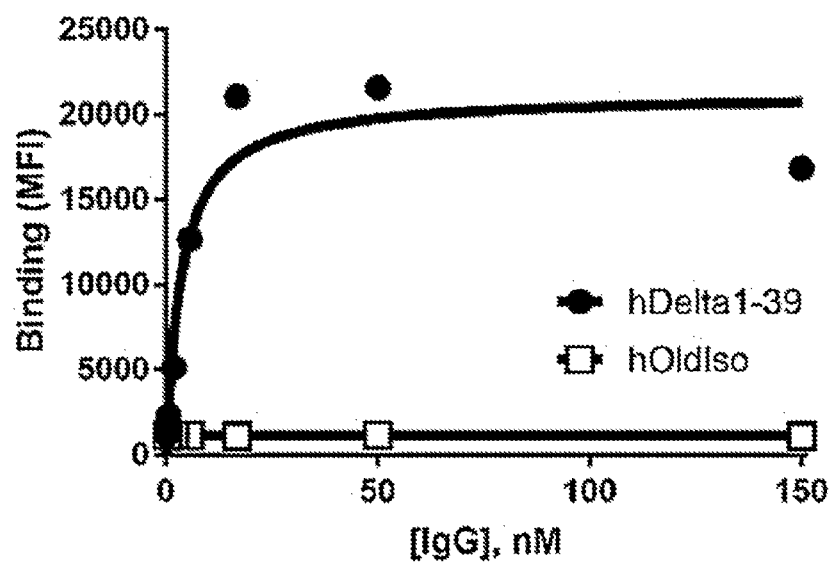
Figure 24E:
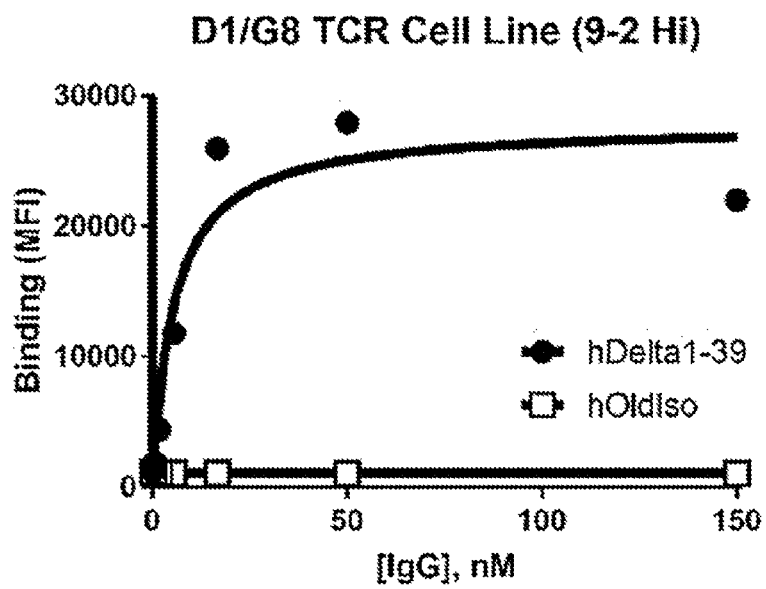
Figure 24F:
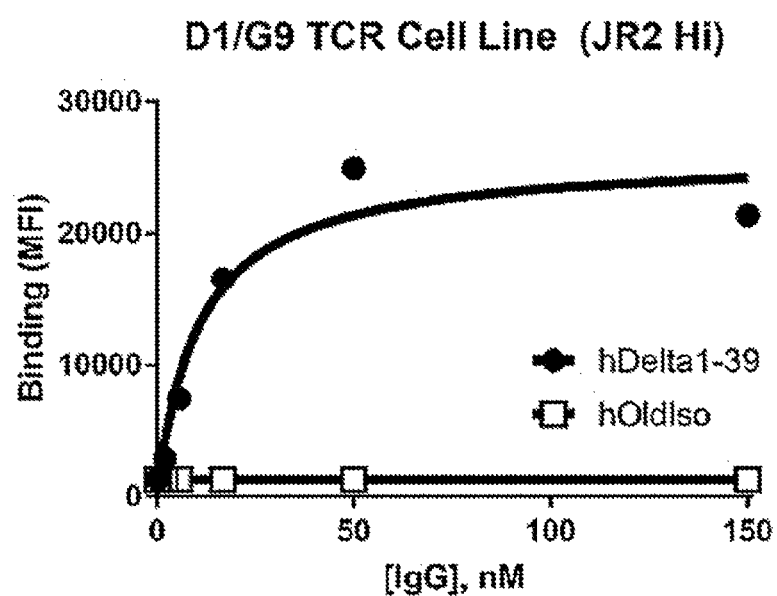
Figure 24G:
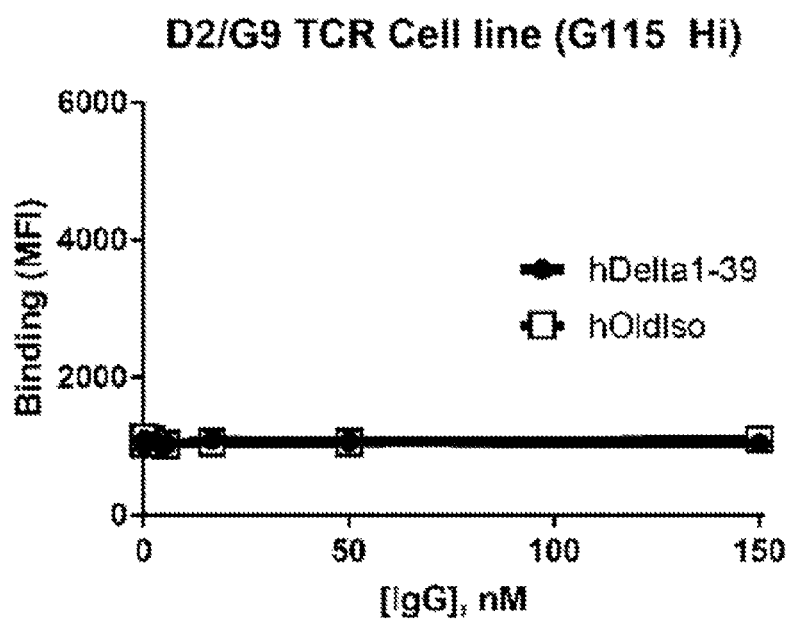
Figure 24H:
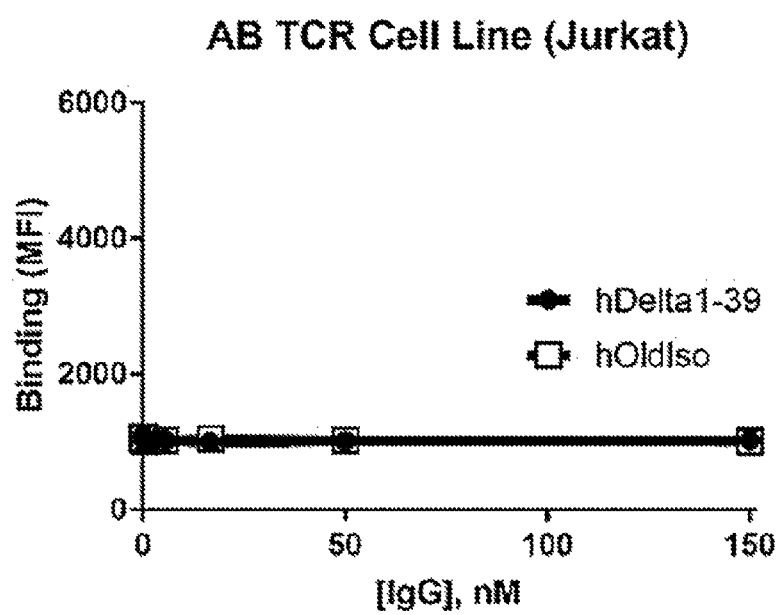

FIGS. 24A-24H show that anti-Delta1 antibodies disclosed herein are specific, regardless of the gamma combination used in the δγ TCRs on the cell surface. FIGS. 24A-24F: graphs showing binding of Delta1-39 antibody to cell surface-expressed δ1γ2, δ1γ3, δ1γ4, δ1γ5, δ1γ8, and δ1γ9, respectively. FIGS. 24G and 24H: are graphs showing a binding study where cell surface-expressed δ2γ9 and TCR alpha beta (from the parental Jurkat (E6-1) cell line) were used as a negative control and show no binding by Delta1-39.

Figure 25A:
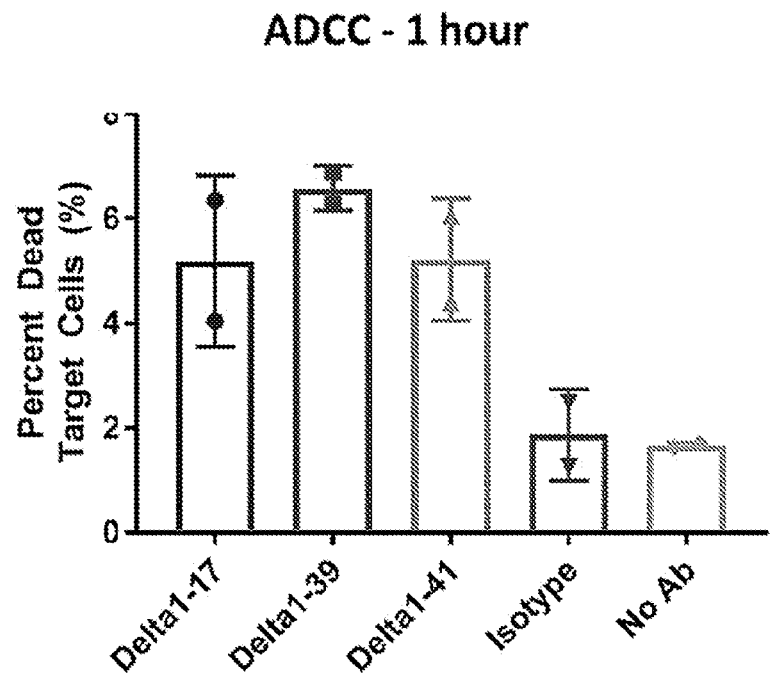
Figure 25B:
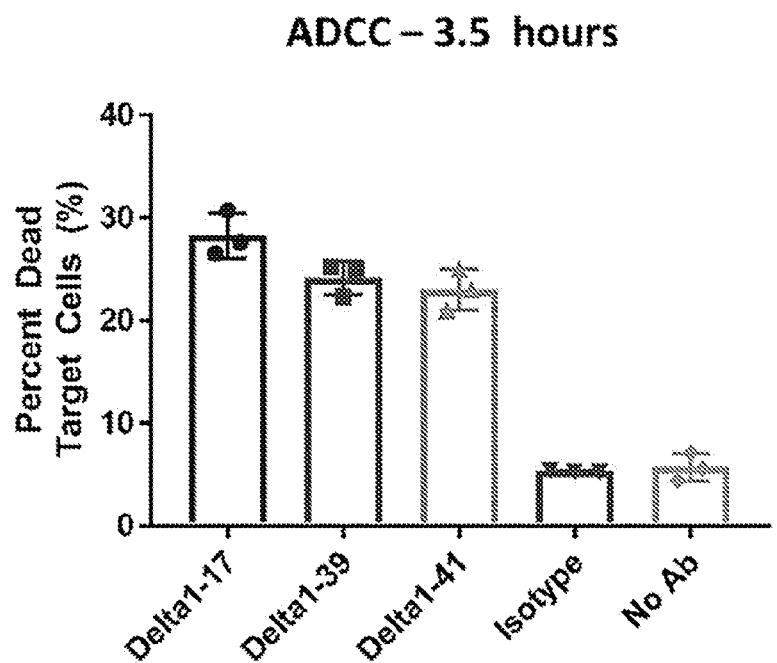

FIGS. 25A and 25B include diagrams showing the antibody-dependent cell cytotoxicity (ADCC) effects of Delta1-17, Delta1-39, and Delta1-41 compared to isotype-treated and untreated cells. NK-92 cells expressing extra FcγR were used as effector cells. Jurkat (J.RT3-T3.5) cell line expressing δ1/γ9 was used as the target cell line and labelled with CFSE dye. The cells were mixed at 4:1 effector to target ratio and the anti-Delta1 antibodies or isotypes s were added at 100 nM for 1 hour (FIG. 25A) or 3.5 hours (FIG. 25B). After the incubation, the cells were stained with a fixable viability dye (FVD660) and quantified by flow cytometry.

Figure 26:
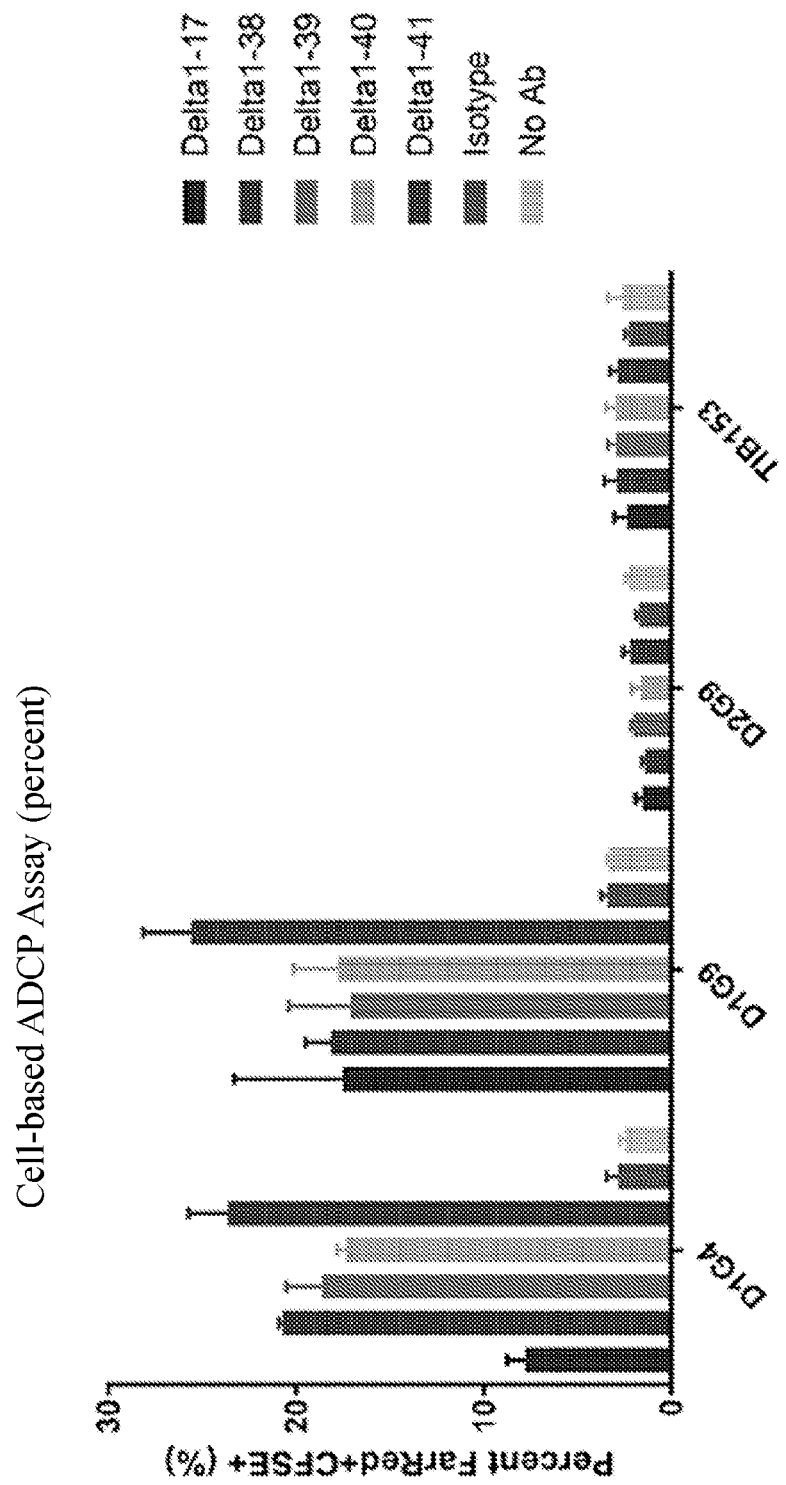

FIG. 26 includes a bar graph showing the ADCP effect of anti-Delta1 antibodies in a cell-based ADCP assay using anti-Delta antibodies, isotype or vehicle on cells expressing Delta1/gamma-4, Delta1/gamma-9, Delta2/gamma-9, or no TCR. For each set of bars, left to right are bars for: Delta1-17, Delta1-38, Delta1-39, Delta1-40, Delta1-41, Isotype, and No Ab.

Figure 27:
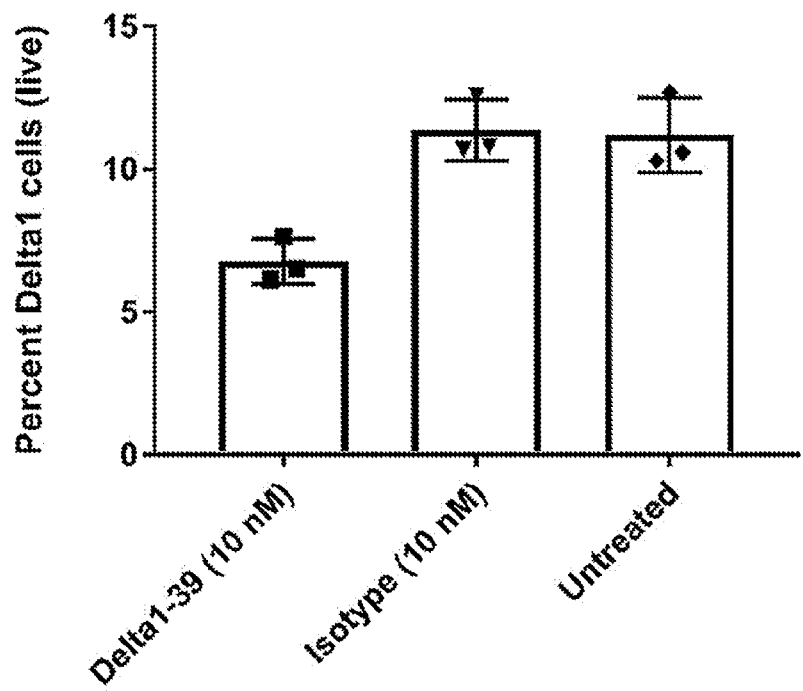

FIG. 27 includes a diagram showing specific cell killing in peripheral blood mononuclear cells (PBMCs) isolated from a healthy human donor that were treated with either Delta1-39, isotype or left untreated after isolation. Healthy PBMCs purchased from Stemcell (cat 70025.1) treated for 1 hour at 37C and processed for staining and flow.

Figure 28A:
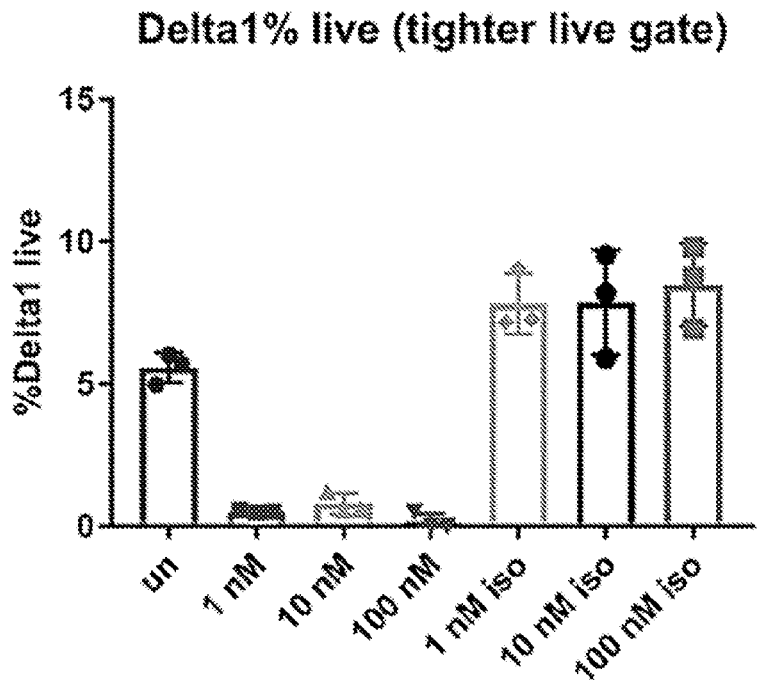
Figure 28B:
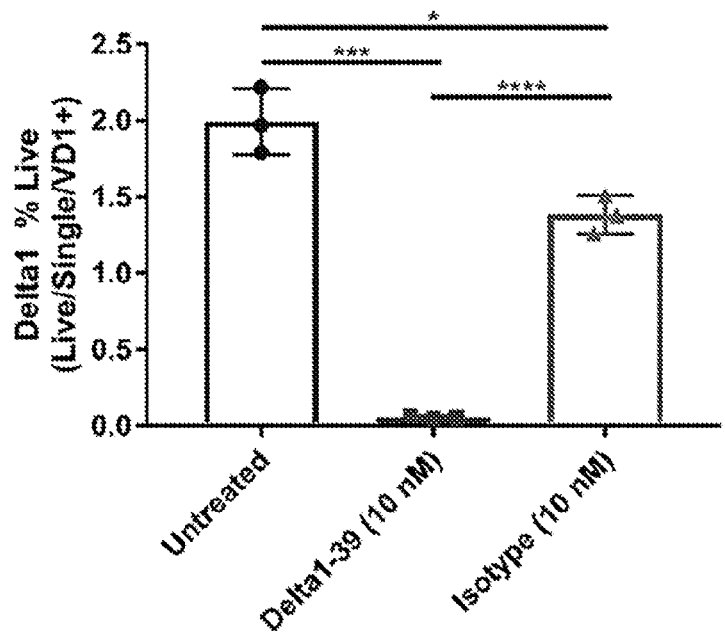
Figure 28C:
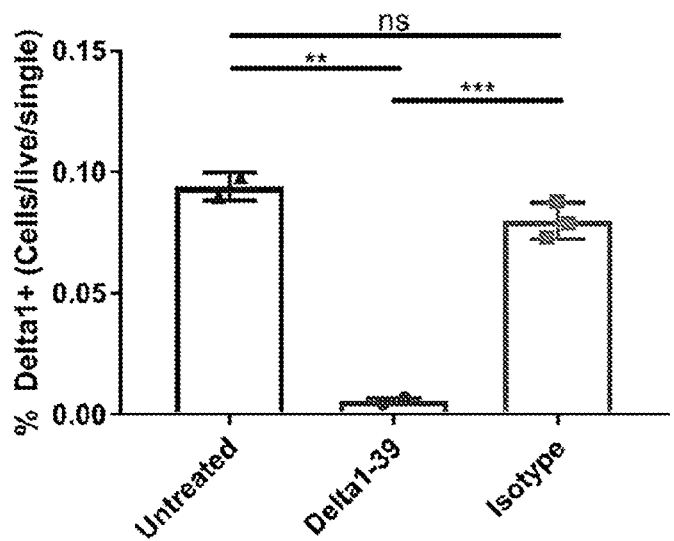

FIG. 28A-C include diagrams showing Delta1-39 mediated killing in various patient camples. FIGS. 28A-28 include diagram showing specific cell killing in patient samples. Lung adenocarcinoma (FIG. 28A), pancreatic ductal carcinoma (PDA; FIG. 28B), and gastrointestinal neuroendocrine tumor (GI-NET; FIG. 28C) single cell tumor suspensions were treated with either Delta1-39, isotype overnight at 37C or left untreated as indicated, and processed for staining and flow.cytometry.

Figure 29:
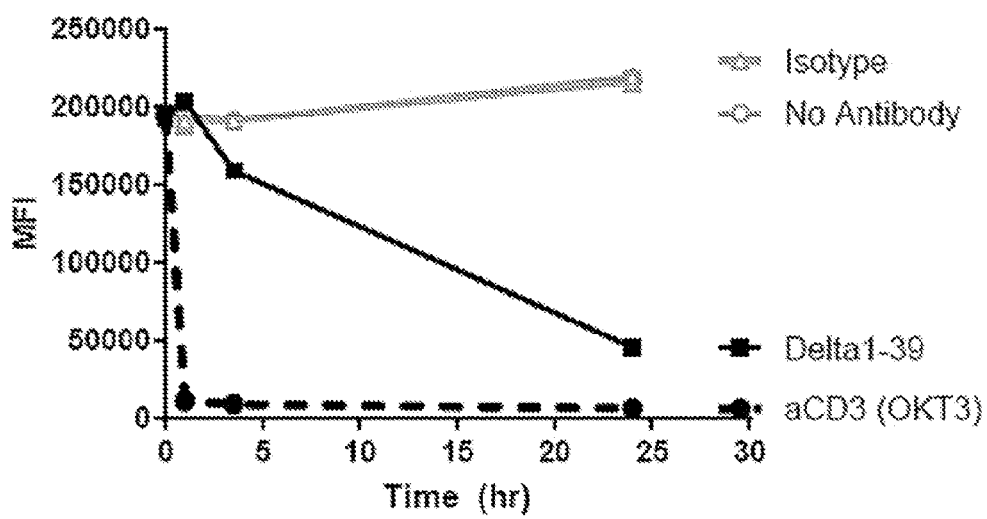

FIG. 29 depicts a graph showing the results of a receptor internalization assay. Cells expressing Delta1/Gamma9 T cell receptor on the surface were incubated in the presence of 100 nM Delta1-39, isotype antibody, anti-CD3 (clone OKT3) (azide free) antibody or in the absence of antibody. The cells were harvested at 1, 3.5 and 24 hours after incubation and processed for staining with anti-Delta1 (clone TS8.2) antibodies for flow cytometry.

Figure 30:
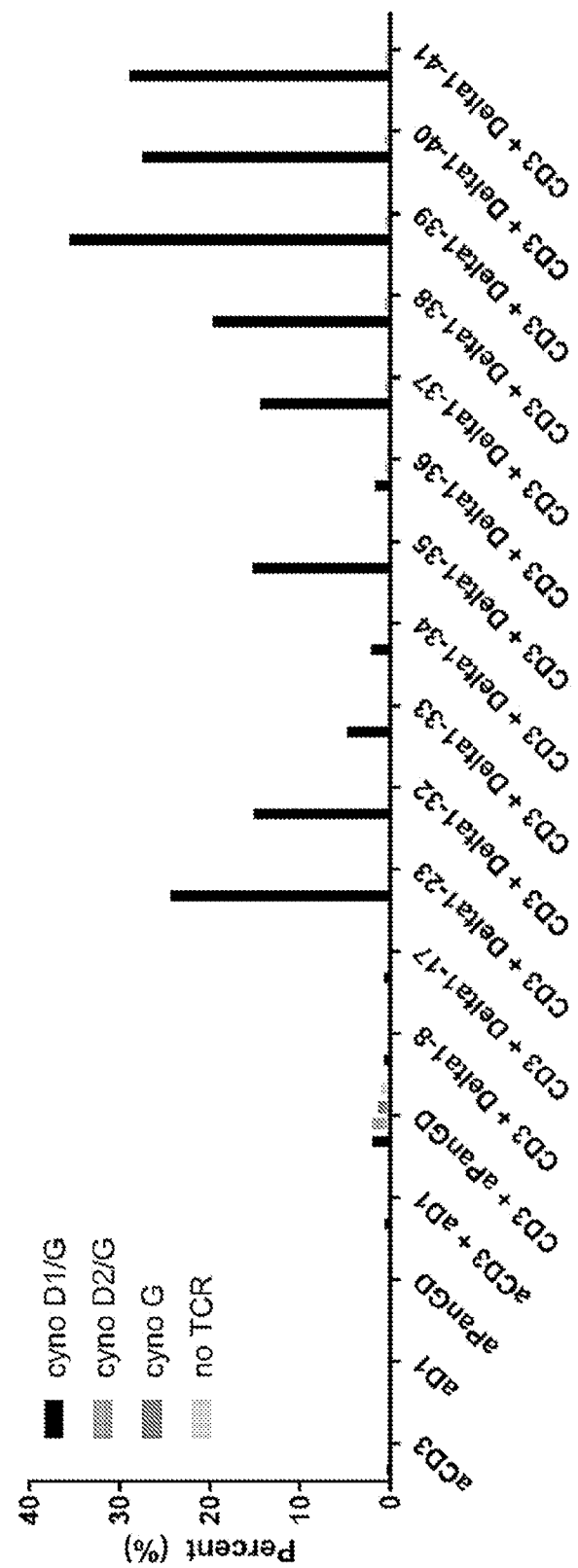

FIG. 30 shows a bar graph demonstrating various delta-1 clones as indicated binding to stable cell lines expressing monkey gamma/delta TCR. Jurkat cells that lack the expression of TCR on the surface were transduced to expressed monkey Delta1/Gamma or Delta2/Gamma receptors. Cells expressing the Gamma chain only or no TCR were stained as negative controls. Anti-Delta1-17 shows no binding to any cyno TCR, while anti-Delta1-23 and anti-Delta1-32-41 show specific binding to monkey Delta1 containing TCR on the cell surface.

Figure 31A:
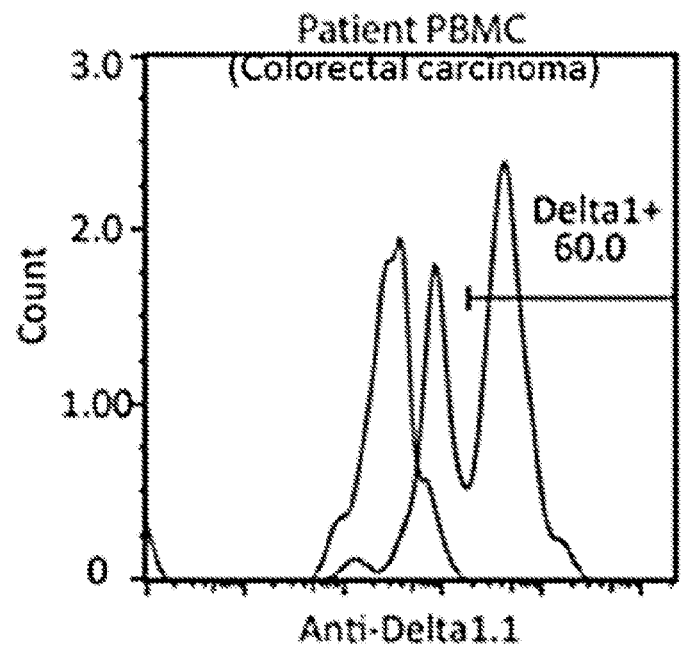
Figure 31B:
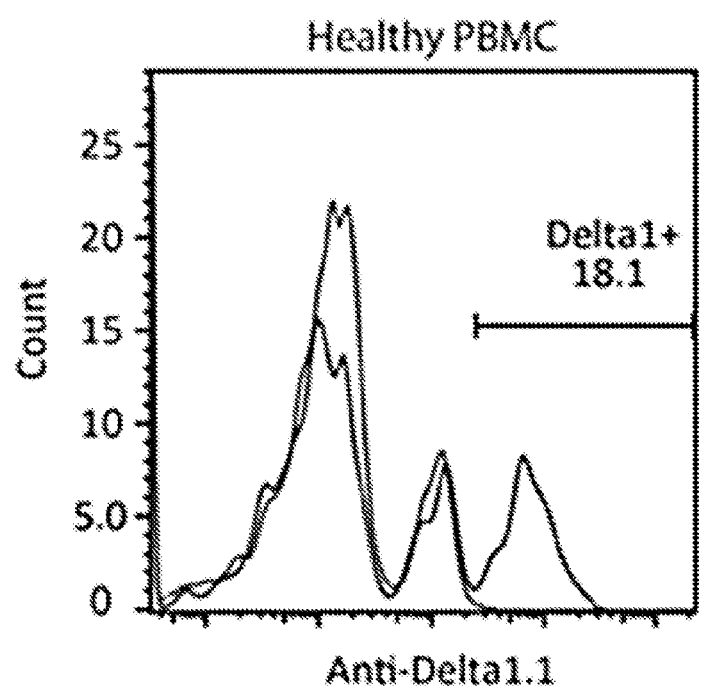

FIGS. 31A-31B include diagrams showing specific Delta1 detection in PBMCs isolated from a human donor with colorectal carcinoma (FIG. 31A) and a healthy human donor (FIG. 31B) using an anti-delta1 antibody (anti-Delta1-39 as an example).

Figure 32:
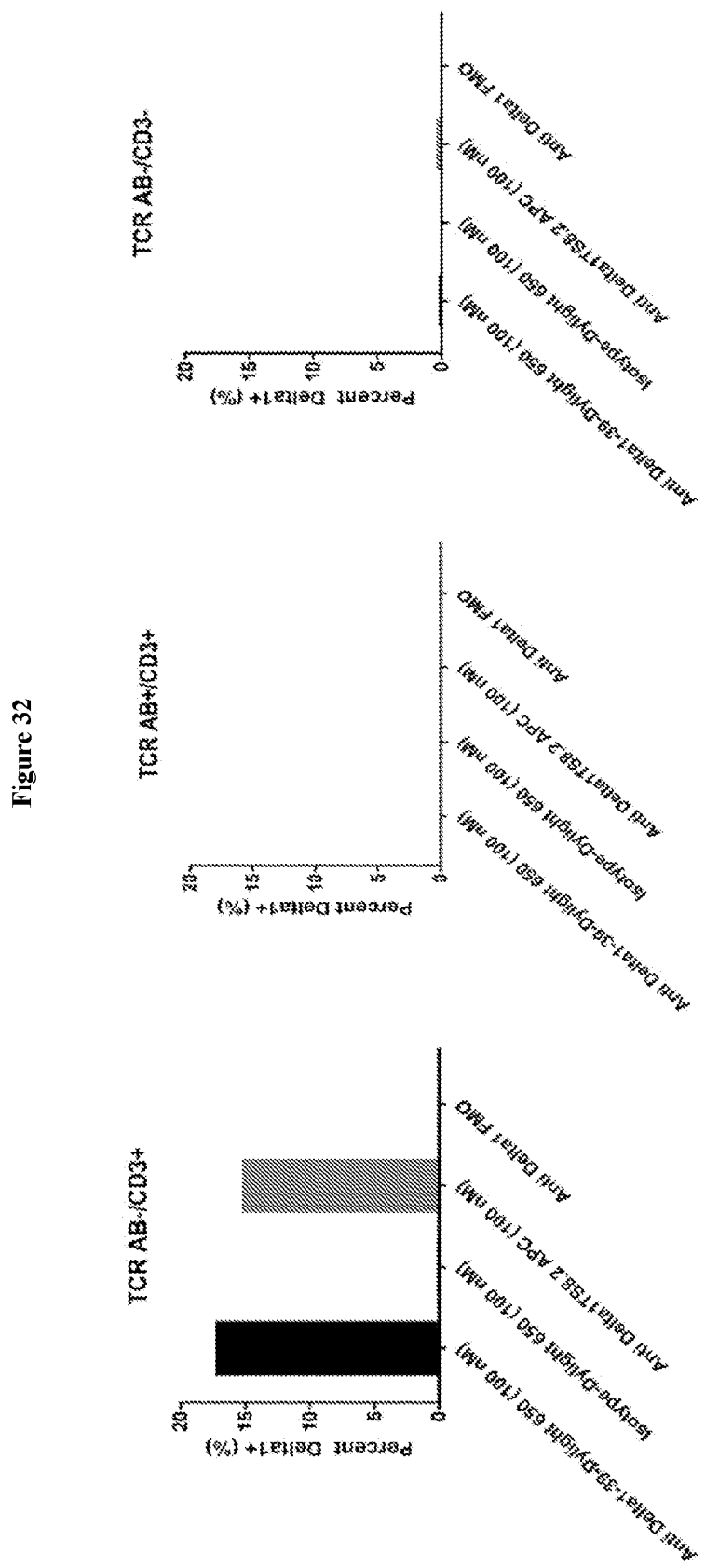

FIG. 32 depicts three bar graphs showing a flow cytometric analysis of PBMCs Dylight-650 conjugated anti-Delta1-39 as well as commercial anti-Delta1 (clone TS8.2), anti-Delta2-PE (clone B6), anti-CD3 (clone UCHT-1), anti TCR AB (clone IP26). Results show the staining profiles of the directly conjugated anti-Delta1-39 and the anti Delta1 (clone TS8.2) are similar.

Figure 33:
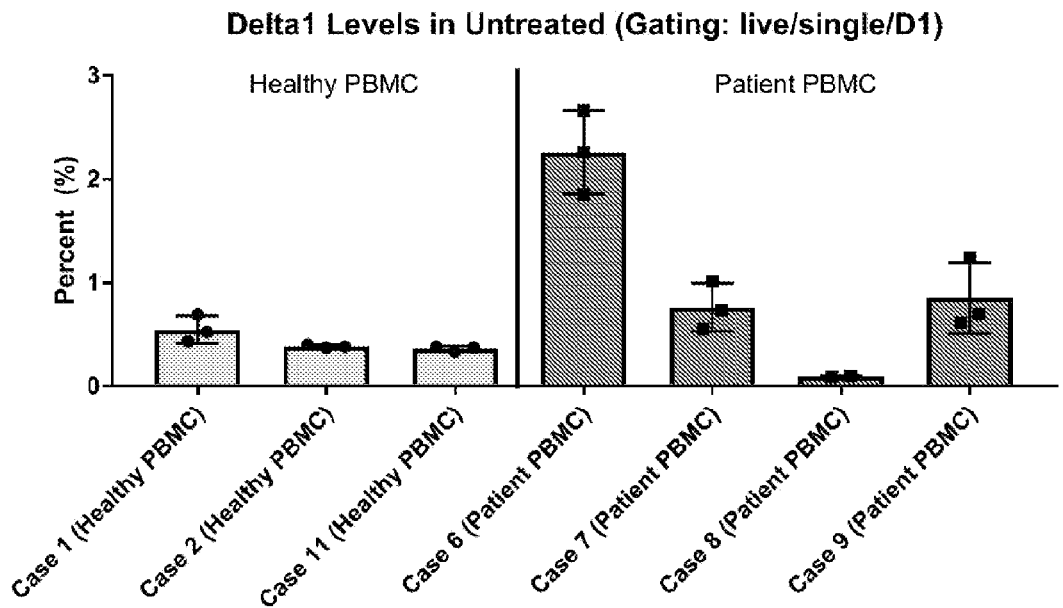

FIG. 33 depicts a flow cytometric analysis of the commercial anti Delta1 (clone TS8.2) to determine the levels of Delta1 positive T cells in healthy and patient PBMC. For most patients tested, the Delta1 levels were higher than in healthy donors. The percentages of Delta1 T cells are calculated as a fraction of total, live and single cells.

Figure 34:
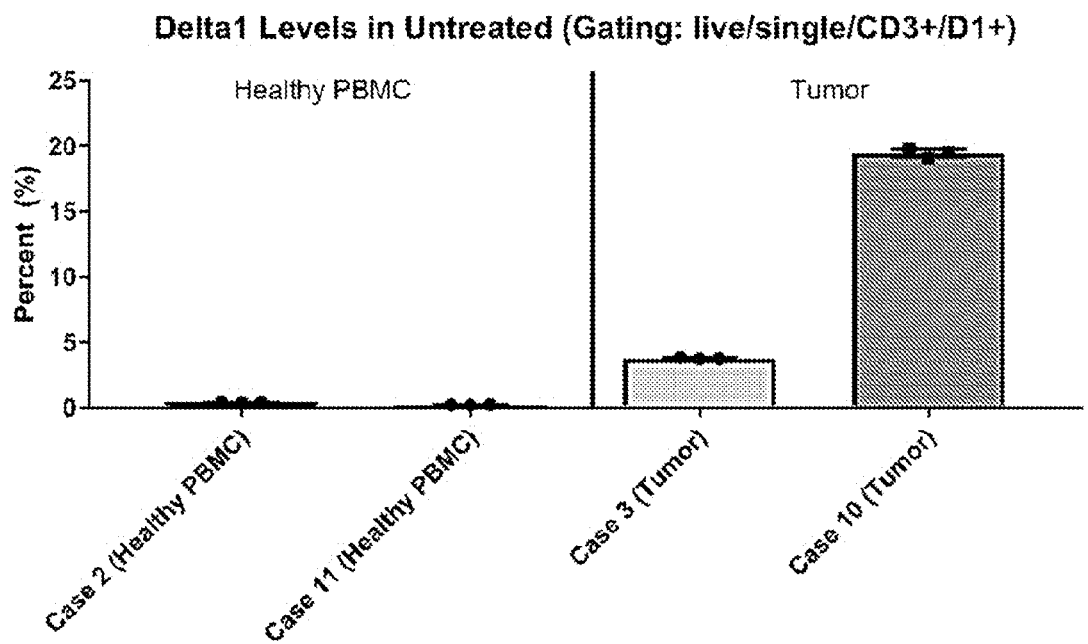

FIG. 34 depicts a flow cytometric analysis of Delta1 T cell levels in healthy PBMCs versus tumors. The Delta1 levels are measured by staining with the commercial anti Delta1 antibody (clone TS8.2). Results show the Delta1 levels are higher in the tumor single cell suspensions than in healthy donor PBMCs. The percentages of Delta1 T cells are calculated as a fraction of total, live, single and CD3 positive cells.

DETAILED DESCRIPTION OF INVENTION

T cell receptors (TCRs) are disulfide-linked membrane-anchored heterodimeric proteins, expressed on the surface of T cells, where they recognize fragments of antigen presented by major histocompatibility complex (MHC) molecules on antigen-presenting cells (APCs) or other types of ligands presented on cell surface. Most T cells have TCRs comprising an alpha (α) and a beta (β) chain (known as αβ T cells), whereas a minority of T cells have TCRs made up of a gamma (γ) chain and a delta (δ) chain (known as γδ T cells).

The γδ TCRs recognize a variety of self and non-self-antigens, such as small peptides, soluble or membrane proteins, phospholipids, prenyl pyrophosphates, and sulfatides. Due to their antigenic diversity, the γδ T cell can exert a wide range of different actions. For example, as γδ T cell activation does not require antigen processing and presentation by antigen-presenting cells (APCs), γδ T cells can be quickly activated and act during the early phase of immune responses. Similar to natural killer (NK) cells, γδ T cells also respond to stimulation by stress- and/or infection-induced ligands (Lafont et al., *Front Immunol.*, 2014, 5: 622). Such ligands are typically weakly or not expressed under normal state, as they are up-regulated only in the presence of stress (DNA damage, heat stress) or infection. In addition, human γδ T cells also express pattern recognition receptors (PRR), such as Toll-like receptors (TLR), which modulate their activation (Shojaei et al., *Cancer Res.*, 2009, 69(22): 8710-8717).

γδ T cells have been found to be both anti-tumorigenic and pro-tumorigenic, depending on a wide variety of conditions (Lafont et al., *Front Immunol.*, 2014, 5: 622). With respect to pancreatic ductal adenocarcinoma (PDA), γδ T cells have been found to make up a substantial fraction of the tumor-infiltrating T cells, where they have inhibitory functions on anti-cancer immunity mediated by αβ T cells. In a mouse model, the deletion, depletion, or blockade of γδ T cell recruitment was found to be protective against PDA and resulted in increased infiltration, activation, and Th1 polarization of αβ T cells (Daley et al., *Cell*, 2016, 166: 1485-

1499). In particular, the Delta1 subtype of γδ T cell receptors was found to be enriched among the tumor-infiltrating T cells.

Thus, antibodies specific to γδ T cells (e.g., specific to delta-1 chain of a TCR comprising the delta-1 chain and a gamma chain; "anti-Delta-1 antibodies") may be promising therapeutic agents for treating diseases associated with tumor-infiltrating γδ T cells (e.g., those in which tumor-infiltrating γδ T cells play an immunosuppressive role) or circulating γδ T cells, which may block conventional T cell activation and thus immune responses against pathologic cells (e.g., cancer cells). Without being bound by theory, an anti-Delta1 antibody may block the inhibitory function of the γδ T cells expressing such, thereby enhancing anti-tumor immune responses. Accordingly, the antibody may prevent direct or indirect suppression of alpha-beta T cell activity. The antibody may inhibit γδ T cell cytokine secretion (e.g., IL-17), and there by prevent induction of angiogenesis, and the attraction of MDSCs, neutrophils and TAMs. The antibody may inhibit the Treg/Th2 type activity of γδ T cells, and thereby prevent the restriction of anti-tumor γδ T cells. Additionally, the antibody may prevent the interface of pro-tumor γδ T cells with dendritic cells (DCs), and thereby prevent the inhibition of DC maturation, the induction of DC and/or T cell senescence and prevent the limitation of DC antigen presentation resulting from the presence of γδ T cells. Alternatively, or in addition, an anti-Delta1 antibody may also exert its therapeutic effect by inducing cytotoxicity, for example, ADCC, ADCP and/or CDC against the target γδ T cells. A pathologic cell refers to a cell that contributes to the initiation and/or development of a disease, either directly or indirectly. In some embodiments, the anti-Delta1 antibody is an antibody drug conjugate, and exerts its effect by targeting a chemotherapeutic agent to the tumor site.

Accordingly, described herein are antibodies specific to T6 T cells (e.g., anti-Delta1 antibodies) and therapeutic uses thereof for rescuing inhibition of conventional T cell activity mediated by γδ T cells and/or treating diseases associated γδ T cell activation.

Antibodies Binding to the Delta1 Chain of γδ T Cells

The present disclosure provides antibodies that are specific to γδ T cells of a suitable species (e.g., human, or a non-human primate such as monkey, chimpanzee, or ape), for example, specific to γδ1 T cells. Such antibodies may specifically bind a delta-1 chain of the TCR expressed on γδ1 T cells. In some embodiments, the antibodies described herein bind the delta-1 chain in a 761 heterodimer (e.g., a heterodimer of delta-1/and a gamma chain, e.g., gamma-9), which may be expressed on the surface of a γδ1 T cell.

The anti-Delta1 chain antibodies disclosed herein may exhibit one or more superior features, including, but not limited to, (i) high binding affinity to multiple human delta 1 TCRs, regardless of their CDR sequences, in particular, regardless of their CDR3 sequences (e.g., $K_D$ lower than 12 nM, for example, clones Delta1-19, Delta1-26, Delta1-29, and Delta-39); (ii) cross-reactivity of human delta1 TCR and non-human primate delta 1 TCR such as cyno delta1 TCR (e.g., difference of $K_D$ value for human and that for cyno delta 1 TCR) is within one order of magnitude, for example, clones Delta1-18, Delta1-19, Delta1-21, Delta1-22, Delta1-23, Delta1-25, Delta1-26, Delta1-28, Delta1-39); (iii) capable of binding to 761 TCRs containing various gamma chains, including gamma 3, 4, 5, 8, or 9, e.g., Delta1-38, Delta1-39, Delta1-40, and Delta1-41; and/or (iv) binding to delta-1 with high specificity, e.g., little or no binding to other targets, e.g. as determineid by protein array analysis (v) inhibiting γδ-T cell activity, i.e., inhibiting γδ-T cell mediated suppression of T cell activation, e.g., of CD4+ and/or CD8+ cells (e.g., Delta1-23, Delta1-39) (vi) promote inflammatory T cell activation (i.e., promotes the activation of CD4+ helper cells and/or CD8+ effector cells) (vii) depletion of γδ-T cells, e.g., through ADCC, CDC, and/or ADCP.

Accordingly, in some embodiments, the anti-Delta1 chain antibodies (also referred to herein as "anti-Delta1 antibodies") disclosed herein exhibit one or more superior features. In some embodiments, the anti-Delta1 chain antibodies disclosed herein have high binding affinity to multiple human delta 1 TCRs, regardless of their CDR sequences, in particular, regardless of their CDR3 sequences. In some embodiments, the $K_D$ value for human delta-1 is lower than 10 nM. In some embodiments, the $K_D$ value for human delta-1 is lower than 5 nM or lower than 2 nM. In some embodiments, the $K_D$ value for human delta-1 is lower than 1 nM. A non-limiting example of an antibody with $K_D$ value for human delta-1 is lower than 1 nM is Delta1-39. In some embodiments, cross-reactivity of human delta1 TCR and non-human primate delta 1 TCR such as cyno delta1 TCR (e.g., difference of $K_D$ value for human and that for cyno delta 1 TCR) is within one order of magnitude. A non-limiting example of an antibody for which difference of $K_D$ value for human and that for cyno delta 1 TCR) is within one order of magnitude is Delta1-39. In some embodiments, the anti-Delta1 chain antibodies disclosed herein have high binding affinity to multiple cyno delta 1 TCRs, regardless of their CDR sequences, in particular, regardless of their CDR3 sequences. In some embodiments, the $K_D$ value for cyno delta-1 is lower than 10 nM. In some embodiments, the $K_D$ value for cyno delta-1 is lower than 5 nM or lower than 2 nM. In some embodiments, the $K_D$ value for cyno delta-1 is lower than 1 nM. A non-limiting example of an antibody with $K_D$ value for cyno delta-1 is lower than 1 nM is Delta1-39. In some embodiments, the anti-Delta1 chain antibodies disclosed herein are capable of binding to 761 TCRs containing various gamma chains. In some embodiments, the anti-Delta1 chain antibodies disclosed herein are capable of binding to γδ1 TCRs containing gamma chains 3, 4, 5, 8, and/or or 9. For example, in one specific embodiment, the anti-Delta1 chain antibodies disclosed herein are capable of binding to γδ1 TCRs containing gamma chains 3, 4, 5, and 8, e.g., include Delta-38, Delta1-39, Delta1-40, and Delta1-41. A non-limiting example of an anti-Delta1 antibodies disclosed herein which is capable of binding to 761 TCRs containing gamma chains 3, 4, 5, and 8, and 9 is Delta1-39. In some embodiments, the anti-Delta1 antibody described herein cross-reacts with a human delta-1 chain and a non-human mammalian delta-1 chain, e.g., a non-human primate delta-1 chain, and is capable of binding to γδ1 TCRs containing various gamma chains, including gamma 3, 4, 5, and 8. Non-limiting examples of such antibodies described herein include Delta1-39 and Delta1-41. Additional examples include Delta1-38 and Delat1-40. In some embodiments, the antibodies bind to Delta-1 with high specificity, e.g., as determined by protein array analysis. A non-limiting example of such and antibody is clone Delta1-39. In some embodiments, the anti-Delta1 chain antibodies disclosed herein inhibit γδ-T cell mediated suppression or inhibition of T cell activation. In some embodiments, the anti-Delta1 antibodies described herein inhibit the suppressive activity of γδ-T cells. In some embodiments, the anti-Delta1 chain antibodies disclosed herein are capable of promoting inflammatory T cell activation e.g., as shown herein for Delta1-39. In some embodiments, the anti-Delta1 chain antibodies disclosed herein are capable activating CD4+ helper cells and/or CD8+ effector cells, e.g., in a tumor or in peripheral blood. In some embodiments, the anti-Delta1 chain antibodies disclosed herein are capable of depletion of γδ-T cells, e.g., through ADCC, CDC, and/or ADCP.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antibody" is also meant to include so-called antibody mimetics. Antibody mimetics refers to small molecules, e.g., 3-30 kDa, which can be single amino acid chain molecules, which can specifically bind antigens but do not have an antibody-related structure. Antibody mimetics and their protein scaffolds, include, but are not limited to, Affibody molecules (Z domain of Protein A), Affilins (Gamma-B crystalline), Ubiquitin, Affimers (Cystatin), Affitins (Sac7d (from *Sulfolobus acidocaldarius*)), Alphabodies (Triple helix coiled coil), Anticalins (Lipocalins), Avimers (domains of various membrane receptors), DARPins (Ankyrin repeat motif), Fynomers (SH3 domain of Fyn), Kunitz domain peptides (Kunitz domains of various protease inhibitors), Ecallantide (Kalbitor), and Monobodies (fibronectin type III domain). Accordingly, some embodiments, the anti-Delta1 antibody is an antibody mimetic.

In some embodiments, the anti-Delta1 antibody is an antibody drug conjugate (ADC). ADCs generally comprise a monoclonal antibody against a target present on a cell, a cytotoxic drug, and a linker that attaches the antibody to the drug. Antibody-drug conjugates for cancer therapy are reviewed by Carter & Senter (2008), Cancer J. 14(3): 154-69, and Chari et al (2014) Angewandte Chemie International Edition 53: 3751. The cytotoxic moiety may be a polypeptide, which may be either directly or indirectly cytotoxic. When indirectly cytotoxic, the polypeptide may have enzymatic activity and can convert a relatively non-toxic prodrug into a cytotoxic drug (e.g. antibody-directed enzyme prodrug therapy; ADEPT). The cytotoxic moiety may comprise a drug selected from the group consisting of: a cytostatic agent (such as a taxane (e.g. docetaxel and, particularly, paclitaxel); an alkylating agent (such as cisplatin, carboplatin); an antimetabolite (such as 25 azathioprine, methotrexate); an antimitotic drug (such as vincristine); a topoisomerase inhibitor (such as doxorubicine, etoposide), etc. The cytotoxic moiety may be any known chemotherapeutic agent. The cytotoxic moiety may be an enterobacterial toxin, especially *Pseudomonas* exotoxin 20 A or calicheamicin. The cytotoxic moiety may also comprise a radioactive atom. The radioactive atom is typically selected from the group consisting of: iodine—123; iodine—125; iodine—131; indium—111; bromine—77; copper—67; arsenic—77; astatine—211; actinium—15 225; bismuth—212; bismuth—213; bismuth—217; lutetium—177; holmium—166; phosphorous—33; platinum—193; platinum—195; rhenium—186; rhenium—188; strontium—89; yttrium—90. gold—199, palladium—100; and antimony—211. In some embodiments, the cytotoxic moiety is capable of inhibiting at least one activity of cells expressing delta1 TCR. In some embodiments, the cytotoxic moiety is capable of inactivating or killing the cell. In order to facilitate the coupling between the cytotoxic moiety and the antibody, it is possible to directly conjugate the two agents, or to introduce a spacer molecule between them. Suitable spacers include poly(alkylene) glycols such as polyethylene glycol, and peptide linkers. Many suitable coupling techniques are well known in the art. Suitable agents allowing covalent, electrostatic or noncovalent binding of the moiety to the antibody include benzoquinone, carbodiimide and more particularly EDC (1-ethyl-3-[3-dimethyl-aminopropyl]-carbodiimide hydrochloride), dimaleimide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)-propionamide (APDP), N-succinimid-yl 3-(2-25 pyridyldithio) propionate (SPDP), 6-hydrazino-nicotinamide (HYNIC). Another form of coupling, especially for the radioelements, includes the use of a bifunctional ion chelator. For example, chelates derived from EDTA or DTPA which have been developed for binding metals, especially radioactive metals, and immunoglobulins. Thus, DTPA and its derivatives can be substituted by different groups on the carbon chain in order to increase the stability and the rigidity of the ligand-metal complex, as is well known in the art.

In some embodiments, the anti-Delta1 antibody is conjugated to a drug to produce an antibody drug conjugate (ADC). In some embodiments, the anti-Delta1 antibody is an antibody drug conjugate (ADC). Suitable cytotoxic agents which can be conjugated to the anti-Delta1 antibody are described herein and known in the art. In some embodiments, the linker is cleavable. Non-limiting examples of linkers include, disulfide containing linkers that are cleavable through disulfide exchange, acid-labile linkers that are cleavable at acidic pH, and linkers that are cleavable by hydrolases (e.g., glycosyl hydrolases such as glucuronidases), esterases, and peptidases (e.g., peptide linkers and glucuronide linkers). In some embodiments, the linker is non-cleavable. In some embodiments, the drug is released via a proteolytic antibody degradation mechanism.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, the EU definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; Edelman et al., Proc Natl Acad Sci USA. 1969 May; 63(1):78-85; and Almagro, J. Mol. Recognit. 17:132-143 (2004). See also hgmp.mrc.ac.uk and bioinf.org.uk/abs). Correspondence or alignments between C numberings according to different definitions can for example be found at http://www.imgt.org/.

The antibodies described herein may be capable of binding to a T cell receptor delta-1 polypeptide (anti-Delta1 antibody), which can be of a suitable source, for example, human or a non-human mammal (e.g., rabbit, primate such as monkey, etc.).

The anti-Delta1 antibody as described herein may be a full-length antibody, which contains two heavy chains and two light chains, each including a variable domain and a constant domain. Alternatively, the anti-Delta1 antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, CL and $C_H 1$ domains; (ii) a F(ab')$_2$ fragment, a bivalent fragment including two Fab fragments linked by a disulfide bridge at the hinge region; (iii) a Fd fragment consisting of the $V_H$ and $C_H 1$ domains; (iv) a Fv fragment consisting of the $V_L$ and $V_H$ domains of a single arm of an antibody (v) a dAb fragment (Ward et al., (1989) *Nature* 341:544-546), which consists of one or more $V_H$ domain(s) (e.g., including but not limited to VHH domains (camelid or nanobodies); and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

In some embodiments, the antibodies described herein specifically bind to the corresponding target antigen or an epitope thereof, e.g., specifically binds a delta-1 chain of a T cell γδ1 receptor. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., a delta-1 chain of a human TCR) or an antigenic epitope therein is an antibody that binds this target antigen with greater affinity, avidity, more readily, and/or with greater duration than it binds to other antigens (e.g., a delta-2 chain of a human TCR) or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen, i.e., only baseline binding activity can be detected in a conventional method. Baseline binding activity refers to the binding activity detected in the conventional method when no antigen (blank control) or a different antigen (negative control) is used.

Specificity of the anti-Delta1 antibodies described herein can be measured using protein arrays, resulting in a specificity score (S score) as described herein and known in the art (see, e.g., Jeong et al., Mol Cell Proteomics. 2012 June; 11(6): 0111.016253). Additionally, specificity of the anti-Delta1 antibodies described herein is assessed by comparing the $K_D$ of binding of the anti-Delta1 antibodies to d1 with the $K_D$ of binding to d2.

In some embodiments, the anti-Delta1 antibody described herein binds a motif that is common to TCR delta-1 chains. Sequences of TCR delta-1 chains (e.g., human TCR delta-1 chains, cynomolgus monkey TCR delta-1 chains, or TCR delta chains from other species) are well known in the art and can be found from publicly available databases, for example, the International Immunogenetics Information System® database (imgt.org), or GenBank. In some examples, the anti-Delta1 antibody may cross-react with different human or cynomolgus monkey delta1 chain.

Exemplary amino acid sequences of the extracellular regions (lacking transmembrane domain and cytoplasmic tail) of Delta1 chains (human and cyno) are provided below:

Human TCR:

(SEQ ID NO: 26)

AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGVYAH

SLTGGYRGGADKLIFGKGTRVTVEPRSQPHTKPSVFVMKNGTNVACLVK

EFYPKDIRINLVSSKKITEFDPAIVISPSGKYNAVKLGKYEDSNSVTCS

VQHDNKTVHSTDFEVKTDSTDHVKPKETENTKQPSKS

Human TCR:

(SEQ ID NO: 27)

AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGPRPS

YSEELGDTHRADKLIFGKGTRVTVEPRSQPHTKPSVFVMKNGTNVACLV

KEFYPKDIRINLVSSKKITEFDPAIVISPSGKYNAVKLGKYEDSNSVTC

SVQHDNKTVHSTDFEVKTDSTDHVKPKETENTKQPSKS

```
Human TCR:
                                        (SEQ ID NO: 28)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGEPNH

FLNTDKLIFGKGTRVTVEPRSQPHTKPSVFVMKNGTNVACLVKEFYPKD

IRINLVSSKKITEFDPAIVISPSGKYNAVKLGKYEDSNSVTCSVQHDNK

TVHSTDFEVKTDSTDHVKPKETENTKQPSKS

Cynomolgus Monkey TCR:
                                        (SEQ ID NO: 32)
AQKVTQAQSSVSMPVEKAVTINCQYETSSWSYDLFWYKQLPGKEMIFLI

RQGSSEQNARDGRYSVNFKKEASFIALTISALQLEDSATYFCALRRPFT

AQLFFGKGTQLIVEPERQPHTKPSVEVMKNGTNVACLVKDFYPKDIRIN

LESSKKITEFDPAIVVSPSGKYNAVKLGQYADSNSVTCSVQHNKEVVYS

TDFEVKTNSTDHLKPTETENTKQPSKS

Cynomolgus Monkey TCR:
                                        (SEQ ID NO: 33)
AQKVTQAQSSVSMPVGKAVTINCQYETSSWSYYLFWYKQLPGKEMIFLI

HQGSSQQNARNGRYSVNFQKAASSITLTISALQLEDSATYFCALRERPP

NPGPFVLGVYATAQLFFGKGTQLIVEPERQPHTKPSVFVMKNGTNVACL

VKDFYPKDIRINLESSKKITEFDPAIVVSPSGKYNAVKLGQYADSNSVT

CSVQHNKEVVYSTDFEVKTNSTDHLKPTETENTKQPSKS

Cynomolgus Monkey TCR:
                                        (SEQ ID NO: 34)
AQKVTQAQSSVSMPVEKAVTLNCQYETSWWSYDLFWYKQLPGKEMIFLI

RQSSSEQNARDGRYSANFKKEASSKSFIALTISALQLEDSATYFCALPL

QVRGPTGGIRVYDKLIFGKGTRVTVEPKRQPHTKPSVFVMKNGTNVACL

VKDFYPKDIRINLESSKKITEFDPAIVVSPSGKYNAVKLGQYADSNSVT

CSVQHNKEVVYSTDFEVKTNSTDHLKPTETENTKQPSKS
```

As used herein, "cross-react" means that an antibody shows binding activity (detectable by a conventional assay) to two or more different antigen sequences (e.g., human delta1 and delta2). Such an antibody may have substantially similar binding affinity to these antigens, e.g., having a binding affinity to one antigen <10 fold (e.g., <5 fold or <2 fold) higher than that to another antigen as determined under the same assay conditions. Alternatively, such an antibody may have substantially higher binding affinity to one of these antigens as relative to another, for example, having a binding affinity to one antigen that is at least 10-fold higher (e.g., 20-fold higher, 50-fold higher, 100-fold higher, or 1,000-fold higher) than that to another antigen as determined under the same assay conditions.

In some embodiments, the anti-Delta1 antibody described herein preferentially binds a single human delta1 chain. In some embodiments, the antibody binds to a delta1 chain regardless of the sequence of the CDR regions, e.g., CDR3 region. In some embodiments, the anti-Delta1 antibody preferentially binds human delta1 as relative to human delta-2 chain, a human delta-3 chain, a gamma chain (such as a gamma-9 chain), and/or a non-human delta1 chain. As used herein, an antibody "preferentially binds" a first antigen or an epitope thereof as compared with a second antigen or another epitope means that the antibody has a substantially higher binding affinity to the first antigen or the epitope thereof as relative to the second antigen or the other epitope, e.g., at least 10-fold higher (e.g., >20 fold, >50 fold, >100 fold, >1,000 fold or higher) as determined under the same assay conditions.

The anti-Delta1 antibody described herein may preferentially bind a human delta1 chain as relative to a non-human counterpart (e.g., a non-human primate delta1 chain), or vice versa. In other instances, the anti-Delta1 antibody described herein may cross-react to human and a non-human delta1 chain. For example, the antibody may cross-react to a human delta1 chain and a non-human primate delta1 chain.

In some instances, the anti-Delta1 antibody described herein does not bind to a human delta-2 chain, a human delta-3 chain, or a gamma chain (such as a gamma-9 chain). In some embodiments, the anti-Delta1 antibody does not bind to a Delta-2 chain. (referred to herein as Delta2). In some embodiments, the anti-Delta1 antibody does not bind to a Delta-3 chain. (referred to herein as Delta3). In some embodiments, the anti-Delta1 antibody binds to neither a Delta-2 or Delta-3 chain. An antibody that does not bind an antigen means that no meaningful binding (e.g., only background binding or no binding at all) can be detected using a conventional assay (e.g., ELISA or surface plasmon resonance).

In some embodiments the antibody the anti-Delta1 antibody described herein binds to a T cell receptor comprising a delta1 chain and a gamma chain. Sequences of gamma chains are known in the art (see, e.g., imgt.org/IMGTrepertoire). Non-limiting examples of gamma chains include Gamma-1, gamma-2, gamma-3, gamma-4, gamma-5, gamma5P, gamma-8, gamma-9, gamma-10, gamma-11, gamma-a. Non-limiting examples of gamma chains are encoded by the following genes: •TRGV1, TRGV2, TRGV3, TRGV4, TRGV5, TRGV5P, TRGV8, TRGV9, TRGV10, TRGV11, and TRGVA. In some embodiments the antibody the anti-Delta1 antibody described herein binds to a T cell receptor comprising a delta1 chain and a gamma chain known in the art. In some embodiments, the anti-Delta1 antibody described herein can bind to a TCR comprising any gamma chains. In some embodiments, the anti-Delta1 antibody described herein can bind to a TCR comprising gamma3, 4, 5, 8 and 9. In some embodiments, the anti-Delta1 antibody described herein can bind to a TCR comprising gamma 3, 4, 5, and 8. The anti-Delta1 antibody as described herein preferably has a suitable binding affinity for the target antigen (e.g., a human delta1 chain) or antigenic epitopes thereof. As used herein, "binding affinity" refers to the apparent association constant or $K_A$. The $K_A$ is the reciprocal of the dissociation constant ($K_D$). The anti-Delta1 antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof, or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-Delta1 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The anti-Delta1 antibodies described herein can inhibit γδ T cell activation, i.e., reducing the overall activity of γδ T cell, e.g., of an immune suppressive γδ T cell. Without being bound by theory, the anti-Delta1 antibodies described herein may inhibit the bioactivity of γδ1 T cells via directly blocking the activity of the γδ1 TCR expressed on the T cells. Alternatively or in addition, via binding to a γδ1 TCR, the anti-Delta1 antibodies may trigger cytotoxicity such as ADCC and/or ADCP and/or CDC, to eliminate T cells expressing the γδ1 TCR, resulting in depletion of γδ1 T cells. Accordingly, the anti-Delta1 antibodies described herein may rescue immune suppression mediated by γδ T cells under, for example, cancer environment.

In some embodiments, the anti-Delta1 antibody as described herein inhibits the activity of γδ1 T cells. In some embodiments, the anti-Delta1 antibody as described herein inhibits the activity of γδ1 T cells by at least 10% (e.g., 10%, 15%, 20%, 25%, 30%, 35%, 40%, 50%, 60%, 70%, 80%, 90%, 95% or greater, including any increment therein). In some embodiments, the inhibitory or suppressive potency of the anti-Delta1 antibody is measured by examining the ability of the antibody to "rescue" immune cells such as αβ T cells from the inhibitory activity of γδ T cells. In some embodiments, the anti-Delta1 antibody described herein may rescue the immune inhibition induced by γδ1 T cells. The anti-Delta1 antibody described herein may rescue the immune inhibition induced by γδ1 T cells by at least 10% (e.g., at least 20%, 30%, 40%, 50%, 60%, 70%, 80%, 90% or greater).

In some embodiments, the anti-Delta1 antibody as described herein is capable of eliminating γδ1 T cells, i.e., depleting γδ1 T cells, e.g., from the tumor microenvironment, and/or from serum, blood or circulation. In some embodiments, the anti-Delta1 antibody as described herein is capable of eliminating γδ1 T cells, i.e., depleting γδ1 T cells, from the tumor microenvironment. In some embodiments, the anti-Delta1 antibody as described herein depletes γδ1 T cells by at least 10% (e.g., 10%, 15%, 20%, 25%, 30%, 35%, 40%, 50%, 60%, 70%, 80%, 90%, 95% or greater, including any increment therein). In some embodiments, the ability of the anti-Delta1 antibody is measured by examining the ability of the antibody to "rescue" immune cells such as αβ T cells from the inhibitory activity of γδ T cells. In some embodiments, the anti-Delta1 antibody described herein may rescue the immune inhibition induced by γδ1 T cells. The anti-Delta1 antibody described herein may rescue the immune inhibition induced by γδ1 T cells by at least 10% (e.g., at least 20%, 30%, 40%, 50%, 60%, 70%, 80%, 90% or greater).

In some embodiments, the anti-Delta1 antibody as described herein is capable of eliminating γδ1 T cells, i.e., depleting γδ1 T cells, from the tumor microenvironment. In some embodiments, the anti-Delta1 antibody as described herein In some embodiments, the anti-Delta1 antibody as described herein depletes γδ1 T cells at least 10% (e.g., 10%, 15%, 20%, 25%, 30%, 35%, 40%, 50%, 60%, 70%, 80%, 90%, 95% or greater, including any increment therein). In some embodiments, the inhibitory or suppressive potency of the anti-Delta1 antibody is measured by examining the ability of the antibody to "rescue" immune cells such as αβ T cells from the inhibitory activity of γδ T cells. In some embodiments, the anti-Delta1 antibody described herein may rescue the immune inhibition induced by γδ1 T cells. The anti-Delta1 antibody described herein may rescue the immune inhibition induced by γδ1 T cells by at least 10% (e.g., at least 20%, 30%, 40%, 50%, 60%, 70%, 80%, 90% or greater).

In some embodiments, the anti-Delta1 antibody as described herein activates ADCC. In some embodiments, the anti-Delta1 antibody as described herein activates ADCC by at least 10% (e.g., 10%, 15%, 20%, 25%, 30%, 35%, 40%, 50%, 60%, 70%, 80%, 90%, 95% or greater, including any increment therein). In some embodiments, the ability of the antibody to activate ADCC is measured according to one or more of the methods described herein.

In some embodiments, the anti-Delta1 antibody as described herein activates ADCP. In some embodiments, the anti-Delta1 antibody as described herein activates ADCP by at least 10% (e.g., 10%, 15%, 20%, 25%, 30%, 35%, 40%, 50%, 60%, 70%, 80%, 90%, 95% or greater, including any increment therein). In some embodiments, the ability of the antibody to activate ADCP is measured according to one or more of the methods described herein.

In some embodiments, the anti-Delta1 antibody as described herein activates or re-activates CD4+ helper cells and/or CD8+ effector cells in a tumor and/or in peripheral blood. In some embodiments, the anti-Delta1 antibody as described herein activates or re-activates CD4+ helper cells and/or CD8+ effector cells in a tumor and/or in peripheral blood by at least 10% (e.g., 10%, 15%, 20%, 25%, 30%, 35%, 40%, 50%, 60%, 70%, 80%, 90%, 95% or greater, including any increment therein). In some embodiments, the ability of the anti-Delta1 antibody to activate CD4+ and/or CD8+ cells is measured by examining levels of proinflammatory cytokines. In some embodiments, the anti-Delta1 antibody is capable of increasing production of pro-inflammatory cytokines, including, but not limited to, IFNγ, TNF-α, and CD44, in the tumor. In some embodiments, the anti-Delta1 antibody is capable of increasing production of pro-inflammatory cytokines, including, but not limited to, IFNγ, TNF-α, and CD44, in the tumor by at least 10% (e.g., 10%, 15%, 20%, 25%, 30%, 35%, 40%, 50%, 60%, 70%, 80%, 90%, 95% or greater, including any increment therein).

In some embodiments, the anti-Delta1 antibody as described herein can modulate, e.g., reduce, the ratio γδ1 T cells to γδ2 T cells. In some embodiments, the anti-Delta1 antibody as described herein modulates, e.g., reduces, the ratio γδ1 T cells to γδ2 T cells by at least 10% (e.g., 10%, 15%, 20%, 25%, 30%, 35%, 40%, 50%, 60%, 70%, 80%, 90%, 95% or greater, including any increment therein).

In some embodiments, the anti-Delta1 antibody as described herein can modulate, e.g., reduce, the fraction γδ1 T cells present in PBMCs and/or the fraction of γδ1 T cells present in tumor localized immune cells. In some embodiments, the anti-Delta1 antibody as described herein modulates, e.g., reduces, the fraction γδ1 T cells present in PBMCs and/or the fraction of γδ1 T cells present in tumor localized immune cells by at least 10% (e.g., 10%, 15%, 20%, 25%, 30%, 35%, 40%, 50%, 60%, 70%, 80%, 90%, 95% or greater, including any increment therein).

In some embodiments, the anti-Delta1 antibody as described herein can deplete a tumor of γδ T cells. In some embodiments, the anti-Delta1 antibody as described herein deplete a tumor of γδ T cells by at least 10% (e.g., 10%, 15%, 20%, 25%, 30%, 35%, 40%, 50%, 60%, 70%, 80%, 90%, 95% or greater, including any increment therein).

In some embodiments, the anti-Delta1 antibody as described herein can prevent direct or indirect suppression of alpha-beta T cell activity. In some embodiments, the anti-Delta1 antibody as described herein can inhibit γδ T cell cytokine secretion (e.g., IL-17), and there by prevent induction of angiogenesis, and the attraction of MDSCs, neutrophils and TAMs. In some embodiments, the anti-Delta1 antibody as described herein can inhibit the Treg/Th2 type activity of γδ T cells, and thereby prevent the restriction of anti-tumor γδ T cells. In some embodiments, the anti-Delta1 antibody as described herein can prevent the interface of pro-tumor γδ T cells with dendritic cells (DCs), and accordingly prevent the inhibition of DC maturation, and/or the induction of DC or T cell senescence. In some embodiments, the anti-Delta1 antibody as described herein can prevent the limitation of DC antigen presentation resulting from the presence of γδ T cells.

The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-Delta1 antibody described herein can be determined by routine methods known in the art.

The $K_i^{app}$ value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_{i,}^{app}$ versus substrate concentration.

$$v = A \cdot \frac{([E] - [I] - K_i^{app}) + \sqrt{([E] - [I] - K_i^{app})^2 + 4[E] \cdot K_i^{app}}}{2} \quad \text{(Equation 1)}$$

Where A is equivalent to vo/E, the initial velocity (vo) of the enzymatic reaction in the absence of inhibitor (I) divided by the total enzyme concentration (E).

In some embodiments, the anti-Delta1 antibody described herein may have a $Ki^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for the target antigen or antigen epitope. In some embodiments, the anti-Delta1 antibody may have a lower $Ki^{app}$ for a first target (e.g., a specific epitope of Delta1) relative to a second target (e.g., a different specific epitope of Delta1). Differences in $Ki^{app}$ (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some examples, the anti-Delta1 antibody inhibits a first antigen (e.g., a first protein in a first conformation or mimic thereof) better relative to a second antigen (e.g., the same first protein in a second conformation or mimic thereof; or a second protein). In some embodiments, any of the anti-Delta1 antibodies may be further affinity matured to reduce the $Ki^{app}$ of the antibody to the target antigen or antigenic epitope thereof.

The antibodies described herein can be murine, rat, monkey, human, or any other origin (including chimeric or humanized antibodies). Such antibodies are non-naturally occurring, i.e., would not be produced in an animal without human act (e.g., immunizing such an animal with a desired antigen or fragment thereof or isolated from antibody libraries).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions can be used to substitute for the corresponding residues in the human acceptor genes.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-Delta 1 antibodies described herein may comprise a heavy chain variable region ($V_H$) that comprises a heavy chain (HC) CDR1, a HC CDR2, and a HC CDR3. The HC CDR1 may comprises the motif set forth as $FTX_1X_2X_3X_4X_5IH$ (SEQ ID NO: 46), in which $X_1$ can be F or V, $X_2$ can be S or T, $X_3$ can be G, A, or S, $X_4$ can be T, N, or S, and $X_5$ can be D or S. In specific examples, the HC CDR1 can be FTVSSSSIH (SEQ ID NO: 52). The HC CDR2 may comprises the motif set forth as SIYSSSGYTYYADSVKG (SEQ ID NO: 53. Alternatively or in addition, the HC CDR3 may comprise the motif set forth as $PGX_6YYWYYSGSAYEGYGLDY$ (SEQ ID NO: 48), in which $X_6$ can be S or M. In specific examples, the HC CDR3 may comprise the sequence of DPGSYYWYYSGSAYEGYGLDY (SEQ ID NO: 54).

Alternatively or in addition, the anti-Delta 1 antibodies described herein may comprise a light chain variable region ($V_L$) that comprises a light chain (LC) CDR1, a LC CDR2, and a LC CDR3. In some instances, the LC CDR1 may comprise the motif set forth as RASQSVSSAVA (SEQ ID NO: 55). The LC CDR2 may comprise the motif set forth as $X_7ASSLX_8S$ (SEQ ID NO: 50), in which $X_7$ can be S or A, and $X_8$ can be Y or Q. In some examples, the LC CDR2 may comprise the sequence of AASSLQS (SEQ ID NO: 56). Alternatively or in addition, the LC CDR3 may comprise the motif set forth as $QQX_9X_{10}X_{11}X_{12}X_{13}X_{14}LIT$ (SEQ ID NO: 51), in which $X_9$ can be S or Q, $X_{10}$ can be G, S, or T, $X_{11}$ can be D, K, or S, $X_{12}$ can be Y, W, or absent, $X_{13}$ can be P or absent, and $X_{14}$ can be D, F, or Y. In some examples, the LC CDR3 may comprise the sequence of QQQSKYPFLIT (SEQ ID NO: 57).

In some embodiments, the antibody comprises a heavy chain variable region ($V_H$) that comprises a HC CDR1, a HC CDR2, and a HC CDR3, wherein the HC CDR1 comprises a motif of $FTFX_1X_2X_3X_4IH$ (SEQ ID NO: 93), in which $X_1$ is S or T, $X_2$ is S, G or A, $X_3$ is T, N, or S, and $X_4$ is D or S. Alternatively or in addition, the HC CDR2 comprises SIYSSSGYTYYADSVKG (SEQ ID NO: 53). Alternatively, or in addition, the HC CDR3 comprises DPGSYYWYYSGSAYEGYGLDY (SEQ ID NO: 54). Alternatively or in addition, the isolated antibody disclosed herein comprises a light chain variable region ($V_L$) that comprises a LC CDR1, a LC CDR2, and a LC CDR3, wherein the LC CDR1 comprises RASQSVSSAVA (SEQ ID NO: 55). Alternatively or in addition, the LC CDR2 comprises AASSLQS (SEQ ID NO: 56). Alternatively or in addition, the LC CDR3 comprises QQQSKYPFLIT (SEQ ID NO: 57).

In some embodiments, the antibody comprises a heavy chain variable region ($V_H$) that comprises a HC CDR1, a HC CDR2, and a HC CDR3, wherein the HC CDR1 comprises a motif of $FTFX_1X_2X_3X_4IH$ (SEQ ID NO: 93), in which $X_1$ is S or T, $X_2$ is S, G or A, $X_3$ is T, N, or S, and $X_4$ is D or S, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody further comprises a light chain variable region ($V_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the antibody comprises a heavy chain variable region ($V_H$) that comprises a HC CDR1, a HC CDR2, and a HC CDR3, wherein the HC CDR1 comprises a motif of $FTFX_1X_2X_3X_4IH$ (SEQ ID NO: 94), in which $X_1$ is S or T, $X_2$ is S, or A, $X_3$ is N, or S, and $X_4$ is D or S, the HC CDR2 comprises SIYSSSGYTYYADSVKG (SEQ ID NO: 53), and the HC CDR3 comprises DPGSYYWYYSGSAYEGYGLDY (SEQ ID NO: 54). In some embodiments, the isolated antibody comprises a light chain variable region ($V_L$) that comprises a LC CDR1, a LC CDR2, and a LC CDR3, wherein the LC CDR1 comprises RASQSVSSAVA (SEQ ID NO: 55), the LC CDR2 comprises AASSLQS (SEQ ID NO: 56), and the LC CDR3 comprises QQQSKYPFLIT (SEQ ID NO: 57).

In some embodiments, the antibody comprises a heavy chain variable region ($V_H$) that comprises a HC CDR1, a HC CDR2, and a HC CDR3, wherein the HC CDR1 is selected from the group consisting of SEQ ID NO: 68, SEQ ID NO: 69, SEQ ID NO: 70, SEQ ID NO: 71, and SEQ ID NO: 72. Alternatively or in addition, the HC CDR2 comprises SIYSSSGYTYYADSVKG (SEQ ID NO: 53). Alternatively, or in addition, the HC CDR3 comprises DPGSYYWYYSGSAYEGYGLDY (SEQ ID NO: 54). Alternatively or in addition, the isolated antibody disclosed herein comprises a light chain variable region ($V_L$) that comprises a LC CDR1, a LC CDR2, and a LC CDR3, wherein the LC CDR1 comprises RASQSVSSAVA (SEQ ID NO: 55). Alternatively or in addition, the LC CDR2 comprises AASSLQS (SEQ ID NO: 56). Alternatively or in addition, the LC CDR3 comprises QQQSKYPFLIT (SEQ ID NO: 57).

In some embodiments, the anti-Delta 1 antibodies described herein comprise all of the heavy chain and/or all of the light chain CDR motifs described herein. In some examples, the antibody does not have the same heavy chain and light chain CDRs as Delta1-17 or does not have the same heavy chain and light chain variable regions as Delta1-17.

A number of exemplary anti-Delta1 antibodies are provided below (CDR residues based on Kabat numbering are indicated by bolding). A listing of CDRs is provided in Table 1.

Delta1-17

$V_H$:

(SEQ ID NO: 1)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGMYYWYYSGSAYEGYGLDYWGQGTLVTVSS $V_L$:

(SEQ ID NO: 2)
DIQMTQSPSSLSASVGDRVTITCRASQSVSSAVAWYQQKPGKAPKLLIY
SASSLYSGVPSRFSGSRSGTDFTLTISSLQPEDFATYYCQQSGDDLITF
GQGTKVEIKR

Delta1-18

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 4)
DIQMTQSPSSLSASVGDRVTITCRASQSVSSAVAWYQQKPGKAPKLLIY
AASSLQSGVPSRFSGSRSGTDFTLTISSLQPEDFATYYC**QQRSRVYSLV
T**FGQGTKVEIKR

Delta1-19

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 5)
DIQMTQSPSSLSASVGDRVTITCRASQSVSSAVAWYQQKPGKAPKLLIY
AASSLQSGVPSRFSGSRSGTDFTLTISSLQPEDFATYYC**QQMDRFYSLI
T**FGQGTKVEIKR

Delta1-20

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 6)
DIQMTQSPSSLSASVGDRVTITCRASQSVSSAVAWYQQKPGKAPKLLIY
AASSLQSGVPSRFSGSRSGTDFTLTISSLQPEDFATYYC**QQYCRKSSLF
T**FGQGTKVEIKR

Delta1-21

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 7)
DIQMTQSPSSLSASVGDRVTITCRASQSVSSAVAWYQQKPGKAPKLLIY
AASSLQSGVPSRFSGSRSGTDFTLTISSLQPEDFATYYC**QQQQRTSYLI
T**FGQGTKVEIKR

Delta1-22

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 8)
DIQMTQSPSSLSASVGDRVTITCRASQSVSSAVAWYQQKPGKAPKLLIY
AASSLQSGVPSRFSGSRSGTDFTLTISSLQPEDFATYYC**QQRSRYYSLI
T**FGQGTKVEIKR

Delta1-23

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQQSKYPFLI
TFGQGTKVEIKR

Delta1-24

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 10)
DIQMTQSPSSLSASVGDRVTITCRASQSVSSAVAWYQQKPGKAPKLLIY
AASSLQSGVPSRFSGSRSGTDFTLTISSLQPEDFATYYC**QQSNRSYPPL
T**FGQGTKVEIKR

Delta1-25

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 11)
DIQMTQSPSSLSASVGDRVTITCRASQSVSSAVAWYQQKPGKAPKLLIY
AASSLQSGVPSRFSGSRSGTDFTLTISSLQPEDFATYYC**QQIGRRSSLI
T**FGQGTKVEIKR

Delta1-26

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 12)
DIQMTQSPSSLSASVGDRVTITCRASQSVSSAVAWYQQKPGKAPKLLIY
AASSLQSGVPSRFSGSRSGTDFTLTISSLQPEDFATYYC**QQQQRYSYLI
T**FGQGTKVEIKR

Delta1-27

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 13)
DIQMTQSPSSLSASVGDRVTITCRASQSVSSAVAWYQQKPGKAPKLLIY
AASSLQSGVPSRFSGSRSGTDFTLTISSLQPEDFATYYC**QQSSRNSKLI
T**FGQGTKVEIKR

Delta1-28

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 14)
DIQMTQSPSSLSASVGDRVTITCRASQSVSSAVAWYQQKPGKAPKLLIY
AASSLQSGVPSRFSGSRSGTDFTLTISSLQPEDFATYYC**QQWMRSSSLF
T**FGQGTKVEIKR

Delta1-29

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 15)
DIQMTQSPSSLSASVGDRVTITCRASQSVSSAVAWYQQKPGKAPKLLIY
AASSLQSGVPSRFSGSRSGTDFTLTISSLQPEDFATYYCQQSGDDLITF
GQGTKVEIKR

Delta1-30

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 2)
DIQMTQSPSSLSASVGDRVTITCRASQSVSSAVAWYQQKPGKAPKLLIY
SASSLYSGVPSRFSGSRSGTDFTLTISSLQPEDFATYYCQQSGDDLITF
GQGTKVEIKR

Delta1-31

$V_H$:

(SEQ ID NO: 3)
EVQLVESGGGLVQPGGSLRLSCAASGFTVSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 16)
DIQMTQSPSSLSASVGDRVTITCRASQSVSSAVAWYQQKPGKAPKLLIY
AASSLQSGVPSRFSGSRSGTDFTLTISSLQPEDFATYYC**QQQTSWPYLI
T**FGQGTKVEIKR

Delta1-32

$V_H$:

(SEQ ID NO: 17)
EVQLVESGGGLVQPGGSLRLSCAASGFTFSSSDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYC**QQQSKYPFLI
T**FGQGTKVEIKR

Delta1-33

$V_H$:

(SEQ ID NO: 18)
EVQLVESGGGLVQPGGSLRLSCAASGFTFSSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYC**QQQSKYPFLI
T**FGQGTKVEIKR

Delta1-34

$V_H$:

(SEQ ID NO: 19)
EVQLVESGGGLVQPGGSLRLSCAASGFTFSGTDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYC**QQQSKYPFLI
T**FGQGTKVEIKR

Delta1-35

$V_H$:

(SEQ ID NO: 20)
EVQLVESGGGLVQPGGSLRLSCAASGFTFSASSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYC**QQQSKYPFLI
T**FGQGTKVEIKR

Delta1-36

$V_H$:

(SEQ ID NO: 21)
EVQLVESGGGLVQPGGSLRLSCAASGFTFSSNDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS $V_L$:

(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYCQQQSKYPFLI
TFGQGTKVEIKR

Delta1-37
V_H:
(SEQ ID NO: 22)
EVQLVESGGGLVQPGGSLRLSCAASGFTFTGSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR Delta1-38
V_H:
(SEQ ID NO: 23)
EVQLVESGGGLVQPGGSLRLSCAASGFTFTSSDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR Delta1-39
V_H:
(SEQ ID NO: 24)
EVQLVESGGGLVQPGGSLRLSCAASGFTFTANDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRESGSRSGTDFTLTISSLQPEDFATYYCQQSKYPFLI
TFGQGTKVEIKR Delta1-40
V_H:
(SEQ ID NO: 25)
EVQLVESGGGLVQPGGSLRLSCAASGFTFTSSSIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR Delta1-41
V_H:
(SEQ ID NO: 43)
EVQLVESGGGLVQPGGSLRLSCAASGFTFSANDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR Delta1-42
V_H:
(SEQ ID NO: 44)
EVQLVESGGGLVQPGGSLRLSCAASGFTFSATDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR Delta1-43
V_H:
(SEQ ID NO: 45)
EVQLVESGGGLVQPGGSLRLSCAASGFTFSGSDIHWVRQAPGKGLEWVA
SIYSSSGYTYYADSVKGRFTISADTSKNTAYLQMNSLRAEDTAVYYCAR
DPGSYYWYYSGSAYEGYGLDYWGQGTLVTVSS V_L:
(SEQ ID NO: 9)
DIQMTQSPSSLSASVGDRVTITCRASQSVSSAVAWYQQKPGKAPKLLIY
AASSLQSGVPSRFSGSRSGTDFTLTISSLQPEDFATYYCQQSKYPFLI
TFGQGTKVEIKR

TABLE 1

Selected Antibody CDR Sequences

| Clone | | Sequence | SEQ ID NO: |
|---|---|---|---|
| Delta1-17 | V_H CDR1 | FTVSSSSIH | 52 |
| | V_H CDR2 | SIYSSSGYTYYADSVKG | 53 |
| | V_H CDR3 | DPGMYYWYYSGSAYEGYGLDY | 82 |
| | V_L CDR1 | RASQSVSSAVA | 55 |
| | V_L CDR2 | SASSLYS | 58 |
| | V_L CDR3 | QQSGDDLIT | 59 |
| Delta1-18 | V_H CDR1 | FTVSSSSIH | 52 |
| | V_H CDR2 | SIYSSSGYTYYADSVKG | 53 |
| | V_H CDR3 | DPGSYYWYYSGSAYEGYGLDY | 54 |
| | V_L CDR1 | RASQSVSSAVA | 55 |
| | V_L CDR2 | AASSLQS | 56 |
| | V_L CDR3 | QQRSRVYSLVT | 83 |
| Delta1-19 | V_H CDR1 | FTVSSSSIH | 52 |
| | V_H CDR2 | SIYSSSGYTYYADSVKG | 53 |
| | V_H CDR3 | DPGSYYWYYSGSAYEGYGLDY | 54 |
| | V_L CDR1 | RASQSVSSAVA | 55 |
| | V_L CDR2 | AASSLQS | 56 |
| | V_L CDR3 | QQMDRFYSLIT | 84 |
| Delta1-20 | V_H CDR1 | FTVSSSSIH | 52 |
| | V_H CDR2 | SIYSSSGYTYYADSVKG | 53 |
| | V_H CDR3 | DPGSYYWYYSGSAYEGYGLDY | 54 |
| | V_L CDR1 | RASQSVSSAVA | 55 |

TABLE 1-continued

Selected Antibody CDR Sequences

| Clone | | Sequence | SEQ ID NO: |
|---|---|---|---|
| | $V_L$ CDR2 | AASSLQS | 56 |
| | $V_L$ CDR3 | QQYCRKSSLFT | 85 |
| Delta1-21 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQQRTSYLIT | 86 |
| Delta1-22 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQRSRYYSLIT | 87 |
| Delta1-23 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-24 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQSNRSYPPLT | 88 |
| Delta1-25 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQIGRRSSLIT | 89 |
| Delta1-26 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQQRYSYLIT | 90 |
| Delta1-27 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQSSRNSKLIT | 91 |
| Delta1-28 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQWMRSSSLFT | 92 |
| Delta1-30 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | SASSLYS | 58 |
| | $V_L$ CDR3 | QQSGDDLIT | 59 |
| Delta1-31 | $V_H$ CDR1 | FTVSSSSIH | 52 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQTSWPYLIT | 60 |
| Delta1-32 | $V_H$ CDR1 | FTFSSSDIH | 61 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-33 | $V_H$ CDR1 | FTFSSSSIH | 62 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |

TABLE 1-continued

Selected Antibody CDR Sequences

| Clone | | Sequence | SEQ ID NO: |
|---|---|---|---|
| Delta1-34 | $V_H$ CDR1 | FTFSGTDIH | 63 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-35 | $V_H$ CDR1 | FTFSASSIH | 64 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-36 | $V_H$ CDR1 | FTFSSNDIH | 65 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-37 | $V_H$ CDR1 | FTFTGSSIH | 66 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-38 | $V_H$ CDR1 | FTFTSSDIH | 67 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-39 | $V_H$ CDR1 | FTFTANDIH | 68 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-40 | $V_H$ CDR1 | FTFTSSSIH | 69 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-41 | $V_H$ CDR1 | FTFSANDIH | 70 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-42 | $V_H$ CDR1 | FTFSATDIH | 71 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |
| Delta1-43 | $V_H$ CDR1 | FTFSGSDIH | 72 |
| | $V_H$ CDR2 | SIYSSSGYTYYADSVKG | 53 |
| | $V_H$ CDR3 | DPGSYYWYYSGSAYEGYGLDY | 54 |
| | $V_L$ CDR1 | RASQSVSSAVA | 55 |
| | $V_L$ CDR2 | AASSLQS | 56 |
| | $V_L$ CDR3 | QQQSKYPFLIT | 57 |

In some embodiments, the anti-Delta1 antibodies described herein bind to the same epitope as any of the exemplary antibodies listed above or competes against the exemplary antibody from binding to the delta-1 chain. An "epitope" refers to the site on a target antigen that is recognized and bound by an antibody. The site can be entirely composed of amino acid components, entirely composed of chemical modifications of amino acids of the protein (e.g., glycosyl moieties), or composed of combinations thereof. Overlapping epitopes include at least one common amino acid residue. An epitope can be linear, which is typically 6-15 amino acids in length. Alternatively, the epitope can be conformational. The epitope to which an antibody binds can be determined by routine technology, for example, the epitope mapping method (see, e.g., descriptions below). An antibody that binds the same epitope as an exemplary antibody described herein may bind to exactly the same epitope or a substantially overlapping epitope (e.g., containing less than 3 non-overlapping amino acid residues, less than 2 non-overlapping amino acid residues, or only 1 non-overlapping amino acid residue) as the exemplary antibody. Whether two antibodies compete against each other from binding to the cognate antigen can be determined by a competition assay, which is well known in the art.

In some examples, the anti-Delta1 antibody described herein comprises the same $V_H$ and/or VL CDRs as an exemplary antibody listed above. Two antibodies having the same $V_H$ and/or VL CDRs means that their CDRs are identical when determined by the same approach (e.g., the Kabat approach or the Chothia approach as known in the art). Such anti-Delta1 antibodies may have the same $V_H$, the same $V_L$, or both as compared to an exemplary antibody described herein.

Also within the scope of the present disclosure are functional variants of any of the exemplary anti-Delta1 antibodies as disclosed herein. Such functional variants are substantially similar to the exemplary antibody, both structurally and functionally. A functional variant comprises substantially the same $V_H$ and/or $V_L$ CDRs as the exemplary antibody. For example, it may comprise only up to 10 (e.g., 9, 8, 7, 6, 5, 4, 3, 2, or 1) amino acid residue variations in the total CDR regions of the antibody and binds the same epitope of Delta1 with substantially similar affinity (e.g., having a $K_D$ value in the same order). Alternatively or in addition, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-Delta1 antibody may comprise heavy chain CDRs that are at least 80% (e.g., 85%, 90%, 95%, or 98%) sequence identity, individually or collectively, as compared with the $V_H$ CDRs of an exemplary antibody described herein. Alternatively or in addition, the anti-Delta1 antibody may comprise light chain CDRs that are at least 80% (e.g., 85%, 90%, 95%, or 98%) sequence identity, individually or collectively, as compared with the $V_L$ CDRs as an exemplary antibody described herein. "Individually" means that one particular heavy chain or light chain CDR of an antibody shares the described sequence identify to the corresponding heavy chain or light chain CDR of an exemplary antibody, e.g., disclosed herein. "Collectively" means that the three heavy chain or light chain CDRs of an antibody, in combination, share the described sequence identity to the three corresponding heavy chain or light chain CDRs of an exemplary antibody, e.g., those described herein. Such antibodies may also comprise the one or more of the heavy chain CDR1, CDR2, and CDR3 motifs and/or one or more of the light chain CDR1, CDR2, and CDR3 motifs described herein, e.g., all of the heavy chain CDR1, CDR1, and CDR3 motifs and/or all of the light chain CDR1, CDR2, and CDR3 motifs described herein.

In some embodiments, the anti-Delta1 antibody described herein may comprise a $V_H$ that has at least 80% (e.g., 85%, 90%, 95%, or 98%) sequence identity to the $V_H$ of an exemplary antibody described herein. Alternatively or in addition, the anti-Delta1 antibody may comprise a $V_L$ that has at least 80% (e.g., 85%, 90%, 95%, or 98%) sequence identity to the $V_L$ of an exemplary antibody described herein. Such antibodies may also comprise the one or more of the heavy chain CDR1, CDR2, and CDR3 motifs and/or one or more of the light chain CDR1, CDR2, and CDR3 motifs described herein, e.g., all of the heavy chain CDR1, CDR1, and CDR3 motifs and/or all of the light chain CDR1, CDR2, and CDR3 motifs described herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the heavy chain of any of the anti-Delta1 antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain) of any IgG subfamily as described herein, such as IgG1. Several mutations in the heavy chain of an antibody to modulate effector function are known in the art (e.g., as listed in Table 1 and described in Wang et al., Protein Cell 2018, 9(1):63-73, the contents of which is herein incorporated by reference in its entirety).

As per special mutations to include, There are many known mutations that exist for enhancing ADCC, ADCP and CDC. I am attaching a review paper which details all of these (See table 1). Non-liming examples of human IgG1 heavy chain mutations include (1) E333A mutation (increased binding to FcγRIIIa and Increased ADCC and CDC); (2) S239D/A330L/I332E mutations (increased binding to FcγRIIIa and Increased ADCC); (3) K326W/E333S mutations (increased binding to C1q and increased CDC); (4) S239D/I332E/G236A mutations (increased FcγRIIa/FcγRIIb ratio and increased macrophage phagocytosis). Alternatively, the LALA mutation prevents all effector function, i.e., essentially functions to ADCC, ADCP and CDC. The hIgG1 LALA sequence includes two mutations, L234A and L235A (EU numbering), which suppress FcgR binding as well as a P329G mutation (EU numbering) to abolish complement C1q binding, thus abolishing all immune effector functions. Exemplary mutation in IgG4 istThe hIgG4 Fab Arm Exchange Mutant sequence includes a mutation to suppress Fab Arm Exchange (S228P; EU numbering). For manufacturing purposes, it may be desirable to delete the C-terminal lysine ("K") residue in the heavy chain sequences below. Therefore, in some embodiments, the C-terminal lysine ("K") residue may not be present in each of the heavy chain sequences presented below. In one example, the constant region is from human IgG1, an exemplary heavy chain amino acid sequence of which is provided below (SEQ ID NO: 31). In some embodiments, one or more of the mutations described above in 1-4 is introduced. In some embodiments, the heavy chain constant region of the anti-Delta1 antibodies described herein may comprise a single domain (e.g., CH1, CH2, or CH3) or a combination of any of the single domains, of a constant region (e.g., SEQ ID NO: 31, 74-77). In some embodiments, the light chain constant region of the antibodies described herein may comprise a single domain (e.g., CL), of a constant region (e.g., SEQ ID NO: 73). Exemplary light and heavy chain sequences are listed below.

Exemplary Constant Region Sequences

Igκ Light Chain (LC) (SEQ ID NO: 73):
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSENRGEC

IgG1 Heavy Chain (HC) (SEQ ID NO: 31):
ASTKGPSVFPLAPSSKSTSGGTAALGCLVKDYFPEPVTVSWNSGALTGV

HTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTV

DKSRWQQGNVFSCSVMHEALHNHYTQKSLSLSPGK

IgG1 Heavy Chain (HC) LALA (SEQ ID NO: 74):
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALGAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

IgG4 HC (SEQ ID NO: 75):
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

IgG4 HC Fab Arm Exchange mutant (SEQ ID NO: 76):
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK hIgG4 HC Fab Arm Exchange mut constant region
(SEQ ID NO: 77)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLIVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSPGK

Delta1-39 with Igk Light Chain (LC)
(SEQ ID NO: 78)
DIQMTQSPSSLSASVGDRVTITCRASQSVSSAVAWYQQKPGKAPKLLIY

AASSLQSGVPSRFSGSRSGTDFTLTISSLQPEDFATYYCQQQSKYPFLI

TFGQGTKVEIKRTVAAPSVFIFPPSDEQLKSGTASVVCLLNNFYPPEAK

VQWKVDNALQSGNSQESVTEQDSKDSTYSLSSTLTLSKADYEKHKVYAC

EVTHQGLSSPVTKSFNRGEC

Delta1-39 with IgG1 Heavy Chain (HC)
(SEQ ID NO: 79)
EVQLVESGGGLVQPGGSLRLSCAASGFTFTANDIHWVRQAPGKGLEWVA

SIYSSSGYTYYADSVKGRFTISADTSKNTAYLQMNSLRAEDTAVYYCAR

DPGSYYWYYSGSAYEGYGLDYWGQGTLVTVSSASTKGPSVFPLAPSSKS

TSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAP

ELLGGPSVFLFPPKPKDTLMISPTPEVTCVVVLVSHEDPEVKFNWYVDG

VEVHNAKTKPREEQYNSTYRVVSVLTVLHQDWLNGKEYKCKVSNKALPA

PIEKTISKAKGQPPEPQVYTLPPSREEMTKNQVSLTCLVKGFYPSDIAV

EWESNGQPENNYKTTPPVLDSDGSFFLYSKLTVDKSRWQQGNVFSCSVM

HEALHNHYTQKSLSESPGK

Delta1-39 with IgG4 HC
(SEQ ID NO: 47)
EVQLVESGGGLVQPGGSLRLSCAASGFTVSSSSIHWVRQAPGKGLEWVA

YISSSSGYTYYADSVKGRFTISADTSKNTAYLQMNSLRAEDTAVYYCAR

YWSYPSWWPYRGMDYWGQGTLVTVSSASTKGPSVEPLAPCSRSTSESTA

ALGCLVKDYFPEPVTVSWNSGALTSGVHTFPAVLQSSGLYSLSSVVTVP

SSSLGTKTYTCNVDHKPSNTKVDKRVESKYGPPCPSCPAPEFLGGPSVE

-continued

LFPPKPKDTLMISRTPEVTCVVVDVSQEDPEVQFNWYVDGVEVHNAKTK

PREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHYT

QKSLSLSPGK

Delta1-39 with IgG4 HC Fab Arm Exchange mutant HC
(SEQ ID NO: 49)
EVQLVESGGGLVQPGGSLRLSCAASGFTFTANDIHWVRQAPGKGLEWVA

SIYSSSGYTYYADSVKGRFTISADTSKNTAYLQMNSLRAEDTAVYYCAR

DPGSYYWYYSGSAYEGYGLDYWGQGTLVTVSSASTKGPSVFPLAPCSRS

TSESTAALGCLVKDYFPEPVTVSWNSGALTSGVHTFPAVLQSSGLYSLS

SVVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIE

KTISKAKGQPREPQVYTLPPSQREEMTKNQVSLTCLVKGFYPSDIAVEW

ESNGQPENNYKTTPPVLDSDGSFFLYSRLTVDKSRWQEGNVFSCSVMHE

ALHNHYTQKSLSLSLGK

Delta1-39 with IgG4 HC Fab Arm Exchange mutant
(SEQ ID NO: 80)
EVQLVESGGGLVQPGGSLRLSCAASGFTFTANDIHWVRQAPGKGLEWVA

SIYSSSGYTYYADSVKGRFTISADTSKNTAYLQMNSLRAEDTAVYYCAR

DPGSYYWYYSGSAYEGYGLDYWGQGTLVTVSSASTKGPSVFPLAPCSRS

TSESTAALGCLVKDYFPEPVTVSWNSGALTSGVHTFPAVLQSSGLYSLS

SVVTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEA

LHNHYTQKSLSLSPGK

In any of the embodiments described herein, an anti-Delta1 antibody of the disclosure may comprise a light chain constant region having the sequence of SEQ ID NO: 73. In any of the embodiments described herein, an anti-Delta1 antibody of the disclosure may comprise the heavy chain constant region having the sequence of SEQ ID NO: 31. In any of the embodiments described herein, an anti-Delta1 antibody of the disclosure may comprise the heavy chain constant region having the sequence of SEQ ID NO: 74. In any of the embodiments described herein, an anti-Delta1 antibody of the disclosure may comprise the heavy chain constant region having the sequence of SEQ ID NO: 75. In any of the embodiments described herein, an anti-Delta1 antibody of the disclosure may comprise the heavy chain constant region having the sequence of SEQ ID NO: 76.

In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 78. In some embodiments, the anti-Delta1 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 79. In some embodiments, the anti-Delta1 antibody has a light chain sequence comprising SEQ ID NO: 78. In some embodiments, the anti-Delta1 antibody has a heavy chain sequence comprising SEQ ID NO: 79. In some embodiments, the isolated antibody has a light chain sequence consisting essentially of SEQ ID NO: 78 or consisting of SEQ ID NO: 78. In some embodiments, the isolated antibody has a heavy chain sequence consisting essentially of SEQ ID NO: 79 or consisting of SEQ ID NO: 79.

In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 78 and has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to SEQ ID NO: 79. In some embodiments, the isolated antibody has a light chain sequence comprising SEQ ID NO: 78 and a heavy chain sequence comprising SEQ ID NO: 79. In some embodiments, the isolated antibody has a light chain sequence consisting essentially of SEQ ID NO: 78 and a heavy chain sequence consisting essentially of SEQ ID NO: 79. In some embodiments, the isolated antibody has a light chain sequence consisting of SEQ ID NO: 78 and a heavy chain sequence consisting of SEQ ID NO: 79.

In some embodiments, the anti-Delta1 antibody has a heavy chain sequence comprising a constant region having a sequence of SEQ ID NO: 31 and a VH region having a sequence selected from SEQ ID NOs: 3, 17, 18, 19, 20, 21, 22, 23, 24, 25, 43, 44, and 45. In some embodiments, the antibody has a the heavy chain sequence which is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the heavy chain sequence comprising a constant region having a sequence of SEQ ID NO: 31 and a $V_H$ region having a sequence selected from SEQ ID NOs: 3, 17, 18, 19, 20, 21, 22, 23, 24, 25, 43, 44, and 45.

In some embodiments, the anti-Delta1 antibody has a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the light chain sequence comprising a constant region having a sequence of SEQ ID NO: 31 and a VL region having a sequence selected from SEQ ID NOs: 4, 5, 6, 7, 8, 9, 10, 11, 12, 13, 14, 15, 2, 16, and 9.

In some embodiments, the anti-Delta1 antibody has a heavy chain sequence comprising a constant region having a sequence of SEQ ID NO: 31 and a VH region having a sequence selected from SEQ ID NOs: 3, 17, 18, 19, 20, 21, 22, 23, 24, 25, 43, 44, and 45. In some embodiments, the anti-Delta1 antibody has a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence consisting essentially a constant region having a sequence of SEQ ID NO: 31 and a VH region having a sequence selected from SEQ ID NOs: 3, 17, 18, 19, 20, 21, 22, 23, 24, 25, 43, 44, and 45 or consisting of a constant region having a sequence of SEQ ID NO: 31 and a VH region having a sequence selected from SEQ ID NOs: 3, 17, 18, 19, 20, 21, 22, 23, 24, 25, 43, 44, and 45. In some embodiments, the isolated antibody has a light chain sequence consisting essentially of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9 or consisting of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9.

In some embodiments, the anti-Delta1 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical heavy chain sequence comprising a constant region having a sequence of SEQ ID NO: 31 and a VH region having a sequence selected from SEQ ID NOs: 3, 17, 18, 19, 20, 21, 22, 23, 24, 25, 43, 44, and 45 and has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence comprising a constant region having a sequence of SEQ ID NO: 31 and a VH region having a sequence selected from SEQ ID NOs: 3, 17, 18, 19, 20, 21, 22, 23, 24, 25, 43, 44, and 45 and a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence consisting essentially of constant region having a sequence of SEQ ID NO: 31 and a VH region having a sequence selected from SEQ ID NOs: 3, 17, 18, 19, 20, 21, 22, 23, 24, 25, 43, 44, and 45 and a light chain sequence consisting essentially of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence consisting of constant region having a sequence of SEQ ID NO: 31 and a $V_H$ region having a sequence selected from SEQ ID NOs: 3, 17, 18, 19, 20, 21, 22, 23, 24, 25, 43, 44, and 45 and a light chain sequence consisting of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9.

In some embodiments, the anti-Delta1 antibody has a heavy chain sequence comprising a constant region having a sequence of SEQ ID NO: 31 and a VH region having a sequence selected from SEQ ID NOs: 17, 18, 19, 20, 21, 22, 23, 24, 25, 43, 44, and 45. In some embodiments, the antibody has the heavy chain sequence which is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the heavy chain sequence comprising a constant region having a sequence of SEQ ID NO: 31 and a $V_H$ region having a sequence selected from SEQ ID NOs: 17, 18, 19, 20, 21, 22, 23, 24, 25, 43, 44, and 45.

In some embodiments, the anti-Delta1 antibody has a light chain sequence comprising a constant region having a sequence of SEQ ID NO: 73 and a VL region having a sequence of SEQ ID NO: 9. In some embodiments, the anti-Delta1 antibody has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to the light chain sequence comprising a constant region having a sequence of SEQ ID NO: 31 and a VL region having a sequence of SEQ ID NO: 9.

In some embodiments, the anti-Delta1 antibody has a heavy chain sequence comprising a constant region having a sequence of SEQ ID NO: 31 and a VH region having a sequence selected from SEQ ID NOs: 17, 18, 19, 20, 21, 22, 23, 24, 25, 43, 44, and 45. In some embodiments, the anti-Delta1 antibody has a light chain sequence comprising a constant region having a sequence of SEQ ID NO: 73 and a VL region having a sequence of SEQ ID NO: 9. In some embodiments, the isolated antibody has a heavy chain sequence consisting essentially a constant region having a sequence of SEQ ID NO: 31 and a VH region having a sequence selected from SEQ ID NOs: 17, 18, 19, 20, 21, 22, 23, 24, 25, 43, 44, and 45 or consisting of a constant region having a sequence of SEQ ID NO: 31 and a VH region having a sequence selected from SEQ ID NOs: 17, 18, 19, 20, 21, 22, 23, 24, 25, 43, 44, and 45. In some embodiments, the isolated antibody has a light chain sequence consisting essentially of a constant region having a sequence of SEQ ID NO: 73 and a VL region having a sequence of SEQ ID NO: 4 9 or consisting of a constant region having a sequence of SEQ ID NO: 73 and a VL region having a sequence of SEQ ID NO: 9.

In some embodiments, the anti-Delta1 antibody has a heavy chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical heavy chain sequence comprising a constant region having a sequence of SEQ ID NO: 31 and a VH region having a sequence selected from SEQ ID NOs: 17, 18, 19, 20, 21, 22, 23, 24, 25, 43, 44, and 45 and has a light chain sequence that is at least 80 or 85% (e.g., at least 80%, 81%, 82%, 83% 84% or at least 85%, 86%, 87%, 88%, 89%, 90%, 91%, 92%, 93%, 94%, 95%, 96%, 97%, 98%, 99%, or 100%) identical to a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence comprising a constant region having a sequence of SEQ ID NO: 31 and a VH region having a sequence selected from SEQ ID NOs: 17, 18, 19, 20, 21, 22, 23, 24, 25, 43, 44, and 45 and a light chain sequence comprising a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence consisting essentially of constant region having a sequence of SEQ ID NO: 31 and a VH region having a sequence selected from SEQ ID NOs: 17, 18, 19, 20, 21, 22, 23, 24, 25, 43, 44, and 45 and a light chain sequence consisting essentially of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9. In some embodiments, the isolated antibody has a heavy chain sequence consisting of constant region having a sequence of SEQ ID NO: 31 and a VH region having a sequence selected from SEQ ID NOs: 17, 18, 19, 20, 21, 22, 23, 24, 25, 43, 44, and 45 and a light chain sequence consisting of a constant region having a sequence of SEQ ID NO: 73 and a VL region having a sequence selected from SEQ ID NOs: 4, 5, 6, 7, 8, 9, 10, 11, 12, 13, 14, 15, 2, 16, and 9.

When needed, the anti-Delta1 antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). In other embodiments, the constant region is modified as described in *Eur. J. Immunol.* (1999) 29:2613-2624; PCT Application No. PCT/GB99/01441; and/or UK Patent Application No. 9809951.8. In other examples, the antibody described herein may contain a modified constant region having an enhanced ADCC activity. Accordingly, the anti-Delta1 antibody described herein can comprise a modified constant region that improves effector function, i.e., improves complement mediated lysis, improves the stimulation of antibody-dependent cell mediated cytotoxicity (ADCC). In some embodiments, the antibody is an IgG1 molecule and comprises one or more mutations described under 1-4 above or in Wang et al. ADCC activity can be assessed using methods disclosed in U.S. Pat. No. 5,500,362.

Any of the anti-Delta1 antibodies described herein may comprise a light chain that further comprises a light chain constant region, which can be any CL known in the art. In some examples, the CL is a kappa light chain. In other examples, the CL is a lambda light chain.

Antibody heavy and light chain constant regions are well known in the art, e.g., those provided in the IMGT database (www.imgt.org) or at www.vbase2.org/vbstat.php., both of which are incorporated by reference herein.

Preparation of Anti-Delta1 Antibodies

Antibodies capable of binding the delta-1 chain of a γδTCR as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., a delta-1 chain of a suitable species such as human or a fragment thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-Delta1 monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with Delta1 (γδ T cell) activity. Hybridomas that produce such antibodies may be grown in vitro or in vivo using known procedures. The monoclonal antibodies may be isolated from the culture media or body fluids by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or $R_1N=C=NR$, where R and $R_1$ are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of a target γδ1 TCR (thus the activity of the target γδ T cells). It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse$^{RTM}$ from Amgen, Inc. (Fremont, Calif.) and HuMAb-Mouse$^{RTM}$ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) *Annu. Rev. Immunol.* 12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

Alternatively, antibodies capable of binding to the target antigens as described herein may be isolated from a suitable antibody library via routine practice. Antibody libraries, which contain a plurality of antibody components, can be used to identify antibodies that bind to a specific target antigen (e.g., an epitope of a delta-1 chain in this case) following routine selection processes as known in the art. In the selection process, an antibody library can be probed with the target antigen or a fragment thereof and members of the library that are capable of binding to the target antigen can be isolated, typically by retention on a support. Such screening process may be performed by multiple rounds (e.g., including both positive and negative selections) to enrich the pool of antibodies capable of binding to the target antigen. Individual clones of the enriched pool can then be isolated and further characterized to identify those having desired binding activity and biological activity. Sequences of the heavy chain and light chain variable domains can also be determined via conventional methodology.

There are a number of routine methods known in the art to identify and isolate antibodies capable of binding to the target antigens described herein, including phage display, yeast display, ribosomal display, or mammalian display technology.

As an example, phage displays typically use a covalent linkage to bind the protein (e.g., antibody) component to a bacteriophage coat protein. The linkage results from translation of a nucleic acid encoding the antibody component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be selected, and then the nucleic acid may be isolated and sequenced.

Other display formats include cell-based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958), and yeast display (Feldhaus et al., *Nat Biotechnol.* 2003; 21:163-70). After display library members are isolated for binding to the target antigen, each isolated library member can be also tested for its ability to bind to a non-target molecule to evaluate its binding specificity. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target. A high-throughput ELISA screen can be used to obtain the data, for example. The ELISA screen can also be used to obtain quantitative data for binding of each library member to the target as well as for cross-species reactivity to related targets or subunits of the target antigen. The non-target and target binding data are compared (e.g., using a computer and software) to identify library members that specifically bind to the target.

After selecting candidate library members that bind to a target, each candidate library member can be further analyzed, e.g., to further characterize its binding properties for the target, e.g., Delta1 chain (referred to herein as Delta1). Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties are described below.

Binding proteins can also be evaluated using an ELISA assay. For example, each protein is contacted to a microtitre plate whose bottom surface has been coated with the target, e.g., a limiting amount of the target. The plate is washed with buffer to remove non-specifically bound polypeptides. Then the amount of the binding protein bound to the target on the plate is determined by probing the plate with an antibody that can recognize the binding protein, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Alternatively, the ability of a binding protein described herein to bind a target antigen can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Surface plasmon resonance (SPR) can be used to analyze the interaction of a binding protein and a target antigen. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of SPR). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

As a further example, cellular assays may be used. Binding proteins can be screened for ability to bind to cells which transiently or stably express and display the target of interest on the cell surface. For example, Delta1 binding proteins can be fluorescently labeled and binding to Delta1 in the presence or absence of antagonistic antibody can be detected by a change in fluorescence intensity using flow cytometry e.g., a FACS machine.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to Delta1 can be identified from the library following routine procedures. Positive clones can be subjected to further screening to identify those that inhibit γδ T cell activity.

In some examples, any of the anti-Delta1 antibodies described herein can be a binding moiety of a bi-specific or tri-specific antibody. In other examples, any of the anti-Delta1 antibodies can be used for constructing a chimeric antigen receptor (CAR), which can be expressed on immune cells such as T cells. Any bi-specific antibodies or CAR-T cells comprising the anti-Delta1 antibodies are also within the scope of the present disclosure.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence, to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the Delta1 polypeptide have been replaced (swapped) with sequences from a closely related, but antigenically distinct protein (such as another member of the β-galactoside-binding soluble lectin family). By assessing binding of the antibody to the mutant Delta1, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-Delta1 antibody is prepared by recombinant technology as exemplified below.

Nucleic acids encoding the heavy and light chain of an anti-Delta1 antibody as described herein can be cloned into one expression vector, each nucleotide sequence being in operable linkage to a suitable promoter. In one example, each of the nucleotide sequences encoding the heavy chain and light chain is in operable linkage to a distinct prompter.

Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell*, 49:603-δ12 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell*, 49:603-δ12 (1987)]; Gossen and Bujard (1992); [M. Gossen et al., *Natl. Acad. Sci. USA*, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy*, 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-Delta1 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-Delta1 antibody and the other encoding the light chain of the anti-Delta1 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-Delta1 antibody as described herein, vectors (e.g., expression vectors) containing such; and host cells comprising the vectors are within the scope of the present disclosure.

Anti-Delta1 antibodies thus prepared can be can be characterized using methods known in the art, whereby reduction, amelioration, or neutralization of γδ T cell biological activity is detected and/or measured. For example, an ELISA-type assay may be suitable for qualitative or quantitative measurement of γδ T cell inhibition of αβ T cell activation or lack thereof.

The bioactivity of an anti-Delta1 antibody can verified by incubating a candidate antibody with stimulated conventional (αβ) T cells and isolated γδ T cells, and monitoring any one or more of the following characteristics: (a) binding between the candidate antibody and γδ T cells (b) an subsequent increase in the level of T cell activation markers; (c) preventing, ameliorating, or treating any aspect of a solid tumor; (c) blocking or decreasing γδ T cell activation; and (d) inhibiting (reducing) synthesis, production or release of γδ T cells (e) reducing or depleting γδ T cell levels.

Accordingly in one aspect, the present disclosure provides an isolated nucleic acid or set of nucleic acids which encode or collectively encode any of the anti-Delta1 antibodies disclosed herein. In some instances, the heavy chain and light chain of the antibody are encoded by two separate nucleic acid molecules (a set of nucleic acids). In other instances, the heavy chain and light chain of the antibody are encoded by one nucleic acid molecule, which may be in multicistronic format, or under the control of distinct promoters. Accordingly, in one aspect the disclosure provides an isolated nucleic acid molecule comprising one or more nucleic acid sequence(s) encoding a heavy chain variable region (VH) and/or a light chain variable region (VL) of an anti-Delta1 antibody described herein. In some embodiments, the nucleic acid molecule comprises one or more nucleic acid sequence(s) encoding a heavy chain variable region (VH) of an anti-Delta1 antibody described herein. Alternatively or in addition, in some embodiments, the nucleic acid molecule comprises one or more nucleic acid sequence(s) encoding a Light chain variable region (VL) of an anti-Delta1 antibody described herein.

In some embodiments, the isolated nucleic acid encodes an antibody which binds to binds to delta1 irrespective of the gamma chain. In some of the nucleic acid embodiments described herein, the nucleic acid molecule comprises the one or more nucleic acid sequences encoding a VH and/or VL of a full-length antibody or an antigen-binding fragment thereof. In some of the nucleic acid embodiments described herein, the nucleic acid molecule comprises the one or more nucleic acid sequences encoding: the VH and/or VL region of a single chain antibody. In some of the nucleic acid embodiments described herein, the nucleic acid molecule comprises the one or more nucleic acid sequences encoding VH and/or VL of a human antibody or a humanized antibody. In some of the nucleic acid embodiments described herein, the nucleic acid molecule comprises the one or more nucleic acid sequences encoding a VH and/or VL of a IgG molecule, e.g., an IgG1 molecule. In some of the nucleic acid embodiments described herein, the nucleic acid molecule comprises the one or more nucleic acid sequences encoding a VH and/or VL of an antibody comprising a HC constant region set forth as SEQ ID NO: 31, and/or a light chain constant region set forth as SEQ ID NO: 71.

In some embodiments, the isolated nucleic acid comprises one or more nucleic acid sequence(s) encoding a heavy chain variable region (VH) and/or a light chain variable region (VL) of an antibody that to binds to a delta1 chain of a gamma/delta T cell receptor, wherein said antibody comprises: a heavy chain complementarity determining region 1 (CDR1) set forth in a sequence selected from SEQ ID NOs: 52, 61, 62, 63, 64, 65, 66, 67, 68, 69, 70, 71, and 72, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56 or 58, and a light chain complementary determining region 3 (CDR3) set forth as in a sequence selected from SEQ ID NO: 83, 84, 85, 86, 87, 57, 88, 89, 90, 91, 92, 59, and 60.

In some embodiments, the isolated nucleic acid comprises one or more nucleic acid sequence(s) encoding a heavy chain variable region (VH) and/or a light chain variable region (VL) of an antibody that to binds to a delta1 chain of a gamma/delta T cell receptor, wherein said antibody comprises: a heavy chain complementarity determining region 1 (CDR1) set forth in a sequence selected from SEQ ID NOs: 5 61, 62, 63, 64, 65, 66, 67, 68, 69, 70, 71, and 72, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR) set forth as SEQ ID NO: 55, a light chain complementary determining region 2 (CDR2) set forth as SEQ ID NO: 56, and a light chain complementary determining region 3 (CDR3) set forth as in SEQ ID NO: 57.

In some embodiments, the isolated nucleic acid comprises one or more nucleic acid sequence(s) encoding a heavy chain variable region (VH) and/or a light chain variable region (VL) of an antibody that to binds to a delta1 chain of a gamma/delta T cell receptor, wherein said antibody comprises: a heavy chain complementarity determining region 1 (CDR1) set forth as SEQ ID NO: 68, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56, and a light chain complementary determining region 3 (CDR3) set forth as SEQ ID NO: 57.

In some of the nucleic acid embodiments described herein the nucleic acid molecule comprises the one or more nucleic acid sequences encoding a VH of an antibody comprising a VH and/or VL selected from SEQ ID NOs: 3, 17, 18, 19, 20, 21, 22, 23, 24, 25, 43, 44, and 45 and/or a VL selected from SEQ ID NOs: 4, 5, 6, 7, 8, 9, 10, 11, 12, 13, 14, 15, 2, 16, and 9. In some of the nucleic acid embodiments described herein, the nucleic acid molecule comprises the one or more nucleic acid sequences encoding a VH of an antibody comprising a VH and/or VL selected from SEQ ID NOs: 17, 18, 19, 20, 21, 22, 23, 24, 25, 43, 44, and 45 and/or a VL set forth in SEQ ID NO: 9.

In some of the nucleic acid embodiments described herein, the nucleic acid molecule comprises the one or more nucleic acid sequences encoding a VH and/or VL of an antibody comprising a VH and/or VL set forth as SEQ ill) NO: 24 and/or a VL set forth as SEQ ID NO: 9. In some of the nucleic acid embodiments described herein, the nucleic acid molecule comprises the one or more nucleic acid sequences encoding a VH and/or VL of an antibody comprising a VH and/or VL set forth as SEQ ID NO: 55 and/or a VL set forth as SEQ ID NO. 54.

In some embodiments, the one or more nucleic acid sequences encode a VH and/or VL of an antibody comprising a VI set forth as SEQ ID NO: 24 and a VT set forth as SEQ ID NO: 9, and a heavy chain constant region set forth as SEQ ID NO: 31 and a light chain constant region set forth as SEQ ID NO: 71. In some embodiments, the one or more nucleic acid sequences encode a VH and/or VL of an antibody comprising a heavy chain set forth as SEQ ID NO: 79 and a light chain set forth as SEQ ID NO:78. In some embodiments, the one or more nucleic acid sequences encode a VH and/or VL of Delta1-39.

In some embodiments, the isolated nucleic acid comprises one or more nucleic acid sequence(s) encoding a heavy chain and/or a light chain of an antibody that to binds to a delta1 chain of a gamma/delta T cell receptor, wherein said antibody comprises: a heavy chain complementarity determining region 1 (CDR1) set forth in a sequence selected from SEQ ID NOs: 52, 61, 62, 63, 64, 65, 66, 67, 68, 69, 70, 71, and 72, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56 or 58, and a light chain complementary determining region 3 (CDR3) set forth as in a sequence selected from SEQ ID NO: 83, 84, 85, 86, 87, 57, 88, 89, 90, 91, 92, 59, and 60.

In some embodiments, the isolated nucleic acid comprises one or more nucleic acid sequence(s) encoding a heavy chain and/or a light chain of an antibody that to binds to a delta1 chain of a gamma/delta T cell receptor, wherein said antibody comprises: a heavy chain complementarity determining region 1 (CDR1) set forth in a sequence selected from SEQ ID NOs: 5 61, 62, 63, 64, 65, 66, 67, 68, 69, 70, 71, and 72, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56, and a light chain complementary determining region 3 (CDR3) set forth as in SEQ ID NO: 57.

In some embodiments, the isolated nucleic acid comprises one or more nucleic acid sequence(s) encoding heavy chain and/or a light chain of an antibody that to binds to a delta1 chain of a gamma/delta T cell receptor, wherein said antibody comprises: a heavy chain complementarity determining region 1 (CDR1) set forth as SEQ ID NO: 68, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56, and a light chain complementary determining region 3 (CDR3) set forth as SEQ ID NO: 57. In some of the nucleic acid embodiments described herein, the nucleic acid molecule comprises the one or more nucleic acid sequences encoding a heavy chain of an antibody comprising a VH and/or VL selected from SEQ ID NOs: 3, 17, 18, 19, 20, 21, 22, 23, 24, 25, 43, 44, and 45 and/or a light chain selected from SEQ ID NOs: 4, 5, 6, 7, 8, 9, 10, 11, 12, 13, 14, 15, 2, 16, and 9. In some of the nucleic acid embodiments described herein, the nucleic acid molecule comprises the one or more nucleic acid sequences encoding a heavy chain of an antibody comprising a VH and/or VL selected from SEQ ID NOs: 17, 18, 19, 20, 21, 22, 23, 24, 25, 43, 44, and 45 and/or a light chain set forth in SEQ ID NO: 9.

In some of the nucleic acid embodiments described herein, the nucleic acid molecule comprises the one or more nucleic acid sequences encoding a heavy chain and/or light chain of an antibody comprising a VH and/or VL set forth as SEQ ID NO: 24 and/or a VL set forth as SEQ ID NO: 9. In some of the nucleic acid embodiments described herein, the nucleic acid molecule comprises the one or more nucleic acid sequences encoding a heavy chain and/or light chain of an antibody comprising a VH and/or VL set forth as SEQ ID NO: 55 and/or a VL set forth as SEQ ID NO: 54.

In some embodiments, the one or more nucleic acid sequences encode a heavy chain and/or light chain of an antibody comprising a VH set forth as SEQ ID NO: 24 and a VL set forth as SEQ ID NO: 9, and a heavy chain constant region set forth as SEQ ID NO: 31 and a light chain constant region set forth as SEQ ID NO: 71. In some embodiments, the one or more nucleic acid sequences encode a heavy chain and/or light chain of an antibody comprising a heavy chain set forth as SEQ ID NO: 79 and a light chain set forth as SEQ ID NO:78. In some embodiments, the one or more nucleic acid sequences encode a heavy chain and/or light chain of Delta1-39.

Any of the isolated nucleic acids described herein are suitable for cloning into a vector. In some embodiments, the vector is an expression vector. In some embodiments, the vector comprises isolated nucleic acid comprising one or more nucleic acid sequence(s) encoding a heavy chain variable region (VH) and/or a light chain variable region (VL) of an antibody that to binds to a delta1 chain of a gamma/delta T cell receptor, wherein said antibody comprises: a heavy chain complementarity determining region 1 (CDR1) set forth as SEQ ID NO: 68, a heavy chain complementary determining region 2 (CDR2) set forth as SEQ ID NO: 53, and a heavy chain complementary determining region 3 (CDR3) set forth as SEQ ID NO: 54 and/or comprises a light chain complementarity determining region 1 (CDR1) set forth as SEQ ID NO: 55, a light chain complementary determining region 2 (CDR2) set forth as SEQ ID NO: 56, and a light chain complementary determining region 3 (CDR3) set forth as SEQ ID NO: 57. In some embodiments, the vector comprises a isolated nucleic acid encoding a VH. In some embodiments, the vector comprises a isolated nucleic acid encoding a VL. In some embodiments, the vector comprises a isolated nucleic acid encoding both VL and VH. Also contemplated in the disclosure are compositions comprising any of the isolated nucleic acids or vectors described herein, including but not limited to for example a vector or nucleic acid described in the instant paragraph. Also contemplated in the disclosure are host cells comprising any of the isolated nucleic acids or vectors described herein, including but not limited to the vectors and nucleic acids described in the instant paragraph. In some embodiments, the host cell is selected from the group consisting of E. coli cells, simian COS cells, Chinese hamster ovary (CHO) cells, or myeloma cells.

Also provided herein are methods of producing an antibody or antigen binding fragment thereof described herein that binds human delta-1, comprising expressing one or more nucleic acid molecules described herein (including but not limited to those described in the previous paragraph, in a host cell, thereby producing the antibody. In one embodiment, the method producing a monoclonal antibody or an antigen-binding fragment thereof that binds human Galectin-9, comprises (i) culturing the host cell under conditions allowing for expression of the anti-Delta1 antibody; and (ii) harvesting the anti-Delta1 antibody thus produced from the cell culture. Antibodies produced according to such methods are also contemplated.

Pharmaceutical Compositions and Uses Thereof

The present disclosure provides pharmaceutical compositions comprising the anti-Delta1 antibody described herein and uses of such for inhibiting signaling mediated by γδ1 T cells or activity mediated by γδ1 T cells, and/or eliminating Delta1-positive cells. Such antibodies can be used for treating diseases associated with activated γδ1 T cells, or for determining presence/level of γδ T cells in a biological sample.

Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Therapeutic Applications

The present disclosure provides pharmaceutical compositions comprising at least one anti-Delta1 antibody described herein or antigen binding fragment thereof and uses of such for inhibiting and/or reducing activity and/or reducing signaling mediated by a γδ1TCR expressing T cells and/or eliminating or reducing number(s) of γδ1 T cells. In some embodiments, the antibodies are useful for treating diseases associated with γδ1 T cells. In some embodiments, the antibodies are useful for treating diseases associated with γδ1 T cells. Any of the anti-Delta1 antibodies described herein can be used in the methods described herein. In some embodiments, the anti-Delta1 antibody is selected from Delta1-23, Delta1-30, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43 or combinations thereof. In some embodiments, the anti-Delta1 antibody is selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43 or combinations thereof. Non-limiting examples of such antibodies include for example Delta1-23. In another aspect, the antibody is Delta1-41. In another aspect, the antibody is Delta1-39. In some aspects, the invention provides methods of treating cancer. In some embodiments, the present disclosure methods for reducing, ameliorating, or eliminating one or more symptom(s) and/or extending survival (disease-free, progression-free, overall), associated with cancer.

In some embodiments, the disclosure provides a method for treating cancer in a subject, the method comprising administering to a subject in need thereof an effective amount of an anti-Delta1 antibody described herein or antigen binding fragment thereof. In some embodiments, the disclosure provides a method for treating cancer in a subject, the method comprising administering to a subject in need thereof an effective amount of a pharmaceutical composition comprising an anti-Delta1 antibody described herein or antigen binding fragment thereof. In some embodiments, the anti-Delta1 antibody is selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or combinations thereof. A non-limiting example of such antibodies includes Delta1-23. In specific examples, the anti-Delta1 antibody is Delta1-17 or a functional variant thereof as disclosed herein. In other specific examples, the anti-Delta1 antibody is Delta1-39 or a functional variant thereof as disclosed herein. In yet specific examples, the anti-Delta1 antibody is Delta1-41 or a functional variants thereof as disclosed herein.

The present disclosure provides methods of inhibiting γδ1 TCR-mediated cell signaling in a subject, the method comprising administering to a subject in need thereof an effective amount of a pharmaceutical composition comprising an anti-Delta1 antibody described herein, including, but not limited to Delta1-23, Delta1-17, Delta1-39, and/or Delta1-41. In one aspect, the antibody is Delta1-41. In another aspect, the antibody is Delta1-39.

To practice the method disclosed herein, an effective amount of the pharmaceutical composition described herein is administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-Delta1 antibodies as described herein are aerosolized using a fluorocarbon formulation and a metered dose inhaler, or inhaled as a lyophilized and milled powder.

In some embodiments, the subject to be treated by the methods described herein is a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a solid tumor.

In some embodiments, the cancer is selected from adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, cholangiocarcinoma, cholangiosarcoma, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, genitourinary cancers, gestational trophoblastic disease, heart cancer, Kaposi sarcoma, kidney cancer, laryngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer (for example, non-small cell lung cancer, NSCLC, and small cell lung cancer, SCLC), lymphoma (e.g., AIDS-related lymphoma, Burkitt lymphoma, cutaneous T cell lymphoma, Hogkin lymphoma, Non-Hogkin lymphoma, primary central nervous system lymphoma), malignant mesothelioma, multiple myeloma, myelodysplastic syndrome, nasal cavity cancer, paranasal sinus cancer, pancreatic duct adenocarcinoma (PDA) nasopharyngeal cancer, neuroblastoma, oral cavity cancer, oropharyngeal cancer, osteosarcoma, liposarcoma, lipomyosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), squamous cell head and neck cancer, small intestine cancer, stomach cancer, teratoid tumor, testicular cancer, throat cancer, thymus cancer, thyroid cancer, unusual childhood cancers, upper and lower gastrointestinal malignancies (including, but not limited to, esophageal, gastric, and hepatobiliary cancer), urethral cancer, uterine cancer, uterine sarcoma, vaginal cancer, vulvar cancer, cancers of the unknown primary, Waldenstrom macroglobulinemia, and Wilms tumor. In some embodiments, the cancer is selected from hematological malignancies include acute lymphoblastic leukemia, chronic lymphocytic leukemia, lymphomas, multiple myeloma, acute myelogenous leukemia, chronic myelogenous leukemia, myelodysplastic syndromes and the myeloproliferative neoplasms, such as essential thrombocythemia, polycythemia vera and myelofibrosis. In some embodiments, the symptom(s) associated thereof include, but are not limited to, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration. The method may comprise preparing a pharmaceutical composition with an anti-Delta1 antibody described herein, and administering the pharmaceutical composition to a subject in a therapeutically effective amount. In certain embodiments, administering the pharmaceutical composition, e.g., one or more of the anti-Delta1 antibodies described herein, including but not limited to antibody Delta1-23, to the subject reduces cell proliferation, tumor growth, and/or tumor volume in a subject, or reduces the number of metastatic lesions over time. In some embodiments, administering the composition results in complete response, partial response, or stable disease.

Examples of solid tumor cancers include pancreatic duct adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, and sarcomas. Hematological malignancies include acute lymphoblastic leukemia, chronic lymphocytic leukemia, lymphomas, multiple myeloma, acute myelogenous leukemia, chronic myelogenous leukemia, myelodysplastic syndromes and the myeloproliferative neoplasms, such as essential thrombocythemia, polycythemia vera and myelofibrosis. A subject having a solid tumor or a hematological malignancy can be identified by routine medical examination, e.g., laboratory tests, organ functional tests relevant imaging modalities. In some embodiments, the subject to be treated by the method described herein may be a human cancer patient who has undergone or is subjecting to an anti-cancer therapy, for example, chemotherapy, radiotherapy, immunotherapy, cell based therapy, surgery or any combination thereof.

Increased numbers of γδ T cells have been found in a number of cancers, including, but not limited to, glioma, melanoma, esophageal cancer, gastric cancer, colorectal cancer, pancreatic cancer, liver cancer, neuroendocrine tumors (e.g., carcinoid tumors), breast cancer, lung cancer, ovarian cancer, renal cancer, bladder cancer, and prostate cancer. In some cases, as explained below, the proportion or number of γδ1 T cells is increased in cancers relative to a non-cancerous control, and/or the proportion or number of γδ2 T cells is decreased in the cancer relative to a non-cancerous control. Without wishing to be bound by theory, blocking or targeting delta1 chain TCRs and thereby reducing an immunosuppressive function of γδ T cells expressing the delta1 TCRs (γδ1 cells), e.g., by using or administering an anti-Delta1 antibody, may present an effective novel therapeutic approach for the treatment of certain cancers, e.g., cancers with high levels of γδ T cells. Accordingly, any of the anti-delta-1 antibodies disclosed herein are suitable for inhibiting immune suppression by γδ T cells, and reactivating the effector T cell response. Accordingly, the anti-Delta1 antibodies described herein are suitable for the treatment of cancers, e.g., cancers associated with γδ T cells (e.g., cancers in which γδ T cells play a role in cancer development and progression). Accordingly, methods of treating cancer are provided herein, comprising administering to a subject in need thereof an effective amount of an anti-Delta1 antibody described herein or antigen binding fragment thereof. In some embodiments, the anti-Delta-1 antibody being administered to the subject, is selected from Delta1-17, Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43 or functional variants thereof as disclosed herein. In one example, the antibody is Delta1-23. In another example, the antibody is Delta1-17. In yet another example, the antibody is Delta1-39. In a further example, the antibody is Delta1-41.

Non-limiting exemplary cancers that are treated by the anti-delta1 antibodies disclosed herein are provided below.

Gliomas, tumors of the glial cells of the brain or the spine, are a deadly form of brain cancer, comprising about 80% of all malignant brain tumors and 50% of primary brain tumors (Goodenberger and Jenkins, Genetics of adult glioma. Cancer Genet. 2012 December;205(12):613-21). The cancer is characterized by infiltrative growth of the tumor without boundary in the brain, leaving behind extensive necrosis, and frequently disrupting the blood-brain barrier Glioblastoma (glioblastoma multiforme, GBM), is the most aggressive type of glioma. High-grade gliomas typically regrow despite complete surgical resection. Other treatments, such as radiotherapy and chemotherapy, have been used with very limited success.

It has been found that, while the ratio of total γδ T cells in peripheral blood in patients with glioma is not significantly different from that of healthy controls, the ratio of γδ1 T cells is significantly higher while the ratio of γδ2 T cells is significantly lower in the peripheral blood of glioma patients, as compared to healthy controls (Liu et al., γδ T Cells in Peripheral Blood of Glioma Patients. Med Sci Monit. 2018; 24:1784-92). Without wishing to be bound by theory, blocking or targeting delta1, and thereby potentially reducing an immunosuppressive function of 7δ1 cells, e.g., by administering an antibody that binds to delta1, may present a novel therapeutic approach for the treatment of glioma.

In some embodiments, the disclosure provides a method for treating glioma (e.g., glioblastoma) in a subject, the method comprising administering to a subject in need thereof an effective amount of an anti-Delta1 antibody described herein or antigen binding fragment thereof. In some embodiments, the anti-Delta1 antibody is one or more of the anti-delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one aspect, the antibody is Delta1-41. In another aspect, the antibody is Delta1-39.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is glioma (e.g., glioblastoma). In one example, the antibody is Delta1-23. In another example, the antibody is Delta1-17. In yet another example, the antibody is Delta1-39. In a further example, the antibody is Delta1-41.

Melanoma is the deadliest form of skin cancer and has been increasing in incidence for the past 30 years, especially in young adults. Accumulation of genetic disorders, most frequently mutations in B-Raf and N-Ras, in the melanocyte are a hallmark of melanoma (Rodríguez-Cerdeira et al., Advances in Immunotherapy for Melanoma: A Comprehensive Review; Mediators Inflamm. 2017; 2017: 3264217, and references therein). Subsequently, these alterations to result in the transformation of a dysplastic melanocyte into a melanoma cell, followed by invasion and metastasis.

Similar to glioma, frequencies of Vδ1 cells are higher in melanoma patients compared to healthy controls (Wistuba-Hamprecht et al., Eur J Cancer. 2016 September;64:116-26). This was found regardless of whether patients were treated with ipilimumab or not. In contrast, levels of γδ2 cells were lower in melanoma patients as compared to healthy controls and ipilimumab reduced γδ2 cell levels in patients with worse outcomes. In this study, high frequencies of γδ2 cells and low frequencies of γδ1 cells were associated with favorable overall survival (OS) of melanoma patients. Without wishing to be bound by theory, blocking or targeting delta1 and potentially reducing an immunosuppressive function of γδ1 cells, e.g., by administering an antibody that binds to delta1, may present a novel therapeutic approach in melanoma, which can lead to improved overall survival in patients, including but not limited to those treated with ipilimimab.

In some embodiments, the disclosure provides a method for treating melanoma in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is melanoma. In one example, the antibody is Delta1-23. In another example, the antibody is Delta1-17. In yet another example, the antibody is Delta1-39. In a further example, the antibody is Delta1-41.

Sarcomas are tumors of mesenchymal (connective) tissue, and include malignant tumors of bone (e.g., osteosarcoma), cartilage (chondrosarcoma), fat (liposarcoma), muscle (e.g., leiomyosarcoma), vascular, and hematopoietic tissues. Sarcomas are typically treated with surgery, although chemotherapy and radiation may also be administered before and/or after surgery to improve outcome.

In some embodiments, the disclosure provides a method for treating a sarcoma in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is a sarcoma. In one example, the antibody is Delta1-23. In another example, the antibody is Delta1-17. In yet another example, the antibody is Delta1-39. In a further example, the antibody is Delta1-41.

Gastrointestinal (GI) cancers include, but are not limited to, esophageal cancer, gastric cancer, colorectal cancer, pancreatic cancer, cholangiocarcinoma, and liver cancer. GI cancers represent the largest number of cancers and most deaths from cancer than any other system of the body.

Esophageal cancer, which is the sixth most common cancer worldwide, is increasing in incidence. There are two main types of esophageal cancer: esophageal squamous cell carcinoma (ESCC) and esophageal adenocarcinoma (EAC), and while the cause of this cancer is unknown, certain risk factors, such as the use of tobacco or alcohol, as well as reflux, Barrett's esophagus, achalasia, Plummer-Vinson syndrome, or esophageal scarring, have been identified (American Cancer Society, Esophageal Cancer, Jun. 14, 2017). Current treatments usually include surgery, as well as chemotherapy, radiotherapy, and/or stenting (Short et al., Esophageal Cancer. Am Fam Physician. 2017 Jan. 1; 95(1): 22-28).

It has been found that adhesion molecules recruit γδ1 T cells from the peripheral blood to the tumor tissue in esophageal patients, as γδ1 T cells are found to be sequestered in tumor tissue of patients having esophageal cancer (Thomas et al., Role of adhesion molecules in recruitment of γδ1 T cells from the peripheral blood to the tumor tissue of esophageal cancer patients. Cancer Immunol Immunother. 2001 June;50(4):218-25). Given the increased levels of γδ1 T cells, blocking or targeting delta1 e.g., by administering an antibody that binds to delta1, may present a novel therapeutic approach in esophageal cancer, which can lead to improved overall survival in patients.

In some embodiments, the disclosure provides a method for treating esophageal cancer in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is esophageal cancer. In one example, the antibody is Delta1-23. In another example, the antibody is Delta1-17. In yet another example, the antibody is Delta1-39. In a further example, the antibody is Delta1-41.

Gastric cancer, which develops in the lining of the stomach, used to be the leading cause of cancer deaths until the 1980s, and is currently the third most common cause of cancer-related death in the world (World Health Organization, Fact Sheets—Cancer, Sep. 12, 2018). There are a number of factors that lead to gastric cancer, including *Helicobacter pylori* infection, smoking, diet, and genetics. One genetic risk factor for gastric cancer is a genetic defect of the CDH1 gene. Generally, treatment of gastric cancer includes surgery, chemotherapy, and radiation therapy, although cures are rare. Treatment with a human epidermal growth factor receptor 2 (HER2) inhibitor, trastuzumab, has been found to increase overall survival in patients with inoperable locally advanced or metastatic gastric carcinoma over-expressing the HER2 neu gene (Orditura et al., Treatment of gastric cancer. World J Gastroenterol. 2014 Feb. 21; 20(7): 1635-1649). However, further anti-treatment strategies are needed to improve outcomes for gastric cancer patients.

It has been found that γδ T cells promote gastric cancer development. In particular, γδ T cells are a major source of IL-17 in the tumor microenvironment, and IL-17 supports angiogenesis in gastric cancer, promoting cancer growth (Wu et al., IL-17 promotes tumor angiogenesis through Stat3 pathway mediated upregulation of VEGF in gastric cancer. Tumour Biol. 2016 April; 37(4):5493-501). Therefore, without wishing to be bound by theory, γδ T cells are key producers of immune suppressive cytokines in gastric cancer and a present a novel target for immunotherapy.

In some embodiments, the disclosure provides a method for treating gastric cancer in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is gastric cancer. In one example, the antibody is Delta1-23. In another example, the antibody is Delta1-17. In yet another example, the antibody is Delta1-39. In a further example, the antibody is Delta1-41.

Colorectal cancer (CRC), also known as bowel cancer, colon cancer, or rectal cancer, is any cancer affecting the colon and the rectum. CRC is known to be driven by genetic alterations of tumor cells and is also influenced by tumor-host interactions. Recent reports have demonstrated a direct correlation between the densities of certain T lymphocyte subpopulations and a favorable clinical outcome in CRC, supporting a major role of T-cell-mediated immunity in repressing tumor progression of CRC. As for most cancers, current treatment for CRC includes surgery, chemotherapy, and radiation. In addition, drugs targeting specific mutations (e.g., bevacizumab, cetuximab, panitumumab, ramucirumab, regorafenib, and ziv-aflibercept) may be administered. Immunotherapy antibodies, such as pembrolizumab and nivolumab, but not limited to pembrolizumab and nivolumab, may be administered as well. However, there exists a need for further anti-tumor treatments to improve patient outcome.

Frequencies of γδ1 cells are higher in rectal tumor tissues from rectal cancer patients, and were found to positively correlate with T stage (Rong et al., Analysis of tumor-infiltrating gamma delta T cells in rectal cancer. World J Gastroenterol. 2016 Apr. 7; 22(13): 3573-3580). In contrast, levels of T62 cells were lower in rectal cancer patients as compared to healthy controls, and negatively correlated with T stage. The tumor-infiltrating γδ1 T cells were found to have strong inhibitory effects, and it was concluded that the percentage imbalance in γδ1 and γδ2 T cells in rectal cancer patients may contribute to the development of rectal cancer. Without wishing to be bound by theory, blocking or targeting delta1 and potentially reducing an inhibitory function of 7δ1 cells, e.g., by administering an antibody that binds to delta1, may present a novel therapeutic approach in CRC, which can lead to improved overall survival in patients.

In some embodiments, the disclosure provides a method for treating colorectal cancer in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is colorectal cancer. In one example, the antibody is Delta1-23. In another example, the antibody is Delta1-17. In yet another example, the antibody is Delta1-39. In a further example, the antibody is Delta1-41.

Pancreatic cancer, which includes pancreatic ductal adenocarcinoma (PDA), accounts for approximately 3% of all cancers and 7% of all cancer deaths in the US (American Cancer Society, 2019). In PDA, which accounts for about 85% of all pancreatic cancers, four genes have found to be mutated in the majority of cases: KRAS, CDKN2A, TP53, and SMAD4 (Wolfgang et al., CA Cancer J Clin. 2013 September; 63(5): 318-348). Treatment of pancreatic cancer typically consists of surgical resection and adjuvant therapy; currently the median overall survival for patients with resected pancreatic cancer is still approximately 20-22 months. Thus, there exists a need for additional anti-tumor strategies to further improve outcomes for pancreatic cancer patients.

In human pancreatic ductal adenocarcinoma (PDA), an activated γδT cell population constitutes up to 75% of tumor-infiltrating T cells (Daley et al., Cell. 2016 Sep. 8; 166(6):1485-1499.e15), and γδT cells produce high levels of tumor-promoting IL-17 in PDA (McAllister et al., Cancer Cell. 2014 May 12; 25(5):621-37). Deletion of intra-pancreatic γδT cells markedly protects against oncogenesis in vivo and results in an influx of immunogenic Th1 cells and $CD8^+$ T cells to the tumor micro environment (TME). Without wishing to be bound by theory, pancreas-infiltrating γδT cells promote PDA progression by inducing adaptive immune suppression, and accordingly, γδT cells are key regulators of effector T cell activation in pancreatic cancer and a new target for cancer immunotherapy.

In some embodiments, the disclosure provides a method for treating pancreatic cancer (e.g., PDA) in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is pancreatic cancer (e.g., PDA). In one example, the antibody is Delta1-23. In another example, the antibody is Delta1-17. In yet another example, the antibody is Delta1-39. In a further example, the antibody is Delta1-41.

Cholangiocarcinoma (CCA) is an epithelial cancer that forms in the bile ducts and is the most common biliary malignancy and the second most common hepatic malignancy after hepatocellular carcinoma. The overall incidence of cholangiocarcinoma has increased progressively worldwide over the past four decades. CCAs are classified into three subtypes based on their anatomic location, intrahepatic cholangiocarcinoma (iCCA), perihilar CCA (pCCA), and distal CCA (dCCA) (see, e.g., Loeuillard et al., Animal models of cholangiocarcinoma; Biochim Biophys Acta Mol Basis Dis. 2018 April 5, and Rizvi et al., Cholangiocarcinoma evolving concepts and therapeutic strategies; Nat Rev Clin Oncol. 2018 February; 15(2): 95-111). Currently, the disease is incurable and lethal, unless the tumor(s) can be fully resected in the early stages. Other treatments include adjuvant chemotherapy and radiation therapy.

In some embodiments, the disclosure provides a method for treating cholangiocarcinoma in a subject, the method comprising administering to a subject in need thereof an effective amount of an anti-Delta1 antibody described herein or antigen binding fragment thereof. In some embodiments, the anti-Delta1 antibody is one or more of the anti-Delta1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is cholangiocarcinoma. In one example, the antibody is Delta1-23. In another example, the antibody is Delta1-17. In yet another example, the antibody is Delta1-39. In a further example, the antibody is Delta1-41.

Hepatocellular carcinoma (HCC) is the most common type of primary liver cancer. It is the sixth most frequent cancer and second leading cause of death from cancer. Hepatocellular carcinoma occurs most often in people with chronic liver diseases, such as cirrhosis caused by hepatitis B or hepatitis C infection. HCC is usually accompanied by cirrhotic liver with extensive lymphocyte infiltration due to chronic viral infection. Current treatments for liver cancer include partial surgical resection, liver transplantation, percutaneous ablation, localized and systemic chemotherapy (e.g., transarterial chemoembolization), small molecule TKIs and immunotherapy. Additional anti-tumor treatments strategies are however needed to further improve liver cancer patients' outcomes.

It has been found that γδ T cells accumulate in liver tumors, as patients with hepatic malignancies have increased levels of γδ T cells as compared to healthy controls (Kenna et al., Distinct subpopulations of gamma delta T cells are present in normal and tumor-bearing human liver. Clin Immunol. 2004; 113:56-63 and Hammerich et al., World J Gastrointest Pathophysiol. 2014 May 15; 5(2): 107-113). In addition, different γδ chains can lead γδ T cells to have protective or damaging effects. γδ1 T cells were found to correlate with higher necroinflammatory scores in hepatitis C virus patients, which could be indicative of how such cells would perform in liver cancer (Rajoriya et al., Front Immunol. 2014; 5: 400). Without wishing to be bound by theory, blocking certain populations of γδ T cells, for example with an anti-Delta1 antibody, may present a novel therapeutic approach in liver cancer, potentially leading to increased overall survival of patients.

In some embodiments, the disclosure provides a method for treating liver cancer in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is liver cancer. In one example, the antibody is Delta1-23. In another example, the antibody is Delta1-17. In yet another example, the antibody is Delta1-39. In a further example, the antibody is Delta1-41.

Neuroendocrine tumors (NETs), which originate in neuroendocrine cells, most often occur in the intestine, but can also occur in the pancreas, lung, and other areas of the body. Carcinoid tumors, slow-growing neuroendocrine tumors occurring in the enterochromaffin cells in the gastrointestinal and bronchopulmonary systems, while rare, are the most type of common gastrointestinal neuroendocrine tumor. There are number of different types of carcinoid tumors, including bronchopulmonary, gastric, small intestinal, appendiceal, and colorectal carcinoid tumors. Typically, treatment includes surgical resection, hepatic chemoembolization (if applicable), and medical therapy (Pinchot et al., Carcinoid tumors. Oncologist. 2008 December; 13(12):1255-1269). Patients have been found to respond to somatostatin analogues (Aparicio et al., Antitumor activity of somatostatin analogues in progressive metastatic neuroendocrine gastroenteropancreatic tumors. Gut. 1996; 38:430-438), in addition to some chemotherapeutic drugs (Maroun et al., J Curr Oncol. 2006 April; 13(2):67-76) and limited number of small molecule inhibitors. However, additional anti-tumor strategies are needed to improve outcomes for NET and carcinoid tumor patients.

In some embodiments, the disclosure provides a method for treating a neuroendocrine tumor (e.g., a carcinoid tumor) in a subject, the method comprising administering to a subject in need thereof an effective amount of an anti-Delta1 antibody described herein or antigen binding fragment thereof. In some embodiments, the anti-Delta1 antibody is one or more of the anti-delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is a neuroendocrine tumor (e.g., a carcinoid tumor). In one example, the antibody is Delta1-23. In another example, the antibody is Delta1-17. In yet another example, the antibody is Delta1-39. In a further example, the antibody is Delta1-41.

Breast cancer is the second leading cause of cancer deaths in women. It is caused by a genetic mutation in the DNA of breast cancer cells most frequent type of cancer in women. Depending on the severity of the cancer, treatments can include surgery, chemotherapy, hormone therapy (e.g., hormone-blocking therapy, selective estrogen receptor modulators, aromatase inhibitors), and/or radiation. However, additional anti-tumor strategies are needed to improve outcomes for NET and carcinoid tumor patients.

γδ1 cells were found to be the dominant tumor-infiltrating T cells in tumors cells from patients with breast cancer compared to normal controls (Peng et al., Tumor-infiltrating γδ T cells suppress T and dendritic cell function via mechanisms controlled by a unique toll-like receptor signaling pathway. Immunity. 2007 August; 27(2):334-48). In contrast, levels of γδ2 cells were lower in breast cancer patients as compared to healthy controls. An additional study, which looked specifically at triple-negative breast cancer, found increased numbers of T6 T cells as compared to the levels in normal breast tissue (Hidalgo et al., Histological analysis of γδ T lymphocytes infiltrating human triple-negative breast carcinomas. Front Immunol. 2014; 5: 632). In fact, the γδ1 T cell subtype has been found to promote tumor growth and spread through its immunosuppressive effects (Morrow et al., The role of gamma delta T lymphocytes in breast cancer: a review. Transl Res. 2019 January;203:88-96). Without wishing to be bound by theory, blocking or targeting delta1 and potentially reducing the immunosuppressive effects of γδ1 T cells in breast cancer, e.g., by administering an antibody that binds to delta1, may present a novel therapeutic approach in breast cancer, which can lead to improved overall survival in patients.

In some embodiments, the disclosure provides a method for treating breast cancer in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is breast cancer. In one example, the antibody is Delta1-23. In another example, the antibody is Delta1-17. In yet another example, the antibody is Delta1-39. In a further example, the antibody is Delta1-41.

Lung cancer is the most common cause of cancer-related death in men and second most common cause of cancer-related death in women. Mutations in the Kras proto-oncogene have been implicated in about 30% of cancers, while mutations in c-MET, NKX2-1, LIB1, PIK3CA, and BRAF have also been implicated (Herbst et al., Lung cancer. N Eng J Med. 2008. 359 (13): 1367-80). Treatment for lung cancer varies depending on its severity, and can include surgery, radiotherapy, chemotherapy, targeted drug therapy (e.g., erlotinib, gefitinib, afatinib, denosumab), and bronchoscopy treatments. However, the prognosis for people with lung cancer is less than 20% for five years after diagnosis. Therefore, additional anti-tumor strategies to further improve patient outcomes are needed.

In a study of non-small cell lung cancer (NSCLC) patients, it was found that the γδ1 T cell populations were enriched relative to the γδ2 T cell populations (Bao et al., Characterization of γδ T cells in patients with non-small cell lung cancer. Oncol Lett. 2017 July; 14(1): 1133-1140). In another study, it was demonstrated that lung cancer cells overexpress tumor-infiltrating γδ T lymphocytes, and that the cells represent "a sizeable fraction" of the tumor-infiltrating cells in lung cancer (Ferrarini et al., Killing of laminin receptor-positive human lung cancers by tumor infiltrating lymphocytes bearing gammadelta(+) t-cell receptors. J Natl Cancer Inst. 1996 Apr. 3; 88(7):436-41). Without wishing to be bound by theory, blocking or targeting delta1 and potentially reducing the immunosuppressive effects of γδ1 T cells in breast cancer, e.g., by administering an antibody that binds to Delta-1, may present a novel therapeutic approach in lung cancer, which can lead to improved overall survival in patients.

In some embodiments, the disclosure provides a method for treating lung cancer in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is lung cancer. In one example, the antibody is Delta1-23. In another example, the antibody is Delta1-17. In yet another example, the antibody is Delta1-39. In a further example, the antibody is Delta1-41.

Genitourinary cancers include, for example, ovarian, endometrial, renal, bladder, and prostate cancers.

Ovarian cancer, which is the most common gynecologic cause of death in Europe and North America, has a diverse progression, making its treatment and management difficult. Generally, treatment is surgery followed by chemotherapy (e.g., platinum-based chemotherapy). Likewise, uterine cancer (e.g., endometrial cancer, uterine sarcoma), the most common gynecologic cancer in the United States, presents with a varied disease progression. Treatment generally comprises surgery, chemotherapy, hormonal therapy, and radiotherapy. Renal cancer (e.g., renal cell carcinoma, transitional cell carcinoma) accounts for approximately 2% of all cancers worldwide, and its highest prevalence is in North America. Treatment generally consists of surgery, biological therapies (e.g., everolimus, torisel, nexavar, sutent, axitinib), immunotherapy (e.g., interferon, interleukin-2), and sunitinib and pazopanib. Renal cancer is generally not responsive to chemotherapy or radiotherapy. Bladder cancer is one of the most common cancers, and is highly treatable if diagnosed early. Current treatments include surgery, chemotherapy, radiation therapy, and immunotherapy (e.g., *Bacillus* Calmette-Guerin (BCG), interferon alfa-2b, atezolizumab). Prostate cancer, which is the most common cancer and the second leading cause of cancer death among men in the United States, may be treated by surgery, radiation therapy, hormone therapy, chemotherapy, and/or immunotherapy. Therefore, there exists a need for further anti-tumor strategies in order to improve outcomes for genitourinary cancer patients.

In a study, γδ T cells were found to be present in the intratumoral T cells of primary advanced untreated ovarian serous carcinomas, while αβ T cells were not (Raspollini et al., Tumour-infiltrating gamma/delta T-lymphocytes are correlated with a brief disease-free interval in advanced ovarian serous carcinoma. Ann Oncol. 2005 April; 16(4):590-6). In a murine ovarian cancer model, δγ T cells were found to accumulate at the later stages of tumor progression (Rei et al. Murine CD27(−) Vgamma6(+) gammadelta T cells producing IL-17A promote ovarian cancer growth via mobilization of protumor small peritoneal macrophages. Proc Natl Acad Sci USA 2014; 111: E3562-E3570). Increased levels of Vδ1 T cells have been found in renal cell cancers as well as prostate cancer (Groh et al., Broad tumor-associated expression and recognition by tumor-derived γδ T cells of MICA and MICB. Proc Natl Acad Sci USA. 1999 Jun. 8; 96(12): 6879-6884). In contrast, the increase in Vδ2 T cells following administration of BCG has found to be beneficial in bladder cancer (Pauza et al., Gamma Delta T Cell Therapy for Cancer: It Is Good to be Local. Front Immunol. 2018; 9:1305).

In some embodiments, the disclosure provides a method for treating a genitourinary cancer (e.g., ovarian cancer, endometrial (uterine) cancer, renal cancer, bladder cancer, prostate cancer) in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is a genitourinary cancer (e.g., ovarian cancer, endometrial (uterine) cancer, renal cancer, bladder cancer, prostate cancer). In one example, the antibody is Delta1-23. In another example, the antibody is Delta1-17. In yet another example, the antibody is Delta1-39. In a further example, the antibody is Delta1-41.

Lymphomas are cancers of the lymphocytes, and include chronic lymphocytic leukemia, cutaneous B-cell lymphoma, cutaneous T-cell lymphoma, Hodgkin's lymphoma (Hodgkin's disease), non-Hodgkin's lymphoma, and Waldenstrom macroglobulinemia. Treatments for lymphoma include chemotherapy, radiation therapy, and immunotherapy. A rare type of lymphoma, γδ T cell lymphoma, is frequently fatal, although treatment with allogenic stem cell transplantation may be possible. However, there exists a need for additional anti-tumor therapies to further improve outcomes for patients with lymphoma.

In some embodiments, the disclosure provides a method for treating a lymphoma in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is a lymphoma. In one example, the antibody is Delta1-23. In another example, the antibody is Delta1-17. In yet another example, the antibody is Delta1-39. In a further example, the antibody is Delta1-41.

Adrenocortical carcinoma is a rare but aggressive form of cancer. The cancer is treated with surgical resection, although most patients are not candidates for this treatment, and are instead treated with radiation and radiofrequency ablation. Chemotherapy (e.g., mitotane, cisplatin, doxorubicin, etoposide and mitotane, streptozotocin and mitotane) may also be administered; however, the overall survival rate remains low. As such, additional anti-tumor strategies are needed to further improve outcomes for patients with adrenocortical carcinoma.

In some embodiments, the disclosure provides a method for treating adrenocortical carcinoma in a subject, the method comprising administering to a subject in need thereof an effective amount of an anti-Delta1 antibody described herein or antigen binding fragment thereof. In some embodiments, the anti-Delta1 antibody is one or more of the anti-Delta 1 antibodies disclosed herein, e.g., selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein. In one example, the antibody is Delta1-23. In another example, the antibody is Delta1-17. In yet another example, the antibody is Delta1-39. In a further example, the antibody is Delta1-41.

In some embodiments, the disclosure provides the use of an anti-Delta1 antibody as a medicament for the treatment of a cancer, wherein the anti-Delta1 antibody is selected from one or more of any of the antibodies described herein (e.g., Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or a functional variant thereof such as those described herein), and wherein the cancer is adrenocortical carcinoma. In one example, the antibody is Delta1-23. In another example, the antibody is Delta1-17. In yet another example, the antibody is Delta1-39. In a further example, the antibody is Delta1-41.

In specific examples, administering to a subject in need thereof an effective amount of Delta1-17 using the methods disclosed herein can treat pancreatic ductal adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, sarcomas, or a combination thereof.

In other specific examples, administering to a subject in need thereof an effective amount of Delta1-39 using the methods disclosed herein can treat pancreatic duct adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, sarcomas, or a combination thereof.

In still other specific examples, administering to a subject in need thereof an effective amount of Delta1-41 using the methods disclosed herein can treat pancreatic duct adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, sarcomas, or a combination thereof.

In still other specific examples, administering to a subject in need thereof an effective amount of Delta1-39 sing the methods disclosed herein can treat pancreatic duct adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, sarcomas, or a combination thereof.

A subject suspected of having any of such target disease/disorder may or may not show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced γδ T cell activity and/or amount/expression or increased anti-tumor immune responses in the tumor microenvironment (e.g., increased αβ T cell activation and/or activity). Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an anti-Delta1 antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the anti-Delta1 antibodies described herein, an initial candidate dosage can be about 2 mg/kg to about 10 mg/kg or 1 mg/kg to about 20 mg/kg. For the purpose of the present disclosure, a typical dosage might range from about any of 0.1 µg/kg to 3 µg/kg to 30 µg/kg to 300 µg/kg to 3 mg/kg, to 30 mg/kg to 100 mg/kg or more, depending on the factors mentioned above. In some embodiments, any of the anti-Delta1 antibodies described herein may be given to a subject in need of the treatment at one or more flat doses i.e., is not dependent on the subject's weight, body surface area, or other factors alike. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 3 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In other embodiments, a flat dose (giving a patient a defined amount of the antibody without taking into consideration body weight, body surface area and other factors alike) can be used for treatment of a target disease as described herein.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. In some examples, the dosage of the anti-Delta1 antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the disclosure provides a method for inhibiting the activity of γδ T cells. In some embodiments, the anti-Delta1 antibodies described herein are administered to a subject in need of the treatment at an amount sufficient to inhibit the activity of γδ T cells. In some embodiments, the anti-Delta1 antibodies described herein are administered to a subject in need of the treatment at an amount sufficient to inhibit the activity of γδ T cells by at least 10% (e.g., 20%, 30%, 40%, 50%, 60%, 70%, 80%, 90% or greater) in vivo. In other embodiments, the anti-Delta1 antibodies are administered in an amount effective in rescuing immune inhibition induced by γδ T cells. In other embodiments, the anti-Delta1 antibodies are administered in an amount effective in rescuing immune inhibition induced by γδ T cells by at least 10% (e.g., 20%, 30%, 40%, 50%, 60%, 70%, 80%, 90% or greater).

In some embodiments, the disclosure provides one or more anti-Delta1 antibodies described herein, including, but not limited to, Delta1-23, Delta1-41, and Delta1-39, for for inhibiting the activity of γδ T cells. In some embodiments, the antibodies described herein, e.g., in Table 1, including, but not limited to, Delta1-23, Delta1-41, and Delta1-39, are administered to a subject in need thereof at an amount sufficient to for inhibiting the activity of γδ T cells. In some embodiments, the antibodies described herein, e.g., in Table 1, including, but not limited to, Delta1-23, Delta1-41, and Delta1-39, are administered to a subject in need of the treatment at an amount sufficient to for inhibiting the activity of γδ T cells by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for reducing tumor volume, tumor size, and/or tumor burden, the method comprising providing or administering an anti-Delta1 antibody described herein, e.g., in Table 1 and/or Table 2, or antigen binding fragment thereof to a subject. In some embodiments, the anti-Delta1 antibody selected from Delta1-23, Delta1-39, and Delta1-41. In some embodiments, the method reduces tumor volume, tumor size, and/or tumor burden by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-41, and Delta1-39, for reducing tumor volume, tumor size, and/or tumor burden. In some embodiments, the antibodies described herein, e.g., in Table 1, including, but not limited to, Delta1-23, Delta1-41, and Delta1-39, are administered to a subject in need thereof at an amount sufficient to reduce tumor volume, tumor size, and/or tumor burden. In some embodiments, the antibodies described herein, e.g., in Table 1, including, but not limited to, Delta1-23, Delta1-41, and Delta1-39, are administered to a subject in need of the treatment at an amount sufficient to reduce tumor volume, tumor size, and/or tumor burden by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for depleting target cells, e.g., γδ T cells, e.g. Vδ1 T cells, in a tumor and/or in the blood, the method comprising providing or administering an anti-Delta1 antibody described herein, e.g., in Table 1 and/or Table 2, or antigen binding fragment thereof to a subject. In some embodiments, the anti-Delta1 antibody selected from Delta1-23, Delta1-39, and Delta1-41. In some embodiments, the method depletes γδ T cells, e.g. Vδ1 T cells by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-41, and Delta1-39, for depleting target cells, e.g., γδ T cells, e.g. γδ1 T cells in a tumor and/or in the blood. In some embodiments, the antibodies described herein, e.g., in Table 1, including, but not limited to, Delta1-23, Delta1-41, and Delta1-39, are administered to a subject in need thereof at an amount sufficient to deplete γδ T cells, e.g. γδ1 T cells, in a tumor and/or in the blood. In some embodiments, the antibodies described herein, e.g., in Table 1, including, but not limited to, Delta1-23, Delta1-41, and Delta1-39, are administered to a subject in need of the treatment at an amount sufficient to deplete γδ T cells, e.g. γδ1 T cells, in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for modulating the ratio of γδ T cells, e.g. modulating, e.g., reducing, the ratio γδ1 T cells to T62 T cells, in a tumor, the method comprising providing or administering an anti-Delta1 antibody described herein, e.g., in Table 1 and/or Table 2, or antigen binding fragment thereof to a subject. In some embodiments, the anti-Delta1 antibody selected from Delta1-23, Delta1-39, and Delta1-41. In some embodiments, the method modulates, e.g., reduces, the ratio γδ1 T cells to T62 T cells in a tumor by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for modulating the ratio of γδ T cells, e.g. modulating, e.g., reducing, the ratio Vδ1 T cells to Vδ2 T cells, in a tumor. In some embodiments, the antibodies described herein, e.g., in Table 1, including, but not limited to, Delta1-23, Delta1-41, and Delta1-39, are administered to a subject in need thereof at an amount sufficient to modulate, e.g., reduce, the ratio γδ1 T cells to γδ2 T cells in a tumor. In some embodiments, the antibodies described herein, e.g., in Table 1, including, but not limited to, Delta1-23, Delta1-41, and Delta1-39, are administered to a subject in need of the treatment at an amount sufficient to modulate, e.g., reduce, the ratio γδ1 T cells to γδ2 T cells in a tumor by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for modulating the ratio γδ1 T cells in PBMCs and/or the ratio γδ1 T cells in immune cells present in a tumor, e.g., isolated from a subject having a cancer, e.g. modulating, e.g., reducing, the ratio γδ1 T cells in PBMCs and/or the ratio γδ1 T cells in immune cells present in a tumor, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the method modulates, e.g., reduces, the ratio γδ1 T cells in PBMCs and/or the ratio γδ1 T cells in immune cells present in a tumor by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for modulating the ratio γδ1 T cells in PBMCs and/or the ratio γδ1 T cells in immune cells present in a tumor, e.g. modulating, e.g., reducing, the ratio 7δ1 to PBMCs, or to immune cells in a tumor. In some embodiments, the antibodies described herein, e.g., in Table 1, including, but not limited to, Delta1-23, Delta1-41, and Delta1-39, are administered to a subject in need thereof at an amount sufficient to modulate, e.g., reduce, the ratio γδ1 T cells in PBMCs and/or the ratio γδ1 T cells in immune cells present in a tumor. In some embodiments, the antibodies described herein, e.g., in Table 1, including, but not limited to, Delta1-23, Delta1-41, and Delta1-39, are administered to a subject in need of the treatment at an amount sufficient to modulate, e.g., reduce, the ratio γδ1 T cells in PBMCs and/or the ratio γδ1 T cells in immune cells present in a tumor by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for elimination or depletion of target cells, wherein the target cells are immune suppressive immune cells, e.g., γδ T cells, e.g. γδ1 T cells, the method comprising providing or administering an anti-Delta1 antibody described herein, e.g., in Table 1 and/or Table 2, or antigen binding fragment thereof to a subject. In some embodiments, the anti-Delta1 antibody is Delta1-39. In some embodiments, the method promotes elimination or depletion of target cells, e.g., immune suppressive immune cells, e.g., γδ T cells, e.g. γδ1 T cells, by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for elimination or depletion of target cells, wherein the target cells are immune suppressive immune cells, e.g., γδ T cells, e.g. γδ1 T cells. In some embodiments, the antibodies described herein, e.g., in Table 1, including, but not limited to, Delta1-23, Delta1-17, Delta1-39, or Delta1-41, are administered to a subject in need thereof at an amount sufficient to eliminate or deplete γδ T cells, e.g. γδ1 T cells, in a tumor and/or in the circulation, e.g., serum or blood. In some embodiments, the antibodies described herein, e.g., in Table 1, including, but not limited to, Delta1-23, Delta1-41, and Delta1-39, are administered to a subject in need of the treatment at an amount sufficient to eliminate or deplete γδ T cells, e.g. γδ1 T cells, in a tumor by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for inducing cell cytotoxicity, such as ADCC, in target cells, wherein the target cells are immune suppressive immune cells, e.g., γδ T cells, e.g. γδ1 T cells, the method comprising providing or administering an anti-Delta1 antibody described herein, e.g., in Table 1 and/or Table 2, or antigen binding fragment thereof to a subject. In some embodiments, the anti-Delta1 antibody selected from Delta1-23, Delta1-39, and Delta1-41. In some embodiments, the method induces cell cytotoxicity, such as ADCC in γδ T cells cells, e.g. Vδ1 T cells by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for inducing cell cytotoxicity, such as ADCC, in target cells, wherein the target cells are immune suppressive immune cells, e.g., γδ T cells, e.g. γδ1 T cells. In some embodiments, the antibodies described herein, e.g., in Table 1, including, but not limited to, Delta1-23, Delta1-17, Delta1-39, or Delta1-41, are administered to a subject in need thereof at an amount sufficient to promote ADCC in γδ T cells, e.g. γδ1 T cells, in a tumor or in circulation, e.g., serum or blood. In some embodiments, the antibodies described herein, e.g., in Table 1, including, but not limited to, Delta1-23, Delta1-41, and Delta1-39, are administered to a subject in need of the treatment at an amount sufficient to promote ADCC in γδ T cells, e.g. γδ1 T cells, in a tumor and/or in the circulation, e.g., serum or blood, by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for inducing cell cytotoxicity such as complement-dependent cytotoxicity (CDC) against target cells expressing delta1, i.e., γδ T cells, e.g. γδ1 T cells, in a subject, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the method induces cell cytotoxicity such as complement-dependent cytotoxicity (CDC) against T6 T cells, e.g. γδ1 T cells, at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for inducing cell cytotoxicity such as complement-dependent cytotoxicity (CDC) against target cells expressing delta1, i.e., γδ T cells, e.g. γδ1 T cells. In some embodiments, the antibodies described herein, e.g., in Table 1, including, but not limited to, Delta1-23, Delta1-41, and Delta1-39, are administered to a subject in need of the treatment at an amount sufficient to promote CDC in γδ T cells, e.g. γδ1 T cells, in a tumor and/or in the circulation, e.g., serum or blood. In some embodiments, the antibodies described herein, e.g., in Table 1, including, but not limited to, Delta1-23, Delta1-41, and Delta1-39, are administered to a subject in need of the treatment at an amount sufficient to promote CDC in γδ T cells, e.g. γδ1 T cells, in a tumor and/or in the circulation, e.g., serum or blood, by at least 20% (e.g., 30%, 40%, 50%, 60%, 70%, 80%, 90% or greater) or in a control subject). In some embodiments, the antibody is Delta1-39.

In some embodiments, the disclosure provides a method for inducing phagocytosis of target cells expressing delta1 (ADCP), the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the anti-Delta1 antibody increases phagocytosis of T6 T cells, e.g. γδ1 T cells, by at least 30% (e.g., 31%, 35%, 40%, 50%, 60%, 70%, 80%, 90%, 95% or greater, including any increment therein).

In some embodiments, the antibodies described herein, e.g., in Table 1, including, but not limited to, Delta1-23, Delta1-17, Delta1-39, or Delta1-41, are administered to a subject in need of the treatment at an amount sufficient to promote ADCP in γδ T cells, e.g. γδ1 T cells, in a tumor and/or in the circulation, e.g., serum or blood.

In some embodiments, the disclosure provides one or more anti-Delta1 antibodies described herein, including, but not limited to, Delta1-23, Delta1-17, Delta1-39, or Delta1-41, for inducing phagocytosis of target cells expressing delta1 (ADCP). In some embodiments, the antibodies described herein, e.g., in Table 1, including, but not limited to, Delta1-23, Delta1-17, Delta1-39, or Delta1-41, are administered to a subject in need of the treatment at an amount sufficient to promote ADCP of γδ T cells, e.g. γδ1 T cells, in a tumor and/or in the circulation, e.g., serum or blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for inducing T cell activation, in a tumor and/or in the blood, e.g., by targeting tumor infiltrating γδ T cells, e.g. γδ1 T cells, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the method promotes T cell activation in a tumor and/or in the blood by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, inducing T cell activation, in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote T cell activation in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote T cell activation in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for promoting CD4+ cell activation in a tumor and/or in the blood, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the method promotes CD4+ cell activation in a tumor and/or in the blood by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-41, and Delta1-39, for promoting CD4+ cell activation in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote CD4+ T cell activation in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote CD4+ T cell activation in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for inducing CD44 expression in CD4+ cells, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the method increases proinflammatory cytokine expression in a tumor and/or in the blood, e.g., CD44, IFNγ, and/or TNF-α expression, in CD4+ cells by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-17, Delta1-39, or Delta1-41, for inducing CD44 expression in CD4+ cells. In some embodiments, the antibodies described herein, e.g., in Table 1, including, but not limited to, Delta1-23, Delta1-41, and Delta1-39, are administered to a subject in need of the treatment at an amount sufficient to induce proinflammatory cytokine expression in a tumor and/or in the blood, e.g., CD44, IFNγ, and/or TNF-α expression, in CD4+ cells in a tumor. In some embodiments, the antibodies described herein, e.g., in Table 1, including, but not limited to, Delta1-23, Delta1-41, and Delta1-39, are administered to a subject in need of the treatment at an amount sufficient to induce proinflammatory cytokine expression, e.g., CD44, IFNγ, and/or TNF-α expression, in CD4+ cells in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for promoting CD8+ cell activation in a tumor and/or in the blood, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the method promotes CD8+ cell activation in a tumor and/or in the blood by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-41, and Delta1-39, for promoting CD8+ cell activation in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote CD8⁺ T cell activation in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to promote CD8⁺ T cell activation in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for inducing CD44 expression in CD8+ cells in a tumor and/or in the blood, the method comprising providing or administering an anti-Delta1 antibody described herein, e.g., in Table 1, or antigen binding fragment thereof to a subject. In some embodiments, the anti-Delta1 antibody selected from Delta1-23, Delta1-39, and Delta1-41. In some embodiments, the anti-Delta1 antibody is Delta1-17. In some embodiments, the anti-Delta1 antibody is Delta1-39. In some embodiments, the anti-Delta1 antibody is Delta1-41. In some embodiments, the method increases proinflammatory cytokine expression, e.g., CD44, IFNγ, and/or TNF-α expression, in CD8+ cells in a tumor and/or in the blood by at least 30% (e.g., 31%, 35%, 40%, 50%, 60%, 70%, 80%, 90%, 95% or greater, including any increment therein).

In some embodiments, the disclosure provides one or more anti-Delta1 antibodies described herein, including, but not limited to, Delta1-23, Delta1-41, and Delta1-39, for inducing CD44 expression in CD8+ cells in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient for inducing CD44 expression in CD8+ cells in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient for inducing CD44 expression in CD8+ cells in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

In some embodiments, the disclosure provides a method for preventing direct or indirect suppression of alpha-beta T cell activity. In some embodiments, the disclosure provides a method for inhibiting γδ T cell cytokine secretion (e.g., IL-17), and accordingly preventing induction of angiogenesis, and the attraction of MDSCs, neutrophils and TAMs. In some embodiments, the disclosure provides a method for inhibiting the Treg/Th2 type activity of γδ T cells, and thereby preventing the restriction of anti-tumor γδ T cells. In some embodiments, the disclosure provides a method for preventing the interface of pro-tumor γδ T cells with dendritic cells (DCs), and accordingly preventing the inhibition of DC maturation, and/or the induction of DC or T cell senescence. In some embodiments, the disclosure provides a method for preventing the limitation of DC antigen presentation resulting from the presence of γδ T cells.

In some embodiments, the disclosure provides one or more anti-Delta1 antibodies described herein, including, but not limited to, Delta1-23, Delta1-17, Delta1-39, or Delta1-41, for inducing CD44 expression in CD8+ cells in a tumor and/or in the blood. In some embodiments, the antibodies described herein, e.g., in Table 1, including, but not limited to, Delta1-23, Delta1-41, and Delta1-39, are administered to a subject in need of the treatment at an amount sufficient to induce proinflammatory cytokine expression, e.g., CD44, IFNγ, and/or TNF-α expression, in CD8+ cells in a tumor and/or in the blood. In some embodiments, the antibodies described herein, e.g., in Table 1, including, but not limited to, Delta1-23, Delta1-17, Delta1-39, or Delta1-41, are administered to a subject in need of the treatment at an amount sufficient to induce proinflammatory cytokine expression, e.g., CD44, IFNγ, and/or TNF-α expression, in CD8+ cells in a tumor and/or in the blood by at least 20% (e.g., 30%, 40%, 50%, 60%, 70%, 80%, 90% or greater) in vivo (as compared to levels prior to treatment or in a control subject). In some embodiments, the antibody is Delta1-39.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* (1993) 11:202; Chiou et al., Gene Therapeutics: Methods and Applications of Direct Gene Transfer (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol.* (1994) 14:2411, and in Woffendin, *Proc. Natl. Acad. Sci.* (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents.

Treatment efficacy for a target disease/disorder can be assessed by methods well-known in the art.

Combination Therapy

Any of the anti-Delta1 antibodies described herein may be utilized in conjunction with other types of therapy for cancer, such as chemotherapy, surgery, radiation, gene therapy, small molecule inhibitors, cell based therapies, anti-hormonal agents, immune-therapy, anti-metabolics, biological agents including bio-similars and/or any combination thereof and so forth. Such therapies can be administered simultaneously or sequentially (in any order) with the immunotherapy according to the present disclosure.

When co-administered with an additional therapeutic agent, suitable therapeutically effective dosages for each agent may be lowered due to the additive action or synergy.

In some embodiments, the anti-Delta1 antibody can be combined with other immunomodulatory treatments such as, e.g., inhibitors of a checkpoint molecule (e.g., PD-1, PD-L1, PD-L2, CTLA-4, LAG3, TIM-3, A2aR, TIGIT or VISTA), activators of a co-stimulatory receptor (e.g., DX40, GITR, CD137, CD40, CD27, and ICOS), and/or inhibitors of an innate immune cell target (e.g., KIR, NKG2A, CD96, TLR, IDO, and/or galectin-9). Without being bound by theory, it is thought that anti-Delta1 antibodies can reprogram immune responses against tumor cells via, e.g., inhibiting the activity of γδ T cells infiltrated into tumor microenvironment. Thus, combined use of an anti-Delta1 antibody and an immunomodulatory agent such as those described herein would be expected to significantly enhance anti-tumor efficacy.

In some embodiments, the treatment method further comprises administering to the subject an inhibitor of a checkpoint molecule, an activator of a co-stimulatory receptor, and/or an inhibitor of an innate immune cell target. In some embodiments, the treatment method further comprises administering to the subject an inhibitor of a checkpoint molecule. In some embodiments, the checkpoint molecule is selected from the group consisting of PD-1, PD-L1, PD-L2, CTLA-4, LAG3, TIM-3 and A2aR, TIGIT and VISTA. In some embodiments, the treatment method further comprises administering to the subject an inhibitor of an activator of a co-stimulatory receptor, and/or an inhibitor of an innate immune cell target. In some embodiments, the co-stimulatory receptor is selected from the group consisting of OX40, GITR, CD137, CD40, CD27, and ICOS. In some embodiments, the treatment method further comprises administering to the subject an inhibitor of an innate immune cell target. In some embodiments, the innate immune cell target is selected from the group consisting of KIR, NKG2A, CD96, TLR, and IDO. In some embodiments, the anti-Delta1 antibody is selected from Delta1-18, Delta1-19, Delta1-20, Delta1-21, Delta1-22, Delta1-23, Delta1-24, Delta1-25, Delta1-26, Delta1-27, Delta1-28, Delta1-31, Delta1-32, Delta1-33, Delta1-34, Delta1-35, Delta1-36, Delta1-37, Delta1-38, Delta1-39, Delta1-40, Delta1-41, Delta1-42, or Delta1-43, or combinations thereof. A non-limiting example of such antibodies include for example antibody Delta1-23. In any of these methods of treatment, the anti-Delta1 antibody is antibody Delta1-23. In some embodiments, the anti-Delta1 antibody is Delta1-17. In some embodiments, the anti-Delta1 antibody is Delta1-39. In some embodiments, the anti-Delta1 antibody is Delta1-41.

In some examples, the treatment method disclosed herein comprises administering to a human patient having a lung cancer an inhibitor of CTLA-4 (e.g., an anti-CTLA-4 antibody) and any of the anti-Delta 1 antibodies disclosed herein. In other examples, the treatment method disclosed herein comprises administering to a human patient having a skin cancer (e.g., melanoma) an inhibitor of PD-1 (e.g., an anti-PD-1 antibody or an anti-PDL1 antibody) and any of the anti-Delta1 antibodies disclosed herein.

Exemplary anti-CTLA-4 antibodies include ipilimumab. Exemplary anti-PD-1 antibodies include pembrolizumab, nivolumab, cemiplimab, AMP-224, AMP-514, and PDR001. Exemplary anti-PD-L1 antibodies include avelumab, atezolizumab, durvalumab, BMS-936559, and CK-301.

In other embodiments, the anti-Delta1 antibody described herein can also be co-used with a chemotherapeutic agent, including alkylating agents, anthracyclines, cytoskeletal disruptors (Taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents, retinoids, vinca alkaloids and derivatives thereof. Non-limiting examples include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof; and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, nanoparticle albumin-bound paclitaxel (Abraxane®), docetaxel), eribulin, vincristine, vinblastine, nocodazole, epothilones, and navelbine, epidipodophyllotoxins (etoposide and teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycin, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, mitoxantrone, topotecan, irinotecan (e.g., irinotecan liposome injections such as Onivyde®), corticosteroids (cortisone, dexamethasone, hydrocortisone, methylprednisolone, prednisone, and prednisolone); growth factor signal transduction kinase inhibitors; nucleotide analog and thymidine phosphorylase inhibitors (e.g., trifluridine-tipiracil or Lonsurf®); mitochondrial dysfunction inducers and caspase activators; and chromatin disruptors. The therapeutic agents described herein include any drug products containing the listed active ingredients and derivatives thereof, as well as any formulations (e.g., sustained release formulations) including those known in the art.

Alternatively or in addition, the anti-Delta1 antibody described herein can also be co-used with an anti-hypertension agent, which includes, but is not limited to, angiotensin-converting enzyme (ACE) inhibitors (e.g., benazepril, captopril, enalapril, fosinopril, Lisinopril, moexipril, perindopril, quinapril, ramipril, or trandolapril), angiotensin II receptor blockers (a.k.a. ARBs or Sartans, e.g., azilsartan, candesartan, eprosartan, irbesartan, telmisartan, valsartan, losartan, or olmesartan), beta blockers (e.g., p1-selective agents such as acebutolol, atenolol, betaxolol, bisoprolol, celiprolol, metoprolol, nebivolol; p2-selective agents such as butaxamine or ICI-118,551; p3-selective agents such as SR 59230A; and non-selective agents such as propranolol, bucindolol, carteolol, carvedilol, labetalol, nadolol, oxprenolol, penbutolol, pindolol, sotalol, timolol) calcium channel blockers (e.g., amlodipine, diltiazem, felodipine, isradipine, nicardipine, nifedipine, nisoldipine, or verapamil), direct renin inhibitors (e.g., aliskiren), or diuretics. See, also US20130287688, and Pinter et al., Sci Transl Med (2017) 9(410).

Additional useful agents can be found in, e.g., Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

It was reported that chemotherapy and/or immune therapy of solid tumors could enhance the level of immune modulators such as checkpoint molecules, resulting in suppressed immunity against tumor cells. Erisson et al., *J. Translational Medicine* (2016), 14:282; Grabosch et al., *J. Immuno-Therapy of Cancer* (2015), 3(suppl 2): P302; and Azad et al., EMBO J. (2016). Anti-Delta1 antibodies have been found to inhibit the activity of γδ T cells, leading to increased T cell activation, particularly in solid tumors. As such, the co-use of an anti-Delta1 antibody and a chemotherapeutic agent (e.g., gemcitabine) or immunotherapeutic agent (e.g., anti-PD-L1 antibody) would be expected to result in significantly enhanced therapeutic activity against solid tumors, such as PDA or CRC.

In some embodiments, the methods are provided, wherein the anti-Delta1 antibody described herein is capable of improving anti-tumor activity of the co-administered checkpoint inhibitors. In some embodiments, the methods are provided, wherein the anti-Delta1 antibody, such as any of the anti-Delta1 antibodies described herein in Table 1 and elsewhere, such as Delta1-23, is capable of improving anti-tumor activity, i.e., efficacy (reducing tumor proliferation, size, volume, weight, burden or load or reduction in number of metastatic lesions over time, improving stable disease, improved survival rate) of the co-administered checkpoint inhibitors (e.g., PD-1, PD-L1 and/or CTLA-4 or others listed herein or known in the art), e.g., by 10%, 20%, 25%, 30%, 40%, 50%, 60%, 70%, 75%, 80%, 85%, 90%, 95%, or more as compared to a checkpoint inhibitor therapy alone under the same conditions. In some embodiments, the anti-Delta1 antibody, such as any of the anti-Delta1 antibodies described herein in Table 1 and elsewhere, for example Delta1-23, is capable of improving anti-tumor activity, i.e., efficacy (reducing tumor proliferation, size, volume, weight, burden or load or reduction in number of metastatic lesions over time, improving stable disease, improved survival rate) of the co-administered checkpoint inhibitors (e.g., PD-1 and/or CTLA-4 e.g., PD-1, PD-L1 and/or CTLA-4 or others listed herein or known in the art), e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to a checkpoint inhibitor therapy alone under the same conditions.

In some embodiments, the co-administered checkpoint inhibitors (e.g., PD-1, PD-L1 and/or CTLA-4 or others listed herein or known in the art) are capable of improving anti-tumor activity of the anti-Delta1 antibody described herein. In some embodiments, the co-administered checkpoint inhibitors (e.g., PD-1, PD-L1 and/or CTLA-4 or others listed herein or known in the art) are capable of improving anti-tumor activity of the anti-Delta1 antibody, such as any of the anti-Delta1 antibodies described herein in Table 1 and elsewhere, including but not limited to Delta1-23, anti-tumor activity, i.e., efficacy (reducing tumor proliferation, size, volume, weight, burden or load or reduction in number of metastatic lesions over time, improving stable disease, improved survival rate), e.g., by 10%, 20%, 25%, 30%, 40%, 50%, 60%, 70%, 75%, 80%, 85%, 90%, 95%, or more as compared to anti-Delta1 therapy alone under the same conditions. In some embodiments, the co-administered checkpoint inhibitors (e.g., PD-1, PD-L1 and/or CTLA-4 or others listed herein or known in the art) are capable of improving anti-tumor activity, i.e., efficacy (reducing tumor proliferation, size, volume, weight, burden or load or reduction in number of metastatic lesions over time, improving stable disease, improved survival rate) of the anti-Delta1 antibody, such as any of the anti-Delta1 antibodies described herein in Table 1 and elsewhere, including but not limited to Delta1-23, e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to an anti-Delta1 therapy alone under the same conditions.

In some embodiments, the methods are provided, wherein the anti-Delta1 antibody described herein is capable of improving the ability of the immunotherapy to activate T cells. In some embodiments, the methods are provided, wherein the anti-Delta1 antibody, such as any of the anti- Delta1 antibodies described herein in Table 1 and elsewhere, including but not limited to, Delta1-23, Delta1-41, and Delta1-39, is capable of improving the ability of the immunotherapy to activate T cells (e.g., as measured by cytokine markers described herein) (e.g., as described herein or known in the art), e.g., by 10%, 20%, 25%, 30%, 40%, 50%, 60%, 70%, 75%, 80%, 85%, 90%, 95%, or more as compared to a immunotherapy therapy alone under the same conditions. In some embodiments, the anti-Delta1 antibody is capable of improving the ability of the immunotherapy to activate T cells (e.g., as measured by cytokine markers described herein) (e.g., as described herein or known in the art), e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to a immunotherapy therapy alone under the same conditions.

In some embodiments, the methods are provided, wherein the co-administered immunotherapies are capable of improving the ability of the anti-Delta1 antibody described herein to activate T cells. In some embodiments, the methods are provided, wherein the co-administered immunotherapies (e.g., as described herein or known in the art) are capable of improving the ability of the anti-Delta1 antibody, such as any of the anti-Delta1 antibodies described herein in Table 1 and elsewhere, including but not limited to, Delta1-23, Delta1-41, and Delta1-39, to activate T cells (e.g., as measured by cytokine markers described herein), e.g., by 10%, 20%, 25%, 30%, 40%, 50%, 60%, 70%, 75%, 80%, 85%, 90%, 95%, or more as compared to an anti-Delta1 therapy alone under the same conditions. In some embodiments, the co-administered immunotherapies (e.g., as described herein or known in the art) are capable of improving the ability of the anti-Delta1 antibody to activate T cells (e.g., as measured by cytokine markers described herein), e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to an anti-Delta1 therapy alone under the same conditions.

In some embodiments, the methods are provided, wherein the anti-Delta1 antibody is capable of improving anti-tumor activity of the co-administered chemotherapeutic and/or other anti-cancer agents. In some embodiments, the methods are provided, wherein the anti-Delta1 antibody, such as any of the antibodies described herein in Table 1 and elsewhere, for example Delta1-23, is capable of improving anti-tumor activity, i.e., efficacy (reducing tumor proliferation, size, volume, weight, burden or load or reduction in number of metastatic lesions over time, improving stable disease, improved survival rate) of the co-administered chemotherapeutic agents (e.g., as described herein or known in the art), e.g., by 10%, 20%, 25%, 30%, 40%, 50%, 60%, 70%, 75%, 80%, 85%, 90%, 95%, or more as compared to a chemotherapeutic agent therapy alone under the same conditions. In some embodiments, the anti-Delta1 antibody is capable of improving anti-tumor activity, i.e., efficacy (reducing tumor proliferation, size, volume, weight, burden or load or reduction in number of metastatic lesions over time, improving stable disease, improved survival rate) of the co-administered chemotherapeutic agents (e.g., as described herein or known in the art), e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to a chemotherapeutic agent therapy alone under the same conditions.

In some embodiments, the anti-Delta1 antibody is administered as a maintenance therapy.

In some embodiments, the methods are provided, wherein the co-administered chemotherapeutic agents are capable of improving anti-tumor activity of the anti-Delta1 antibody. In some embodiments, the methods are provided, wherein the co-administered chemotherapeutic agents (e.g., as described herein or known in the art) are capable of improving anti-tumor activity of the anti-Delta1 antibody, such as any of the antibodies described herein in Table 1 and elsewhere, for example Delta1-23, (reducing tumor proliferation, size, volume, weight, burden or load or reduction in number of metastatic lesions over time, improving stable disease, improved survival rate) by, e.g., by 10%, 20%, 25%, 30%, 40%, 50%, 60%, 70%, 75%, 80%, 85%, 90%, 95%, or more as compared to an anti-Delta1 therapy alone under the same conditions. In some embodiments, the co-administered chemotherapeutic agents (e.g., as described herein or known in the art) are capable of improving anti-tumor activity, i.e., efficacy (e.g., reducing tumor proliferation, size, volume, weight, burden or load or reduction in number of metastatic lesions over time, improving stable disease, improved survival rate) of the anti-Delta1 antibody, e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to an anti-Delta1 therapy alone under the same conditions.

In some embodiments methods are provided herein, wherein the anti-Delta1 antibody is capable of improving the ability of the chemotherapeutic agent to activate T cells. In some embodiments methods are provided herein, wherein the anti-Delta1 antibody, such as any of the antibodies described herein in Table 1 and elsewhere, for example Delta1-23, Delta1-17, Delta1-39, or Delta1-41, is capable of improving the ability of the chemotherapeutic agent to activate T cells (e.g., as measured by cytokine markers described herein) (e.g., as described herein or known in the art), e.g., by 10%, 20%, 25%, 30%, 40%, 50%, 60%, 70%, 75%, 80%, 85%, 90%, 95%, or more as compared to a chemotherapeutic agent therapy alone under the same conditions. In some embodiments, the anti-Delta1 antibody is capable of improving the ability of the chemotherapeutic agent to activate T cells (e.g., as measured by cytokine markers described herein) (e.g., as described herein or known in the art e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to a chemotherapeutic agent therapy alone under the same conditions.

In some embodiments, methods are provided herein, wherein the co-administered chemotherapeutic agents are capable of improving the ability of the anti-Delta1 antibody to activate T cells. In some embodiments, methods are provided herein, wherein the co-administered chemotherapeutic agents (e.g., as described herein or known in the art) are capable of improving the ability of the anti-Delta1 antibody, such as any of the antibodies described herein in Table 1 and elsewhere, for example Delta1-23, Delta1-17, Delta1-39, or Delta1-41, to activate T cells (e.g., as measured by cytokine markers described herein), e.g., by 10%, 20%, 25%, 30%, 40%, 50%, 60%, 70%, 75%, 80%, 85%, 90%, 95%, or more as compared to an anti-Delta1 therapy alone under the same conditions. In some embodiments, the co-administered chemotherapeutic agents (e.g., as described herein or known in the art) are capable of improving the ability of the anti-Delta1 antibody to activate T cells (e.g., as measured by cytokine markers described herein), e.g., 1.0-1.2-fold, 1.2-1.4-fold, 1.4-1.6-fold, 1.6-1.8-fold, 1.8-2-fold, or two-fold, three-fold, four-fold, ten-fold more or more as compared to an anti-Delta1 therapy alone under the same conditions.

In any of these combination therapy methods the cancer to be treated is selected from Examples of solid tumor cancers include pancreatic duct adenocarcinoma (PDA), colorectal cancer (CRC), melanoma, breast cancer, lung cancer (for example, non-small cell lung cancer, NSCLC, and small cell lung cancer, SCLC), glioblastoma, upper and lower gastrointestinal malignancies (including, but not limited to, esophageal, gastric, colorectal, pancreatic, bile duct (cholangiocarcinoma), and hepatobiliary cancer), squamous cell head and neck cancer, genitourinary cancers, endometrial cancer, renal cancer, bladder cancer, prostate cancer, ovarian cancer, neuroendocrine cancer (carcinoid and pancreatic neuroendocrine tumors), adrenocortical cancer, and sarcomas. Hematological malignancies include acute lymphoblastic leukemia, chronic lymphocytic leukemia, lymphomas, multiple myeloma, acute myelogenous leukemia, chronic myelogenous leukemia, myelodysplastic syndromes and the myeloproliferative neoplasms, such as essential thrombocythemia, polycythemia vera and myelofibrosis, and others described herein.

Other Applications

Any of the anti-Delta1 antibodies described herein may also be used for detecting presence of $\gamma\delta1$ T cells and/or measuring the level of $\gamma\delta1$ T cells in a sample, such as a biological sample, using a conventional immunoassay (e.g., Western blotting, FACS, immunohistochemistry, immunocytochemistry, etc.). Briefly, the antibody can be incubated with a sample for a suitable period of time under suitable conditions allowing for binding of the antibody to the target $\gamma\delta1$ if present in the sample. Such a binding can then be detected using a conventional method, for example, using a labeled second antibody that binds the anti-Delta1 antibody. Performing such an immunoassay for detecting the target $\gamma\delta1$ TCR or T cells expressing such a TCR is well within the knowledge of those skilled in the art.

Also provided herein are methods for identifying a cancer patient and methods for selecting a cancer patient for immunotherapy, e.g. an immunotherapy comprising administering to the subject an anti-Delta1 antibody, and optionally treating the cancer patient. In some embodiments, the identification is based on levels of Delta1 measured in a subject, e.g., in a biological sample from the subject. In some embodiments, Delta1 levels are measured in serum or plasma of a patient. In some embodiments, Delta1 levels are measured in a biological sample from the patient, e.g., a tumor or tumor derived organoids. In some embodiments, Delta1 levels are measured using an antibody, e.g., as described herein, including but not limited to Delta1-39. In some embodiments a different antibody known in the art is used to detect Delta1 in the sample.

Accordingly, in some embodiments, the method comprises: (i) providing a biological sample of a subject, e.g., a human subject, in need thereof, (ii) measuring the level of Delta1 in the biological sample, and (iii) identifying the subject as having a cancer or being at risk for the cancer based on the level of Delta1 in the biological sample. In some embodiments, the elevated level of Delta1 in the biological sample of the subject is relative to a control and indicates that the subject has the cancer or is at risk for the cancer. In some embodiments, the elevated level of Delta1 in the biological sample of the subject is relative to a control and indicates the subject may be a suitable cancer patient for immunotherapy, e.g. an immunotherapy comprising administering to the subject an anti-Delta1 antibody. In some embodiments, the control comprises a biological sample from a subject without cancer. In some embodiments, the control comprises a pre-determined reference value or range of values. In some embodiments, the biological sample is a serum sample or a plasma sample. In some embodiments, other diagnostic tests known in the art are used in conjunction with the method. In some embodiments, the control is a reference value, i.e. a range which is established and which reflects a range of Delta1 in healthy people. Accordingly, levels higher than the reference values be indicative of an increased level.

Accordingly, in some embodiments, the method comprises: (i) providing a blood sample of a subject, e.g., a human subject, in need thereof, (ii) measuring the level of Delta1 in the blood sample, and (iii) identifying the subject as having a cancer or being at risk for the cancer based on the level of Delta1 in the blood sample. In some embodiments, the elevated level of Delta1 in the blood sample of the subject is relative to a control and indicates that the subject has the cancer or is at risk for the cancer. In some embodiments, the elevated level of Delta1 in the blood sample of the subject is relative to a control and indicates the subject may be a suitable cancer patient for immunotherapy, e.g. an immunotherapy comprising administering to the subject an anti-Delta1 antibody. In some embodiments, the control comprises a blood sample from a subject without cancer. In some embodiments, the control comprises a pre-determined reference value or range of values. In some embodiments, the blood sample is a serum sample or a plasma sample. In some embodiments, other diagnostic tests known in the art are used in conjunction with the method. In some embodiments, the control is a reference value, i.e. a range which is established and which reflects a range of Delta1 in healthy people. Accordingly, levels higher than the reference values be indicative of an increased level.

In some embodiments, the methods comprise (i) providing a biopsy sample of a subject, e.g., a human subject, in need thereof, (ii) measuring the level of Delta1 in the biopsy sample from a subject or in a sample derived from a biological sample of a subject, e.g., patient-derived organotypic tumor spheroids (PDOTs), single cell tumor suspensions, e.g., prepared as described herein, and (iii) identifying the subject as having a cancer or being at risk for the cancer based on the level of Delta1 in the sample. In some embodiments, the elevated level of Delta1 in the sample of the subject is relative to a control and indicates that the subject has the cancer or is at risk for the cancer. In some embodiments, the elevated level of Delta1 in the biological sample, e.g. biopsy sample of the subject is relative to a control and indicates the subject may be a suitable cancer patient for immunotherapy, e.g. an immunotherapy comprising administering to the subject an anti-Delta1 antibody. In some embodiments, the control is cancer negative tissue from the same subject. In some embodiments, the control is a reference value or range of values. In some embodiments, the control is derived from a healthy subject. In some embodiments, the measuring involves determining levels of Delta1 protein or gene expression, e.g., mRNA levels. In some embodiments, the measuring involves detecting Delta1 protein, e.g., e.g., using one or more anti-Delta1 antibodies described herein, including but not limited to, Delta1-39.

In another aspect, provided herein are methods for predicting the responsiveness of a cancer patient to anti-Delta1 immunotherapy. Accordingly, in some embodiments, the methods comprise (i) determining the level of Delta1 in a biological sample, e.g., blood plasma, serum, biopsy or biopsy derived samples, e.g., PDOTs, single cell tumor suspensions, or other tissue, from the patient; (ii) comparing the level of Delta1 in the biological sample with a control level, wherein levels of Delta1 in the biological sample above the control level is indicative that the patient is likely to respond to anti-Delta1 immunotherapy and levels below the control level is indicative that the patient is unlikely to respond to anti-Delta1 immunotherapy (iii) if the levels of Delta1 are above the control level, then predicting the patient is responsive to anti-Delta1 immunotherapy. In some embodiments, the control level corresponds to the levels observed in blood or tissue from a healthy subject. In some embodiments, the control level corresponds to the levels observed in tumor adjacent healthy tissue of the subject having cancer. In some embodiments, other diagnostic tests known in the art are used in conjunction with the method.

In another aspect, provided herein are methods for predicting the responsiveness of a cancer patient to anti-Delta1 immunotherapy. Accordingly, in some embodiments, the methods comprise (i) using an anti-Delta1 antibody to determine the level of Delta1 in a biological sample, e.g., blood plasma, serum, biopsy or biopsy derived samples, e.g., PDOTs, single cell tumor suspensions, or tissue, from the patient; (ii) using an anti-Delta1 antibody to compare the level of Delta1 in the biological sample with a control level, wherein levels of Delta1 above the control level is indicative that the patient is likely to respond to anti-Delta1 immunotherapy and levels below the control level is indicative that the patient is unlikely to respond to anti-Delta1 immunotherapy (iii) if the levels of Delta1 are above the control level, then predicting the patient is responsive to anti-Delta1 immunotherapy. In some embodiments, the anti-Delta1 antibody is any of the anti-Delta1 antibodies provided herein, including but not limited to, Delta1-39. In some embodiments, the antibody is a different antibody known in the art. In some embodiments, Delta1 levels are determined using flow cytometry, e.g., using any of the anti-Delta1 antibodies provided herein, including but not limited to, Delta1-39. In some embodiments, Delta1 levels are determined using flow cytometry, e.g., using a different antibody known in the art. In some embodiments, Delta1 levels are determined using immunohistochemistry, e.g., using a Delta1 antibody described herein or a different antibody known in the art. In some embodiments, the control level corresponds to the levels observed in blood or tissue from a healthy subject. In some embodiments, the control level corresponds to the levels observed in tumor adjacent healthy tissue of the subject having cancer. In some embodiments, other diagnostic tests known in the art are used in conjunction with the method.

In another aspect, provided herein are methods for treating a cancer patient having a predicted responsiveness to anti-Delta1 immunotherapy. Accordingly, in some embodiments, the methods comprise (i) determining the level of Delta1 in a biological sample, e.g., blood plasma, serum, biopsy or biopsy derived samples, e.g., PDOTs, single cell tumor suspensions, or other tissue, from the patient; (ii) comparing the level of Delta1 in the biological sample with a control level, wherein the level of Delta1 in the biological sample above the control level is indicative that the patient is likely to respond to anti-Delta1 immunotherapy and levels below the control level is indicative that the patient is unlikely to respond to anti-Delta1 immunotherapy (iii) if the levels of Delta1 are above the control level, then predicting the patient is responsive to anti-Delta1 immunotherapy and (iv) if the patient is predicted to be responsive to anti-Delta1 immunotherapy, then treating the cancer patient. In some embodiments, the treatment comprises administering an anti-Delta1 antibody, e.g., any of the anti-Delta1 antibodies provided herein. In some embodiments, the treatment comprises administering Delta1-39. In some embodiments, the control level corresponds to the levels observed in blood or tissue from a healthy subject. In some embodiments, the control level corresponds to the levels observed in tumor adjacent healthy tissue of the subject having cancer. In some embodiments, other diagnostic tests known in the art are used in conjunction with the method. In some embodiments, Delta1 levels are determined using flow cytometry, e.g., using any of the anti-Delta1 antibodies provided herein, including but not limited to, Delta1-39.

Kits for Use in Treatment of Diseases Associated with γδ T Cell Activation

The present disclosure also provides kits for use in treating or alleviating a disease associated with γδ T cell activation. Examples include solid tumors such as PDA and others described herein. Such kits can include one or more containers comprising an anti-Delta1 antibody, e.g., any of those described herein, and optionally a second therapeutic agent to be co-used with the anti-Delta1 antibody, which is also described herein.

In some embodiments, the kit can comprise instructions for use in accordance with any of the methods described herein. The included instructions can comprise a description of administration of the anti-Delta1 antibody, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-Delta1 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease associated with γδ T cell activation. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-Delta1 antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation of Anti-Delta1 Antibodies

Antigen Production

Expression vectors for the gamma and delta chains of human and cynomolgus T cell receptors (TCR) fused to the Fc portion of mouse immunoglobulin G (IgG) were constructed using standard recombinant DNA methods. To make purification and immobilization more efficient, the expression vectors for the delta chains were further modified to include an AviTag™ and a His6 tag attached to the C-terminus of the Fc portion. Expression vectors for six different delta1 clones (human Delta1A (SEQ ID NO: 26), human Delta1B (SEQ ID NO: 27), human Delta1C (SEQ ID NO: 28), cynomolgus monkey Delta1A (SEQ ID NO: 32), cynomolgus monkey Delta1B (SEQ ID NO: 33), and cynomolgus monkey Delta1C (SEQ ID NO: 34)), four delta2 clones (human Delta2A (SEQ ID NO: 29), human Delta2B (SEQ ID NO: 35), human Delta2C (SEQ ID NO: 36), and cynomolgus monkey Delta2 (SEQ ID NO: 37)), and six gamma9 clones (human Gamma9 (SEQ ID NO: 30), human Gamma3 (SEQ ID NO: 38), human Gamma4 (SEQ ID NO: 39), human Gamma5 (SEQ ID NO: 40), human Gamma8 (SEQ ID NO: 41), cynomolgus monkey gamma (SEQ ID NO: 42)) were generated. The amino acid sequences of the extracellular region of the Delta1 chains are provided above and the amino acid sequences of the Delta2 and Gamma chains are given below. Mammalian cells were transfected with the vector for a delta chain clone (one of the 10 vectors described above) and a vector for the gamma chain (one of six gamma chains) to produce gamma/delta heterodimers. The resulting gamma/delta TCR-Fc fusion protein was extracted from the culture supernatant and purified using Ni Sepharose® chromatography followed by in vitro using recombinant BirA and gel filtration to apparent homogeneity.

Human TCR Delta2A:
(SEQ ID NO: 29)
AIELVPEHQTVPVSIGVPATLRCSMKGEAIGNYYINWYRKTQGNTMTFI

YREKDIYGPGFKDNFQGDIDIAKNLAVLKILAPSERDEGSYYCACDTLG

MGGEYTDKLIFGKGTRVTVEPRSQPHTKPSVFVMKNGTNVACLVKEFYP

KDIRINLVSSKKITEFDPAIVISPSGKYNAVKLGKYEDSNSVTCSVQHD

NKTVHSTDFEVKTDSTDHVKPKETENTKQPSKS

Human TCR Delta2B:
(SEQ ID NO: 35)
AIELVPEHQTVPVSIGVPATLRCSMKGEAIGNYYINWYRKTQGNTMTFI

YREKDIYGPGFKDNFQGDIDIAKNLAVLKILAPSERDEGSYYCACDTSS

SSGTDKLIFGKGTRVTVEPRSQPHTKPSVFVMKNGTNVACLVKEFYPKD

IRINLVSSKKITEFDPAIVISPSGKYNAVKLGKYEDSNSVTCSVQHDNK

TVHSTDFEVKTDSTDHVKPKETENTKQPSKS

Human TCR Delta2C:
(SEQ ID NO: 36)
AIELVPEHQTVPVSIGVPATLRCSMKGEAIGNYYINWYRKTQGNTMTFI

YREKDIYGPGFKDNFQGDIDIAKNLAVLKILAPSERDEGSYYCACDILG

DKGNTDKLIFGKGTRVTVEPRSQPHTKPSVFVMKNGTNVACLVKEFYPK

DIRINLVSSKKITEFDPAIVISPSGKYNAVKLGKYEDSNSVTCSVQHDN

KTVHSTDFEVKTDSTDHVKPKETENTKQPSKS

Cynomolgus Monkey TCR Delta2:
(SEQ ID NO: 37)
AVELVPEHQTVIVSVGDPATLKCSMKGEAISNYYINWYRKTQGNTMTFI

YREKGIYGPGFKDNFQGDIDTEENQAVLKILAPSERDEGSYYCASDILS

WVDSYTDKLIFGKGTRVTVEPKRQPHTKPSVFVMKNGTNVACLVKDFYG

KDIRINLESSKKITEFDPAIVVSPSGKYNAVKLGQYADSNSVTCSVQHN

KEVVYSTDFEVKTNSTDHLKPTETENTKQPSKS

Human TCR Gamma3:
(SEQ ID NO: 38)
SSNLEGRTKSVTRQTGSSAEITCDLTVTNTFYIHWYLHQEGKAPQRLLY

YDVSTARDVLESGLSPGKYYTHTPRRWSWILRLQNLIENDSGVYYCATW

-continued

DRPLNAWIKTFAKGTRLIVTSPDKQLDADVSPKPTIFLPSIAETKLQKA

GTYLCLLEKFFPDVIKIHWQEKKSNTILGSQEGNTMKTNDTYMKFSWLT

VPEKSLDKEHRCIVRHENNKNGVDQEIIFPPIKTDVITMDPKDN

Human TCR Gamma4:
(SEQ ID NO: 39)
SSNLEGRTKSVIRQTGSSAEITCDLAEGSTGYIHWYLHQEGKAPQRLLY

YDSYTSSVVLESGISPGKYDTYGSTRKNLRMILRNLIENDSGVYYCATW

DEKYYKKLFGSGTTLVVTDKQLDADVSPKPTIFLPSIAETKLQKAGTYL

CLLEKFFPDVIKIHWQEKKSNTILGSQEGNTMKTNDTYMKFSWLTVPEK

SLDKEHRCIVRHENNKNGVDQEIIFPPIKTDVITMDPKDN

Human TCR Gamma5:
(SEQ ID NO: 40)
SSNLEGGTKSVTRPTRSSAEITCDLTVINAFYIHWYLHQEGKAPQRLLY

YDVSNSKDVLESGLSPGKYYTHTPRRWSWILILRNLIENDSGVYYCATW

DRLRKKLFGSGTTLVVTDKQLDADVSPKPTIFLPSIAETKLQKAGTYLC

LLEKFFPDVIKIHWQEKKSNTILGSQEGNTMKTNDTYMKFSWLTVPEKS

LDKEHRCIVRHENNKNGVDQEIIFPPIKTDVITMDPKDN

Human TCR Gamma8:
(SEQ ID NO: 41)
SSNLEGRTKSVTRPTGSSAVITCDLPVENAVYTHWYLHQEGKAPQRLLY

YDSYNSRVVLESGISREKYHTYASTGKSLKFILENLIERDSGVYYCATW

DWGKKLFGSGTTLVVTDKQLDADVSPKPTIFLPSIAETKLQKAGTYLCL

LEKFFPDVIKIHWQEKKSNTILGSQEGNTMKINDTYMKFSWLTVPEKSL

DKEHRCIVRHENNKNGVDQEIIFPPIKTDVITMDPKDN

Human TCR Gamma9:
(SEQ ID NO: 30)
AGHLEQPQISSTKTLSKTARLECVVSGITISATSVYWYRERPGEVIQFL

VSISYDGTVRKESGIPSGKFEVDRIPETSTSTLTIHNVEKQDIATYYCA

LWEAQQELGKKIKVFGPGTKLIITDKOLDADVSPKPTIFLPSIAETKLQ

KAGTYLCLLEKFFPDVIKIHWEEKKSNTILGSQEGNTMKINDTYMKFSW

LTVPEKSLDKEHRCIVRHENNKNGVDQEIIFPPIKTDVITMDPKDN

Cynomolgus Monkey TCR Gamma:
(SEQ ID NO: 42)
AGHLEQPQISSTKMLSKTARLECVVSGVTISETSIYWYRERPGEVIQFL

VCIFYDGTVKKESSIPSGKFEVDRIPKTSTSTLTIHNVEKQDIATYYCA

LWEVQQFGRKVKLFGPGTKLIITDKHLDADVSPKPTIFLPSIAETNLHK

AGTYLCLLENFFPDVIKIHWQEKKSNTILGSQEGNTVKINDTYMKFSWL

TVPEKSLDKEHRCIVRHENNKNGVDQEIIFPPIKTDVTTMDPKDN

Synthetic Antibody Generation

Antibody clones having intended binding specificity were isolated from a phage-display library in the Fab format, following the design of an earlier-described library (Miller et al., *PloS One.* 2012, 7:e43746) with improvements. Phage library sorting was performed essentially following published procedures (Miller et al., *PloS One.* 2012, 7:e43746; Fellouse et al., *J Mol Biol.* 2007, 373:924-940). To enrich clones binding to the common regions of the delta1 chain, TCR samples consisting of different delta1 chains were used in successive rounds of library sorting. To eliminate clones binding to the delta2 chain or gamma chain, negative sorting using the sample consisting of the delta2 chain was also incorporated. To eliminate clones binding to the Fc portion of the TCR construct, the purified Fc was used as a competitor during sorting. Four rounds of phage selection were performed.

Binding to TCR clones was determined by phage ELISA (Sidhu et al., *Methods Enzymol.* 2000, 328:333-363). Biotinylated TCR samples ("targets"; TCR (Delta1A/Gamma9), TCR (Delta1B/Gamma9), TCR (Delta1C/Gamma9), TCR (Delta2/Gamma9) or Fc) were immobilized to neutravidin-coated wells and blocked with an excess of biotin. The wells were incubated with phages displaying single Fab clones. Bound phages were detected with HRP-conjugated anti-M13 phage antibody.

Affinity Maturation

In order to improve the affinity and cross-species reactivity (human and cynomolgus TCRs) of the Fab clones, yeast surface display was used to construct libraries, which were then quantitatively sorted, by essentially following published procedures (Boder et al., *Nat Biotechnol.* 1997; 15:553-7; Koide et al., *J Mol Biol.* 2007; 373:941-53).

Briefly, CDR-H3 affinity maturation was performed using Delta1-17 as a parent clone. Delta1-30 was identified from the CDR-H3 affinity maturation, which contains a S→M mutation in the CDR-H3 relative to Delta1-17. Delta1-30 was converted into a single-chain Fv (scFv) format, which was fused to the yeast Aga2 protein and a V5 tag and placed under the control of the Pgal promoter. CDR-L2 was converted into the predicted germline sequence derived from alignments with entries in the NCBI Germline (www.ncbi.nlm.nih.gov/igblast/) and V-BASE (www2.mrc-lmb.cam.ac.uk/vbase/) giving rise to Delta1-29. Then, sequence diversity as described in (Miller et al., *PloS One,* 2012;7:e43746. PMCID: 3423377), was introduced into the CDR-L3. The biotinylated TCR targets were conjugated to DyLight 650 labeled streptavidin (Thermo Fisher Scientific) and used for library sorting and binding assay by flow cytometry. Clones of Delta1-18 to Delta1-28 and Delta1-31 were identified via yeast display for their activity of binding to Delta 1. The amino acid sequences of their $V_H$ and $V_L$ chains ($V_H/V_L$) are provided above. Subsequently, sequence diversity was introduced into the CDR-H1 portion of Delta1-23. Affinity maturation was carried out as above giving rise to Delta1-32 to Delta1-43.

IgG Protein Production

The genes for the antibody clones described above were transferred into mammalian expression vectors for human IgG production. The proteins were produced by transient transfection of ExpiCHO or Expi293 cells (ThermoFisher) and purified using Protein G Sepharose chromatography followed by Superdex S200 or ResourceS chromatography (GE Healthcare).

Example 2: Characterization of Anti-Delta1 Antibody Clones

Affinity Measurements

The affinity of the antibodies was assessed using surface plasmon resonance (SPR). A biotinylated TCR sample was immobilized on an Avicap chip (Pall ForteBio) that had been preloaded with neutravidin (ThermoFisher). IgG samples were flowed using the OneStep method on a Pioneer SPR instrument (Pall ForteBio). The analyzed IgG samples had dissociation constant ($K_D$) values in the low nanomolar range to their respective targets (FIG. 10A). In some cases, bio-layer interferometry (BLI) was used to measure affinity. Similarly, biotinylated TCR samples were immobilized on the streptavidin sensors and incubated with antibody in solution (FIGS. 22A and 22B).

Alternatively, the affinity was assessed using bead-binding assay, as described previously (Nishikori S, Hattori T, Fuchs S M, Yasui N, Wojcik J, Koide A, Strahl B D, Koide S. Broad ranges of affinity and specificity of anti-histone antibodies revealed by a quantitative Peptide immunoprecipitation assay. *J Mol Biol.* 2012; 424:391-9. PMCID: 3502729). A biotinylated TCR sample was immobilized on a streptavidin-coated beads (Thermo Fisher) and the beads were incubated with various concentrations of an IgG sample. After washing, IgG bound to the beads were stained with fluorescently labeled secondary antibody and quantified using a flow cytometer (e.g., FIGS. 6, 7, 9) and others).

KD values are shown in Table 2.

TABLE 2

Apparent dissociation constants for cyno and human delta1 TCRs of identified antibody clones in the IgG format as determined using the bead binding assay

| Clone | $K_D$ apparent (nM) for cyno delta1 TCR | $K_D$ apparent (nM) for human delta1 TCR |
| --- | --- | --- |
| Delta1-17 | 13.7 | 0.16 |
| Delta1-18 | 0.15 | 1.73 |
| Delta1-19 | 0.25 ± 0.04 | 0.35 ± 0.15 |
| Delta1-20 | 0.34 | 5.46 |
| Delta1-21 | 1.74 ± 0.15 | 3.1 ± 0.3 |
| Delta1-22 | 0.61 ± 0.07 | 2.0 ± 0.3 |
| Delta1-23 | 1.3 ± 0.3 | 1.82 ± 0.11 |
| Delta1-24 | 1.16 | 10.2 |
| Delta1-25 | 0.48 ± 0.06 | 3.90 ± 0.12 |
| Delta1-26 | 0.26 ± 0.03 | 0.98 ± 0.18 |
| Delta1-27 | 0.78 | 9.6 |
| Delta1-28 | 0.36 ± 0.12 | 2.2 ± 0.2 |
| Delta1-29 | 30.4 | 0.63 |
| Delta1-41 | 2.7 | 4.9 |
| Delta1-39 | 0.28 | 0.23 |

Errors shown are s.d from triplicate experiments. Where no error is shown, the measurement was done once. Biotinylated TCR samples were immobilized on streptavidin-coated beads, and the antibodies were titrated and their binding was quantified using flow cytometry.

Cell Based Analysis for Delta1 Vs Delta2 Specificity

The specificity of anti-Delta1 antibody Delta1-17 to Delta1 relative to Delta2 was examined. Three different Delta1 variants, differing from each other only in the CDR3 loop, were produced (D1A, D1B, D1C). Delta1 and Delta2 Fc fusion proteins were attached to streptavidin-coated beads and binding titrations were performed using Delta1-17 hIgG1. As shown in FIG. 10B, Delta1-17 is highly specific to Delta1 (all three variants) and does not cross-react with Delta2. Similar specificity was observed for Delta1-41. As shown in FIG. 10D, Delta1-41 is highly specific to Delta1 as relative to Delta2.

Cell Based Analysis of Gamma Binding

The effect of different Gamma chains on anti-Delta1 antibody binding was examined. Fc fusion proteins containing Gamma 3, 4, 5, 8, and 9 were generated and attached to streptavidin-coated beads. Binding titrations were performed using anti-Delta1-17 antibody. As shown in FIG. 11A, anti-Delta1-17 binding is Gamma-independent; that is, the binding is Delta1-specific, regardless of the Gamma chain used in the δγ TCRs.

The effect of different Gamma chains on anti-Delta1 antibody binding was examined using binding titrations performed with anti-Delta1-39 antibody. Fc fusion proteins containing Gamma 3, 4, 5, 8, and 8 were generated and attached to streptavidin-coated beads. As shown in FIG. 23, anti-Delta1-39 binding was also Gamma-independent.

J.RT3-T3.5 (ATCC® TIB-153) cell lines were virally transduced to express the various Delta and Gamma combinations shown in FIG. 11B. The TIB153 cell line was used as a negative control, as it is a Jurkat cell line that does not express CD3 or any TCR. Accordingly, it can be used to confirm that there is no background binding to any other cell surface receptors found on T cells. These cells were stained with commercial anti-human CD3 FITC (clone UCHT1, Biolegend #300440), anti-human Delta1 APC (clone TS8.2, eBioscience #17-5679-42), and anti-human TCR Gamma/Delta Alexa Fluor 647 (clone B1, Biolegend #331214). Anti-human IgG Fc APC (clone M1310G05, Biolegend #410712) was used to detect staining with selected anti-Delta1 antibodies described herein, as shown in FIG. 11B. Delta1-39 and Delta1-41 were found to be better pan-Gamma binders than other clones tested. Their binding profiles are comparable with that of the commercially available anti-Delta1 antibody.

Stable Jurkat (J.RT3-T3.5; ATCC® TIB-153) cell lines were prepared (same as in FIG. 11B) to express the following gamma chains on anti-Delta1 antibody combinations: 1) anti-Delta1 and gamma 2; 2) anti-Delta1 and gamma 3; 3) anti-Delta1 and gamma 4; 5) anti-Delta1 and gamma 5; 6) anti-Delta1 and gamma 8; 7) anti-Delta1 and gamma 9; 8) anti-Delta2 antibody and gamma 9. Binding was examined using increasing titrations of Delta1-39. For binding studies, the parental Jurakat (E6-1) cell line expressing alpha beta TCR was used as a control. As shown in FIGS. 24A-24H, Delta1-39 binding was specific, regardless of the gamma combination used in the δγ TCRs on the cell surface and it had no binding to TCR containing d2 or alpha beta TCRs (FIGS. 24G-H).

Cell Based Analysis of Cyno Binding

The reactivity of Delta1-41 antibody with human and cynomolgus monkey was examined. Human and cynomolgus monkey Delta1 Fc fusion proteins were attached to streptavidin-coated beads and binding titrations were performed with Delta1-41. As shown in FIG. 10C, Delta1-41 antibody binds to human Delta1 with essentially the same affinity as cynomolgus monkey Delta1. See also FIG. 10D.

Figure 9A:
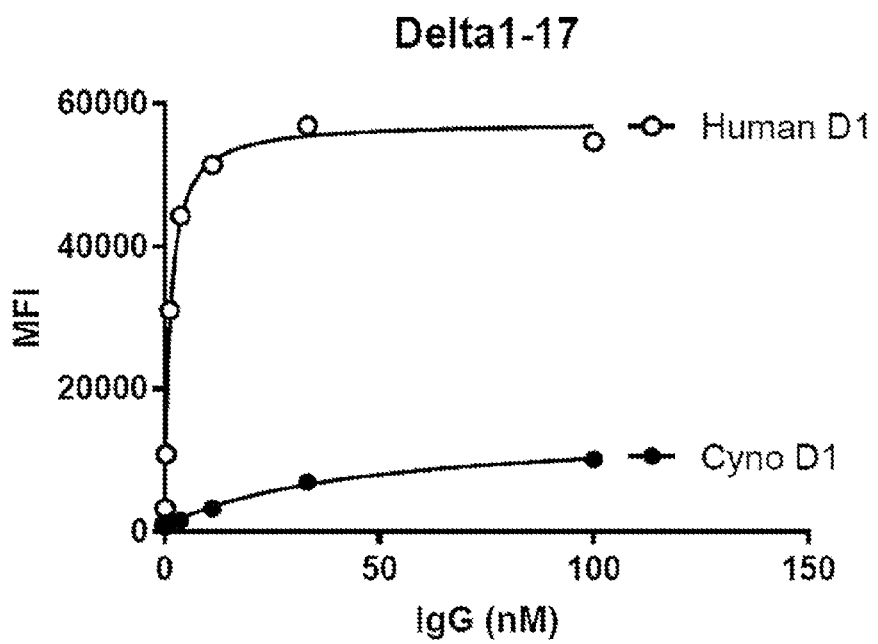
Figure 9B:
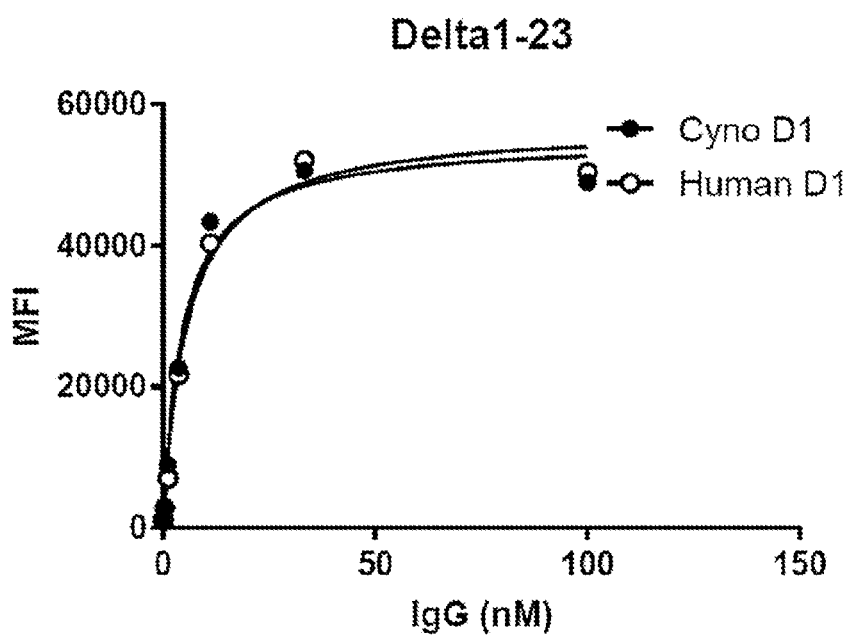
Figure 9C:
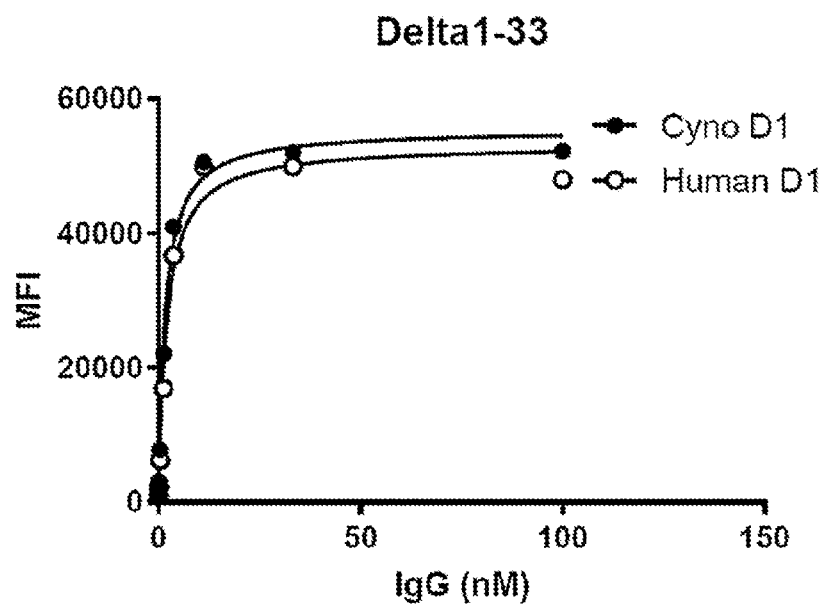
Figure 9D:
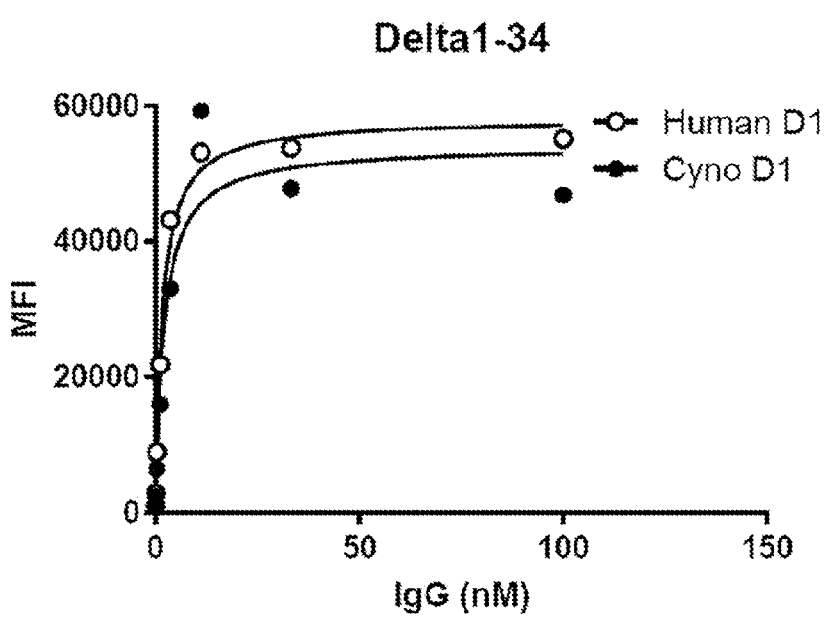
Figure 9E:
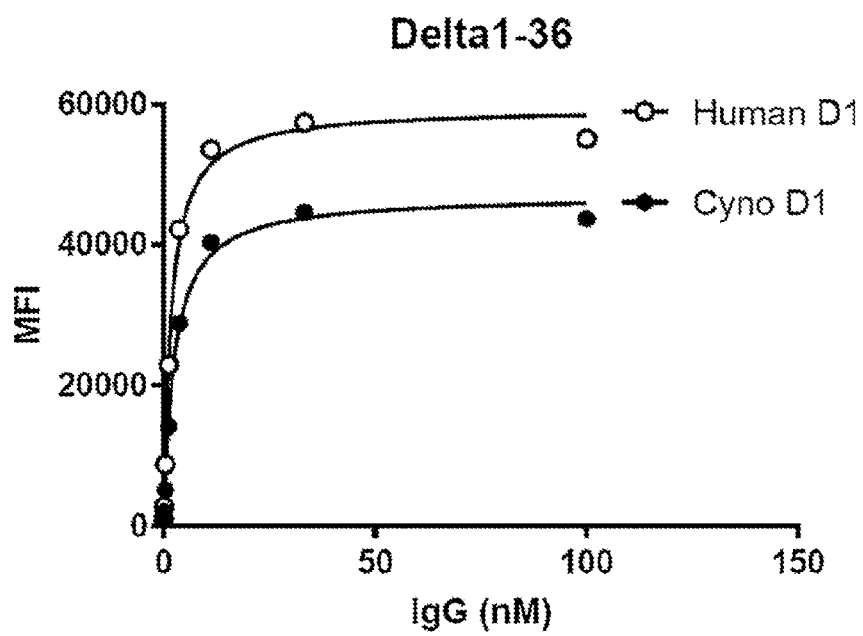
Figure 9F:
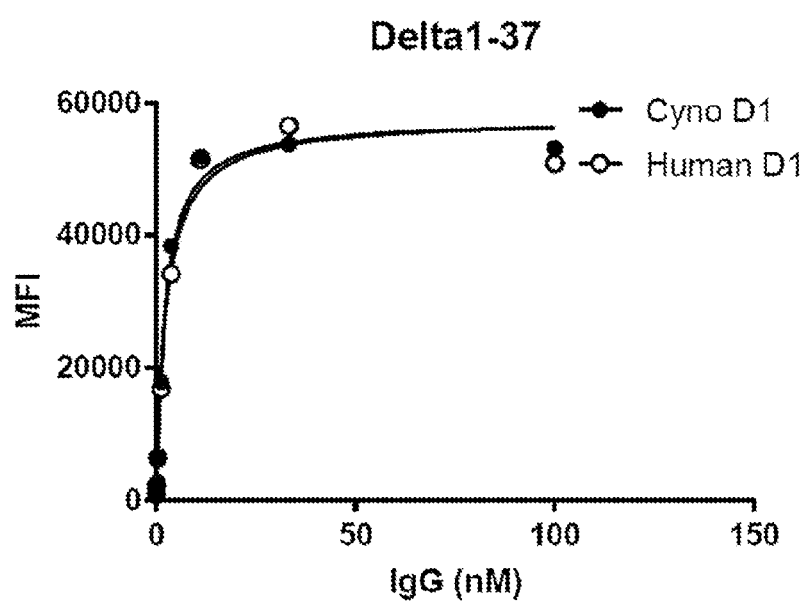
Figure 9G:
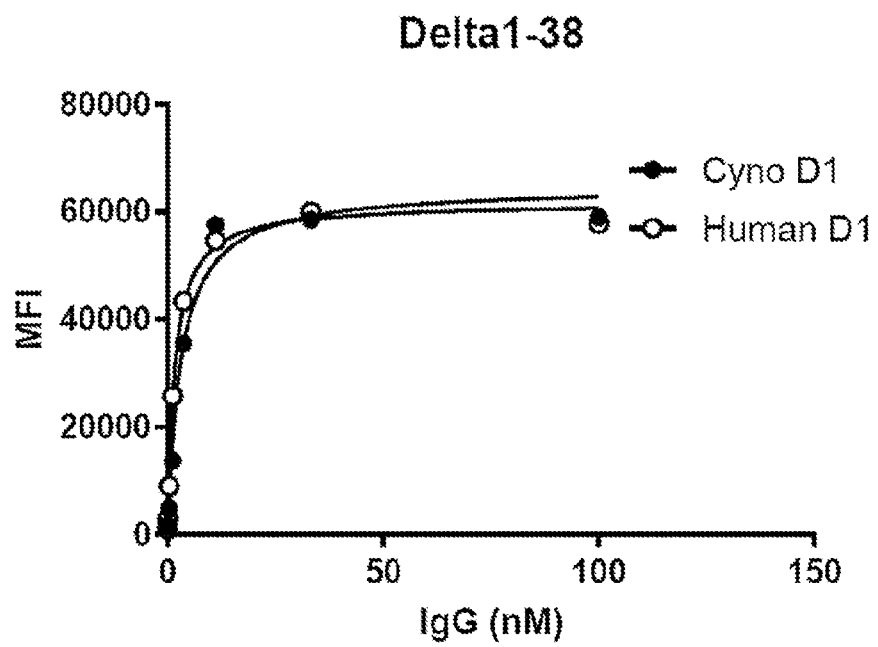
Figure 9H:
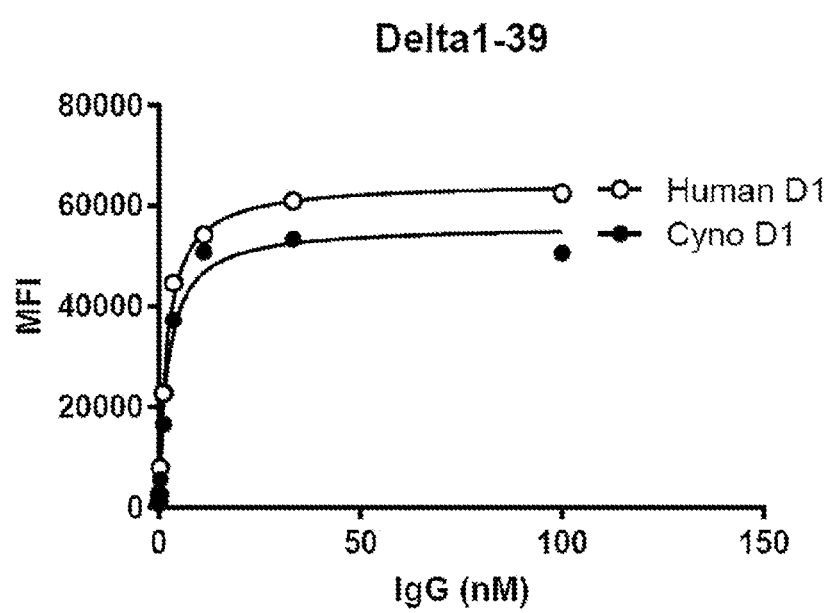
Figure 9I:
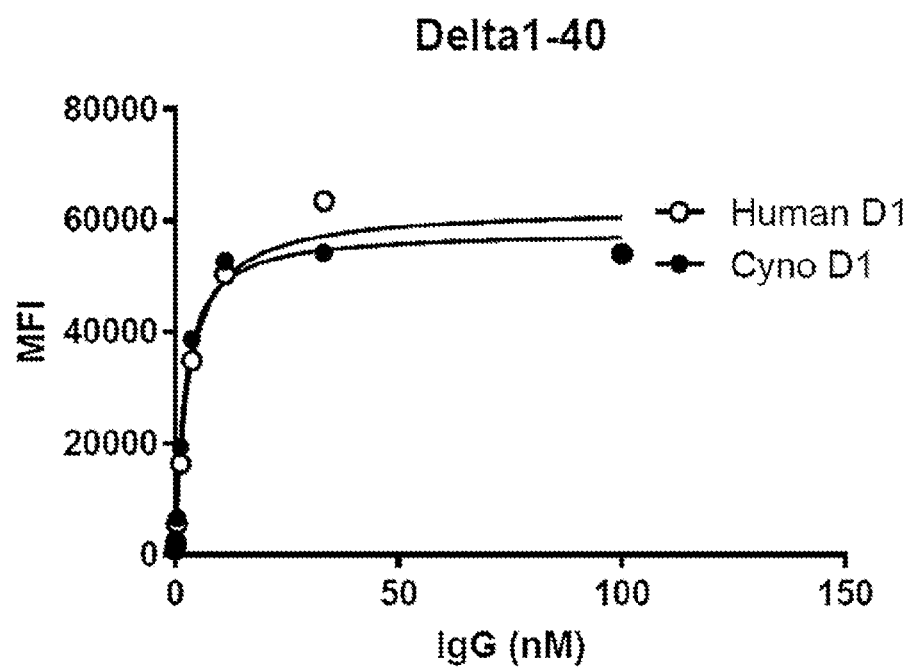

The reactivity of Delta1-39 antibody with human and cynomolgus monkey was also examined. Human and cynomolgus monkey Delta1 Fc fusion proteins were attached to streptavidin-coated beads and binding titrations were performed with Delta1-39(FIG. 9H). As shown in FIG. 22A, Delta1-39 antibody binds to human Delta1 with essentially the same affinity (KD=0.23 nM) as to cynomolgus monkey Delta1 (KD=0.28 nM) shown in FIG. 22B. Affinity measurements were carried out using Octet Bio-Layer Interferometry (BLI). Biotinylated human or monkey receptors were immobilized on stretpavidin sensor tips and Delta1.1 mAb was titrated as shown.

Thermostability

Purified proteins were incubated with SYPRO-Orange at temperatures ranging from 25° C. to 99° C. in 0.5° C. increments. Fluorescence was measured at each increment. The average change in fluorescence versus temperature (i.e., the first derivative) was plotted for the 40° C. to 90° C. range, and is shown in FIG. 8. The curves are vertically offset for clarity.

Example 3: Spheroid Preparation and Microfluidic Culture of Patient Tumor Samples Fresh tumor specimens (human patients) are received in media (DMEM) on ice and minced in a 10-cm dish (on ice) using sterile forceps and scalpel. Minced tumor is resuspended in DMEM (4.5 mmol/L glucose, 100 mmol/L Na pyruvate, 1:100 penicillin-streptomycin; Corning CellGro)+ 10% FBS (Gemini Bio-Products), 100 U/mL collagenase type IV (Life Technologies), and 15 mmol/L HEPES (Life Technologies). Samples are pelleted and resuspended in 10 to 20 mL media. Red blood cells (RBC) are removed from visibly bloody samples using RBC lysis buffer (Boston Bio-Products). Samples are pelleted and then resuspended in fresh DMEM+10% FBS and strained over 100-μm filter and 40-μm filters to generate S1 (>100 μm), S2 (40-100 μm), and S3 (<40 μm) spheroid fractions, which are subsequently maintained in ultralow-attachment tissue culture plates. S2 fractions are used for ex vivo culture. An aliquot of the S2 fraction is pelleted and resuspended in type I rat tail collagen (Corning) at a concentration of 2.5 mg/mL following the addition of 10× PBS with phenol red with pH adjusted using NaOH. pH 7.0-7.5 is confirmed using PANPEHA Whatman paper (Sigma-Aldrich). The spheroid-collagen mixture is then injected into the center gel region of a 3-D microfluidic culture device as described in Jenkins et al., Cancer Discov. 2018 February;8(2):196-215; Ex Vivo Profiling of PD-1 Blockade Using Organotypic Tumor Spheroids, the contents of which is herein incorporated by reference in its entirety. Collagen hydrogels containing patient-derived organotypic tumor spheroids (PDOTS) are hydrated with media with or without anti-γδ monoclonal antibodies after 30 minutes at 37° C.

In some cases, to test synergy with checkpoint inhibitors or other immunotherapy agents, PDOTS are treated with anti-PD-1 (pembrolizumab, 250 μg/mL), anti-CTLA4 (ipilimumab, 50 μg/mL), or combination (250 μg/mL pembrolizumab+50 μg/mL ipilimumab). For indicated PDOTS studies, anti-human PD-L1 is atezolizumab at 600 μg/mL+ human IFNgamma.

Immune profiling is performed by flow cytometry as described in Jenkins et al.

Example 4: Co-Culture Preparation, Treatment, and Analysis

Figure 1:
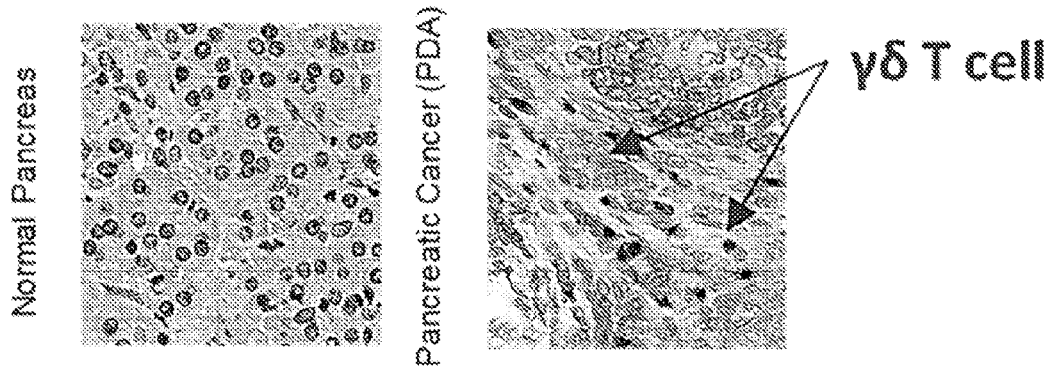
FIG. 1 is a photograph of an immunohistochemical analysis of human pancreatic cancer tissue compared to normal pancreas, demonstrating the enrichment of γδ T cells in pancreatic cancer tissue compared to normal tissue.
Figure 2:
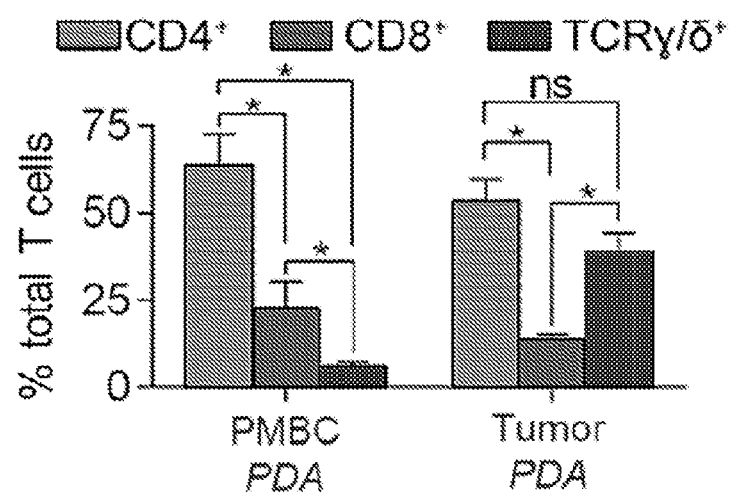
FIG. 2 is a bar graph depicting the percentage of total T cells in peripheral blood and in tumors, demonstrating the enrichment of γδ T cells in pancreatic cancer tissue compared to peripheral blood.

In vitro culture assays using cells from a pancreatic cancer patient were performed to examine the effects of γδ T cells on αβ T cells. Blood αβ T cells were cultured alone or co-cultured with intratumoral or blood γδ T cells. Blood αβ T cells were activated by ligation to CD3/CD28, resulting in an increase of TNF-α measured by FACS. As shown in FIG. 2, co-culture of activated αβ T cells with blood and tumor γδ T cells (bars 3 and 4, respectively) showed a significantly suppressed TNF-α signal, as compared to activated αβ T cells (bar 2). Bar 1 represents inactivated αβ T cells. The results demonstrate that γδ T cells from pancreatic cancer patients are immunosuppressive.

Figure 3A:
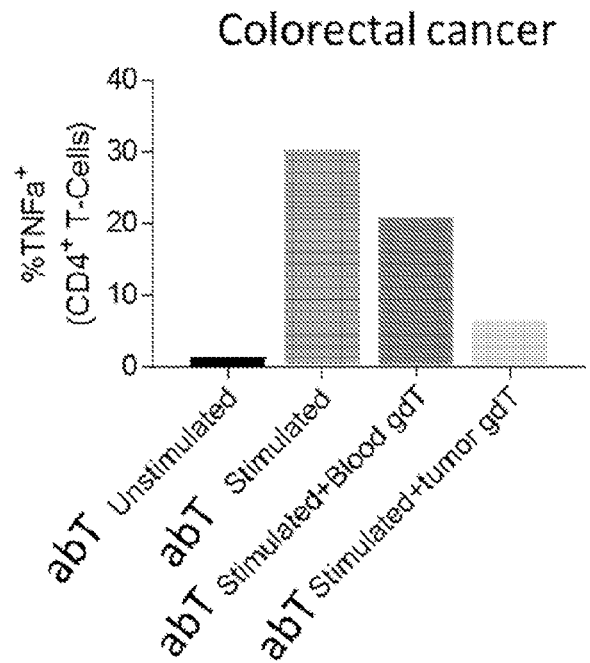
FIGS. 3A-3C depict bar graphs showing co-culture assay of gamma delta (gdT) and alpha beta T cells (abT). Gamma delta cells are derived from tumor or blood, as indicated, alpha beta T cells are derived from blood of the same patient. The figure depicts % TNF-α+ cells obtained upon culture of blood αβ T cells, alone or upon co-culture with intratumoral and blood T6 T cells. Blood alpha beta T cells were activated by ligation to CD3/CD28, resulting in increase in TNF-α measured by FACS. Bar 1: non-activated αβ T cell; Bar 2: activated αβ T cell; Bar 3: activated αβ T cell co-cultured with blood γδ T cells; Bar 4: activated αβ T cell co-cultured with tumor γδ T cells.
Figure 3B:
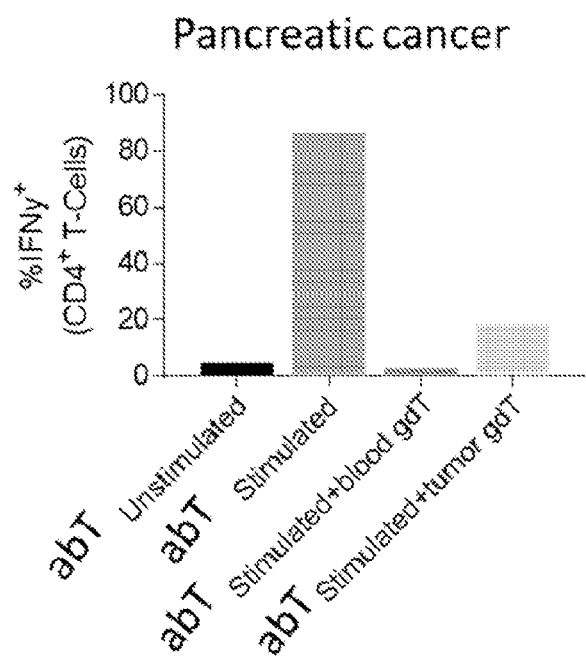
Figure 3C:
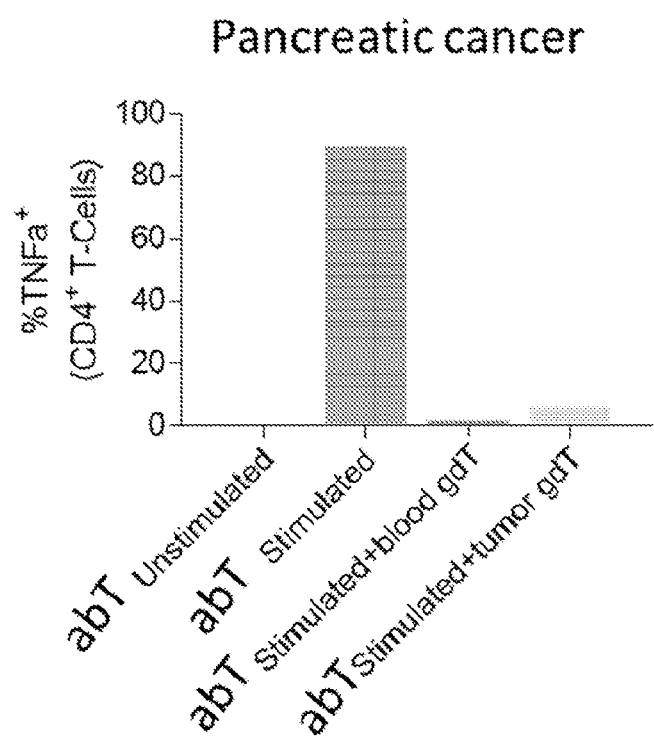

Gamma delta T cell (GDT) and conventional T cells (αβ T cells) were sorted from human surgically resected tumor specimens and paired blood samples which were received fresh. For antibody-based T cell proliferation assays, blood or tumor CD3+ T cells were activated using a human T cell activation kit (130-091-441, Miltenyi Biotec, MA) in 96-well plates. In selected wells, Gamma delta T cells were added in a 1:5 GDT: T cell ratio. T cell activation, as indicated by TNF-α and IFNγ, was determined at 72 hr by flow cytometry. Co-culture of activated αβ T cells with blood and tumor γδ T cells resulted in suppressed TNF-α and IFNγ signaling, demonstrating that the γδ T cells from three cancer patients (colorectal cancer, FIG. 3A, pancreatic cancer, FIG. 3B, and pancreatic cancer, FIG. 3C) are immunosuppressive.

Example 5: PDOTS Preparation, Treatment, and Analysis

PDOTS were prepared as described in the Example above with slight modifications (Jenkins et al., 2017, Ex Vivo Profiling of PD-1 Blockade Using Organotypic Tumor Spheroids. Cancer Discov February;8(2):196-215). Briefly, human surgically resected tumor specimens were received fresh in DMEM media on ice and minced in 10 cm dishes. Minced tumors were resuspended in DMEM+10% FBS with 100 U/mL collagenase type IV to obtain spheroids. Partially digested samples were pelleted and then re-suspended in fresh DMEM+10% FBS and strained over both 100 mm and 40 mm filters to generate S1 (>100 mm), S2 (40-100 mm), and S3 (<40 mm) spheroid fractions, which were subsequently maintained in ultra-low-attachment tissue culture plates. An aliquot of the S2 fraction was pelleted and resuspended in type I rat tail collagen at a concentration of 2.5 mg/mL following addition of 10× PBS with phenol red with pH adjusted using NaOH. An aliquot of the S2 fraction was pelleted and re-suspended in type I rat tail collagen and the spheroid-collagen mixture was then injected into the center gel region of the DAX-1 3D microfluidic cell culture chip (Aim Biotech, Singapore). After 30 min at 37° C., collagen hydrogels containing PDOTS were hydrated with media with indicated treatments including two anti-Delta1 antibodies (using Delta1-17 and Delta1-23 as examples) and associated isotypes. PDOTS were kept in a sterile container and incubated in the standard cell culture incubator. PDOTS were collected after incubating for 3 days and further analyses of immune change were done by flow cytometry.

Figure 4A:
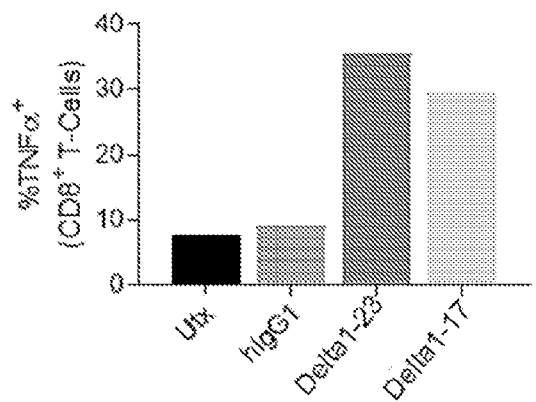
FIGS. 4A-4C depict bar graphs showing immune profile expression in a gastrointestinal neuroendocrine tumor sample (PDOTS) untreated (Utx) and treated with isotype (hIgG1), as compared to two anti-Delta1 IgG1 antibodies (Delta1-23 and Delta1-17 as examples). The percent TNF-α in CD8+ T cells (FIG. 4A), percent IFNγ in CD8+ T cells (FIG. 4B), and percent CD44 in CD8+ T cells (FIG. 4C) are shown.
Figure 4B:
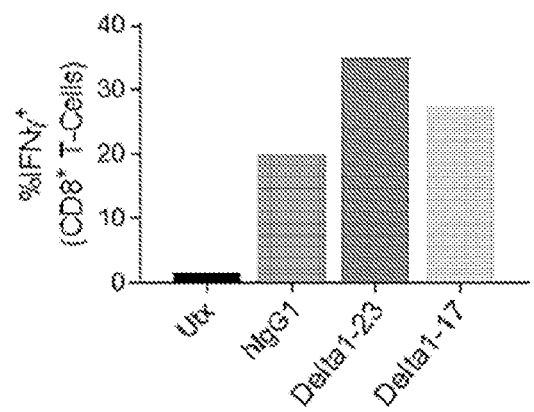
Figure 4C:
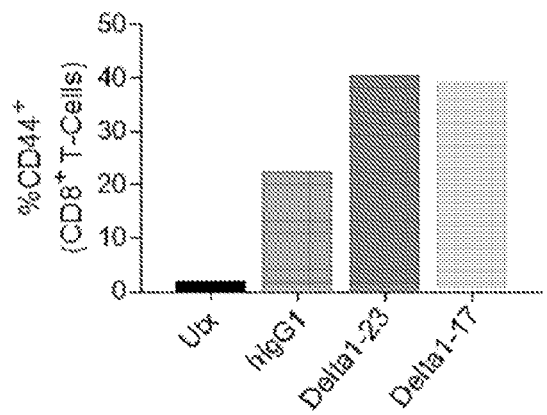

As shown in Table 3 below, 20 PDOTS were treated. "Responders" were PDOTS that showed an increase of greater than 20% in response compared to the isotype control in two out of three markers (CD44, TNFα, and IFNγ). Representative results are shown in FIGS. 4, 5, and 12. Treatment of the PDOTS with the anti-Delta1 antibodies described herein resulted in an increase in activated T cells in a gastrointestinal neuroendocrine tumor sample (FIG. 4), a breast cancer liver metastasis tumor sample (FIG. 5), a colorectal carcinoma liver metastasis tumor sample (FIG. 12A), a liver neuroendocrine tumor sample (FIG. 12B), a colorectal carcinoma neuroendocrine tumor sample (FIG. 12C), a hepatocellular carcinoma tumor sample (FIG. 12D), and a colorectal carcinoma (CRC) sample (FIG. 12E). Similar increases in activated T cells were obtained using Delta1-41 in colorectal cancer tumor sample (FIG. 20A) and liver metastasis tumor sample (FIG. 20B).

These results suggest that anti-Delta1 antibodies block the inhibitory function of the γδ T cells and allow activation of CD4+ and CD8+ T cells within the tumor spheroids. Compared side by side, both antibodies tested achieved T cell activation to a similar extent (FIGS. 4 and 5).

TABLE 3

Summary of PDOTS Data

| Diagnosis | Total Cases | Number of Responders | Response Rate (%) |
|---|---|---|---|
| CRC Liver Mets | 7 | 5 | 71 |
| HCC | 6 | 5 | 83 |
| CRC | 4 | 3 | 75 |
| CRC NET | 1 | 1 | 100 |
| Liver NET | 1 | 1 | 100 |
| PDA | 1 | 0 | 0 |
| Total | 20 | 15 | 75 |

Example 6. Immunophenotyping Cynomolgus and Rhesus Monkey Whole Blood

To further characterize the anti-Delta1 antibodies described herein, a γ/δ T cell FACS panel is developed for use with whole blood from cynomolgus macaque and rhesus monkeys. The panel is then used to evaluate the binding specificity of the anti-Delta1 antibodies.

Whole blood samples from cynomolgus and/or rhesus monkeys is drawn in NaHep tubes and are stored overnight. Samples are derived from normal or pancreatic cancer model animals. First, a FACS panel for the evaluation of γ/δ T-cells in NHP whole blood is developed and optimized which is then used to assess binding specificity of anti-Delta1 antibodies described herein.

Commercially available antibodies are used as controls (AF647-anti-pan γ/δ T: Biolegend 331214 (reported cross-reactive cyno/rhesus); APC-anti-vδ2 T: Biolegend 331418 (negative control; cross-reactive rhesus)). To develop and optimize a control panel, commercially available antibodies are titrated on fresh whole blood, from diseased NHP subjects, using an 8-point titration, with 2-fold dilutions, beginning at twice the manufacturer's recommendation. After selecting the optimal titrations, whole blood from cynomolgus (n=6) and rhesus subjects (n=6) (with three normal and three diseased subjects each) is stained with the complete optimized control panel as follows: CD45/CD3/CD4/CD8/AF647-Pan γ/δ T/APC-vδ2T/Live-Dead. An appropriate control tube is be used for gating.

Upon confirmation of staining with the commercially available antibodies, whole blood from 2 diseased subject (1 rhesus and 1 cynomolgus) is used for staining with anti-Delta1 antibodies described herein. Anti-Delta1 antibodies, e.g., clone Delta1-39, is fluorescently conjugated and is titrated on whole blood, using an 8-point titration curve. Control staining using the full optimized panel set with commercially available antibodies is included. Upon confirmation of antibody binding, whole blood from 6 cynomolgus and 6 rhesus subjects (three normal and three diseased subjects each) is stained with the complete optimized panel as follows: Control Panel: CD45/CD3/CD4/CD8/AF647-Pan γ/δ T/APC-vδ2T/Live-Dead; Test Panel: CD45/CD3/CD4/CD8/Delta1-23 γ/δ T/APC-vδ2T/Live-Dead; Staining CTRL:CD45/CD3/CD4/CD8/isotype ctrl/APC-vδ2T/Live-Dead. All samples are acquired on the 3-laser or 5-laser Fortessa cytometer and are analyzed with FlowJo software.

Example 7. In Vivo Evaluation of Two Immune Checkpoint Inhibitors in Syngeneic Models of Murine Lewis Lung Carcinoma and Skin Melanoma, in B6-TCRdelta- and Control C57BL/6J Mice This study aims at evaluating the antitumor activity of two immune checkpoint inhibitors, anti-PD1 and anti-CTLA-4, in syngeneic models of murine Lewis lung carcinoma (LLC) and skin melanoma (B16F10), in female (LLC) and male (B16F10) B6-TCRdelta- and control C57BL/6J mice.

Test Agents:

The test agents used in this study (shown in Table 5 below) were formulated following the instructions provided by Champions and prepared on the day of dosing for the duration of the study.

TABLE 5

Test Agents

| Agent | Master Stock Storage | Master Stock Stability | State | Working Stock Storage | Working Stock Stability |
|---|---|---|---|---|---|
| Anti-mCTLA-4 | 2-8° C. | Study duration | Liquid | 2-8° C. | Study duration |
| Anti-mPD-1 | 2-8° C. | Study duration | Liquid | 2-8° C. | Study duration |
| Isotype Control mIgG2a (PD-1) | 2-8° C. | Study duration | Liquid | 2-8° C. | Study duration |
| Isotype Control mIgG2b (CTLA-4) | 2-8° C. | Study duration | Liquid | 2-8° C. | Study duration |

Experimental Design:

Pre-study Animals:

Pre-study animals (female C57BL/6J mice or female GammaDelta KO C57BL/6J mice) were unilaterally implanted subcutaneously in the left flank with $3 \times 10^5$ LLC cells resuspended in 100 μl PBS.

Pre-study animals (male C57BL/6J mice or male C57BL/6J GammaDelta KO mice) were unilaterally implanted subcutaneously in the left flank with $5 \times 10^5$ B16F10 cells resuspended in 100 μl PBS.

Study Animals:

Pre-study tumor volumes were recorded for each experiment 2-3 days after implantation. When tumors reached an average tumor volume of 50-100 mm³ (preferably 50-75 mm³), animals were matched by tumor volume into treatment or control groups to be used for dosing and dosing was initiated on Day 0.

The wild-type C57BL/6J mice or GammaDelta KO mice were randomly assigned into five groups, each being treated as shown in Table 6 below:

TABLE 6

Treatment Conditions

| Group | -n- | Agent | Dose Level | Dose Volume | ROA/ Schedule | Total Doses |
|---|---|---|---|---|---|---|
| 1 | 9* | Untreated control | — | 0 mL/kg | / | 0 |
| 2 | 10* | Isotype control mIgG2a (PD-1) | 10 mg/kg | 10 mL/kg | IP/BIW × 4 | 8 |
| 3 | 10* | Isotype control mIgG2b (CTLA-4) | 10 mg/kg | 10 mL/kg | IP/BIW × 4 | 8 |
| 4 | 10* | Anti-mPD-1 | 10 mg/kg | 10 mL/kg | IP/BIW × 4 | 8 |
| 5 | 10* | Anti-mCTLA-4 | 10 mg/kg | 10 mL/kg | IP/BIW × 4 | 8 |

*Up to 9 or 10 mice per group

Efficacy Tumor Volumes:

Tumor volumes were measured three times weekly. A final tumor volume was measured on the day study reaches endpoint. If possible, a final tumor volume was measured if an animal is found moribund.

Tumor Ulceration:

Tumors can start developing ulceration at early time points. Triple antibiotic ointment was applied three times per week on all tumors after tumor volume measurements. Mice with ulceration greater than 50% of the tumor total surface area or an impact on overall health and well-being would be euthanized.

Efficacy Animal Weights:

Animals were weighed three times weekly. A final weight was measured on the day the study reaches endpoint or if an animal was found moribund, if possible. Animals exhibiting ≥10% weight loss when compared to Day 0 would be provided with DietGel® ad libitum. Any animal exhibiting >20% net weight loss for a period lasting 7 days or if mice display >30% net weight loss when compared to Day 0 would be considered moribund and euthanized.

Study Termination:

Efficacy: The study endpoint was defined to be when the mean tumor volume of the control group (uncensored) reaches 1500 mm³. If this occured before Day 28, treatment groups and individual mice were dosed and measured up to Day 28. If the mean tumor volume of the control group (uncensored) did not reach 1500 mm³ by Day 28, then the endpoint for all animals was set as the day when the mean tumor volume of the control group (uncensored) reached 1500 mm³ up to a maximum of Day 60.

In-Life Blood Collection: 150 μL of blood were collected from the submandibular vein. Blood was transferred to serum separator tubes and allowed to clot at room temperature for at least 15 minutes. Samples were centrifuged at 3500 RPM for 10 minutes at room temperature. The resultant serum was separated, transferred to uniquely labeled clear polypropylene tubes, and frozen immediately over dry ice or in a freezer set to maintain −80° C. until shipment.

Data Collection, Analysis, and Reporting

Agent Toxicity: Beginning Day 0, animals were observed daily and weighed three times weekly using a digital scale; data including individual and mean gram weights (Mean We±SD), mean percent weight change versus Day 0 (% vD0) was recorded for each group and % vD0 plotted at study completion. Maximum mean % vD0 (weight nadir) for each treatment group was reported at study completion.

Results

Beginning Day 0, tumor dimensions were measured three times weekly by digital caliper and data including individual and mean estimated tumor volumes (Mean TV±SEM) recorded for each group. Tumor volume was calculated using the formula (1): TV=width2×length×0.52. At study completion, percent tumor growth inhibition (% TGI) values was calculated and reported for each treatment group (T) versus control (C) using initial (i) and final (f) tumor measurements by the formula (2): % TGI=1−(Tf−Ti)/(Cf−Ci). Individual mice reporting a tumor volume=30% of the Day 0 measurement for two consecutive measurements were considered partial responders (PR). Individual mice lacking palpable tumors (0.00 mm³ for two consecutive measurements) were classified as complete responders (CR). A CR that persists until study completion was considered a tumor-free survivor (TFS). Tumor doubling time (DT) was determined for the vehicle treated groups using the formula DT=(Di−Df)*log 2/(log TVi−log TV)f where D=Day and TV=Tumor Volume.

As shown in FIG. 13A and FIG. 13B, an anti-CTLA-4 antibody successfully reduced tumor volume in γδ knock-out LCC mice as compared with untreated mice or mice treated with an IgG isotype control as indicated, while such anti-tumor effects were not observed in wild-type mice.

In γδ knock-out melanoma mice, the anti-tumor effects of an anti-PD-1 antibody were observed on about day 14 after doing and onward (e.g., on day 17 after dosing). FIGS. 13C and 13D. The non-balanced 2-Way ANOVA (Bonferroni's multiple comparison's test) for groups 4c (anti-PD-1 C57BL/6J) versus 4d (anti-PD-1 GammaDelta KO) was used for the B16F10 model, up to day 17. The reduction observed in the mean TV is significant at the level of $p<0.05$ ($p=0.0410$; interaction factor). The treatment effect is significant on day 17 (Bonferroni's multiple comparison's test).

These data indicate that checkpoint inhibitors are more effective in the absence of γδ T cells. The data also suggests that a therapeutic that blocks/inhibits/depletes immunosuppressive gamma delta T cells, combined with checkpoint inhibitors (anti-PD1, anti-CTLA4, anti-PDL1) would benefit cancer treatment, e.g., by enabling, rescuing and augmenting anti-cancer immune responses. Such anti-cancer immune responses, which are suppressed by γδ T cells, include but are not limited to responses mediated by αβ T cells and other anti-cancer effector pathways, such as macrophages, NK cells, dentritic cells in the tumor microenvironment.

Example 8. Stability Analysis of Anti-Delta1 Antibodies

Anti-Delta1 antibody Delta1-17 and Delta1-41 were stored at −80° C. until use. Prior to analysis, samples were thawed in a 37° C. water bath and stored on ice until analysis. Prior to handling, absorbance at 280 nm was measured using Nanodrop. The samples were then concentrated to 12 mg/ml and filtered through a 0.22 μm filter (Millipore; SLGV004SL). The samples were analyzed by SEC using a TOSOH TSKgel SuperSW mAb HR column. Different thawing, storage and handling conditions were assessed by SEC and monitored for the appearance of higher molecular weight peaks.

Stability of the antibody clones undergone one cycle of freeze and thaw, concentration, and/or filtration were analyzed in this study. The results shown in FIGS. 14A and 14B indicate that both Delta1-17 and Delta1-41 remain aggregate free at high concentration (12 mg/ml) and can withstand a single freeze thaw cycle as well as filtration through a 0.22 uM filter. After 10 day storage at 4° C., Delta1-17 an Delta1-41 remain aggregate free at the same conditions as shown in FIGS. 14C and 14D. Further, Delta1-17 and Delta1-41 remain aggregate free after overnight storage at 37° C. and room temperature (24° C.) as well as after 4 freeze/thaw cycles as shown in FIGS. 14E and 14F. Similar experiments were conducted with clone Delta1-39 and are shown in FIG. 14G.

Example 9. Antibody Dependent Cell Phagocytosis (ADCP) and Antibody Dependent Cell Cytotoxicity (ADCC) Analysis of Delta1-17 and Delta1-41

The antibody dependent cell phagocytosis (ADCP) effect of Delta1-17 and Delta1-41 was evaluated using bead-based ADCP assay and cell-based ADCP assay as described below.
(i) ADCP Assay with Beads Nuetravidin FluoSpheres Yellow/Green (505/515) (Invitrogen #F8776) were used at 1:100 dilution and conjugated with biotinylated Gamma/Delta complexes at 10 nM. Total 5 ul of the bead suspension was used per well. The THP-1 monocyte cell line (ATCC #TIB-202) was used as effector cells and was stained with CellTrace™ Far Red Cell Proliferation dye (Thermo cat #C34572). $2 \times 10^4$ effector cells were added to each well containing Delta1-17 and Delta1-41 at different concentrations, and incubated for 1 hour at 37° C. After the incubation the cells were resuspended in PBS with 0.1% BSA and analyzed by FACS.

As shown in FIGS. 15A-15C, both Delta1-17 and Delta1-41 were able to mediate ADCP at all 3 target immobilization ratios, with 10 nM providing the best specificity versus Isotype. The results indicate that Delta1-17 and Delta1-41 can mediate antibody dependent cell phagocytosis (ADCP) using beads as targets at different target coating densities.

Further, ADCP effects were investigated at 1-hour, 4-hour, and 24-hour time points. As shown in FIGS. 16A-16C, the 1 hour incubation showed the best phagocytic profile allowing for distinction between efficacy of the two antibody clones. The phagocytic score is calculate as (% bead-positive cells×MFI of positive population)/$10^6$. The results indicate that Delta1-17 and Delta1-41 can mediate antibody dependent cell phagocytosis (ADCP) using beads as targets over a wide range of times.

Further, different biotinylated targets were immobilized on neutravidin coated fluorescent beads at 10 nM. Delta1-1-17, Delta1-39, and Delta1-41 were able to mediate ADCP with beads coated with human Delta1 and monkey Delta1 receptors, while the Isotype antibody produced no response. FIG. 17. The phagocytic score was calculated as (% bead-positive cells×MFI of positive population)/$10^6$. The results show that Delta1-17 and Delta1-41 can mediate antibody dependent cell phagocytosis (ADCP) using beads coated with human and monkey targets.
(ii) Cell-Based ADCP Assay Target cells expressing different Delta and Gamma chain combinations on the cell surface were stained with carboxyfluorescein succinimidyl ester (CFSE; eBioscience #65-0850-84). The THP-1 monocyte cell line (ATCC #TIB-202) was used as effector cells and was stained with Cell-Trace™ Far Red Cell Proliferation dye (Thermo cat #C34572). The target and effector cells were mixed in a 1:1 ratio ($2 \times 10^4$ cells each) and incubated with Delta1-17 and Delta1-41 at different concentrations, as indicated, for 1 hour at 37° C. After the incubation, the cells were resuspended in PBS with 0.1% BSA and analyzed by FACS.

Target cells expressing Delta1/Gamma9 TCR on the surface were incubated with the antibodies and THP-1 effector cells for various periods of time as indicated in FIG. 18A. The 1 hour incubation showed the best phagocytic profile allowing for distinction between efficacy of the two antibody clones. The results indicate that Delta1-17 and Delta1-41 can mediate antibody dependent cell phagocytosis (ADCP) using target cells expressing Delta1 TCR on the surface.

Further, target cells expressing Delta1/Gamma9 TCR on the surface were incubated with the antibodies and THP-1 effector cells for 1 hour. From the different antibody concentrations tested, the 5 nM concentration showed the best response. FIG. 18B. The results indicate that Delta1-17 and Delta1-41 can mediate antibody dependent cell phagocytosis (ADCP) using target cells expressing Delta1 TCR on the surface at a wide range of antibody concentrations.

Moreover, target cells expressing different TCRs on the surface were incubated with the antibodies at 5 nM and THP-1 effector cells for 1 hour. All antibody clones tested showed high specificity for mediating ADCP with Delta1 expressing, and not Delta2 expressing target cells. FIG. 18C. The results show that Delta1-17 and Delta1-41 specifically mediate antibody dependent cell phagocytosis (ADCP) using target cells expressing Delta1 TCR and not Delta2 TCR.

A similar experiment was performed to assess whether Delta1-39 can mediate antibody dependent cell phagocytosis (ADCP) and if antibody dependent cell phagocytosis (ADCP) mediated by Delta1-39 was specific to delta1 TCR containing cells. Jurkat cell lines expressing delta1/gamma-4, delta1/gamma-9, or delta2/gamma-9 were used as the target cell lines. The cells were mixed at a 1:1 effector cell (THP-1 monocytes) to target cell. Delta1-39 antibody, isotype, or vehicle was added at 5 nM for 1 hour. Degree of phagocytosis was measured by flow cytometry by first gatng on FarRed positive effector cells and then gating on CFSE positive target cells. As shown in FIG. 26, antibody dependent cell phagocytosis (ADCP) mediated by Delta1-39 was specific to delta1 TCR, but not to Delta2 TCR, regardless of gamma combination with delta1.
(iii) Antibody Dependent Cell Cytotoxicity (ADCC)

Target cells expressing different Delta and Gamma combinations on the cell surface were stained with carboxyfluorescein succinimidyl ester (CFSE; eBioscience #65-0850-84). The THP-1 monocyte cell line (ATCC #TIB-202) was used as effector cells and were not stained. Prior to the beginning of the ADCC assay, the effector cells were separated on a Ficoll Paque Plus gradient (Sigma #GE17-1440-02) to remove dead cells. The target and effector cells were mixed in a 1:8 ratio and incubated with Delta-17, Delta-39, Delta1-41 or isotype controls at 100 nM, as indicated, for 1 hour at 37° C. After the incubation, the cells were washed with PBS and stained with the Fixable Viability Dye 660 (FVD660; eBioscience #65-0864-14) for 30 minutes at 4° C. The cells were then washed with PSB with 0.1% BSA and analyzed by FACS.

Target cells expressing Delta1/Gamma9 TCR on the surface were incubated with the antibodies and NK92+CD16 effector cells for 1 hour and 3.5 hours. Delta-17, Delta-39, and Delta1-41 were able to mediate ADCC (FIGS. 19A and 19B).

A similar cell based ADCC assay was also performed to assess the ADCC effects of Delta1-39. NK-92 cells expressing extra FcγR were used as effector cells. Jurkat (J.RT3-T3.5) cell line expressing δ1/γ9 was used as the target cell line and labelled with CFSE dye. The cells were mixed at 4:1 effector to target ratio and the antibodies (either Delta1-39 antibody or isotype) were added at 100 nM for 3.5 hours (FIGS. 25A and 25B) After the incubation, the cells were stained with a fixable viability dye (FVD660) and quantified by flow cytometry. As shown in FIG. 25, the Delta1-39 antibody promoted antibody dependent cell cytotoxicity (ADCC).

Example 10. Neutralizing δ1 Cells Enables ICOS-Based Immunotherapy in Human HCC PDOTS Human HCC PDOTS were prepared as described in the Examples above. Levels of T cell activation were measured in tumor samples (PDOTS) treated with isotype (hIgG1) as compared to an anti-Delta1 IgG1 antibody (Delta1-41 as an example), or an anti-PD1 antibody. The percent TNF-α in $CD8^+$ T cells and percent IFNγ in $CD8^+$ T cells were both increased in PDOTS treated with Delta1-41.

Next, ability to activate T cells was compared between anti-Delta1 antibody and PD-1 antibody treatment. Treatment of PDOTS from a hepatocellular carcinoma tumor sample with the anti-Delta1 antibody (Delta1-17 as an example), resulted in an increase in activated T cells as compared to the PD-1 antibody and the isotype control, suggesting that targeting gamma delta T cells is more effective than targeting a single check point molecule in blocking the inhibitory function of gamma delta T cells. (FIG. 20B).

The ability to activate T cells in the presence of a co-stimulatory receptor agonist (ICOS agonist as an example) was examined. Treatment of PDOTS from a hepatocellular carcinoma tumor sample with the anti-Delta1 antibody (Delta1-17 as an example) in combination with ICOS agonist, resulted in an increase in activated T cells as compared to the anti-Delta1 antibody alone (FIGS. 21A-21C).

Example 11. Anti-Delta1 Antibody Mediates Specific Cell Killing in Peripheral Blood Mononuclear Cells (PBMCs)

First, PBMCs were isolated from a healthy human donor and then incubated with 10 nM anti-delta1 antibody (Delta1-39 as an example) for 1 hour. After incubation, cells were stained with DAPI, antiCD3, anti TCR antibody and with delta1 using commercially available agents. The percentages of total live cells, shown in FIG. 27, indicate that delta1 antibody was more effective at killing in PBMCs compared to isotype-treated cells or untreated cells.

Next, PBMCs were collected from a healthy human donor and a human subject diagnosed with colorectal carcinoma. The anti-Delta1-39 was used to specifically identify delta T cells in both healthy human PBMCs (FIG. 31B) and PBMCs from a human donor with colorectal carcinoma (FIG. 31A), showing that an Anti-Delta1-39 mAb, such as those described herein, can be used to specifically identify Delta1 T cells in patients Example 12. Testing Delta1 Antibodies for Flow Cytometry The utility of Delta1-39 for use in flow cytometry to detect delta1 positive cells was assessed. Anti-Delta1-39 was conjugated to Dylight650 using an amine reactive NHS ester dye kit (Thermo cat 62266). The conjugated antibody was desalted and assessed for purity, degree of conjugation and binding properties using Delta1 immobilized on beads as well as expressed on cells (data not shown).

Healthy PBMCs were obtained from Stemcell (cat 70025.1) and processed for staining with Dylight-650 conjugated anti-Delta1-39 as well as commercial anti-Delta1 (clone TS8.2), anti-Delta2-PE (clone B6), anti-CD3 (clone UCHT-1), anti TCR AB (clone IP26). Flow cytometric analysis, as shown in FIG. 32, indicates that Delta1 positive staining is observed only in the CD3+/TCR AB-subset of cells (Q3 gate, boxed region). No staining with either anti Delta1 specific antibodies is observed in the TCR AB+/CD3+ or the TCR AB-/CD3-gates. Moreover, the staining profiles obtained with anti-Delta1-39-Dylight-650 recapitulates the profile obtained with the commercial anti Delta1 (clone TS8.2). Results indicate that the anti-Delta1-39 specifically identifies delta T cells in healthy human PBMCs, suggesting that an Anti-Delta1 mAb, such as those described herein, including but not limited to Delta1-39, can be used to specifically identify Delta1 T cells in patients.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody, which binds a delta-1 chain of a T cell receptor, wherein the antibody comprises a heavy chain complementarity determining region 1 (VH-CDR1) set forth as SEQ ID NO: 68, a heavy chain complementarity determining region 2 (VH-CDR2) set forth as SEQ ID NO: 53, and a heavy chain complementarity determining region 3 (VH-CDR3) set forth as SEQ ID NO: 54 and comprises a light chain complementarity determining region 1 (VL-CDR1) set forth as SEQ ID NO: 55, a light chain complementarity determining region 2 (VL-CDR2) set forth as SEQ ID NO: 56, and a light chain complementarity determining region 3 (VL-CDR3) set forth as SEQ ID NO: 57.

2. The isolated antibody of claim 1, which is a full-length antibody or an antigen-binding fragment thereof.

3. The isolated antibody of claim 1, which is a single chain antibody.

4. The isolated antibody of claim 1, which is a human antibody or a humanized antibody.

5. The isolated antibody of claim 1, which is an IgG molecule.

6. The isolated antibody of claim 5, wherein the antibody is an IgG1 or IgG4 molecule.

7. The isolated antibody of claim 6, wherein the antibody is an IgG1 molecule.

8. The isolated antibody of claim 7, wherein the IgG1 has one or more mutations selected from (1) E333A mutation; (2) S239D/A330L/I332E mutation; (3) K326W/E333S mutations; (4) S239D/I332E/G236A mutation.

9. The isolated antibody of claim 7, wherein the antibody comprises a heavy chain constant region set forth as SEQ ID NO: 31, and a light chain constant region set forth as SEQ ID NO: 73.

10. The isolated antibody of claim 1, wherein the antibody comprises a heavy chain variable region (VH) set forth as SEQ ID NO: 24 and a light chain variable region (VL) set forth as SEQ ID NO: 9.

11. The isolated antibody of claim 10, which is a full-length antibody or an antigen-binding fragment thereof.

12. The isolated antibody of claim 10, which is a single chain antibody.

13. The isolated antibody of claim 10, which is a human antibody or a humanized antibody.

14. The isolated antibody of claim 10, which is an IgG molecule.

15. The isolated antibody of claim 14, wherein the antibody is an IgG1 or IgG4 molecule.

16. The isolated antibody of claim 15, wherein the antibody is an IgG1 molecule.

17. The isolated antibody of claim 16, wherein the IgG1 has one or more mutations selected from (1) E333A mutation; (2) S239D/A330L/I332E mutation; (3) K326W/E333S mutations; (4) S239D/I332E/G236A mutation.

18. The isolated antibody of claim 16, wherein the antibody comprises a heavy chain constant region set forth as SEQ ID NO: 31, and a light chain constant region set forth as SEQ ID NO: 73.

19. The isolated antibody of claim 10, wherein the antibody comprises a VH set forth as SEQ ID NO: 24 and a VL set forth as SEQ ID NO: 9, and comprises a heavy chain constant region set forth as SEQ ID NO: 31 and a light chain constant region set forth as SEQ ID NO: 73.

20. The isolated antibody of claim 19, wherein the antibody comprises a heavy chain set forth as SEQ ID NO: 79 and a light chain set forth as SEQ ID NO:78.

21. A pharmaceutical composition comprising the antibody of claim 1 and a pharmaceutically acceptable carrier.

22. A pharmaceutical composition comprising the antibody of claim 9 and a pharmaceutically acceptable carrier.

23. A pharmaceutical composition comprising the antibody of claim 10 and a pharmaceutically acceptable carrier.

24. A pharmaceutical composition comprising the antibody of claim 19 and a pharmaceutically acceptable carrier.

25. A pharmaceutical composition comprising the antibody of claim 20 and a pharmaceutically acceptable carrier.

26. A method of inhibiting γδ T cell activation in a subject, the method comprising administering to a subject in need thereof an effective amount of a pharmaceutical composition of comprising the isolated antibody of claim 1.

27. The method of claim 26, wherein the subject in need thereof is a human patient having, suspected of having, or at risk for, a solid cancer.

28. The method of claim 27, wherein the subject is a human patient having a solid tumor selected from the group consisting of pancreatic ductal adenocarcinoma (PDA), colorectal cancer (CRC), melanoma, breast cancer, lung cancer, upper and lower gastrointestinal malignancies, squamous cell head and neck cancer, genitourinary cancer, ovarian cancer, and sarcomas.

29. The method of claim 26, further comprising administering to the subject an inhibitor of a checkpoint molecule, an activator of a co-stimulatory receptor, an inhibitor of an innate immune cell target, a chemotherapeutic agent, or an anti-hypertension agent.

30. The method of claim 29, wherein the checkpoint molecule is selected from the group consisting of PD-1, PD-L1, PD-L2, CTLA-4, LAG3, TIM-3, A2aR, TIGIT and VISTA.

31. The method of claim 29, wherein the co-stimulatory receptor is selected from the group consisting of OX40, GITR, CD137, CD40, CD27, and ICOS.

32. The method of claim 29, wherein the innate immune cell target is selected from the group consisting of KIR, NKG2A, CD96, TLR, IDO, and galectin-9.

* * * * *

SEQUENCE LISTING

```
<160> NUMBER OF SEQ ID NOS: 94

<210> SEQ ID NO 1
<211> LENGTH: 130
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Tyr Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Met Tyr Tyr Trp Tyr Tyr Ser Gly Ser Ala Tyr
            100                 105                 110
```

```
Glu Gly Tyr Gly Leu Asp Tyr Trp Gly Gln Gly Thr Leu Val Thr Val
            115                 120                 125
Ser Ser
    130

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Asp Asp Leu Ile
                85                  90                  95

Thr Phe Gly Gln Gly Thr Lys Val Glu Ile Lys Arg
            100                 105

<210> SEQ ID NO 3
<211> LENGTH: 130
<212> TYPE: PRT
<213> ORGANISM: Homo sapiens

<400> SEQUENCE: 3

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Ser Ile Tyr Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
            115                 120                 125

Ser Ser
    130

<210> SEQ ID NO 4
<211> LENGTH: 110
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Ser Val Ser Ser Ala
                20                 25                 30

Val Ala Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Arg Ser Gly Thr Asp Phe Thr Leu Thr Ile Ser Ser Leu Gln Pro
65                 70                 75                 80

Glu Asp Phe Ala Thr Tyr Tyr Cys Gln Gln Arg Ser Arg Val Tyr Ser
                85                 90                 95

Leu Val Thr Phe Gly Gln Gly Thr Lys Val Glu Ile Lys Arg
            100                105                110
```

<210> SEQ ID NO 5
<211> LENGTH: 110
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Val Ser Ser Ala
                20                 25                 30

Val Ala Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Arg Ser Gly Thr Asp Phe Thr Leu Thr Ile Ser Ser Leu Gln Pro
65                 70                 75                 80

Glu Asp Phe Ala Thr Tyr Tyr Cys Gln Gln Met Asp Arg Phe Tyr Ser
                85                 90                 95

Leu Ile Thr Phe Gly Gln Gly Thr Lys Val Glu Ile Lys Arg
            100                105                110
```

<210> SEQ ID NO 6
<211> LENGTH: 110
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Val Ser Ser Ala
                20                 25                 30

Val Ala Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Arg Ser Gly Thr Asp Phe Thr Leu Thr Ile Ser Ser Leu Gln Pro
65                 70                 75                 80

Glu Asp Phe Ala Thr Tyr Tyr Cys Gln Gln Tyr Cys Arg Lys Ser Ser
                85                 90                 95

Leu Phe Thr Phe Gly Gln Gly Thr Lys Val Glu Ile Lys Arg
            100                105                110
```

```
<210> SEQ ID NO 7
<211> LENGTH: 110
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Arg Thr Ser Tyr
                85                  90                  95

Leu Ile Thr Phe Gly Gln Gly Thr Lys Val Glu Ile Lys Arg
            100                 105                 110

<210> SEQ ID NO 8
<211> LENGTH: 110
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ser Arg Tyr Tyr Ser
                85                  90                  95

Leu Ile Thr Phe Gly Gln Gly Thr Lys Val Glu Ile Lys Arg
            100                 105                 110

<210> SEQ ID NO 9
<211> LENGTH: 110
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Lys Tyr Pro Phe
                85                  90                  95

Leu Ile Thr Phe Gly Gln Gly Thr Lys Val Glu Ile Lys Arg
            100                 105                 110

<210> SEQ ID NO 10
<211> LENGTH: 110
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Arg Ser Tyr Pro
                85                  90                  95

Pro Leu Thr Phe Gly Gln Gly Thr Lys Val Glu Ile Lys Arg
            100                 105                 110

<210> SEQ ID NO 11
<211> LENGTH: 110
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Gly Arg Arg Ser Ser
                85                  90                  95

Leu Ile Thr Phe Gly Gln Gly Thr Lys Val Glu Ile Lys Arg
            100                 105                 110

<210> SEQ ID NO 12
<211> LENGTH: 110
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30
```

```
Val Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Gln Gln Arg Tyr Ser Tyr
                 85                  90                  95

Leu Ile Thr Phe Gly Gln Gly Thr Lys Val Glu Ile Lys Arg
                100                 105                 110

<210> SEQ ID NO 13
<211> LENGTH: 110
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Arg Asn Ser Lys
                 85                  90                  95

Leu Ile Thr Phe Gly Gln Gly Thr Lys Val Glu Ile Lys Arg
                100                 105                 110

<210> SEQ ID NO 14
<211> LENGTH: 110
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Met Arg Ser Ser Ser
                 85                  90                  95

Leu Phe Thr Phe Gly Gln Gly Thr Lys Val Glu Ile Lys Arg
                100                 105                 110

<210> SEQ ID NO 15
<211> LENGTH: 108
<212> TYPE: PRT
<213> ORGANISM: Homo sapiens
```

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Asp Asp Leu Ile
                85                  90                  95

Thr Phe Gly Gln Gly Thr Lys Val Glu Ile Lys Arg
            100                 105

<210> SEQ ID NO 16
<211> LENGTH: 110
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Thr Ser Trp Pro Tyr
                85                  90                  95

Leu Ile Thr Phe Gly Gly Gly Thr Lys Val Glu Ile Lys Arg
            100                 105                 110

<210> SEQ ID NO 17
<211> LENGTH: 130
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr

-continued

```
                  100                 105                 110
Glu Gly Tyr Gly Leu Asp Tyr Trp Gly Gln Gly Thr Leu Val Thr Val
            115                 120                 125

Ser Ser
    130

<210> SEQ ID NO 18
<211> LENGTH: 130
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Ile His Trp Val Arg Gln Ala Pro Gly Lys Gly Leu Glu Trp Val
            35                  40                  45

Ala Ser Ile Tyr Ser Ser Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
            115                 120                 125

Ser Ser
    130

<210> SEQ ID NO 19
<211> LENGTH: 130
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Thr
            20                  25                  30

Asp Ile His Trp Val Arg Gln Ala Pro Gly Lys Gly Leu Glu Trp Val
            35                  40                  45

Ala Ser Ile Tyr Ser Ser Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
            115                 120                 125

Ser Ser
    130
```

```
<210> SEQ ID NO 20
<211> LENGTH: 130
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Ser
            20                  25                  30

Ser Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser
    130

<210> SEQ ID NO 21
<211> LENGTH: 130
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser
    130

<210> SEQ ID NO 22
<211> LENGTH: 130
<212> TYPE: PRT
<213> ORGANISM: Homo sapiens

<400> SEQUENCE: 22

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Gly Ser
            20                  25                  30

Ser Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
                100                 105                 110

Glu Gly Tyr Gly Leu Asp Tyr Trp Gly Gln Gly Thr Leu Val Thr Val
            115                 120                 125

Ser Ser
    130

<210> SEQ ID NO 23
<211> LENGTH: 130
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Ser Ser
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
                100                 105                 110

Glu Gly Tyr Gly Leu Asp Tyr Trp Gly Gln Gly Thr Leu Val Thr Val
            115                 120                 125

Ser Ser
    130

<210> SEQ ID NO 24
<211> LENGTH: 130
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Ala Asn
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
 50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser
    130

<210> SEQ ID NO 25
<211> LENGTH: 130
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Ser Ser
                 20                  25                  30

Ser Ile His Trp Val Arg Gln Ala Pro Gly Lys Gly Leu Glu Trp Val
            35                  40                  45

Ala Ser Ile Tyr Ser Ser Ser Gly Tyr Thr Tyr Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser
    130

<210> SEQ ID NO 26
<211> LENGTH: 233
<212> TYPE: PRT
<213> ORGANISM: Homo sapiens

<400> SEQUENCE: 26

Ala Gln Lys Val Thr Gln Ala Gln Ser Ser Val Ser Met Pro Val Arg
  1               5                  10                  15

Lys Ala Val Thr Leu Asn Cys Leu Tyr Glu Thr Ser Trp Trp Ser Tyr
                 20                  25                  30

Tyr Ile Phe Trp Tyr Lys Gln Leu Pro Ser Lys Glu Met Ile Phe Leu
            35                  40                  45

Ile Arg Gln Gly Ser Asp Glu Gln Asn Ala Lys Ser Gly Arg Tyr Ser
         50                  55                  60

Val Asn Phe Lys Lys Ala Ala Lys Ser Val Ala Leu Thr Ile Ser Ala
 65                  70                  75                  80

Leu Gln Leu Glu Asp Ser Ala Lys Tyr Phe Cys Ala Leu Gly Val Tyr
                 85                  90                  95

Ala His Ser Leu Thr Gly Gly Tyr Arg Gly Gly Ala Asp Lys Leu Ile
            100                 105                 110
```

```
Phe Gly Lys Gly Thr Arg Val Thr Val Glu Pro Arg Ser Gln Pro His
            115                 120                 125
Thr Lys Pro Ser Val Phe Val Met Lys Asn Gly Thr Asn Val Ala Cys
130                 135                 140
Leu Val Lys Glu Phe Tyr Pro Lys Asp Ile Arg Ile Asn Leu Val Ser
145                 150                 155                 160
Ser Lys Lys Ile Thr Glu Phe Asp Pro Ala Ile Val Ile Ser Pro Ser
                165                 170                 175
Gly Lys Tyr Asn Ala Val Lys Leu Gly Lys Tyr Glu Asp Ser Asn Ser
            180                 185                 190
Val Thr Cys Ser Val Gln His Asp Asn Lys Thr Val His Ser Thr Asp
            195                 200                 205
Phe Glu Val Lys Thr Asp Ser Thr Asp His Val Lys Pro Lys Glu Thr
    210                 215                 220
Glu Asn Thr Lys Gln Pro Ser Lys Ser
225                 230

<210> SEQ ID NO 27
<211> LENGTH: 234
<212> TYPE: PRT
<213> ORGANISM: Homo sapiens

<400> SEQUENCE: 27

Ala Gln Lys Val Thr Gln Ala Gln Ser Ser Val Ser Met Pro Val Arg
1               5                   10                  15
Lys Ala Val Thr Leu Asn Cys Leu Tyr Glu Thr Ser Trp Trp Ser Tyr
                20                  25                  30
Tyr Ile Phe Trp Tyr Lys Gln Leu Pro Ser Lys Glu Met Ile Phe Leu
            35                  40                  45
Ile Arg Gln Gly Ser Asp Glu Gln Asn Ala Lys Ser Gly Arg Tyr Ser
        50                  55                  60
Val Asn Phe Lys Lys Ala Ala Lys Ser Val Ala Leu Thr Ile Ser Ala
65                  70                  75                  80
Leu Gln Leu Glu Asp Ser Ala Lys Tyr Phe Cys Ala Leu Gly Pro Arg
                85                  90                  95
Pro Ser Tyr Ser Glu Glu Leu Gly Asp Thr His Arg Ala Asp Lys Leu
            100                 105                 110
Ile Phe Gly Lys Gly Thr Arg Val Thr Val Glu Pro Arg Ser Gln Pro
        115                 120                 125
His Thr Lys Pro Ser Val Phe Val Met Lys Asn Gly Thr Asn Val Ala
    130                 135                 140
Cys Leu Val Lys Glu Phe Tyr Pro Lys Asp Ile Arg Ile Asn Leu Val
145                 150                 155                 160
Ser Ser Lys Lys Ile Thr Glu Phe Asp Pro Ala Ile Val Ile Ser Pro
                165                 170                 175
Ser Gly Lys Tyr Asn Ala Val Lys Leu Gly Lys Tyr Glu Asp Ser Asn
            180                 185                 190
Ser Val Thr Cys Ser Val Gln His Asp Asn Lys Thr Val His Ser Thr
        195                 200                 205
Asp Phe Glu Val Lys Thr Asp Ser Thr Asp His Val Lys Pro Lys Glu
    210                 215                 220
Thr Glu Asn Thr Lys Gln Pro Ser Lys Ser
225                 230
```

-continued

<210> SEQ ID NO 28
<211> LENGTH: 227
<212> TYPE: PRT
<213> ORGANISM: Homo sapiens

<400> SEQUENCE: 28

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Pro
                85                  90                  95

Asn His Phe Leu Asn Thr Asp Lys Leu Ile Phe Gly Lys Gly Thr Arg
            100                 105                 110

Val Thr Val Glu Pro Arg Ser Gln Pro His Thr Lys Pro Ser Val Phe
        115                 120                 125

Val Met Lys Asn Gly Thr Asn Val Ala Cys Leu Val Lys Glu Phe Tyr
    130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
            180                 185                 190

His Asp Asn Lys Thr Val His Ser Thr Asp Phe Glu Val Lys Thr Asp
        195                 200                 205

Ser Thr Asp His Val Lys Pro Lys Glu Thr Glu Asn Thr Lys Gln Pro
    210                 215                 220

Ser Lys Ser
225

<210> SEQ ID NO 29
<211> LENGTH: 229
<212> TYPE: PRT
<213> ORGANISM: Homo sapiens

<400> SEQUENCE: 29

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Asp Ile Tyr Gly Pro Gly Phe Lys Asp Asn Phe
    50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95

Leu Gly Met Gly Gly Glu Tyr Thr Asp Lys Leu Ile Phe Gly Lys Gly

```
            100                 105                 110
Thr Arg Val Thr Val Glu Pro Arg Ser Gln Pro His Thr Lys Pro Ser
            115                 120                 125
Val Phe Val Met Lys Asn Gly Thr Asn Val Ala Cys Leu Val Lys Glu
            130                 135                 140
Phe Tyr Pro Lys Asp Ile Arg Ile Asn Leu Val Ser Ser Lys Lys Ile
145                 150                 155                 160
Thr Glu Phe Asp Pro Ala Ile Val Ile Ser Pro Ser Gly Lys Tyr Asn
                        165                 170                 175
Ala Val Lys Leu Gly Lys Tyr Glu Asp Ser Asn Ser Val Thr Cys Ser
            180                 185                 190
Val Gln His Asp Asn Lys Thr Val His Ser Thr Asp Phe Glu Val Lys
            195                 200                 205
Thr Asp Ser Thr Asp His Val Lys Pro Lys Glu Thr Glu Asn Thr Lys
            210                 215                 220
Gln Pro Ser Lys Ser
225

<210> SEQ ID NO 30
<211> LENGTH: 242
<212> TYPE: PRT
<213> ORGANISM: Homo sapiens

<400> SEQUENCE: 30

Ala Gly His Leu Glu Gln Pro Gln Ile Ser Ser Thr Lys Thr Leu Ser
1               5                   10                  15
Lys Thr Ala Arg Leu Glu Cys Val Val Ser Gly Ile Thr Ile Ser Ala
                20                  25                  30
Thr Ser Val Tyr Trp Tyr Arg Glu Arg Pro Gly Glu Val Ile Gln Phe
            35                  40                  45
Leu Val Ser Ile Ser Tyr Asp Gly Thr Val Arg Lys Glu Ser Gly Ile
        50                  55                  60
Pro Ser Gly Lys Phe Glu Val Asp Arg Ile Pro Glu Thr Ser Thr Ser
65                  70                  75                  80
Thr Leu Thr Ile His Asn Val Glu Lys Gln Asp Ile Ala Thr Tyr Tyr
                85                  90                  95
Cys Ala Leu Trp Glu Ala Gln Gln Glu Leu Gly Lys Lys Ile Lys Val
            100                 105                 110
Phe Gly Pro Gly Thr Lys Leu Ile Ile Thr Asp Lys Gln Leu Asp Ala
            115                 120                 125
Asp Val Ser Pro Lys Pro Thr Ile Phe Leu Pro Ser Ile Ala Glu Thr
            130                 135                 140
Lys Leu Gln Lys Ala Gly Thr Tyr Leu Cys Leu Leu Glu Lys Phe Phe
145                 150                 155                 160
Pro Asp Val Ile Lys Ile His Trp Glu Glu Lys Lys Ser Asn Thr Ile
                        165                 170                 175
Leu Gly Ser Gln Glu Gly Asn Thr Met Lys Thr Asn Asp Thr Tyr Met
            180                 185                 190
Lys Phe Ser Trp Leu Thr Val Pro Glu Lys Ser Leu Asp Lys Glu His
            195                 200                 205
Arg Cys Ile Val Arg His Glu Asn Asn Lys Asn Gly Val Asp Gln Glu
            210                 215                 220
Ile Ile Phe Pro Pro Ile Lys Thr Asp Val Ile Thr Met Asp Pro Lys
225                 230                 235                 240
```

Asp Asn

<210> SEQ ID NO 31
<211> LENGTH: 330
<212> TYPE: PRT
<213> ORGANISM: Homo sapiens

<400> SEQUENCE: 31

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 32
<211> LENGTH: 223
<212> TYPE: PRT
<213> ORGANISM: Macaca fascicularis

```
<400> SEQUENCE: 32

Ala Gln Lys Val Thr Gln Ala Gln Ser Ser Val Ser Met Pro Val Glu
1               5                   10                  15

Lys Ala Val Thr Leu Asn Cys Gln Tyr Glu Thr Ser Ser Trp Ser Tyr
                20                  25                  30

Asp Leu Phe Trp Tyr Lys Gln Leu Pro Gly Lys Glu Met Ile Phe Leu
            35                  40                  45

Ile Arg Gln Gly Ser Ser Glu Gln Asn Ala Arg Asp Gly Arg Tyr Ser
    50                  55                  60

Val Asn Phe Lys Lys Glu Ala Ser Phe Ile Ala Leu Thr Ile Ser Ala
65                  70                  75                  80

Leu Gln Leu Glu Asp Ser Ala Thr Tyr Phe Cys Ala Leu Arg Arg Pro
                85                  90                  95

Phe Thr Ala Gln Leu Phe Phe Gly Lys Gly Thr Gln Leu Ile Val Glu
            100                 105                 110

Pro Glu Arg Gln Pro His Thr Lys Pro Ser Val Phe Val Met Lys Asn
        115                 120                 125

Gly Thr Asn Val Ala Cys Leu Val Lys Asp Phe Tyr Pro Lys Asp Ile
130                 135                 140

Arg Ile Asn Leu Glu Ser Ser Lys Lys Ile Thr Glu Phe Asp Pro Ala
145                 150                 155                 160

Ile Val Val Ser Pro Ser Gly Lys Tyr Asn Ala Val Lys Leu Gly Gln
                165                 170                 175

Tyr Ala Asp Ser Asn Ser Val Thr Cys Ser Val Gln His Asn Lys Glu
            180                 185                 190

Val Val Tyr Ser Thr Asp Phe Glu Val Lys Thr Asn Ser Thr Asp His
        195                 200                 205

Leu Lys Pro Thr Glu Thr Glu Asn Thr Lys Gln Pro Ser Lys Ser
    210                 215                 220

<210> SEQ ID NO 33
<211> LENGTH: 235
<212> TYPE: PRT
<213> ORGANISM: Macaca fascicularis

<400> SEQUENCE: 33

Ala Gln Lys Val Thr Gln Ala Gln Ser Ser Val Ser Met Pro Val Gly
1               5                   10                  15

Lys Ala Val Thr Leu Asn Cys Gln Tyr Glu Thr Ser Ser Trp Ser Tyr
                20                  25                  30

Tyr Leu Phe Trp Tyr Lys Gln Leu Pro Gly Lys Glu Met Ile Phe Leu
            35                  40                  45

Ile His Gln Gly Ser Ser Gln Gln Asn Ala Arg Asn Gly Arg Tyr Ser
    50                  55                  60

Val Asn Phe Gln Lys Ala Ala Ser Ser Ile Thr Leu Thr Ile Ser Ala
65                  70                  75                  80

Leu Gln Leu Glu Asp Ser Ala Thr Tyr Phe Cys Ala Leu Arg Glu Arg
                85                  90                  95

Pro Pro Asn Pro Gly Pro Phe Val Leu Gly Val Tyr Ala Thr Ala Gln
            100                 105                 110

Leu Phe Phe Gly Lys Gly Thr Gln Leu Ile Val Glu Pro Glu Arg Gln
        115                 120                 125

Pro His Thr Lys Pro Ser Val Phe Val Met Lys Asn Gly Thr Asn Val
    130                 135                 140
```

Ala Cys Leu Val Lys Asp Phe Tyr Pro Lys Asp Ile Arg Ile Asn Leu
145                 150                 155                 160

Glu Ser Ser Lys Lys Ile Thr Glu Phe Asp Pro Ala Ile Val Val Ser
            165                 170                 175

Pro Ser Gly Lys Tyr Asn Ala Val Lys Leu Gly Gln Tyr Ala Asp Ser
            180                 185                 190

Asn Ser Val Thr Cys Ser Val Gln His Asn Lys Glu Val Val Tyr Ser
            195                 200                 205

Thr Asp Phe Glu Val Lys Thr Asn Ser Thr Asp His Leu Lys Pro Thr
            210                 215                 220

Glu Thr Glu Asn Thr Lys Gln Pro Ser Lys Ser
225                 230                 235

<210> SEQ ID NO 34
<211> LENGTH: 235
<212> TYPE: PRT
<213> ORGANISM: Macaca fascicularis

<400> SEQUENCE: 34

Ala Gln Lys Val Thr Gln Ala Gln Ser Ser Val Ser Met Pro Val Glu
1               5                   10                  15

Lys Ala Val Thr Leu Asn Cys Gln Tyr Glu Thr Ser Trp Trp Ser Tyr
            20                  25                  30

Asp Leu Phe Trp Tyr Lys Gln Leu Pro Gly Lys Glu Met Ile Phe Leu
            35                  40                  45

Ile Arg Gln Ser Ser Ser Glu Gln Asn Ala Arg Asp Gly Arg Tyr Ser
        50                  55                  60

Ala Asn Phe Lys Lys Glu Ala Ser Ser Lys Ser Phe Ile Ala Leu Thr
65                  70                  75                  80

Ile Ser Ala Leu Gln Leu Glu Asp Ser Ala Thr Tyr Phe Cys Ala Leu
                85                  90                  95

Pro Leu Gln Val Arg Gly Pro Thr Gly Gly Ile Arg Val Tyr Asp Lys
            100                 105                 110

Leu Ile Phe Gly Lys Gly Thr Arg Val Thr Val Glu Pro Lys Arg Gln
        115                 120                 125

Pro His Thr Lys Pro Ser Val Phe Val Met Lys Asn Gly Thr Asn Val
130                 135                 140

Ala Cys Leu Val Lys Asp Phe Tyr Pro Lys Asp Ile Arg Ile Asn Leu
145                 150                 155                 160

Glu Ser Ser Lys Lys Ile Thr Glu Phe Asp Pro Ala Ile Val Val Ser
            165                 170                 175

Pro Ser Gly Lys Tyr Asn Ala Val Lys Leu Gly Gln Tyr Ala Asp Ser
            180                 185                 190

Asn Ser Val Thr Cys Ser Val Gln His Asn Lys Glu Val Val Tyr Ser
            195                 200                 205

Thr Asp Phe Glu Val Lys Thr Asn Ser Thr Asp His Leu Lys Pro Thr
            210                 215                 220

Glu Thr Glu Asn Thr Lys Gln Pro Ser Lys Ser
225                 230                 235

<210> SEQ ID NO 35
<211> LENGTH: 227
<212> TYPE: PRT
<213> ORGANISM: Homo sapiens

<400> SEQUENCE: 35

```
Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
                35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95

Ser Ser Ser Ser Gly Thr Asp Lys Leu Ile Phe Gly Lys Gly Thr Arg
                100                 105                 110

Val Thr Val Glu Pro Arg Ser Gln Pro His Thr Lys Pro Ser Val Phe
            115                 120                 125

Val Met Lys Asn Gly Thr Asn Val Ala Cys Leu Val Lys Glu Phe Tyr
        130                 135                 140

Pro Lys Asp Ile Arg Ile Asn Leu Val Ser Ser Lys Lys Ile Thr Glu
145                 150                 155                 160

Phe Asp Pro Ala Ile Val Ile Ser Pro Ser Gly Lys Tyr Asn Ala Val
                165                 170                 175

Lys Leu Gly Lys Tyr Glu Asp Ser Asn Ser Val Thr Cys Ser Val Gln
                180                 185                 190

His Asp Asn Lys Thr Val His Ser Thr Asp Phe Glu Val Lys Thr Asp
            195                 200                 205

Ser Thr Asp His Val Lys Pro Lys Glu Thr Glu Asn Thr Lys Gln Pro
        210                 215                 220

Ser Lys Ser
225

<210> SEQ ID NO 36
<211> LENGTH: 228
<212> TYPE: PRT
<213> ORGANISM: Homo sapiens

<400> SEQUENCE: 36

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Met Thr Phe
                35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Ile
                85                  90                  95

Leu Gly Asp Lys Gly Asn Thr Asp Lys Leu Ile Phe Gly Lys Gly Thr
                100                 105                 110

Arg Val Thr Val Glu Pro Arg Ser Gln Pro His Thr Lys Pro Ser Val
            115                 120                 125

Phe Val Met Lys Asn Gly Thr Asn Val Ala Cys Leu Val Lys Glu Phe
        130                 135                 140
```

```
Tyr Pro Lys Asp Ile Arg Ile Asn Leu Val Ser Ser Lys Lys Ile Thr
145                 150                 155                 160

Glu Phe Asp Pro Ala Ile Val Ile Ser Pro Ser Gly Lys Tyr Asn Ala
                165                 170                 175

Val Lys Leu Gly Lys Tyr Glu Asp Ser Asn Ser Val Thr Cys Ser Val
            180                 185                 190

Gln His Asp Asn Lys Thr Val His Ser Thr Asp Phe Glu Val Lys Thr
        195                 200                 205

Asp Ser Thr Asp His Val Lys Pro Lys Glu Thr Glu Asn Thr Lys Gln
    210                 215                 220

Pro Ser Lys Ser
225

<210> SEQ ID NO 37
<211> LENGTH: 229
<212> TYPE: PRT
<213> ORGANISM: Macaca fascicularis

<400> SEQUENCE: 37

Ala Val Glu Leu Val Pro Glu His Gln Thr Val Ile Val Ser Val Gly
1               5                   10                  15

Asp Pro Ala Thr Leu Lys Cys Ser Met Lys Gly Glu Ala Ile Ser Asn
            20                  25                  30

Tyr Tyr Ile Asn Trp Tyr Arg Lys Thr Gln Gly Asn Thr Met Thr Phe
        35                  40                  45

Ile Tyr Arg Glu Lys Gly Ile Tyr Gly Pro Gly Phe Lys Asp Asn Phe
    50                  55                  60

Gln Gly Asp Ile Asp Thr Glu Glu Asn Gln Ala Val Leu Lys Ile Leu
65                  70                  75                  80

Ala Pro Ser Glu Arg Asp Gly Ser Tyr Tyr Cys Ala Ser Asp Ile
                85                  90                  95

Leu Ser Trp Val Asp Ser Tyr Thr Asp Lys Leu Ile Phe Gly Lys Gly
            100                 105                 110

Thr Arg Val Thr Val Glu Pro Lys Arg Gln Pro His Thr Lys Pro Ser
        115                 120                 125

Val Phe Val Met Lys Asn Gly Thr Asn Val Ala Cys Leu Val Lys Asp
    130                 135                 140

Phe Tyr Gly Lys Asp Ile Arg Ile Asn Leu Glu Ser Ser Lys Lys Ile
145                 150                 155                 160

Thr Glu Phe Asp Pro Ala Ile Val Ser Pro Ser Gly Lys Tyr Asn
                165                 170                 175

Ala Val Lys Leu Gly Gln Tyr Ala Asp Ser Asn Ser Val Thr Cys Ser
            180                 185                 190

Val Gln His Asn Lys Glu Val Val Tyr Ser Thr Asp Phe Glu Val Lys
        195                 200                 205

Thr Asn Ser Thr Asp His Leu Lys Pro Thr Glu Thr Glu Asn Thr Lys
    210                 215                 220

Gln Pro Ser Lys Ser
225

<210> SEQ ID NO 38
<211> LENGTH: 240
<212> TYPE: PRT
<213> ORGANISM: Homo sapiens

<400> SEQUENCE: 38
```

```
Ser Ser Asn Leu Glu Gly Arg Thr Lys Ser Val Thr Arg Gln Thr Gly
1               5                   10                  15

Ser Ser Ala Glu Ile Thr Cys Asp Leu Thr Val Thr Asn Thr Phe Tyr
            20                  25                  30

Ile His Trp Tyr Leu His Gln Glu Gly Lys Ala Pro Gln Arg Leu Leu
            35                  40                  45

Tyr Tyr Asp Val Ser Thr Ala Arg Asp Val Leu Glu Ser Gly Leu Ser
50                  55                  60

Pro Gly Lys Tyr Tyr Thr His Thr Pro Arg Arg Trp Ser Trp Ile Leu
65              70                  75                  80

Arg Leu Gln Asn Leu Ile Glu Asn Asp Ser Gly Val Tyr Tyr Cys Ala
                85                  90                  95

Thr Trp Asp Arg Pro Leu Asn Ala Trp Ile Lys Thr Phe Ala Lys Gly
            100                 105                 110

Thr Arg Leu Ile Val Thr Ser Pro Asp Lys Gln Leu Asp Ala Asp Val
        115                 120                 125

Ser Pro Lys Pro Thr Ile Phe Leu Pro Ser Ile Ala Glu Thr Lys Leu
130                 135                 140

Gln Lys Ala Gly Thr Tyr Leu Cys Leu Leu Glu Lys Phe Phe Pro Asp
145                 150                 155                 160

Val Ile Lys Ile His Trp Gln Glu Lys Lys Ser Asn Thr Ile Leu Gly
                165                 170                 175

Ser Gln Glu Gly Asn Thr Met Lys Thr Asn Asp Thr Tyr Met Lys Phe
            180                 185                 190

Ser Trp Leu Thr Val Pro Glu Lys Ser Leu Asp Lys Glu His Arg Cys
        195                 200                 205

Ile Val Arg His Glu Asn Asn Lys Asn Gly Val Asp Gln Glu Ile Ile
    210                 215                 220

Phe Pro Pro Ile Lys Thr Asp Val Ile Thr Met Asp Pro Lys Asp Asn
225                 230                 235                 240

<210> SEQ ID NO 39
<211> LENGTH: 236
<212> TYPE: PRT
<213> ORGANISM: Homo sapiens

<400> SEQUENCE: 39

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
            35                  40                  45

Tyr Tyr Asp Ser Tyr Thr Ser Ser Val Val Leu Glu Ser Gly Ile Ser
50                  55                  60

Pro Gly Lys Tyr Asp Thr Tyr Gly Ser Thr Arg Lys Asn Leu Arg Met
65              70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
            100                 105                 110

Leu Val Val Thr Asp Lys Gln Leu Asp Ala Asp Val Ser Pro Lys Pro
        115                 120                 125

Thr Ile Phe Leu Pro Ser Ile Ala Glu Thr Lys Leu Gln Lys Ala Gly
```

```
                130                 135                 140
Thr Tyr Leu Cys Leu Leu Glu Lys Phe Phe Pro Asp Val Ile Lys Ile
145                 150                 155                 160

His Trp Gln Glu Lys Lys Ser Asn Thr Ile Leu Gly Ser Gln Glu Gly
                165                 170                 175

Asn Thr Met Lys Thr Asn Asp Thr Tyr Met Lys Phe Ser Trp Leu Thr
                180                 185                 190

Val Pro Glu Lys Ser Leu Asp Lys Glu His Arg Cys Ile Val Arg His
                195                 200                 205

Glu Asn Asn Lys Asn Gly Val Asp Gln Glu Ile Ile Phe Pro Pro Ile
                210                 215                 220

Lys Thr Asp Val Ile Thr Met Asp Pro Lys Asp Asn
225                 230                 235

<210> SEQ ID NO 40
<211> LENGTH: 235
<212> TYPE: PRT
<213> ORGANISM: Homo sapiens

<400> SEQUENCE: 40

Ser Ser Asn Leu Glu Gly Gly Thr Lys Ser Val Thr Arg Pro Thr Arg
1               5                   10                  15

Ser Ser Ala Glu Ile Thr Cys Asp Leu Thr Val Ile Asn Ala Phe Tyr
                20                  25                  30

Ile His Trp Tyr Leu His Gln Glu Gly Lys Ala Pro Gln Arg Leu Leu
            35                  40                  45

Tyr Tyr Asp Val Ser Asn Ser Lys Asp Val Leu Glu Ser Gly Leu Ser
50                  55                  60

Pro Gly Lys Tyr Tyr Thr His Thr Pro Arg Arg Trp Ser Trp Ile Leu
65                  70                  75                  80

Ile Leu Arg Asn Leu Ile Glu Asn Asp Ser Gly Val Tyr Tyr Cys Ala
                85                  90                  95

Thr Trp Asp Arg Leu Arg Lys Lys Leu Phe Gly Ser Gly Thr Thr Leu
                100                 105                 110

Val Val Thr Asp Lys Gln Leu Asp Ala Asp Val Ser Pro Lys Pro Thr
            115                 120                 125

Ile Phe Leu Pro Ser Ile Ala Glu Thr Lys Leu Gln Lys Ala Gly Thr
130                 135                 140

Tyr Leu Cys Leu Leu Glu Lys Phe Phe Pro Asp Val Ile Lys Ile His
145                 150                 155                 160

Trp Gln Glu Lys Lys Ser Asn Thr Ile Leu Gly Ser Gln Glu Gly Asn
                165                 170                 175

Thr Met Lys Thr Asn Asp Thr Tyr Met Lys Phe Ser Trp Leu Thr Val
                180                 185                 190

Pro Glu Lys Ser Leu Asp Lys Glu His Arg Cys Ile Val Arg His Glu
                195                 200                 205

Asn Asn Lys Asn Gly Val Asp Gln Glu Ile Ile Phe Pro Pro Ile Lys
                210                 215                 220

Thr Asp Val Ile Thr Met Asp Pro Lys Asp Asn
225                 230                 235

<210> SEQ ID NO 41
<211> LENGTH: 234
<212> TYPE: PRT
<213> ORGANISM: Homo sapiens
```

```
<400> SEQUENCE: 41

Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
            20                  25                  30

Thr His Trp Tyr Leu His Gln Glu Gly Lys Ala Pro Gln Arg Leu Leu
        35                  40                  45

Tyr Tyr Asp Ser Tyr Asn Ser Arg Val Val Leu Glu Ser Gly Ile Ser
    50                  55                  60

Arg Glu Lys Tyr His Thr Tyr Ala Ser Thr Gly Lys Ser Leu Lys Phe
65                  70                  75                  80

Ile Leu Glu Asn Leu Ile Glu Arg Asp Ser Gly Val Tyr Tyr Cys Ala
                85                  90                  95

Thr Trp Asp Trp Gly Lys Lys Leu Phe Gly Ser Gly Thr Thr Leu Val
            100                 105                 110

Val Thr Asp Lys Gln Leu Asp Ala Asp Val Ser Pro Lys Pro Thr Ile
        115                 120                 125

Phe Leu Pro Ser Ile Ala Glu Thr Lys Leu Gln Lys Ala Gly Thr Tyr
    130                 135                 140

Leu Cys Leu Leu Glu Lys Phe Phe Pro Asp Val Ile Lys Ile His Trp
145                 150                 155                 160

Gln Glu Lys Lys Ser Asn Thr Ile Leu Gly Ser Gln Glu Gly Asn Thr
                165                 170                 175

Met Lys Thr Asn Asp Thr Tyr Met Lys Phe Ser Trp Leu Thr Val Pro
            180                 185                 190

Glu Lys Ser Leu Asp Lys Glu His Arg Cys Ile Val Arg His Glu Asn
        195                 200                 205

Asn Lys Asn Gly Val Asp Gln Glu Ile Ile Phe Pro Pro Ile Lys Thr
    210                 215                 220

Asp Val Ile Thr Met Asp Pro Lys Asp Asn
225                 230

<210> SEQ ID NO 42
<211> LENGTH: 241
<212> TYPE: PRT
<213> ORGANISM: Macaca fascicularis

<400> SEQUENCE: 42

Ala Gly His Leu Glu Gln Pro Gln Ile Ser Ser Thr Lys Met Leu Ser
1               5                   10                  15

Lys Thr Ala Arg Leu Glu Cys Val Val Ser Gly Val Thr Ile Ser Glu
            20                  25                  30

Thr Ser Ile Tyr Trp Tyr Arg Glu Arg Pro Gly Glu Val Ile Gln Phe
        35                  40                  45

Leu Val Cys Ile Phe Tyr Asp Gly Thr Val Lys Lys Glu Ser Ser Ile
    50                  55                  60

Pro Ser Gly Lys Phe Glu Val Asp Arg Ile Pro Lys Thr Ser Thr Ser
65                  70                  75                  80

Thr Leu Thr Ile His Asn Val Glu Lys Gln Asp Ile Ala Thr Tyr Tyr
                85                  90                  95

Cys Ala Leu Trp Glu Val Gln Gln Phe Gly Arg Lys Val Lys Leu Phe
            100                 105                 110

Gly Pro Gly Thr Lys Leu Ile Ile Thr Asp Lys His Leu Asp Ala Asp
        115                 120                 125
```

```
Val Ser Pro Lys Pro Thr Ile Phe Leu Pro Ser Ile Ala Glu Thr Asn
    130                 135                 140

Leu His Lys Ala Gly Thr Tyr Leu Cys Leu Leu Glu Asn Phe Phe Pro
145                 150                 155                 160

Asp Val Ile Lys Ile His Trp Gln Glu Lys Lys Ser Asn Thr Ile Leu
                165                 170                 175

Gly Ser Gln Glu Gly Asn Thr Val Lys Thr Asn Asp Thr Tyr Met Lys
                180                 185                 190

Phe Ser Trp Leu Thr Val Pro Glu Lys Ser Leu Asp Lys Glu His Arg
                195                 200                 205

Cys Ile Val Arg His Glu Asn Asn Lys Asn Gly Val Asp Gln Glu Ile
210                 215                 220

Ile Phe Pro Pro Ile Lys Thr Asp Val Thr Thr Met Asp Pro Lys Asp
225                 230                 235                 240

Asn
```

<210> SEQ ID NO 43
<211> LENGTH: 130
<212> TYPE: PRT
<213> ORGANISM: Homo sapiens

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Asn
                20                  25                  30

Asp Ile His Trp Val Arg Gln Ala Pro Gly Lys Gly Leu Glu Trp Val
            35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
                100                 105                 110

Glu Gly Tyr Gly Leu Asp Tyr Trp Gly Gln Gly Thr Leu Val Thr Val
            115                 120                 125

Ser Ser
    130
```

<210> SEQ ID NO 44
<211> LENGTH: 130
<212> TYPE: PRT
<213> ORGANISM: Homo sapiens

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Thr
                20                  25                  30

Asp Ile His Trp Val Arg Gln Ala Pro Gly Lys Gly Leu Glu Trp Val
            35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                    85                  90                  95

Ala Arg Asp Pro Gly Ser Tyr Tyr Trp Tyr Ser Gly Ser Ala Tyr
                100                 105                 110

Glu Gly Tyr Gly Leu Asp Tyr Trp Gly Gln Gly Thr Leu Val Thr Val
            115                 120                 125

Ser Ser
    130

<210> SEQ ID NO 45
<211> LENGTH: 130
<212> TYPE: PRT
<213> ORGANISM: Homo sapiens

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Ser Gly Ser Ala Tyr
                100                 105                 110

Glu Gly Tyr Gly Leu Asp Tyr Trp Gly Gln Gly Thr Leu Val Thr Val
            115                 120                 125

Ser Ser
    130

<210> SEQ ID NO 46
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X may be F or V
<220> FEATURE:
<221> NAME/KEY: MISC_FEATURE
<222> LOCATION: (4)..(4)
<223> OTHER INFORMATION: X may be S or T
<220> FEATURE:
<221> NAME/KEY: MISC_FEATURE
<222> LOCATION: (5)..(5)
<223> OTHER INFORMATION: X may be G, A, or S
<220> FEATURE:
<221> NAME/KEY: MISC_FEATURE
<222> LOCATION: (6)..(6)
<223> OTHER INFORMATION: X may be T, N, or S
<220> FEATURE:
<221> NAME/KEY: MISC_FEATURE
<222> LOCATION: (7)..(7)
<223> OTHER INFORMATION: X may be D or S
<220> FEATURE:
<221> NAME/KEY: MISC_FEATURE
<222> LOCATION: (7)..(7)
<223> OTHER INFORMATION: X may be D or S
```

```
<400> SEQUENCE: 46

Phe Thr Xaa Xaa Xaa Xaa Ile His
1               5

<210> SEQ ID NO 47
<211> LENGTH: 451
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Ser
            20                  25                  30

Ser Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Trp Ser Tyr Pro Ser Trp Trp Pro Tyr Arg Gly Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Gln Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
   450

<210> SEQ ID NO 48
<211> LENGTH: 20
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X may be S or M

<400> SEQUENCE: 48

Pro Gly Xaa Tyr Tyr Trp Tyr Tyr Ser Gly Ser Ala Tyr Glu Gly Tyr
1               5                   10                  15

Gly Leu Asp Tyr
            20

<210> SEQ ID NO 49
<211> LENGTH: 457
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ala Asn
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175
```

-continued

```
Thr Ser Gly Val His Thr Phe Pro Ala Val Leu Gln Ser Ser Gly Leu
            180                 185                 190
Tyr Ser Leu Ser Ser Val Val Thr Val Pro Ser Ser Ser Leu Gly Thr
        195                 200                 205
Lys Thr Tyr Thr Cys Asn Val Asp His Lys Pro Ser Asn Thr Lys Val
210                 215                 220
Asp Lys Arg Val Glu Ser Lys Tyr Gly Pro Pro Cys Pro Pro Cys Pro
225                 230                 235                 240
Ala Pro Glu Phe Leu Gly Gly Pro Ser Val Phe Leu Phe Pro Pro Lys
            245                 250                 255
Pro Lys Asp Thr Leu Met Ile Ser Arg Thr Pro Glu Val Thr Cys Val
        260                 265                 270
Val Val Asp Val Ser Gln Glu Asp Pro Glu Val Gln Phe Asn Trp Tyr
    275                 280                 285
Val Asp Gly Val Glu Val His Asn Ala Lys Thr Lys Pro Arg Glu Glu
290                 295                 300
Gln Phe Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
            325                 330                 335
Gly Leu Pro Ser Ser Ile Glu Lys Thr Ile Ser Lys Ala Lys Gly Gln
        340                 345                 350
Pro Arg Glu Pro Gln Val Tyr Thr Leu Pro Pro Ser Gln Glu Glu Met
    355                 360                 365
Thr Lys Asn Gln Val Ser Leu Thr Cys Leu Val Lys Gly Phe Tyr Pro
370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
            405                 410                 415
Tyr Ser Arg Leu Thr Val Asp Lys Ser Arg Trp Gln Glu Gly Asn Val
        420                 425                 430
Phe Ser Cys Ser Val Met His Glu Ala Leu His Asn His Tyr Thr Gln
    435                 440                 445
Lys Ser Leu Ser Leu Ser Leu Gly Lys
450                 455
```

```
<210> SEQ ID NO 50
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X may be S or A
<220> FEATURE:
<221> NAME/KEY: MISC_FEATURE
<222> LOCATION: (6)..(6)
<223> OTHER INFORMATION: X may be Y or Q

<400> SEQUENCE: 50

Xaa Ala Ser Ser Leu Xaa Ser
1               5

<210> SEQ ID NO 51
<211> LENGTH: 11
<212> TYPE: PRT
<213> ORGANISM: Homo sapiens
```

```
<220> FEATURE:
<221> NAME/KEY: MISC_FEATURE
<222> LOCATION: (3)..(3)
<223> OTHER INFORMATION: X may be S or Q
<220> FEATURE:
<221> NAME/KEY: MISC_FEATURE
<222> LOCATION: (4)..(4)
<223> OTHER INFORMATION: X may be G, S, or T
<220> FEATURE:
<221> NAME/KEY: MISC_FEATURE
<222> LOCATION: (5)..(5)
<223> OTHER INFORMATION: X may be D, K, or S
<220> FEATURE:
<221> NAME/KEY: MISC_FEATURE
<222> LOCATION: (6)..(6)
<223> OTHER INFORMATION: X may be Y, W, or absent
<220> FEATURE:
<221> NAME/KEY: MISC_FEATURE
<222> LOCATION: (7)..(7)
<223> OTHER INFORMATION: X may be P or absent
<220> FEATURE:
<221> NAME/KEY: MISC_FEATURE
<222> LOCATION: (8)..(8)
<223> OTHER INFORMATION: X may be D, F, or Y

<400> SEQUENCE: 51

Gln Gln Xaa Xaa Xaa Xaa Xaa Xaa Leu Ile Thr
1               5                   10

<210> SEQ ID NO 52
<211> LENGTH: 9
<212> TYPE: PRT
<213> ORGANISM: Homo sapiens

<400> SEQUENCE: 52

Phe Thr Val Ser Ser Ser Ser Ile His
1               5

<210> SEQ ID NO 53
<211> LENGTH: 17
<212> TYPE: PRT
<213> ORGANISM: Homo sapiens

<400> SEQUENCE: 53

Ser Ile Tyr Ser Ser Ser Gly Tyr Thr Tyr Tyr Ala Asp Ser Val Lys
1               5                   10                  15
Gly

<210> SEQ ID NO 54
<211> LENGTH: 21
<212> TYPE: PRT
<213> ORGANISM: Homo sapiens

<400> SEQUENCE: 54

Asp Pro Gly Ser Tyr Tyr Trp Tyr Tyr Ser Gly Ser Ala Tyr Glu Gly
1               5                   10                  15
Tyr Gly Leu Asp Tyr
            20

<210> SEQ ID NO 55
<211> LENGTH: 11
<212> TYPE: PRT
<213> ORGANISM: Homo sapiens

<400> SEQUENCE: 55

Arg Ala Ser Gln Ser Val Ser Ser Ala Val Ala
1               5                   10
```

```
<210> SEQ ID NO 56
<211> LENGTH: 7
<212> TYPE: PRT
<213> ORGANISM: Homo sapiens

<400> SEQUENCE: 56

Ala Ala Ser Ser Leu Gln Ser
1               5

<210> SEQ ID NO 57
<211> LENGTH: 11
<212> TYPE: PRT
<213> ORGANISM: Homo sapiens

<400> SEQUENCE: 57

Gln Gln Gln Ser Lys Tyr Pro Phe Leu Ile Thr
1               5                   10

<210> SEQ ID NO 58
<211> LENGTH: 7
<212> TYPE: PRT
<213> ORGANISM: Homo sapiens

<400> SEQUENCE: 58

Ser Ala Ser Ser Leu Tyr Ser
1               5

<210> SEQ ID NO 59
<211> LENGTH: 9
<212> TYPE: PRT
<213> ORGANISM: Homo sapiens

<400> SEQUENCE: 59

Gln Gln Ser Gly Asp Asp Leu Ile Thr
1               5

<210> SEQ ID NO 60
<211> LENGTH: 11
<212> TYPE: PRT
<213> ORGANISM: Homo sapiens

<400> SEQUENCE: 60

Gln Gln Gln Thr Ser Trp Pro Tyr Leu Ile Thr
1               5                   10

<210> SEQ ID NO 61
<211> LENGTH: 9
<212> TYPE: PRT
<213> ORGANISM: Homo sapiens

<400> SEQUENCE: 61

Phe Thr Phe Ser Ser Ser Asp Ile His
1               5

<210> SEQ ID NO 62
<211> LENGTH: 9
<212> TYPE: PRT
<213> ORGANISM: Homo sapiens

<400> SEQUENCE: 62

Phe Thr Phe Ser Ser Ser Ser Ile His
1               5

<210> SEQ ID NO 63
```

```
<211> LENGTH: 9
<212> TYPE: PRT
<213> ORGANISM: Homo sapiens

<400> SEQUENCE: 63

Phe Thr Phe Ser Gly Thr Asp Ile His
1               5

<210> SEQ ID NO 64
<211> LENGTH: 9
<212> TYPE: PRT
<213> ORGANISM: Homo sapiens

<400> SEQUENCE: 64

Phe Thr Phe Ser Ala Ser Ser Ile His
1               5

<210> SEQ ID NO 65
<211> LENGTH: 9
<212> TYPE: PRT
<213> ORGANISM: Homo sapiens

<400> SEQUENCE: 65

Phe Thr Phe Ser Ser Asn Asp Ile His
1               5

<210> SEQ ID NO 66
<211> LENGTH: 9
<212> TYPE: PRT
<213> ORGANISM: Homo sapiens

<400> SEQUENCE: 66

Phe Thr Phe Thr Gly Ser Ser Ile His
1               5

<210> SEQ ID NO 67
<211> LENGTH: 9
<212> TYPE: PRT
<213> ORGANISM: Homo sapiens

<400> SEQUENCE: 67

Phe Thr Phe Thr Ser Ser Asp Ile His
1               5

<210> SEQ ID NO 68
<211> LENGTH: 9
<212> TYPE: PRT
<213> ORGANISM: Homo sapiens

<400> SEQUENCE: 68

Phe Thr Phe Thr Ala Asn Asp Ile His
1               5

<210> SEQ ID NO 69
<211> LENGTH: 9
<212> TYPE: PRT
<213> ORGANISM: Homo sapiens

<400> SEQUENCE: 69

Phe Thr Phe Thr Ser Ser Ser Ile His
1               5

<210> SEQ ID NO 70
<211> LENGTH: 9
<212> TYPE: PRT
```

```
<213> ORGANISM: Homo sapiens

<400> SEQUENCE: 70

Phe Thr Phe Ser Ala Asn Asp Ile His
1               5

<210> SEQ ID NO 71
<211> LENGTH: 9
<212> TYPE: PRT
<213> ORGANISM: Homo sapiens

<400> SEQUENCE: 71

Phe Thr Phe Ser Ala Thr Asp Ile His
1               5

<210> SEQ ID NO 72
<211> LENGTH: 9
<212> TYPE: PRT
<213> ORGANISM: Homo sapiens

<400> SEQUENCE: 72

Phe Thr Phe Ser Gly Ser Asp Ile His
1               5

<210> SEQ ID NO 73
<211> LENGTH: 106
<212> TYPE: PRT
<213> ORGANISM: Homo sapiens

<400> SEQUENCE: 73

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 74
<211> LENGTH: 330
<212> TYPE: PRT
<213> ORGANISM: Homo sapiens

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 327
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 76
<211> LENGTH: 327
<212> TYPE: PRT
<213> ORGANISM: Homo sapiens

<400> SEQUENCE: 76

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

-continued

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 77
<211> LENGTH: 327
<212> TYPE: PRT
<213> ORGANISM: Homo sapiens

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 78
<211> LENGTH: 216
<212> TYPE: PRT
<213> ORGANISM: Homo sapiens

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Lys Tyr Pro Phe
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 79
<211> LENGTH: 460
```

<212> TYPE: PRT
<213> ORGANISM: Homo sapiens

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ala Asn
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400
```

```
Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 80
<211> LENGTH: 457
<212> TYPE: PRT
<213> ORGANISM: Homo sapiens

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ala Asn
            20                  25                  30

Asp Ile His Trp Val Arg Gln Ala Pro Gly Lys Gly Leu Glu Trp Val
        35                  40                  45

Ala Ser Ile Tyr Ser Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Ser Tyr Tyr Trp Tyr Tyr Ser Gly Ser Ala Tyr
            100                 105                 110

Glu Gly Tyr Gly Leu Asp Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
```

```
            305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
                340                 345                 350

Pro Arg Glu Pro Gln Val Tyr Thr Leu Pro Pro Ser Gln Glu Glu Met
                355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
                450                 455
```

<210> SEQ ID NO 81

<400> SEQUENCE: 81

000

<210> SEQ ID NO 82
<211> LENGTH: 21
<212> TYPE: PRT
<213> ORGANISM: Homo sapiens

<400> SEQUENCE: 82

```
Asp Pro Gly Met Tyr Tyr Trp Tyr Tyr Ser Gly Ser Ala Tyr Glu Gly
1               5                   10                  15

Tyr Gly Leu Asp Tyr
                20
```

<210> SEQ ID NO 83
<211> LENGTH: 11
<212> TYPE: PRT
<213> ORGANISM: Homo sapiens

<400> SEQUENCE: 83

```
Gln Gln Arg Ser Arg Val Tyr Ser Leu Val Thr
1               5                   10
```

<210> SEQ ID NO 84
<211> LENGTH: 11
<212> TYPE: PRT
<213> ORGANISM: Homo sapiens

<400> SEQUENCE: 84

```
Gln Gln Met Asp Arg Phe Tyr Ser Leu Ile Thr
1               5                   10
```

<210> SEQ ID NO 85
<211> LENGTH: 11
<212> TYPE: PRT
<213> ORGANISM: Homo sapiens

<400> SEQUENCE: 85

Gln Gln Tyr Cys Arg Lys Ser Ser Leu Phe Thr
1               5                   10

<210> SEQ ID NO 86
<211> LENGTH: 11
<212> TYPE: PRT
<213> ORGANISM: Homo sapiens

<400> SEQUENCE: 86

Gln Gln Gln Gln Arg Thr Ser Tyr Leu Ile Thr
1               5                   10

<210> SEQ ID NO 87
<211> LENGTH: 11
<212> TYPE: PRT
<213> ORGANISM: Homo sapiens

<400> SEQUENCE: 87

Gln Gln Arg Ser Arg Tyr Tyr Ser Leu Ile Thr
1               5                   10

<210> SEQ ID NO 88
<211> LENGTH: 11
<212> TYPE: PRT
<213> ORGANISM: Homo sapiens

<400> SEQUENCE: 88

Gln Gln Ser Asn Arg Ser Tyr Pro Pro Leu Thr
1               5                   10

<210> SEQ ID NO 89
<211> LENGTH: 11
<212> TYPE: PRT
<213> ORGANISM: Homo sapiens

<400> SEQUENCE: 89

Gln Gln Ile Gly Arg Arg Ser Ser Leu Ile Thr
1               5                   10

<210> SEQ ID NO 90
<211> LENGTH: 11
<212> TYPE: PRT
<213> ORGANISM: Homo sapiens

<400> SEQUENCE: 90

Gln Gln Gln Gln Arg Tyr Ser Tyr Leu Ile Thr
1               5                   10

<210> SEQ ID NO 91
<211> LENGTH: 11
<212> TYPE: PRT
<213> ORGANISM: Homo sapiens

<400> SEQUENCE: 91

Gln Gln Ser Ser Arg Asn Ser Lys Leu Ile Thr
1               5                   10

<210> SEQ ID NO 92
<211> LENGTH: 11
<212> TYPE: PRT
<213> ORGANISM: Homo sapiens

<400> SEQUENCE: 92

Gln Gln Trp Met Arg Ser Ser Ser Leu Phe Thr

```
<210> SEQ ID NO 93
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X may be S or T
<220> FEATURE:
<221> NAME/KEY: MISC_FEATURE
<222> LOCATION: (5)..(5)
<223> OTHER INFORMATION: X may be S, G, or A
<220> FEATURE:
<221> NAME/KEY: MISC_FEATURE
<222> LOCATION: (6)..(6)
<223> OTHER INFORMATION: X may be T, N, or S
<220> FEATURE:
<221> NAME/KEY: MISC_FEATURE
<222> LOCATION: (7)..(7)
<223> OTHER INFORMATION: X may be D or S

<400> SEQUENCE: 93

Phe Thr Phe Xaa Xaa Xaa Xaa Ile His
1               5

<210> SEQ ID NO 94
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X may be S or T
<220> FEATURE:
<221> NAME/KEY: MISC_FEATURE
<222> LOCATION: (5)..(5)
<223> OTHER INFORMATION: X may be S or A
<220> FEATURE:
<221> NAME/KEY: MISC_FEATURE
<222> LOCATION: (6)..(6)
<223> OTHER INFORMATION: X may be N or S
<220> FEATURE:
<221> NAME/KEY: MISC_FEATURE
<222> LOCATION: (7)..(7)
<223> OTHER INFORMATION: X may be D or S

<400> SEQUENCE: 94

Phe Thr Phe Xaa Xaa Xaa Xaa Ile His
1               5
```